United States Patent [19]

Yamamoto et al.

[11] Patent Number: 4,844,728
[45] Date of Patent: Jul. 4, 1989

[54] PYRAZOLESULFONAMIDE DERIVATIVE, AND HERBICIDE CONTAINING IT

[75] Inventors: Susumu Yamamoto; Kakuta Takuya; Toshiaki Sato; Katsushi Morimoto, all of Funabashi; Eiichi Oya, Narashino; Takasi Ikai, Tokyo; Tsutomu Nawamaki, Yono; Kenji Hattori, Urawa, all of Japan

[73] Assignee: Nissan Chemical Industries, Ltd., Tokyo, Japan

[21] Appl. No.: 934,400

[22] Filed: Nov. 24, 1986

[30] Foreign Application Priority Data

Nov. 26, 1985 [JP] Japan ............... 60-265835

[51] Int. Cl.⁴ ............... A01N 43/54; C07D 239/69; C07D 401/14; C07D 403/14
[52] U.S. Cl. ............... 71/92; 71/90
[58] Field of Search ............... 71/90, 92; 544/183, 544/284, 237, 295, 321, 324, 331, 278

[56] References Cited

U.S. PATENT DOCUMENTS

| | | | |
|---|---|---|---|
| 4,602,940 | 7/1986 | Wolf | 71/92 |
| 4,655,823 | 4/1987 | Shapiro | 71/93 |
| 4,675,045 | 6/1987 | Petersen | 71/90 |
| 4,685,955 | 8/1987 | Christensen | 71/92 |
| 4,685,958 | 8/1987 | Pearson | 71/93 |
| 4,687,508 | 8/1987 | Hay | 71/92 |
| 4,689,069 | 8/1987 | Artz | 71/90 |
| 4,689,070 | 8/1987 | Shapiro | 71/90 |
| 4,689,072 | 8/1987 | Levitt | 71/93 |
| 4,693,741 | 9/1987 | Meyer | 71/92 |
| 4,693,743 | 9/1987 | Wexler | 71/92 |
| 4,705,558 | 11/1987 | Hartzell | 71/92 |

FOREIGN PATENT DOCUMENTS 0155767 9/1985 European Pat. Off. .

*Primary Examiner*—John M. Ford
*Attorney, Agent, or Firm*—Frishauf, Holtz, Goodman & Woodward

[57] ABSTRACT

Disclosed are a pyrazolesulfonamide derivative represented by Formula (I):

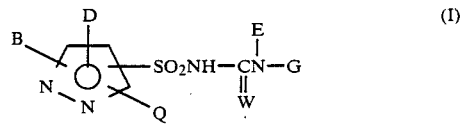

wherein B, D, Q, E, W and G have the same meaning as defined in the specification, a process for its production and a herbicide containing it.

34 Claims, No Drawings

PYRAZOLESULFONAMIDE DERIVATIVE, AND HERBICIDE CONTAINING IT

BACKGROUND OF THE INVENTION

This invention relates to a novel pyrazolesulfonamide derivative compound, a process for preparing the compound and a herbicide containing the compounds as an active component.

In order to protect important crops such as rice plants, wheat, cotton, sugar beets, corn and soybean from damages by weeds to achieve an increased yield, it is indispensable to use a herbicide. In recent years in particular, a herbicide having selectivity (or discriminativity) is sought after as it can kill only weeds selectively without damages to crops even when a foliage treatment is applied simultaneously on crops and weeds in a cultivated land wherein useful crops and weeds are grown together. Also, from viewpoints of the prevention of environmental pollution, the transportation, and the economical cost reduction in application of chemicals, studies and researches have been made over many years on such compounds that may achieve a higher herbicidal activity with use of chemicals in a lower amount. Some of the compounds having such a property are presently used as the herbicide having selectivity. Still, however, there are further demands for new compounds having such a property.

SUMMARY OF THE INVENTION

The present inventors have made researches over many years to develop herbicides having the selectivity on important crops, and have examined herbicidal properties of a number of compounds to create compounds having a higher herbicidal effect and the selectivity. As a result, it was found that a pyrazolesulfonamide derivative represented by Formula (I) (hereinafter referred to as "the compound of this invention"):

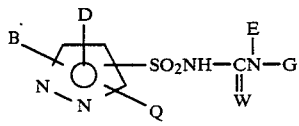

wherein Q represents a group of;

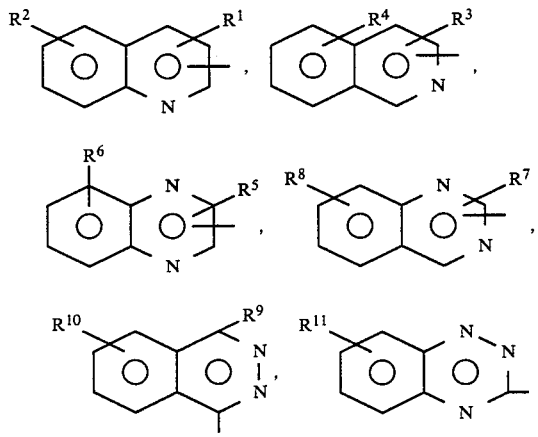

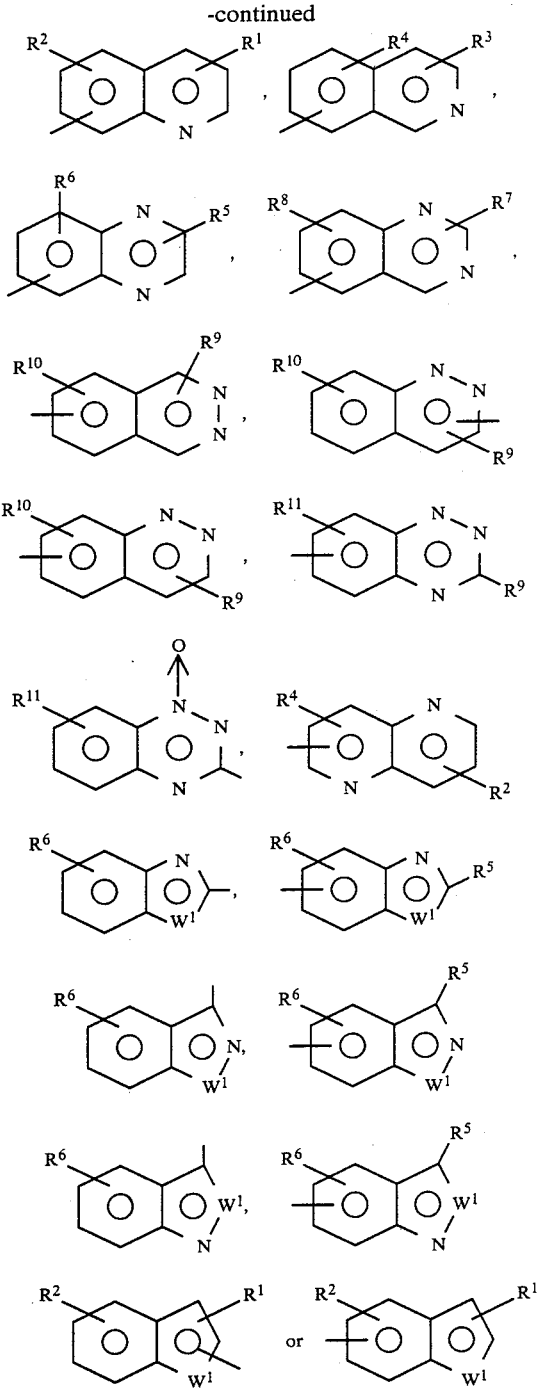

wherein
$R^1$, $R^3$, $R^9$ and $R^{10}$ each represent a hydrogen atom, a halogen atom, a $C_1$-$C_8$ alkyl group, a cyano group or a group of $CO_2R^{13}$;
$R^2$ and $R^4$ each represent a hydrogen atom, a halogen atom, a nitro group, a $C_1$-$C_8$ alkyl group, a halogenated $C_1$-$C_8$ alkyl group or a $C_1$-$C_8$ alkoxy group;
$R^5$ represents a hydrogen atom, a halogen atom, a $C_1$-$C_8$ alkyl group, a $C_1$-$C_8$ alkoxy group or a group of $S(O)_nR^{12}$;
$R^6$ represents a hydrogen atom, a halogen atom, a nitro group, a $C_1$-$C_8$ alkyl group, a halogenated $C_1$–$C_8$ alkyl group, a $C_1$–$C_2$ alkoxy group or a group of $CO_2R^{13}$;

$R^7$ represents a hydrogen atom, a halogen atom, a $C_1$–$C_8$ alkyl group, a $C_1$–$C_8$ alkoxy group or a dialkylamino group;

$R^8$ represents a hydrogen atom, a halogen atom, a $C_1$–$C_8$ alkyl group or a nitro group;

$R^{11}$ represents a hydrogen atom, a halogen atom, a $C_1$–$C_8$ alkyl group or a halogenated $C_1$–$C_8$ alkyl group;

$W^1$ represents an oxygen atom, a sulfur atom or a group of $NR^{13}$;

$R^{12}$ represents a $C_1$–$C_8$ alkyl group;

$R^{13}$ represents a hydrogen atom or a $C_1$–$C_8$ alkyl group; and n represents an integer of 0, 1 or 2;

B and D each independently represent a hydrogen atom, a halogen atom, a nitro group, a $C_1$–$C_8$ alkyl group, a $C_1$–$C_8$ alkenyl group, a $C_1$–$C_8$ alkynyl group, a $C_1$–$C_8$ alkoxy group, a $C_1$–$C_8$ alkoxy-$C_1$–$C_8$ alkyl group, a $C_1$–$C_8$ alkylthio-$C_1$–$C_8$ alkyl group, a halogenated $C_1$–$C_8$ alkyl group, a group of $COOR^{14}$, a group of $CH_2COOR^{14}$, a group of $CONR^{15}R^{16}$, a group of $S(O)_nR^{17}$, a cyano group, a group of $CH_2CN$, a group of $NR^{18}R^{19}$, a group of $SO_2NR^{20}R^{21}$, a group of $COR^{13}$, a group of OH, a benzoyl group which may be substituted (the substituent is selected from a halogen atom or a $C_1$–$C_8$ alkyl group) or a phenyl group which may be substituted (the substituent is selected from a halogen atom, a nitro group, a group of $COOR^{13}$ or a $C_1$–$C_8$ alkyl group);

$R^{14}$ represents a hydrogen atom, an unsubstituted $C_1$–$C_8$ alkyl group (or a $C_1$–$C_8$ alkyl group substituted with an unsubstituted $C_1$–$C_8$ alkoxy group or a $C_1$–$C_8$ alkoxy group substituted with a group of $OR^{13}$, a halogenated $C_1$–$C_8$ alkoxy group, a cyano group, a phenoxy group, a $C_1$–$C_8$ alkoxycarbonyl group, a group of $NR^{12}R^{13}$, a $C_3$–$C_7$ cycloalkyl group, a $C_1$–$C_8$ alkylthio group or a $C_1$–$C_8$ alkylcarbonyl group), an unsubstituted $C_1$–$C_8$ alkenyl group or a $C_1$–$C_8$ alkenyl group substituted with a halogen atom, an unsubstituted $C_1$–$C_8$ alkynyl group or a $C_1$–$C_8$ alkynyl group substituted with a halogen atom, a halogenated $C_1$–$C_8$ alkyl group, a $C_3$–$C_7$ cycloalkyl group or a benzyl group;

$R^{15}$ represents a hydrogen atom, a $C_1$–$C_8$ alkyl group or a phenyl group;

$R^{16}$ represents a hydrogen atom, a $C_1$–$C_8$ alkyl group or a $C_1$–$C_8$ alkoxy group;

$R^{17}$ represents a $C_1$–$C_8$ alkyl group, a $C_1$–$C_8$ alkoxy group, a phenyl group, a halogenated $C_1$–$C_8$ alkyl group, a $C_1$–$C_8$ alkenyloxy group or a $C_1$–$C_8$ alkynyloxy group; n represents an integer of 0, 1 or 2;

$R^{18}$ and $R^{19}$ each independently represent a hydrogen atom, a $C_1$–$C_8$ alkyl group, a $C_1$–$C_8$ alkylcarbonyl group or a $C_1$–$C_8$ alkylsulfonyl group;

$R^{20}$ and $R^{21}$ each independently represent a hydrogen atom, a $C_1$–$C_8$ alkyl group, a $C_1$–$C_8$ alkenyl group or a $C_1$–$C_8$ alkynyl group;

E represents a hydrogen atom, a $C_1$–$C_8$ alkyl group, a $C_1$–$C_8$ alkenyl group, a $C_1$–$C_8$ alkynyl or a $C_1$–$C_8$ alkoxy group;

W represents an oxygen atom, a sulfur atom or a group of $NR^{16}$;

G represents

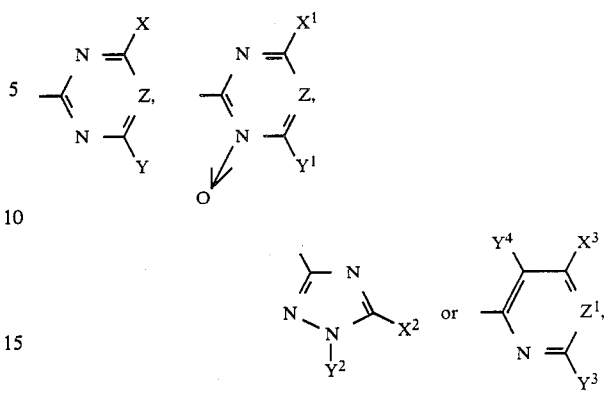

wherein X and Y each independently represent a hydrogen atom, a halogen atom, a $C_1$–$C_8$ alkyl group, a $C_1$–$C_8$ alkoxy group, a $C_1$–$C_8$ alkoxyalkyl group, a halogenated $C_1$–$C_8$ alkyl group, a halogenated $C_1$–$C_8$ alkoxy group, a group of $NR^{22}R^{23}$, a group of $OCH(R^{13})COOR^{13}$, a group of $COOR^{13}$, a cyclopropyl group, a group of $CH(OR^{24})_2$, a $C_1$–$C_8$ alkylthio group or a halogenated $C_1$–$C_8$ alkylthio group;

$R^{22}$ and $R^{23}$ each independently represent a hydrogen atom, a $C_1$–$C_8$ alkyl group or a $C_1$–$C_8$ alkoxy group;

$R^{24}$ represents a $C_1$–$C_8$ alkyl group; $X^1$ and $Y^1$ each independently represent a hydrogen atom, a halogen atom, a $C_1$–$C_8$ alkyl group or a $C_1$–$C_8$ alkoxy group;

$X^2$ represents a $C_1$–$C_8$ alkyl group, a $C_1$–$C_8$ alkylthio group or a $C_1$–$C_8$ alkoxy group;

$Y^2$ represents a $C_1$–$C_8$ alkyl group;

$X^3$ represents a $C_1$–$C_8$ alkyl group, a $C_1$–$C_8$ alkoxy group, a $C_1$–$C_8$ alkoxy-$C_1$–$C_8$ alkyl group or a halogen atom;

$Y^3$ represents a $C_1$–$C_8$ alkyl group, a $C_1$–$C_8$ alkoxy group, a halogen atom, a monoalkylamino group or a dialkylamino group;

$Y^4$ represents a cyano group, a group of $CO_2R^{13}$, a nitro group, a group of $S(O)_nR^{12}$, a $C_1$–$C_8$ alkyl group or a halogenated $C_1$–$C_8$ alkyl group;

Z represents a nitrogen atom or a group of $C-R^{25}$;

$Z^1$ represents a nitrogen atom or a group of CH;

$R^{25}$ represents a hydrogen atom, a $C_1$–$C_8$ alkyl group, a halogenated $C_1$–$C_8$ alkyl group, a halogen atom, a $C_1$–$C_8$ alkoxy group or a 5-membered ring structure containing an oxygen atom together with Y or $Y^1$;

with the proviso that the group:

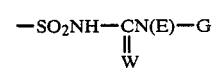

in Formula (I) is not substituted on the nitrogen atom in the pyrazole ring, and, when Q is not substituted on the nitrogen atom in the pyrazole ring, the substituent for B or D on the nitrogen atom is selected from a hydrogen atom, a $C_1$–$C_8$ alkyl group, a $C_1$–$C_8$ alkenyl group, a $C_1$–$C_8$ alkynyl group, a group of —$CH_2CN$, a $C_1$–$C_8$ alkoxy-$C_1$–$C_8$ alkyl group, a $C_1$–$C_8$ alkylthio-$C_1$–$C_8$ alkyl group, a group of —$CH_2COOR^{13}$, a group of —$COR^{13}$, a group of —$SO_2R^{24}$, a group of $-SO_2NR^{13}R^{24}$ or a phenyl group which may be substituted (the substituent is selected from a halogen atom, a nitro group, a group of $COOR^{13}$ or a $C_1-C_8$ alkyl group).

has a strong herbicidal effect to various weeds while retaining high safety to the important crops in either case of the soil treatment or the foliage treatment, whereby this invention has been accomplished. Particularly, some of these compounds show extremely high selectivity to sugar beets. Conventionally, a number of compounds having sulfonylurea structure have been known. Any of these, however, show very strong activities to sugar beets. For example, sugar beets have extremely high sensibility to chlorsulfuron which is known as a herbicide for wheat, and accordingly the sugar beets which are cultured as second crops after wheat are known to be seriously suffered from damages by the agricultural chemicals even after two years, because of a trace amount of the active component remaining in the soil. Also, other sulfonylurea compounds than the chlorsulfuron are also considered to have very particularly strong effect on sugar beets, and, of the sulfonylurea type compounds, almost no compound which may have the selectivity to sugar beets have been hitherto unknown. Also, certain compounds of the compounds of this invention have the selectivity not only to beets but also to rice plants, wheat, cotton, corn, etc. The compound of this invention, on the other hand, shows a high herbicidal activity in an application of a very low amount of the active component as compared with the conventional herbicides, and accordingly it is useful also as a herbicide for orchards and uncultivated lands. As a prior technique, European Patent Publication No. 87,780 discloses a pyrazolesulfonylurea which has the structure similar to the compound of this invention. However, there has been nothing disclosing the compound wherein a fused heterocyclic ring is substituted on a pyrazole ring as the compound of this invention. Thus, the compound of this invention can be said to be a novel one.

DESCRIPTION OF THE PREFERRED EMBODIMENTS

The compound of this invention, represented by Formula (I) can be readily prepared by selecting any of reaction schemes 1 to 3 shown below.

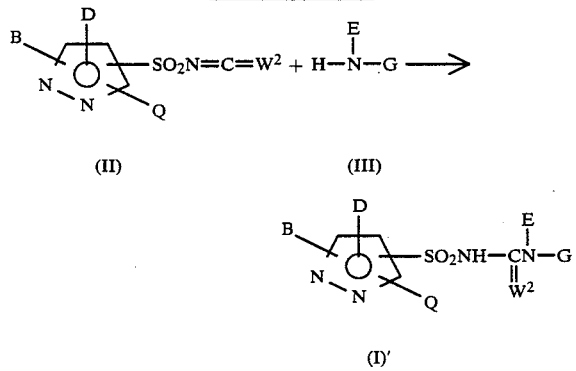

wherein $W^2$ represents an oxygen atom or a sulfur atom, and B, D, Q, E and G have the same meanings as defined above.

Namely, the pyrazolesulfonyl(thio)isocyanate derivative (II) is dissolved in a sufficiently dried inert solvent such as dioxane and acetonitrile and thereto is added a pyrimidine, triazine or triazole derivative represented by Formula (III), with stirring. Thus, the reactants generally are reacted with each other rapidly to give the compound (I)' which is a part of the compound of this invention. In cases where it is difficult for the reaction to proceed, a trace or small amount of a suitable base, such as triethylamine, triethylenediamine, pyridine, a sodium alkoxide, sodium hydride and the like, may be added to the reaction system to allow the reaction to proceed readily.

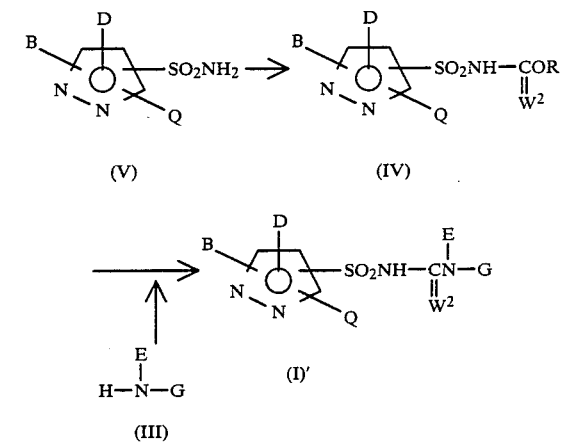

wherein R represents a $C_1-C_8$ alkyl group or a phenyl group and B, D, Q, E, $W^2$ and G have the same meanings as defined above.

Namely, the pyrazolesulfonamide derivative (V) is reacted with a chloroformic acid (thio)ester or a carbonic acid (thio)ester in such a solvent as acetone, methyl ethyl ketone and acetonitrile in the presence of a base such as potassium carbonate to give the compound (IV). Then, the resulting compound (IV) is heated with the compound (III) in such a solvent as toluene to give the compound (I)' which is a part of the compound of this invention.

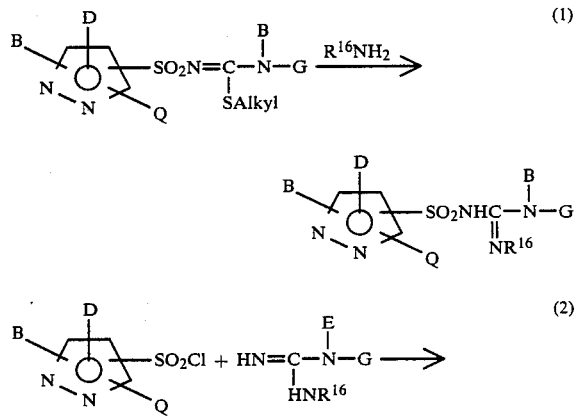

-continued
Reaction scheme 3

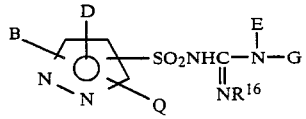

wherein B, D, Q, E, G and $R^{16}$ have the same meanings as defined above.

Namely, the above sulfonylguanidine type compound which is a part of the compound of this invention can be synthesized in accordance with the process disclosed in Japanese Unexamined Patent Publication No. 167570/1984, No. 6654/1985 and No. 36467/1985.

The starting materials, the pyrazolesulfonyl (thio)isocyanate (II) and the pyrazolesulfonyl (thio)carbamate derivatives (IV) which is used in Reaction Schemes 1 and 2 may be synthesized by selecting appropriately the methods as will be described hereinafter to synthesize the pyrazolesulfonamide (V) and further it can be led to a final product with reference to the methods as described in Published European Patent Application No. 87,780 and Japanese Unexamined Patent Publication No. 13266/1980.

The pyrazolesulfonamide which is an intermediate compound to be used in the present invention is also a novel compound, which can be obtained by selecting appropriately one of the following Reaction schemes 4 to 8.

Reaction scheme 4

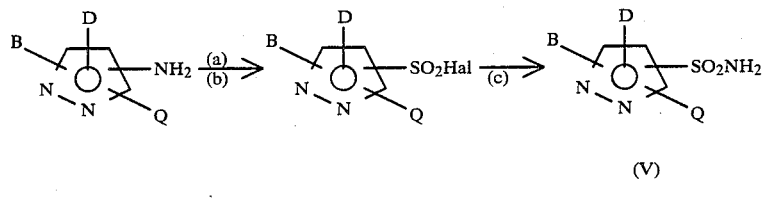

Reaction scheme 5

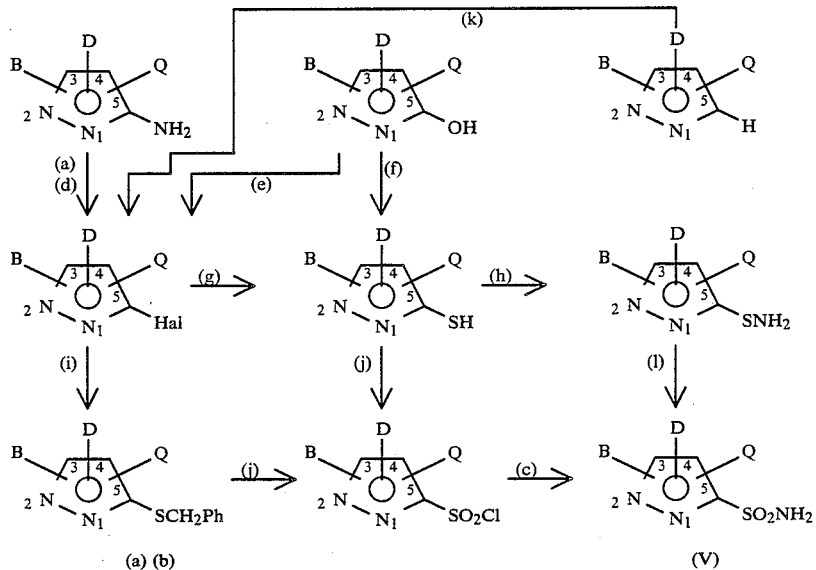

Reaction scheme 6

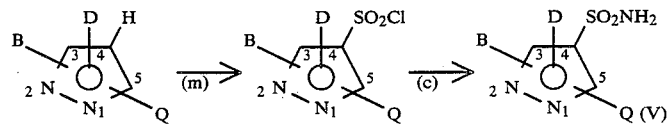

Reaction scheme 7

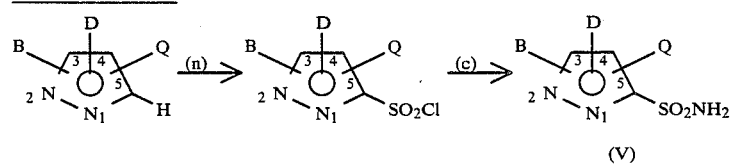

Reaction scheme 8

-continued

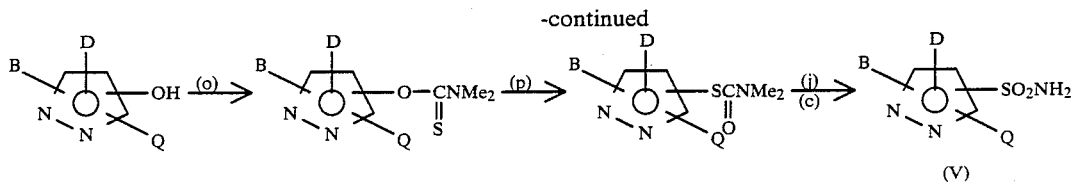

Reaction scheme 9

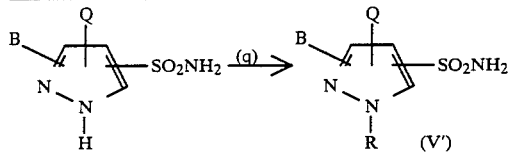

(a) NaNO$_2$.HCl or NaNO$_2$.HBr
(b) SO$_2$.Cu salt
(c) NH$_4$OH or ammonium carbonate
(d) Cu salt
(e) POCl$_3$ or POBr$_3$
(f) P$_2$S$_5$
(g) NaSH
(h) NaOH.NH$_4$OH.NaOCl
(i) NaSCH$_2$Ph
(j) Cl$_2$/CH$_3$COOH.H$_2$O or NaOCl/HCl
BuLi or LiN(i—Pr)$_2$ subsequently, Cl$_2$ or Br$_2$
(l) Oxidizing agent
(m) (1) ClSO$_3$H [2]SOCl$_2$ or PCl$_5$]
(n) (1) BuLi or LiN(i—Pr)$_2$
(2) SO$_2$
(3) N-chlorosuccinimide ClC($=$S)NMe$_2$/base
(p) heating
(q) RHal/base wherein B, D, Q and E, have the same meanings as defined above; R represents a $C_1$-$C_8$ alkyl group, a $C_1$-$C_8$ alkenyl group, a $C_1$-$C_8$ alkynyl group, a group, of —CH$_2$CN, a $C_1$-$C_8$ alkoxy-$C_1$-$C_8$ alkyl group, a $C_1$-$C_8$ alkylthio-$C_1$-$C_8$ alkyl group, a group of —CH$_2$COOR$^{13}$, a group of —COR$^{13}$, a group of —SO$_2$R$^{24}$ or a group of —SO$_2$NR$^{13}$R$^{24}$; and R$^{13}$ and R$^{24}$ have the same meanings as defined above.

The pyrazolesulfonamide (V) may usually be obtained by reacting a corresponding pyrazolesulfonyl chloride with an aqueous ammonia or ammonium carbonate. In order to introduce a sulfonyl group into a pyrazole, there may be adopted such a method as follows:

(1) The amino group is subjected to diazonium decomposition in the presence of sulfur dioxide to give a pyrazolesulfonyl chloride;

(2) A hydroxypyrazole is converted into an O-pyrazole thiocarbamate, which is then subjected to rearrangement reaction to introduce a sulfur atom in the pyrazole ring followed by oxidation to give a pyrazolesulfonyl chloride;

(3) A sulfur atom is introduced in the pyrazole ring by a nucleophilic substitution reaction with a halogen atom or the like and optionally the resulting compound is further oxidized to give a pyrazolesulfonyl chloride;

(4) A carbanion of a pyrazole is formed by using a base and the sulfur dioxide is reacted therewith followed by halogenation to give a pyrazolesulfonyl chloride;

(5) Chlorosulfonic acid or the like is directly used to give a pyrazolesulfonyl chloride;

(6) The pyrazole derivative, which has been obtained by any of the above-mentioned methods, is functionally modified by utilizing the properties of the pyrazole.

Namely, (1) according to Reaction scheme 4, an aminopyrazole is converted into a diazonium salt by using sodium nitrite or the like in hydrochloric acid, hydrobromic acid or the like and then sulfur dioxide is reacted with the resulting diazonium salt in the presence of a catalyst which is used usually for diazonium decomposition such as a copper salt or the like, to afford a corresponding pyrazolesulfonyl chloride. With the resulting compound was reacted an aqueous ammonia to give the desired pyrazolesulfonamide (V).

(2) According to Reaction scheme 8, starting from a hydroxypyrazole, an O-pyrazole thiocarbamate is obtained and then the resulting compound is rearranged under heating to give an S-pyrazole thiolcarbamate which is then oxidized with chlorine in such a solvent as acetic acid to afford a pyrazolesulfonyl chloride. As in Reaction scheme 4, action of an aqueous ammonia gives the desired pyrazolesulfonamide (V).

Be noted that these Reaction schemes 4 and 8 may be applied without any dependency upon the position(s) of the substituent(s).

(3) In the nucleophilic substitution reaction on the pyrazole, the 5 position on the pyrazole ring is usually reacted most easily, but there may be a case where the nucleophilic substitution reaction further occurs at the 3 position when an electron attracting group is substituted at the 4 position.

By using this property, according to Reaction scheme 5, a pyrazole halogenated at the 5 position is treated with sodium sulfide, sodium salt of benzylmercaptan or the like to introduce a sulfur atom into the 5 position followed by oxidation with chlorine in such a solvent as acetic acid to give a pyrazolesulfonyl chloride. As in Reaction scheme 4, a reaction with an aqueous ammonia gives the desired pyrazolesulfonamide (V). The desired pyrazolesulfonamide may also be obtained by converting the intermediate 5-mercaptopyrazole into a sulfenamide which is then oxidized. The starting material, the pyrazole halogenated at the 5 position, may be obtained by diazo-decomposition of an aminopyrazole; by the reaction of a hydroxypyrazole with phosphorus oxychloride or phosphorus oxybromide; or by formation of an anion at the 5 position by using such a strong base as butyl lithium, lithium diisopropylamide or the like, followed by halogenation.

(4) In cases where there is a substituent at the 1 position, the hydrogen atom at the 5 position on the pyrazole ring has a relatively strong acidity. According to Reaction scheme 7, an anion may be formed by using such a strong base as butyl lithium, lithium diisopropylamide or the like, and the resulting anion may further be treated by sulfur dioxide and subsequently with an N-halogenosuccinimide to form a pyrazolesulfonyl chloride which is then treated with an aqueous ammonia to give the pyrazolesulfonamide (V).

(5) As compared with the nucleophilic substitution reaction, the electrophilic substitution reaction on the pyrazole ring may usually occur more easily at the 4 position. According to Reaction scheme 6, use of chlorosulfonic acid may give directly a pyrazolesulfonyl chloride.

(6) According to Reaction scheme 9, when a pyrazolesulfonamide having no substituent on the 1 position is subjected to alkylation, acylation or sulfonylation, the 1 or 2 position may be alkylated, acylated or sulfonylated, respectively. According to this method, there may be obtained, depending upon the starting material used, a mixture of two kinds of compounds in which substituents on the 3 and 5 positions have been switched with each other. However, these compounds may be separated by recrystallization, column chromatography or the like and used as an intermediate compound for the compound of this invention.

Further, various kinds of pyrazolesulfonamide (V) may be obtained by newly introducing a substituent in the pyrazolesulfonamide or by modifying the introduced substituent, utilizing the properties of a pyrazole.

As to the synthesis of pyrazolesulfonamide in which a hetero ring is substituted on the pyrazole ring, specifications of Japanese Patent Application No. 78784/1985 and No. 236780/1985 can be referred to.

The pyrazoles used as starting materials in the above-mentioned reactions may be synthesized in many cases with reference to A. N. Kost & I. I. Groundberg, Advances in Heterocyclic Chemistry Vol. 6, 347 (1966); T. L. Yacobs, Heterocyclic Compounds, R. C. Elderfield, Vol. 5, 45, Wiley, New York (1957); K. Shofield, M. R. Grimmett and B. R. T. Keene, Heterocyclic Nitrogen Compounds, The Azoles, Cambridge University Press, London, New York, Melbourne (1976); and Kevin T. Potts, Comprehensive Heterocyclic Chemistry, Vol. 5, 167 (1984), Pergamon Press. In cases where Q is substituted at the 1 position of the pyrazole ring, $QNHNH_2$ may be used in many cases for the synthesis in place of hydrazine, methlyhydrazine, phenylhydrazine and so on as described in the above-mentioned literatures.

A person skilled in the art would be able to obtain an intermediate for the compound of the present invention by investigating reaction conditions and the like taking into consideration the above descriptions and the prior art technologies as mentioned above.

Hereinafter, there will be described Synthesis examples of the present compounds and the intermediate compounds therefor as working examples or referential examples, which however should not be construed to limit the present invention.

REFERENCE EXAMPLE 1

Synthesis of 4-ethoxycarbonyl-1-(2-quinolyl)pyrazole-5-sulfonamide (1) Synthesis of ethyl 5-amino-1-(2-quinolyl)pyrazole-4-carboxylate:

17.1 g of ethyl ethoxymethylene cyanoacetate was dissolved in 200 ml of n-butyl alcohol and 16 g of 2-hydradinoquinoline was added thereto, followed by stirring at room temperature for 12 hours. The suspension obtained was refluxed for 2.5 hours and then cooled. Crystals precipitated were filtered, washed with n-hexane and dried to obtain 25.7 g of the title compound. m.p.: 146° to 147° C.

(2) Synthesis of ethyl 5-chloro-1-(2-quinolyl)-pyrazole-4-carboxylate:

24.7 g of ethyl 5-amino-1-(2-quinolyl)pyrazole-4-carboxylate was suspended in 400 ml of conc. hydrochloric acid, and the suspension obtained was cooled to −5° C., to which 7.9 g of sodium nitrite dissolved in 15 ml of water was added dropwise, and thereafter stirred for 30 minutes, followed by addition of 1.45 g of urea. The solution thus obtained was added dropwise at 5° C. to a solution obtained by adding 14 g of sulfur dioxide and 1.5 g of cuprous chloride to 150 ml of 1,2-dichloroethane. After stirring at room temperature for 1 hour, 1000 ml of ice water was added thereto, followed by extraction with chloroform. Seperation of the layer of chloroform, washing with water, drying and concentration were then carried out to obtain 23 g of the mixture of the title compound and ethyl 1-(2-quinolyl)pyrazole-4-carboxylate (about 3:2). The mixture obtained can be used in the next procedure without purification.

(3) Synthesis of ethyl 5-mercapto-1-(2-quinolyl)-pyrazole-4-carboxylate:

23 g of the mixture of ethyl 5-chloro-1-(2-quinolyl)-pyrazole-4-carboxylate and ethyl 1-(2-quinolyl)-pyrazole-4-carboxylate (about 3:2) was dissolved in 100 ml of dimethylformamide, to which 15.3 g of 70% sodium hydrosulfide was added and then heated at 80° to 85° C. for 1.5 hours. After the reaction was completed, ice water was added, followed by the filtration of ethyl 1-(2-quinolyl)pyrazole-4-carboxylate which was insoluble, to make the aqueous layer acidic with use of conc. hydrochloric acid. The orange crystal precipitated was filtered, washed with water and dried to obtain 13.1 g of the title compound. m.p.: 113° to 117° C.

(4) Synthesis of 4-ethoxycarbonyl-1-(2-quinolyl)-pyrazole-5-sulfonamide:

13 g of ethyl 5-mercapto-1-(2-quinolyl)pyrazole-4-carboxylate was suspended in 100 ml of 80% acetic acid, into which chlorine was introduced at 5° to 15° C. until it became light yellow homogeneous solution. After the reaction was completed, 500 ml of ice water was added, and crystals precipitated were filtered and washed with water to obtain 4-ethoxycarbonyl-1-(2-quinolyl)pyrazole-5-sulfonylchloride. The sulfonylchloride obtained was dissolved in 50 ml of tetrahydrofuran, followed by addition of 8 ml of 28% aqueous ammonia and stirring at room temperature for 0.5 hour. After solvent was evaporated, crystals precipitated were washed with water and dried to obtain 7 g of the title compound. m.p.: 140° to 141° C.

REFERENCE EXAMPLE 2

Synthesis of 4-ethoxycarbonyl-1-(1-isoquinolyl)pyrazole-5-sulfoamide

Synthesis was carried out following the procedures in Reference Example 1. m.p.: 165° to 170° C.

Each of the intermediates had the following property.

Ethyl 5-amino-1-(1-isoquinolyl)pyrazole-4-carbonylate (it was obtained by heating 1-hydrazinoisoquinoline and ethyl ethoxymethylene cyanoacetate ester in n-butyl alcohol), m.p.: 126° to 128° C.

Ethyl 5-chloro-1-(1-isoquinolyl)pyrazole-4-carboxylate, m.p.: 89° to 90° C.

Ethyl 5-mercapto-1-(1-isoquinolyl)pyrazole-4-carboxylate, m.p.: 121° to 122° C.

EXAMPLE 1

Synthesis of N-[(4,6-dimethoxyprimidine-2-yl)aminocarbonyl]-4-ethoxycarbonyl-1-(2-quinolyl)pyrazole-5-sulfonamide (Compound No. 11)

To a mixture of 6 g of 4-ethoxycarbonyl-1-(2-quinolyl)pyrazole-5-sulfonamide and 3.6 g of anhydrous potassium carbonate dissolved in 40 ml of acetonitrile, was added 1.9 g of n-butylisocyanate at room temperature, followed by heating under reflux for 1.5 hours. After the reaction was completed, acetonitrile was evaporated under reduced pressure, and then the residue was poured into ice water to filter insolubles off, and then the filtrate was precipitated with hydrochloric acid. Crystals precipitated were filtered, washed with water and dried to obtain 7 g of N-(n-butylcarbamoyl)-4-ethoxycarbonyl-1-(2-quinolyl)pyrazole-5-sulfonamide. m.p: 140° to 142° C.

Subsequently, the above compound was added to 70 ml of dried toluene, into which 7.5 g of phosgene was introduced while heating under reflux, and thereafter the reaction mixture was further heated under reflux for 1.5 hours. After the reaction was completed, solvent was evaporated under reduced pressure to obtain 6 g of crude 4-ethoxycarbonyl-1-(2-quinolyl)pyrazole-5-sulfonylisocyanate. 1.0 g of this crude suflonylisocyanate was added to a solution containing 0.37 g of 2-amino-4,6-dimethoxyprimidine dissolved in 5 ml of dried acetonitrile, followed by stirring at room temperature. Crystals precipitated were filtered, washed and dried to obtain 1.2 g of the title compound. m.p: 179° to 182° C.

EXAMPLE 2

Synthesis of N-[(4,6-dimethoxypyrimidin-2-yl)aminocarbonyl]-4-ethoxycarbonyl-1-(1-isoquinolyl)pyrazole-5-sulfonamide (Compound No. 315)

Synthesis was carried out following the procedures in Example 1. m.p.: 213° to 214° C.

The intermediate of N-(n-butylcarbamoyl)-4-ethoxycarbonyl-1-(1-isoquinolyl)pyrazole-5-sulfonamide had a melting point of 131° to 132° C.

In the following, examples of specific compounds included in the compound of this invention are shown in Table 1 to Table 7 in addition to the compounds synthesized in the above Examples, which, however, should not be construed to limit this invention.

TABLE 1

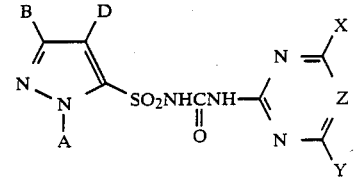

| No. | A | B | D | X | Y | Z |
|---|---|---|---|---|---|---|
| 1 | $Q_1$ | H | COOMe | Me | Me | CH |
| 2 | $Q_1$ | H | COOMe | Me | OMe | CH |
| 3 | $Q_1$ | H | COOMe | OMe | OMe | CH |
| 4 | $Q_1$ | H | COOMe | Me | Me | N |
| 5 | $Q_1$ | H | COOMe | Me | OMe | N |
| 6 | $Q_1$ | H | COOMe | OMe | OMe | N |
| 7 | $Q_1$ | H | COOMe | Me | OCHF$_2$ | CH |
| 8 | $Q_1$ | H | COOMe | Cl | OMe | CH |
| 9 | $Q_1$ | H | COOEt | Me | Me | CH |
| 10 | $Q_1$ | H | COOEt | Me | OMe | CH |
| 11 | $Q_1$ | H | COOEt | OMe | OMe | CH |
| 12 | $Q_1$ | H | COOEt | Me | Me | N |
| 13 | $Q_1$ | H | COOEt | Me | OMe | N |
| 14 | $Q_1$ | H | COOEt | OMe | OMe | N |
| 15 | $Q_1$ | H | COOEt | Me | OCHF$_2$ | CH |
| 16 | $Q_1$ | H | COOEt | Cl | OMe | CH |
| 17 | $Q_1$ | H | COOPr—n | Me | OMe | CH |
| 18 | $Q_1$ | H | COOPr—n | OMe | OMe | CH |
| 19 | $Q_1$ | H | COOPr—n | Me | OMe | N |
| 20 | $Q_1$ | H | COOPr—i | Me | OMe | CH |
| 21 | $Q_1$ | H | COOPr—i | OMe | OMe | CH |
| 22 | $Q_1$ | H | COOPr—i | Me | OMe | N |
| 23 | $Q_1$ | H | COOCH$_2$CH$_2$Cl | Me | OMe | CH |
| 24 | $Q_1$ | H | COOCH$_2$CH$_2$Cl | OMe | OMe | CH |
| 25 | $Q_1$ | H | COOCH$_2$CH$_2$Cl | Me | OMe | N |
| 26 | $Q_1$ | H | COOCH$_2$CH=CH$_2$ | Me | OMe | CH |
| 27 | $Q_1$ | H | COOCH$_2$CH=CH$_2$ | OMe | OMe | CH |
| 28 | $Q_1$ | H | COOCH$_2$CH=CH$_2$ | Me | OMe | N |
| 29 | $Q_1$ | H | COOCH$_2$C≡CH | Me | OMe | CH |
| 30 | $Q_1$ | H | COOCH$_2$C≡CH | OMe | OMe | CH |
| 31 | $Q_1$ | H | COOCH$_2$C≡CH | Me | OMe | N |
| 32 | $Q_1$ | Me | COOMe | Me | Me | CH |
| 33 | $Q_1$ | Me | COOMe | Me | OMe | CH |
| 34 | $Q_1$ | Me | COOMe | OMe | OMe | CH |
| 35 | $Q_1$ | Me | COOMe | Me | OMe | N |
| 36 | $Q_1$ | Me | COOMe | OMe | OMe | N |
| 37 | $Q_1$ | Me | COOEt | Me | Me | CH |
| 38 | $Q_1$ | Me | COOEt | Me | OMe | CH |
| 39 | $Q_1$ | Me | COOEt | OMe | OMe | CH |
| 40 | $Q_1$ | Me | COOEt | Me | OMe | N |
| 41 | $Q_1$ | Me | COOEt | OMe | OMe | N |
| 42 | $Q_1$ | Cl | COOMe | Me | OMe | CH |
| 43 | $Q_1$ | Cl | COOMe | OMe | OMe | CH |
| 44 | $Q_1$ | Cl | COOMe | Me | OMe | N |
| 45 | $Q_1$ | Cl | COOEt | Me | OMe | CH |
| 46 | $Q_1$ | Cl | COOEt | OMe | OMe | CH |
| 47 | $Q_1$ | Cl | COOEt | Me | OMe | N |
| 48 | $Q_1$ | OMe | COOMe | Me | OMe | CH |
| 49 | $Q_1$ | OMe | COOMe | OMe | OMe | CH |
| 50 | $Q_1$ | OMe | COOMe | Me | OMe | N |
| 51 | $Q_1$ | OMe | COOEt | Me | OMe | CH |
| 52 | $Q_1$ | OMe | COOEt | OMe | OMe | CH |
| 53 | $Q_1$ | OMe | COOEt | Me | OMe | N |
| 54 | $Q_1$ | H | Cl | Me | OMe | CH |
| 55 | $Q_1$ | H | Cl | OMe | OMe | CH |
| 56 | $Q_1$ | H | Cl | Me | OMe | N |
| 57 | $Q_1$ | H | NO$_2$ | Me | OMe | CH |
| 58 | $Q_1$ | H | NO$_2$ | OMe | OMe | CH |
| 59 | $Q_1$ | H | NO$_2$ | Me | OMe | N |
| 60 | $Q_1$ | H | SO$_2$NMe$_2$ | Me | OMe | CH |
| 61 | $Q_1$ | H | SO$_2$NMe$_2$ | OMe | OMe | CH |
| 62 | $Q_1$ | H | SO$_2$NMe$_2$ | Me | OMe | N |
| 63 | $Q_1$ | H | CN | Me | OMe | CH |
| 64 | $Q_1$ | H | CN | OMe | OMe | CH |
| 65 | $Q_1$ | H | CN | Me | OMe | N |
| 66 | $Q_1$ | Me | CN | Me | OMe | CH |
| 67 | $Q_1$ | Me | CN | OMe | OMe | CH |
| 68 | $Q_1$ | Me | CN | Me | OMe | N |
| 69 | $Q_1$ | H | Me | Me | OMe | CH |
| 70 | $Q_1$ | H | Me | OMe | OMe | CH |
| 71 | $Q_1$ | H | Me | Me | OMe | N |
| 72 | $Q_1$ | H | Et | Me | OMe | CH |
| 73 | $Q_1$ | H | Et | OMe | OMe | CH |
| 74 | $Q_1$ | H | Et | Me | OMe | N |
| 75 | $Q_1$ | H | H | Me | OMe | CH |
| 76 | $Q_1$ | H | H | OMe | OMe | CH |
| 77 | $Q_1$ | H | H | Me | OMe | N |
| 78 | $Q_1$ | H | COPh | Me | OMe | CH |

TABLE 1-continued

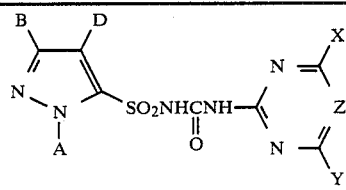

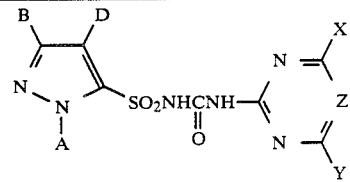

| No. | A | B | D | X | Y | Z |
|---|---|---|---|---|---|---|
| 79 | Q1 | H | COPh | OMe | OMe | CH |
| 80 | Q1 | H | COPh | Me | OMe | N |
| 81 | Me | Q1 | COOMe | Me | OMe | CH |
| 82 | Me | Q1 | COOMe | OMe | OMe | CH |
| 83 | Me | Q1 | COOMe | Me | OMe | N |
| 84 | H | H | Q1 | Me | OMe | CH |
| 85 | H | H | Q1 | OMe | OMe | CH |
| 86 | H | H | Q1 | Me | OMe | N |
| 87 | Me | H | Q1 | Me | Me | CH |
| 88 | Me | H | Q1 | Me | OMe | CH |
| 89 | Me | H | Q1 | OMe | OMe | CH |
| 90 | Me | H | Q1 | Me | OMe | N |
| 91 | Me | H | Q1 | OMe | OMe | N |
| 92 | Me | Me | Q1 | Me | OMe | CH |
| 93 | Me | Me | Q1 | OMe | OMe | CH |
| 94 | Me | Me | Q1 | Me | OMe | N |
| 95 | Q2 | H | COOMe | Me | Me | CH |
| 96 | Q2 | H | COOMe | Me | OMe | CH |
| 97 | Q2 | H | COOMe | OMe | OMe | CH |
| 98 | Q2 | H | COOMe | Me | OMe | N |
| 99 | Q2 | H | COOMe | OMe | OMe | N |
| 100 | Q2 | H | COOEt | Me | Me | CH |
| 101 | Q2 | H | COOEt | Me | OMe | CH |
| 102 | Q2 | H | COOEt | OMe | OMe | CH |
| 103 | Q2 | H | COOEt | Me | OMe | N |
| 104 | Q2 | H | COOEt | OMe | OMe | N |
| 105 | Q2 | Me | COOMe | Me | OMe | CH |
| 106 | Q2 | Me | COOMe | OMe | OMe | CH |
| 107 | Q2 | Me | COOMe | Me | OMe | N |
| 108 | Q2 | Me | COOEt | Me | OMe | CH |
| 109 | Q2 | Me | COOEt | OMe | OMe | CH |
| 110 | Q2 | Me | COOEt | Me | OMe | N |
| 111 | Q2 | H | CN | Me | OMe | CH |
| 112 | Q2 | H | CN | OMe | OMe | CH |
| 113 | Q2 | H | CN | Me | OMe | N |
| 114 | Q2 | H | H | Me | OMe | CH |
| 115 | Q2 | H | H | OMe | OMe | CH |
| 116 | Q2 | H | H | Me | OMe | N |
| 117 | Me | H | Q2 | Me | Me | CH |
| 118 | Me | H | Q2 | Me | OMe | CH |
| 119 | Me | H | Q2 | OMe | OMe | CH |
| 120 | Me | H | Q2 | Me | OMe | N |
| 121 | Me | H | Q2 | OMe | OMe | N |
| 122 | Q3 | H | COOMe | Me | Me | CH |
| 123 | Q3 | H | COOMe | Me | OMe | CH |
| 124 | Q3 | H | COOMe | OMe | OMe | CH |
| 125 | Q3 | H | COOMe | Me | OMe | N |
| 126 | Q3 | H | COOMe | OMe | OMe | N |
| 127 | Q3 | H | COOEt | Me | Me | CH |
| 128 | Q3 | H | COOEt | Me | OMe | CH |
| 129 | Q3 | H | COOEt | OMe | OMe | CH |
| 130 | Q3 | H | COOEt | Me | OMe | N |
| 131 | Q3 | H | COOEt | OMe | OMe | N |
| 132 | Q3 | Me | COOMe | Me | OMe | CH |
| 133 | Q3 | Me | COOMe | OMe | OMe | CH |
| 134 | Q3 | Me | COOMe | Me | OMe | N |
| 135 | Q3 | Me | COOEt | Me | OMe | CH |
| 136 | Q3 | Me | COOEt | OMe | OMe | CH |
| 137 | Q3 | Me | COOEt | Me | OMe | N |
| 138 | Q3 | H | CN | Me | OMe | CH |
| 139 | Q3 | H | CN | OMe | OMe | CH |
| 140 | Q3 | H | CN | Me | OMe | N |
| 141 | Q3 | H | H | Me | OMe | CH |
| 142 | Q3 | H | H | OMe | OMe | CH |
| 143 | Q3 | H | H | Me | OMe | N |
| 144 | Me | H | Q3 | Me | Me | CH |
| 145 | Me | H | Q3 | Me | OMe | CH |
| 146 | Me | H | Q3 | OMe | OMe | CH |
| 147 | Me | H | Q3 | Me | OMe | N |
| 148 | Me | H | Q3 | OMe | OMe | N |
| 149 | Q4 | H | COOMe | Me | Me | CH |
| 150 | Q4 | H | COOMe | Me | OMe | CH |
| 151 | Q4 | H | COOMe | OMe | OMe | CH |
| 152 | Q4 | H | COOMe | Me | OMe | N |
| 153 | Q4 | H | COOMe | OMe | OMe | N |
| 154 | Q4 | H | COOEt | Me | Me | CH |
| 155 | Q4 | H | COOEt | Me | OMe | CH |
| 156 | Q4 | H | COOEt | OMe | OMe | CH |
| 157 | Q4 | H | COOEt | Me | OMe | N |
| 158 | Q4 | H | COOEt | OMe | OMe | N |
| 159 | Q4 | Me | COOMe | Me | OMe | CH |
| 160 | Q4 | Me | COOMe | OMe | OMe | CH |
| 161 | Q4 | Me | COOMe | Me | OMe | N |
| 162 | Q4 | Me | COOEt | Me | OMe | CH |
| 163 | Q4 | Me | COOEt | OMe | OMe | CH |
| 164 | Q4 | Me | COOEt | Me | OMe | N |
| 165 | Q4 | H | CN | Me | OMe | CH |
| 166 | Q4 | H | CN | OMe | OMe | CH |
| 167 | Q4 | H | CN | Me | OMe | N |
| 168 | Q4 | H | H | Me | OMe | CH |
| 169 | Q4 | H | H | OMe | OMe | CH |
| 170 | Q4 | H | H | Me | OMe | N |
| 171 | Me | H | Q4 | Me | Me | CH |
| 172 | Me | H | Q4 | Me | OMe | CH |
| 173 | Me | H | Q4 | OMe | OMe | CH |
| 174 | Me | H | Q4 | Me | OMe | N |
| 175 | Me | H | Q4 | OMe | OMe | N |
| 176 | Q5 | H | COOMe | Me | Me | CH |
| 177 | Q5 | H | COOMe | Me | OMe | CH |
| 178 | Q5 | H | COOMe | OMe | OMe | CH |
| 179 | Q5 | H | COOMe | Me | OMe | N |
| 180 | Q5 | H | COOMe | OMe | OMe | N |
| 181 | Q5 | H | COOEt | Me | Me | CH |
| 182 | Q5 | H | COOEt | Me | OMe | CH |
| 183 | Q5 | H | COOEt | OMe | OMe | CH |
| 184 | Q5 | H | COOEt | Me | OMe | N |
| 185 | Q5 | H | COOEt | OMe | OMe | N |
| 186 | Q5 | Me | COOMe | Me | OMe | CH |
| 187 | Q5 | Me | COOMe | OMe | OMe | CH |
| 188 | Q5 | Me | COOMe | Me | OMe | N |
| 189 | Q5 | Me | COOEt | Me | OMe | CH |
| 190 | Q5 | Me | COOEt | OMe | OMe | CH |
| 191 | Q5 | Me | COOEt | Me | OMe | N |
| 192 | Q5 | H | CN | Me | OMe | CH |
| 193 | Q5 | H | CN | OMe | OMe | CH |
| 194 | Q5 | H | CN | Me | OMe | N |
| 195 | Q5 | H | H | Me | OMe | CH |
| 196 | Q5 | H | H | OMe | OMe | CH |
| 197 | Q5 | H | H | Me | OMe | N |
| 198 | Me | H | Q5 | Me | Me | CH |
| 199 | Me | H | Q5 | Me | OMe | CH |
| 200 | Me | H | Q5 | OMe | OMe | CH |
| 201 | Me | H | Q5 | Me | OMe | N |
| 202 | Me | H | Q5 | OMe | OMe | N |
| 203 | Q6 | H | COOMe | Me | Me | CH |
| 204 | Q6 | H | COOMe | Me | OMe | CH |
| 205 | Q6 | H | COOMe | OMe | OMe | CH |
| 206 | Q6 | H | COOMe | Me | OMe | N |
| 207 | Q6 | H | COOMe | OMe | OMe | N |
| 208 | Q6 | H | COOEt | Me | Me | CH |
| 209 | Q6 | H | COOEt | Me | OMe | CH |
| 210 | Q6 | H | COOEt | OMe | OMe | CH |
| 211 | Q6 | H | COOEt | Me | OMe | N |
| 212 | Q6 | H | COOEt | OMe | OMe | N |
| 213 | Q6 | Me | COOMe | Me | OMe | CH |
| 214 | Q6 | Me | COOMe | OMe | OMe | CH |
| 215 | Q6 | Me | COOMe | Me | OMe | N |
| 216 | Q6 | Me | COOEt | Me | OMe | CH |
| 217 | Q6 | Me | COOEt | OMe | OMe | CH |
| 218 | Q6 | Me | COOEt | Me | OMe | N |
| 219 | Q6 | H | CN | Me | OMe | CH |
| 220 | Q6 | H | CN | OMe | OMe | CH |

TABLE 1-continued

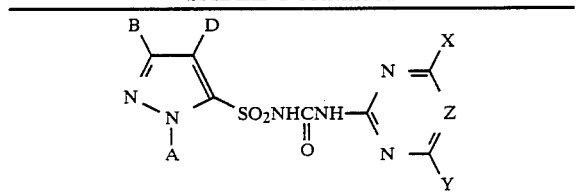

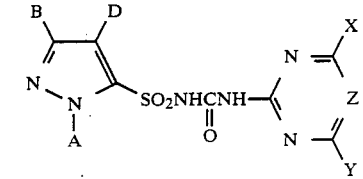

| No. | A | B | D | X | Y | Z | No. | A | B | D | X | Y | Z |
|---|---|---|---|---|---|---|---|---|---|---|---|---|---|
| 221 | Q6 | H | CN | Me | OMe | N | 292 | Q11 | Me | COOEt | OMe | OMe | CH |
| 222 | Q6 | H | H | Me | OMe | CH | 293 | Q11 | Me | COOEt | Me | OMe | N |
| 223 | Q6 | H | H | OMe | OMe | CH | 294 | Q11 | H | CN | Me | OMe | CH |
| 224 | Q6 | H | H | Me | OMe | N | 295 | Q11 | H | CN | OMe | OMe | CH |
| 225 | Me | H | Q6 | Me | Me | CH | 296 | Q11 | H | CN | Me | OMe | N |
| 226 | Me | H | Q6 | Me | OMe | CH | 297 | Q11 | H | H | Me | OMe | CH |
| 227 | Me | H | Q6 | OMe | OMe | CH | 298 | Q11 | H | H | OMe | OMe | CH |
| 228 | Me | H | Q6 | Me | OMe | N | 299 | Q11 | H | H | Me | OMe | N |
| 229 | Me | H | Q6 | OMe | OMe | N | 300 | Me | H | Q11 | Me | Me | CH |
| 230 | Q7 | H | COOMe | Me | OMe | CH | 301 | Me | H | Q11 | Me | OMe | CH |
| 231 | Q7 | H | COOMe | OMe | OMe | CH | 302 | Me | H | Q11 | OMe | OMe | CH |
| 232 | Q7 | H | COOEt | Me | OMe | CH | 303 | Me | H | Q11 | Me | OMe | N |
| 233 | Q7 | H | COOEt | OMe | OMe | CH | 304 | Me | H | Q11 | OMe | OMe | N |
| 234 | Q7 | Me | COOMe | Me | OMe | CH | 305 | Q12 | H | COOMe | Me | Me | CH |
| 235 | Q7 | Me | COOMe | OMe | OMe | CH | 306 | Q12 | H | COOMe | Me | OMe | CH |
| 236 | Q7 | Me | COOEt | Me | OMe | CH | 307 | Q12 | H | COOMe | OMe | OMe | CH |
| 237 | Q7 | Me | COOEt | OMe | OMe | CH | 308 | Q12 | H | COOMe | Me | Me | N |
| 238 | Q7 | H | H | Me | OMe | CH | 309 | Q12 | H | COOMe | Me | OMe | N |
| 239 | Q7 | H | H | OMe | OMe | CH | 310 | Q12 | H | COOMe | OMe | OMe | N |
| 240 | Me | H | Q7 | Me | OMe | CH | 311 | Q12 | H | COOMe | Me | OCHF2 | CH |
| 241 | Me | H | Q7 | OMe | OMe | CH | 312 | Q12 | H | COOMe | Cl | OCHF2 | CH |
| 242 | Q8 | H | COOMe | Me | OMe | CH | 313 | Q12 | H | COOEt | Me | Me | CH |
| 243 | Q8 | H | COOMe | OMe | OMe | CH | 314 | Q12 | H | COOEt | Me | OMe | CH |
| 244 | Q8 | H | COOEt | Me | OMe | CH | 315 | Q12 | H | COOEt | OMe | OMe | CH |
| 245 | Q8 | H | COOEt | OMe | OMe | CH | 316 | Q12 | H | COOEt | Me | Me | N |
| 246 | Q8 | Me | COOMe | Me | OMe | CH | 317 | Q12 | H | COOEt | Me | OMe | N |
| 247 | Q8 | Me | COOMe | OMe | OMe | CH | 318 | Q12 | H | COOEt | OMe | OMe | N |
| 248 | Q8 | Me | COOEt | Me | OMe | CH | 319 | Q12 | H | COOEt | Me | OCHF2 | CH |
| 249 | Q8 | Me | COOEt | OMe | OMe | CH | 320 | Q12 | H | COOEt | Cl | OCHF2 | CH |
| 250 | Q8 | H | H | Me | OMe | CH | 321 | Q12 | H | COOPr—n | Me | OMe | CH |
| 251 | Q8 | H | H | OMe | OMe | CH | 322 | Q12 | H | COOPr—n | OMe | OMe | CH |
| 252 | Me | H | Q8 | Me | OMe | CH | 323 | Q12 | H | COOPr—n | Me | OMe | N |
| 253 | Me | H | Q8 | OMe | OMe | CH | 324 | Q12 | H | COOPr—i | Me | OMe | CH |
| 254 | Q9 | H | COOMe | Me | OMe | CH | 325 | Q12 | H | COOPr—i | OMe | OMe | CH |
| 255 | Q9 | H | COOMe | OMe | OMe | CH | 326 | Q12 | H | COOPr—i | Me | OMe | N |
| 256 | Q9 | H | COOEt | Me | OMe | CH | 327 | Q12 | H | COOCH2CH2Cl | Me | OMe | CH |
| 257 | Q9 | H | COOEt | OMe | OMe | CH | 328 | Q12 | H | COOCH2CH2Cl | OMe | OMe | CH |
| 258 | Q9 | Me | COOMe | Me | OMe | CH | 329 | Q12 | H | COOCH2CH2Cl | Me | OMe | N |
| 259 | Q9 | Me | COOMe | OMe | OMe | CH | 330 | Q12 | H | COOCH2CH=CH2 | Me | OMe | CH |
| 260 | Q9 | Me | COOEt | Me | OMe | CH | 331 | Q12 | H | COOCH2CH=CH2 | OMe | OMe | CH |
| 261 | Q9 | Me | COOEt | OMe | OMe | CH | 332 | Q12 | H | COOCH2CH=CH2 | Me | OMe | N |
| 262 | Q9 | H | H | Me | OMe | CH | 333 | Q12 | H | COOCH2C≡CH | Me | OMe | CH |
| 263 | Q9 | H | H | OMe | OMe | CH | 334 | Q12 | H | COOCH2C≡CH | OMe | OMe | CH |
| 264 | Me | H | Q9 | Me | OMe | CH | 335 | Q12 | H | COOCH2C≡CH | Me | OMe | N |
| 265 | Me | H | Q9 | OMe | OMe | CH | 336 | Q12 | Me | COOMe | Me | Me | CH |
| 266 | Q10 | H | COOMe | Me | OMe | CH | 337 | Q12 | Me | COOMe | Me | OMe | CH |
| 267 | Q10 | H | COOMe | OMe | OMe | CH | 338 | Q12 | Me | COOMe | OMe | OMe | CH |
| 268 | Q10 | H | COOEt | Me | OMe | CH | 339 | Q12 | Me | COOMe | Me | OMe | N |
| 269 | Q10 | H | COOEt | OMe | OMe | CH | 340 | Q12 | Me | COOMe | OMe | OMe | N |
| 270 | Q10 | Me | COOMe | Me | OMe | CH | 341 | Q12 | Me | COOEt | Me | Me | CH |
| 271 | Q10 | Me | COOMe | OMe | OMe | CH | 342 | Q12 | Me | COOEt | Me | OMe | CH |
| 272 | Q10 | Me | COOEt | Me | OMe | CH | 343 | Q12 | Me | COOEt | OMe | OMe | CH |
| 273 | Q10 | Me | COOEt | OMe | OMe | CH | 344 | Q12 | Me | COOEt | Me | OMe | N |
| 274 | Q10 | H | H | Me | OMe | CH | 345 | Q12 | Me | COOEt | OMe | OMe | N |
| 275 | Q10 | H | H | OMe | OMe | CH | 346 | Q12 | Cl | COOMe | Me | OMe | CH |
| 276 | Me | H | Q10 | Me | OMe | CH | 347 | Q12 | Cl | COOMe | OMe | OMe | CH |
| 277 | Me | H | Q10 | OMe | OMe | CH | 348 | Q12 | Cl | COOMe | Me | OMe | N |
| 278 | Q11 | H | COOMe | Me | Me | CH | 349 | Q12 | Cl | COOEt | Me | OMe | CH |
| 279 | Q11 | H | COOMe | Me | OMe | CH | 350 | Q12 | Cl | COOEt | OMe | OMe | CH |
| 280 | Q11 | H | COOMe | OMe | OMe | CH | 351 | Q12 | Cl | COOEt | Me | OMe | N |
| 281 | Q11 | H | COOMe | Me | OMe | N | 352 | Q12 | OMe | COOMe | Me | OMe | CH |
| 282 | Q11 | H | COOMe | OMe | OMe | N | 353 | Q12 | OMe | COOMe | OMe | OMe | CH |
| 283 | Q11 | H | COOEt | Me | Me | CH | 354 | Q12 | OMe | COOMe | Me | OMe | N |
| 284 | Q11 | H | COOEt | Me | OMe | CH | 355 | Q12 | OMe | COOEt | Me | OMe | CH |
| 285 | Q11 | H | COOEt | OMe | OMe | CH | 356 | Q12 | OMe | COOEt | OMe | OMe | CH |
| 286 | Q11 | H | COOEt | Me | OMe | N | 357 | Q12 | OMe | COOEt | Me | OMe | N |
| 287 | Q11 | H | COOEt | OMe | OMe | N | 358 | Q12 | H | Cl | Me | OMe | CH |
| 288 | Q11 | Me | COOMe | Me | OMe | CH | 359 | Q12 | H | Cl | OMe | OMe | CH |
| 289 | Q11 | Me | COOMe | OMe | OMe | CH | 360 | Q12 | H | Cl | Me | OMe | N |
| 290 | Q11 | Me | COOMe | Me | OMe | N | 361 | Q12 | H | NO2 | Me | OMe | CH |
| 291 | Q11 | Me | COOEt | Me | OMe | CH | 362 | Q12 | H | NO2 | OMe | OMe | CH |

TABLE 1-continued

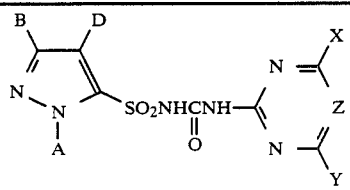

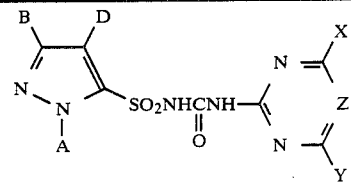

| No. | A | B | D | X | Y | Z |
|---|---|---|---|---|---|---|
| 363 | Q12 | H | NO2 | Me | OMe | N |
| 364 | Q12 | H | SO2NMe2 | Me | OMe | CH |
| 365 | Q12 | H | SO2NMe2 | OMe | OMe | CH |
| 366 | Q12 | H | SO2NMe2 | Me | OMe | N |
| 367 | Q12 | H | CN | Me | OMe | CH |
| 368 | Q12 | H | CN | OMe | OMe | CH |
| 369 | Q12 | H | CN | Me | OMe | N |
| 370 | Q12 | Me | CN | Me | OMe | CH |
| 371 | Q12 | Me | CN | OMe | OMe | CH |
| 372 | Q12 | Me | CN | Me | OMe | N |
| 373 | Q12 | H | Me | Me | OMe | CH |
| 374 | Q12 | H | Me | OMe | OMe | CH |
| 375 | Q12 | H | Me | Me | OMe | N |
| 376 | Q12 | H | Et | Me | OMe | CH |
| 377 | Q12 | H | Et | OMe | OMe | CH |
| 378 | Q12 | H | Et | Me | OMe | N |
| 379 | Q12 | H | H | Me | OMe | CH |
| 380 | Q12 | H | H | OMe | OMe | CH |
| 381 | Q12 | H | H | Me | OMe | N |
| 382 | Q12 | H | COPh | Me | OMe | CH |
| 383 | Q12 | H | COPh | OMe | OMe | CH |
| 384 | Q12 | H | COPh | Me | OMe | N |
| 385 | Me | Q12 | COOMe | Me | OMe | CH |
| 386 | Me | Q12 | COOMe | OMe | OMe | CH |
| 387 | Me | Q12 | COOMe | Me | OMe | N |
| 388 | H | H | Q12 | Me | OMe | CH |
| 389 | H | H | Q12 | OMe | OMe | CH |
| 390 | H | H | Q12 | Me | OMe | N |
| 391 | Me | H | Q12 | Me | Me | CH |
| 392 | Me | H | Q12 | Me | OMe | CH |
| 393 | Me | H | Q12 | OMe | OMe | CH |
| 394 | Me | H | Q12 | Me | OMe | N |
| 395 | Me | H | Q12 | OMe | OMe | N |
| 396 | Me | Me | Q12 | Me | OMe | CH |
| 397 | Me | Me | Q12 | OMe | OMe | CH |
| 398 | Me | Me | Q12 | Me | OMe | N |
| 399 | Q13 | H | COOMe | Me | Me | CH |
| 400 | Q13 | H | COOMe | Me | OMe | CH |
| 401 | Q13 | H | COOMe | OMe | OMe | CH |
| 402 | Q13 | H | COOMe | Me | OMe | N |
| 403 | Q13 | H | COOMe | OMe | OMe | N |
| 404 | Q13 | H | COOEt | Me | Me | CH |
| 405 | Q13 | H | COOEt | Me | OMe | CH |
| 406 | Q13 | H | COOEt | OMe | OMe | CH |
| 407 | Q13 | H | COOEt | Me | OMe | N |
| 408 | Q13 | H | COOEt | OMe | OMe | N |
| 409 | Q13 | Me | COOMe | Me | OMe | CH |
| 410 | Q13 | Me | COOMe | OMe | OMe | CH |
| 411 | Q13 | Me | COOMe | Me | OMe | N |
| 412 | Q13 | Me | COOEt | Me | OMe | CH |
| 413 | Q13 | Me | COOEt | OMe | OMe | CH |
| 414 | Q13 | Me | COOEt | Me | OMe | N |
| 415 | Q13 | H | CN | Me | OMe | CH |
| 416 | Q13 | H | CN | OMe | OMe | CH |
| 417 | Q13 | H | CN | Me | OMe | N |
| 118 | Q13 | H | H | Me | OMe | CH |
| 419 | Q13 | H | H | OMe | OMe | CH |
| 420 | Q13 | H | H | Me | OMe | N |
| 421 | Me | H | Q13 | Me | Me | CH |
| 422 | Me | H | Q13 | Me | OMe | CH |
| 423 | Me | H | Q13 | OMe | OMe | CH |
| 424 | Me | H | Q13 | Me | OMe | N |
| 425 | Me | H | Q13 | OMe | OMe | N |
| 426 | Q14 | H | COOMe | Me | Me | CH |
| 427 | Q14 | H | COOMe | Me | OMe | CH |
| 428 | Q14 | H | COOMe | OMe | OMe | CH |
| 429 | Q14 | H | COOMe | Me | OMe | N |
| 430 | Q14 | H | COOMe | OMe | OMe | N |
| 431 | Q14 | H | COOEt | Me | Me | CH |
| 432 | Q14 | H | COOEt | Me | OMe | CH |
| 433 | Q14 | H | COOEt | OMe | OMe | CH |
| 434 | Q14 | H | COOEt | Me | OMe | N |
| 435 | Q14 | H | COOEt | OMe | OMe | N |
| 436 | Q14 | Me | COOMe | Me | OMe | CH |
| 437 | Q14 | Me | COOMe | OMe | OMe | CH |
| 438 | Q14 | Me | COOMe | Me | OMe | N |
| 439 | Q14 | Me | COOEt | Me | OMe | CH |
| 440 | Q14 | Me | COOEt | OMe | OMe | CH |
| 441 | Q14 | Me | COOEt | Me | OMe | N |
| 442 | Q14 | H | CN | Me | OMe | CH |
| 443 | Q14 | H | CN | OMe | OMe | CH |
| 444 | Q14 | H | CN | Me | OMe | N |
| 445 | Q14 | H | H | Me | OMe | CH |
| 446 | Q14 | H | H | OMe | OMe | CH |
| 447 | Q14 | H | H | Me | OMe | N |
| 448 | Me | H | Q14 | Me | Me | CH |
| 449 | Me | H | Q14 | Me | OMe | CH |
| 450 | Me | H | Q14 | OMe | OMe | CH |
| 451 | Me | H | Q14 | Me | OMe | N |
| 452 | Me | H | Q14 | OMe | OMe | N |
| 453 | Q15 | H | COOMe | Me | OMe | CH |
| 454 | Q15 | H | COOMe | OMe | OMe | CH |
| 455 | Q15 | H | COOEt | Me | OMe | CH |
| 456 | Q15 | H | COOEt | OMe | OMe | CH |
| 457 | Q15 | Me | COOMe | Me | OMe | CH |
| 458 | Q15 | Me | COOMe | OMe | OMe | CH |
| 459 | Q15 | Me | COOEt | Me | OMe | CH |
| 460 | Q15 | Me | COOEt | OMe | OMe | CH |
| 461 | Q15 | H | H | Me | OMe | CH |
| 462 | Q15 | H | H | OMe | OMe | CH |
| 463 | Me | H | Q15 | Me | OMe | CH |
| 464 | Me | H | Q15 | OMe | OMe | CH |
| 465 | Q16 | H | COOMe | Me | OMe | CH |
| 466 | Q16 | H | COOMe | OMe | OMe | CH |
| 467 | Q16 | H | COOEt | Me | OMe | CH |
| 468 | Q16 | H | COOEt | OMe | OMe | CH |
| 469 | Q16 | Me | COOMe | Me | OMe | CH |
| 470 | Q16 | Me | COOMe | OMe | OMe | CH |
| 471 | Q16 | Me | COOEt | Me | OMe | CH |
| 472 | Q16 | Me | COOEt | OMe | OMe | CH |
| 473 | Q16 | H | H | Me | OMe | CH |
| 474 | Q16 | H | H | OMe | OMe | CH |
| 475 | Me | H | Q16 | Me | OMe | CH |
| 476 | Me | H | Q16 | OMe | OMe | CH |
| 477 | Q17 | H | COOMe | Me | OMe | CH |
| 478 | Q17 | H | COOMe | OMe | OMe | CH |
| 479 | Q17 | H | COOEt | Me | OMe | CH |
| 480 | Q17 | H | COOEt | OMe | OMe | CH |
| 481 | Q17 | Me | COOMe | Me | OMe | CH |
| 482 | Q17 | Me | COOMe | OMe | OMe | CH |
| 483 | Q17 | Me | COOEt | Me | OMe | CH |
| 484 | Q17 | Me | COOEt | OMe | OMe | CH |
| 485 | Q17 | H | H | Me | OMe | CH |
| 486 | Q17 | H | H | OMe | OMe | CH |
| 487 | Me | H | Q17 | Me | OMe | CH |
| 488 | Me | H | Q17 | OMe | OMe | CH |
| 489 | Q18 | H | COOMe | Me | OMe | CH |
| 490 | Q18 | H | COOMe | OMe | OMe | CH |
| 491 | Q18 | H | COOEt | Me | OMe | CH |
| 492 | Q18 | H | CCOOEt | OMe | OMe | CH |
| 493 | Q18 | H | COOMe | Me | OMe | CH |
| 494 | Q18 | Me | COOMe | OMe | OMe | CH |
| 495 | Q18 | Me | COOEt | Me | OMe | CH |
| 496 | Q18 | Me | COOEt | OMe | OMe | CH |
| 497 | Q18 | H | H | Me | OMe | CH |
| 498 | Q18 | H | H | OMe | OMe | CH |
| 499 | Me | H | Q18 | Me | OMe | CH |
| 500 | Me | H | Q18 | OMe | OMe | CH |
| 501 | Q19 | H | COOMe | Me | Me | CH |
| 502 | Q19 | H | COOMe | Me | OMe | CH |
| 503 | Q19 | H | COOMe | OMe | OMe | CH |
| 504 | Q19 | H | COOMe | Me | OMe | N |

TABLE 1-continued

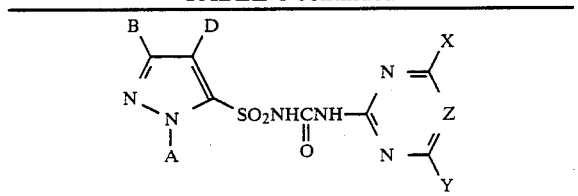

| No. | A | B | D | X | Y | Z |
|---|---|---|---|---|---|---|
| 505 | Q19 | H | COOMe | OMe | OMe | N |
| 506 | Q19 | H | COOEt | Me | Me | CH |
| 507 | Q19 | H | COOEt | Me | OMe | CH |
| 508 | Q19 | H | COOEt | OMe | OMe | CH |
| 509 | Q19 | H | COOEt | Me | OMe | N |
| 510 | Q19 | H | COOEt | OMe | OMe | N |
| 511 | Q19 | Me | COOMe | Me | OMe | CH |
| 512 | Q19 | Me | COOMe | OMe | OMe | CH |
| 513 | Q19 | Me | COOMe | Me | OMe | N |
| 514 | Q19 | Me | COOEt | Me | OMe | CH |
| 515 | Q19 | Me | COOEt | OMe | OMe | CH |
| 516 | Q19 | Me | COOEt | Me | OMe | N |
| 517 | Q19 | H | CN | Me | OMe | CH |
| 518 | Q19 | H | CN | OMe | OMe | CH |
| 519 | Q19 | H | CN | Me | OMe | N |
| 520 | Q19 | H | H | Me | OMe | CH |
| 521 | Q19 | H | H | OMe | OMe | CH |
| 522 | Q19 | H | H | Me | OMe | N |
| 523 | Me | H | Q19 | Me | Me | CH |
| 524 | Me | H | Q19 | Me | OMe | CH |
| 525 | Me | H | Q19 | OMe | OMe | CH |
| 526 | Me | H | Q19 | Me | OMe | N |
| 527 | Me | H | Q19 | OMe | OMe | N |
| 528 | Q20 | H | COOMe | Me | OMe | CH |
| 529 | Q10 | H | COOMe | OMe | OMe | CH |
| 530 | Q10 | H | COOEt | Me | OMe | CH |
| 531 | Q10 | H | COOEt | OMe | OMe | CH |
| 532 | Q20 | Me | COOMe | Me | OMe | CH |
| 533 | Q20 | Me | COOMe | OMe | OMe | CH |
| 534 | Q20 | Me | COOEt | Me | OMe | CH |
| 535 | Q20 | Me | COOEt | OMe | OMe | CH |
| 536 | Q20 | H | H | Me | OMe | CH |
| 537 | Q20 | H | H | OMe | OMe | CH |
| 538 | Me | H | Q20 | Me | OMe | CH |
| 539 | Me | H | Q20 | OMe | OMe | CH |
| 540 | Q21 | H | COOMe | Me | OMe | CH |
| 541 | Q21 | H | COOMe | OMe | OMe | CH |
| 542 | Q21 | H | COOEt | Me | OMe | CH |
| 543 | Q21 | H | COOEt | OMe | OMe | CH |
| 544 | Q21 | Me | COOMe | Me | OMe | CH |
| 545 | Q21 | Me | COOMe | OMe | OMe | CH |
| 546 | Q21 | Me | COOEt | Me | OMe | CH |
| 547 | Q21 | Me | COOEt | OMe | OMe | CH |
| 548 | Q21 | H | H | Me | OMe | CH |
| 549 | Q21 | H | H | OMe | OMe | CH |
| 550 | Me | H | Q21 | Me | OMe | CH |
| 551 | Me | H | Q21 | OMe | OMe | CH |
| 552 | Q22 | H | COOMe | Me | Me | CH |
| 553 | Q22 | H | COOMe | Me | OMe | CH |
| 554 | Q22 | H | COOMe | OMe | OMe | CH |
| 555 | Q22 | H | COOMe | Me | Me | N |
| 556 | Q22 | H | COOMe | Me | OMe | N |
| 557 | Q22 | H | COOMe | OMe | OMe | N |
| 558 | Q22 | H | COOMe | Me | OCHF2 | CH |
| 559 | Q22 | H | COOMe | Cl | OMe | CH |
| 560 | Q22 | H | COOEt | Me | Me | CH |
| 561 | Q22 | H | COOEt | Me | OMe | CH |
| 562 | Q22 | H | COOEt | OMe | OMe | CH |
| 563 | Q22 | H | COOEt | Me | Me | N |
| 564 | Q22 | H | COOEt | Me | OMe | N |
| 565 | Q22 | H | COOEt | OMe | OMe | CH |
| 566 | Q22 | H | COOEt | Me | OCHF2 | CH |
| 567 | Q22 | H | COOEt | Cl | OMe | CH |
| 568 | Q22 | H | COOPr—n | Me | OMe | CH |
| 569 | Q22 | H | COOPr—n | OMe | OMe | CH |
| 570 | Q22 | H | COOPr—n | Me | OMe | N |
| 571 | Q22 | H | COOPr—i | Me | OMe | CH |
| 572 | Q22 | H | COOPr—i | OMe | OMe | CH |
| 573 | Q22 | H | COOPr—i | Me | OMe | N |
| 574 | Q22 | H | COOCH2CH2Cl | Me | OMe | CH |
| 575 | Q22 | H | COOCH2CH2Cl | OMe | OMe | CH |
| 576 | Q22 | H | COOCH2CH2Cl | Me | OMe | N |
| 577 | Q22 | H | COOCH2CH=CH2 | Me | OMe | CH |
| 578 | Q22 | H | COOCH2CH=CH2 | OMe | OMe | CH |
| 579 | Q22 | H | COOCH2CH=CH2 | Me | OMe | N |
| 580 | Q22 | H | COOCH2C≡CH | Me | OMe | CH |
| 581 | Q22 | H | COOCH2C≡CH | OMe | OMe | CH |
| 582 | Q22 | H | COOCH2C≡CH | Me | OMe | N |
| 583 | Q22 | Me | COOMe | Me | Me | CH |
| 584 | Q22 | Me | COOMe | Me | OMe | CH |
| 585 | Q22 | Me | COOMe | OMe | OMe | CH |
| 586 | Q22 | Me | COOMe | Me | OMe | N |
| 587 | Q22 | Me | COOMe | OMe | OMe | N |
| 588 | Q22 | Me | COOEt | Me | Me | CH |
| 589 | Q22 | Me | COOEt | Me | OMe | CH |
| 590 | Q22 | Me | COOEt | OMe | OMe | CH |
| 591 | Q22 | Me | COOEt | Me | OMe | N |
| 592 | Q22 | Me | COOEt | OMe | OMe | N |
| 593 | Q22 | Cl | COOMe | Me | OMe | CH |
| 594 | Q22 | Cl | COOMe | OMe | OMe | CH |
| 595 | Q22 | Cl | COOMe | Me | OMe | N |
| 596 | Q22 | Cl | COOEt | Me | OMe | CH |
| 597 | Q22 | Cl | COOEt | OMe | OMe | CH |
| 598 | Q22 | Cl | COOEt | Me | OMe | N |
| 599 | Q22 | OMe | COOMe | Me | OMe | CH |
| 600 | Q22 | OMe | COOMe | OMe | OMe | CH |
| 601 | Q22 | OMe | COOMe | Me | OMe | N |
| 602 | Q22 | OMe | COOEt | Me | OMe | CH |
| 603 | Q22 | OMe | COOEt | OMe | OMe | CH |
| 604 | Q22 | OMe | COOEt | Me | OMe | N |
| 605 | Q22 | H | Cl | Me | OMe | CH |
| 606 | Q22 | H | Cl | OMe | OMe | CH |
| 607 | Q22 | H | Cl | Me | OMe | N |
| 608 | Q22 | H | NO2 | Me | OMe | CH |
| 609 | Q22 | H | NO2 | OMe | OMe | CH |
| 610 | Q22 | H | NO2 | Me | OMe | N |
| 611 | Q22 | H | SO2NMe2 | Me | OMe | CH |
| 612 | Q22 | H | SO2NMe2 | OMe | OMe | CH |
| 613 | Q22 | H | SO2NMe2 | Me | OMe | N |
| 614 | Q22 | H | CN | Me | OMe | CH |
| 615 | Q22 | H | CN | OMe | OMe | CH |
| 616 | Q22 | H | CN | Me | OMe | N |
| 617 | Q22 | Me | CN | Me | OMe | CH |
| 618 | Q22 | Me | CN | OMe | OMe | CH |
| 619 | Q22 | Me | CN | Me | OMe | N |
| 620 | Q22 | H | Me | Me | OMe | CH |
| 621 | Q22 | H | Me | OMe | OMe | CH |
| 622 | Q22 | H | Me | Me | OMe | N |
| 623 | Q22 | H | Et | Me | OMe | CH |
| 624 | Q22 | H | Et | OMe | OMe | CH |
| 625 | Q22 | H | Et | Me | OMe | N |
| 626 | Q22 | H | H | Me | OMe | CH |
| 627 | Q22 | H | H | OMe | OMe | CH |
| 628 | Q22 | H | H | Me | OMe | N |
| 629 | Q22 | H | COPh | Me | OMe | CH |
| 630 | Q22 | H | COPh | OMe | OMe | CH |
| 631 | Q22 | H | COPh | Me | OMe | N |
| 632 | Me | Q22 | COOMe | Me | OMe | CH |
| 633 | Me | Q22 | COOMe | OMe | OMe | CH |
| 634 | Me | Q22 | COOMe | Me | OMe | N |
| 635 | H | H | Q22 | Me | OMe | CH |
| 636 | H | H | Q22 | OMe | OMe | CH |
| 637 | H | H | Q22 | Me | OMe | N |
| 638 | Me | H | Q22 | Me | Me | CH |
| 639 | Me | H | Q22 | Me | OMe | CH |
| 640 | Me | H | Q22 | OMe | OMe | CH |
| 641 | Me | H | Q22 | Me | OMe | N |
| 642 | Me | H | Q22 | OMe | OMe | N |
| 643 | Me | Me | Q22 | Me | OMe | CH |
| 644 | Me | Me | Q22 | OMe | OMe | CH |
| 645 | Me | Me | Q22 | Me | OMe | N |
| 646 | Q23 | H | COOMe | Me | Me | CH |

TABLE 1-continued

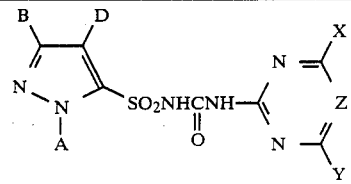

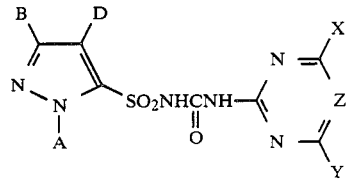

| No. | A | B | D | X | Y | Z |
|---|---|---|---|---|---|---|
| 647 | Q23 | H | COOMe | Me | OMe | CH |
| 648 | Q23 | H | COOMe | OMe | OMe | CH |
| 649 | Q23 | H | COOMe | Me | OMe | N |
| 650 | Q23 | H | COOMe | OMe | OMe | N |
| 651 | Q23 | H | COOEt | Me | Me | CH |
| 652 | Q23 | H | COOEt | Me | OMe | CH |
| 653 | Q23 | H | COOEt | OMe | OMe | CH |
| 654 | Q23 | H | COOEt | Me | OMe | N |
| 655 | Q23 | H | COOEt | OMe | OMe | N |
| 656 | Q23 | Me | COOMe | Me | OMe | CH |
| 657 | Q23 | Me | COOMe | OMe | OMe | CH |
| 658 | Q23 | Me | COOMe | Me | OMe | N |
| 659 | Q23 | Me | COOEt | Me | OMe | CH |
| 660 | Q23 | Me | COOEt | OMe | OMe | CH |
| 661 | Q23 | Me | COOEt | Me | OMe | N |
| 662 | Q23 | H | CN | Me | OMe | CH |
| 663 | Q23 | H | CN | OMe | OMe | CH |
| 664 | Q23 | H | CN | Me | OMe | N |
| 665 | Q23 | H | H | Me | OMe | CH |
| 666 | Q23 | H | H | OMe | OMe | CH |
| 667 | Q23 | H | H | Me | OMe | N |
| 668 | Me | H | Q23 | Me | Me | CH |
| 669 | Me | H | Q23 | Me | OMe | CH |
| 670 | Me | H | Q23 | OMe | OMe | CH |
| 671 | Me | H | Q23 | Me | OMe | N |
| 672 | Me | H | Q23 | OMe | OMe | N |
| 673 | Q24 | H | COOMe | Me | Me | CH |
| 674 | Q24 | H | COOMe | Me | OMe | CH |
| 675 | Q24 | H | COOMe | OMe | OMe | CH |
| 676 | Q24 | H | COOMe | Me | OMe | N |
| 677 | Q24 | H | COOMe | OMe | OMe | N |
| 678 | Q24 | H | COOEt | Me | Me | CH |
| 679 | Q24 | H | COOEt | Me | OMe | CH |
| 680 | Q24 | H | COOEt | OMe | OMe | CH |
| 681 | Q24 | H | COOEt | Me | OMe | N |
| 682 | Q24 | H | COOEt | OMe | OMe | N |
| 683 | Q24 | Me | COOMe | Me | OMe | CH |
| 684 | Q24 | Me | COOMe | OMe | OMe | CH |
| 685 | Q24 | Me | COOMe | Me | OMe | N |
| 686 | Q24 | Me | COOEt | Me | OMe | CH |
| 687 | Q24 | Me | COOEt | OMe | OMe | CH |
| 688 | Q24 | Me | COOEt | Me | OMe | N |
| 689 | Q24 | H | CN | Me | OMe | CH |
| 690 | Q24 | H | CN | OMe | OMe | CH |
| 691 | Q24 | H | CN | Me | OMe | N |
| 692 | Q24 | H | H | Me | OMe | CH |
| 693 | Q24 | H | H | OMe | OMe | CH |
| 694 | Q24 | H | H | Me | OMe | N |
| 695 | Me | H | Q24 | Me | Me | CH |
| 696 | Me | H | Q24 | Me | OMe | CH |
| 697 | Me | H | Q24 | OMe | OMe | CH |
| 698 | Me | H | Q24 | Me | OMe | N |
| 699 | Me | H | Q24 | OMe | OMe | N |
| 700 | Q25 | H | COOMe | Me | Me | CH |
| 701 | Q25 | H | COOMe | Me | OMe | CH |
| 702 | Q25 | H | COOMe | OMe | OMe | CH |
| 703 | Q25 | H | COOMe | Me | OMe | N |
| 704 | Q25 | H | COOMe | OMe | OMe | N |
| 705 | Q25 | H | COOEt | Me | Me | CH |
| 706 | Q25 | H | COOEt | Me | OMe | CH |
| 707 | Q25 | H | COOEt | OMe | OMe | CH |
| 708 | Q25 | H | COOEt | Me | OMe | N |
| 709 | Q25 | H | COOEt | OMe | OMe | N |
| 710 | Q25 | Me | COOMe | Me | OMe | CH |
| 711 | Q25 | Me | COOMe | OMe | OMe | CH |
| 712 | Q25 | Me | COOMe | Me | OMe | N |
| 713 | Q25 | Me | COOEt | Me | OMe | CH |
| 714 | Q25 | Me | COOEt | OMe | OMe | CH |
| 715 | Q25 | Me | COOEt | Me | OMe | N |
| 716 | Q25 | H | CN | Me | OMe | CH |
| 717 | Q25 | H | CN | OMe | OMe | CH |
| 718 | Q25 | H | CN | Me | OMe | N |
| 719 | Q25 | H | H | Me | OMe | CH |
| 720 | Q25 | H | H | OMe | OMe | CH |
| 721 | Q25 | H | H | Me | OMe | N |
| 722 | Me | H | Q25 | Me | Me | CH |
| 723 | Me | H | Q25 | Me | OMe | CH |
| 724 | Me | H | Q25 | OMe | OMe | CH |
| 725 | Me | H | Q25 | Me | OMe | N |
| 726 | Me | H | Q25 | OMe | OMe | N |
| 727 | Q26 | H | COOMe | Me | OMe | CH |
| 728 | Q26 | H | COOMe | OMe | OMe | CH |
| 729 | Q26 | H | COOEt | Me | OMe | CH |
| 730 | Q26 | H | COOEt | OMe | OMe | CH |
| 731 | Q26 | Me | COOMe | Me | OMe | CH |
| 732 | Q26 | Me | COOMe | OMe | OMe | CH |
| 733 | Q26 | Me | COOEt | Me | OMe | CH |
| 734 | Q26 | Me | COOEt | OMe | OMe | CH |
| 735 | Q26 | H | H | Me | OMe | CH |
| 736 | Q26 | H | H | OMe | OMe | CH |
| 737 | Me | H | Q26 | Me | OMe | CH |
| 738 | Me | H | Q26 | OMe | OMe | CH |
| 739 | Q27 | H | COOMe | Me | OMe | CH |
| 740 | Q27 | H | COOMe | OMe | OMe | CH |
| 741 | Q27 | H | COOEt | Me | OMe | CH |
| 742 | Q27 | H | COOEt | OMe | OMe | CH |
| 743 | Q27 | Me | COOMe | Me | OMe | CH |
| 744 | Q27 | Me | COOMe | OMe | OMe | CH |
| 745 | Q27 | Me | COOEt | Me | OMe | CH |
| 746 | Q27 | Me | COOEt | OMe | OMe | CH |
| 747 | Q27 | H | H | Me | OMe | CH |
| 748 | Q27 | H | H | OMe | OMe | CH |
| 749 | Me | H | Q27 | Me | OMe | CH |
| 750 | Me | H | Q27 | OMe | OMe | CH |
| 751 | Q28 | H | COOMe | Me | OMe | CH |
| 752 | Q28 | H | COOMe | OMe | OMe | CH |
| 753 | Q28 | H | COOEt | Me | OMe | CH |
| 754 | Q28 | H | COOEt | OMe | OMe | CH |
| 755 | Q28 | Me | COOMe | Me | OMe | CH |
| 756 | Q28 | Me | COOMe | OMe | OMe | CH |
| 757 | Q28 | Me | COOEt | Me | OMe | CH |
| 758 | Q28 | Me | COOEt | OMe | OMe | CH |
| 759 | Q28 | H | H | Me | OMe | CH |
| 760 | Q28 | H | H | OMe | OMe | CH |
| 761 | Me | H | Q28 | Me | OMe | CH |
| 762 | Me | H | Q28 | OMe | OMe | CH |
| 763 | Q29 | H | COOMe | Me | OMe | CH |
| 764 | Q29 | H | COOMe | OMe | OMe | CH |
| 765 | Q29 | H | COOEt | Me | OMe | CH |
| 766 | Q29 | H | COOEt | OMe | OMe | CH |
| 767 | Q29 | Me | COOMe | Me | OMe | CH |
| 768 | Q29 | Me | COOMe | OMe | OMe | CH |
| 769 | Q29 | Me | COOEt | Me | OMe | CH |
| 770 | Q29 | Me | COOEt | OMe | OMe | CH |
| 771 | Q29 | H | H | Me | OMe | CH |
| 772 | Q29 | H | H | OMe | OMe | CH |
| 773 | Me | H | Q29 | Me | OMe | CH |
| 774 | Me | H | Q29 | OMe | OMe | CH |
| 775 | Q30 | H | COOMe | Me | OMe | CH |
| 776 | Q30 | H | COOMe | OMe | OMe | CH |
| 777 | Q30 | H | COOEt | Me | OMe | CH |
| 778 | Q30 | H | COOEt | OMe | OMe | CH |
| 779 | Q30 | Me | COOMe | Me | OMe | CH |
| 780 | Q30 | Me | COOMe | OMe | OMe | CH |
| 781 | Q30 | Me | COOEt | Me | OMe | CH |
| 782 | Q30 | Me | COOEt | OMe | OMe | CH |
| 783 | Q30 | H | H | Me | OMe | CH |
| 784 | Q30 | H | H | OMe | OMe | CH |
| 785 | Me | H | Q30 | Me | OMe | CH |
| 786 | Me | H | Q30 | OMe | OMe | CH |
| 787 | Q31 | H | COOMe | Me | OMe | CH |
| 788 | Q31 | H | COOMe | OMe | OMe | CH |

TABLE 1-continued

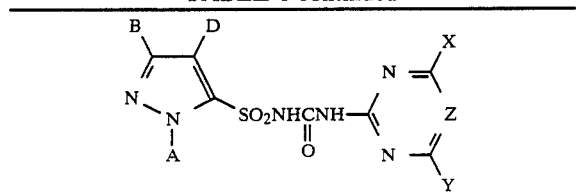

| No. | A | B | D | X | Y | Z |
|---|---|---|---|---|---|---|
| 789 | Q31 | H | COOEt | Me | OMe | CH |
| 790 | Q31 | H | COOEt | OMe | OMe | CH |
| 791 | Q31 | Me | COOMe | Me | OMe | CH |
| 792 | Q31 | Me | COOMe | OMe | OMe | CH |
| 793 | Q31 | Me | COOEt | Me | OMe | CH |
| 794 | Q31 | Me | COOEt | OMe | OMe | CH |
| 795 | Q31 | H | H | Me | OMe | CH |
| 796 | Q31 | H | H | OMe | OMe | CH |
| 797 | Me | H | Q31 | Me | OMe | CH |
| 798 | Me | H | Q31 | OMe | OMe | CH |
| 799 | Q32 | H | COOMe | Me | Me | CH |
| 800 | Q32 | H | COOMe | Me | OMe | CH |
| 801 | Q32 | H | COOMe | OMe | OMe | CH |
| 802 | Q32 | H | COOMe | Me | OMe | N |
| 803 | Q32 | H | COOMe | OMe | OMe | N |
| 804 | Q32 | H | COOEt | Me | Me | CH |
| 805 | Q32 | H | COOEt | Me | OMe | CH |
| 806 | Q32 | H | COOEt | OMe | OMe | CH |
| 807 | Q32 | H | COOEt | Me | OMe | N |
| 808 | Q32 | H | COOEt | OMe | OMe | N |
| 809 | Q32 | Me | COOMe | Me | OMe | CH |
| 810 | Q32 | Me | COOMe | OMe | OMe | CH |
| 811 | Q32 | Me | COOMe | Me | OMe | N |
| 812 | Q32 | Me | COOEt | Me | OMe | CH |
| 813 | Q32 | Me | COOEt | OMe | OMe | CH |
| 814 | Q32 | Me | COOEt | Me | OMe | N |
| 815 | Q32 | H | CN | Me | OMe | CH |
| 816 | Q32 | H | CN | OMe | OMe | CH |
| 817 | Q32 | H | CN | Me | OMe | N |
| 818 | Q32 | H | H | Me | OMe | CH |
| 819 | Q32 | H | H | OMe | OMe | CH |
| 820 | Q32 | H | H | Me | OMe | N |
| 821 | Me | H | Q32 | Me | Me | CH |
| 822 | Me | H | Q32 | Me | OMe | CH |
| 823 | Me | H | Q32 | OMe | OMe | CH |
| 824 | Me | H | Q32 | Me | OMe | N |
| 825 | Me | H | Q32 | OMe | OMe | N |
| 826 | Q33 | H | COOMe | Me | OMe | CH |
| 827 | Q33 | H | COOMe | OMe | OMe | CH |
| 828 | Q33 | H | COOEt | Me | OMe | CH |
| 829 | Q33 | H | COOEt | OMe | OMe | CH |
| 830 | Q33 | Me | COOMe | Me | OMe | CH |
| 831 | Q33 | Me | COOMe | OMe | OMe | CH |
| 832 | Q33 | Me | COOEt | Me | OMe | CH |
| 833 | Q33 | Me | COOEt | OMe | OMe | CH |
| 834 | Q33 | H | H | Me | OMe | CH |
| 835 | Q33 | H | H | OMe | OMe | CH |
| 836 | Me | H | Q33 | Me | OMe | CH |
| 837 | Me | H | Q33 | OMe | OMe | CH |
| 838 | Q34 | H | COOMe | Me | OMe | CH |
| 839 | Q34 | H | COOMe | OMe | OMe | CH |
| 840 | Q34 | H | COOEt | Me | OMe | CH |
| 841 | Q34 | H | COOEt | OMe | OMe | CH |
| 842 | Q34 | Me | COOMe | Me | OMe | CH |
| 843 | Q34 | Me | COOMe | OMe | OMe | CH |
| 844 | Q34 | Me | COOEt | Me | OMe | CH |
| 845 | Q34 | Me | COOEt | OMe | OMe | CH |
| 846 | Q34 | H | H | Me | OMe | CH |
| 847 | Q34 | H | H | OMe | OMe | CH |
| 848 | Me | H | Q34 | Me | OMe | CH |
| 849 | Me | H | Q34 | OMe | OMe | CH |
| 850 | Q35 | H | COOMe | Me | OMe | CH |
| 851 | Q35 | H | COOMe | OMe | OMe | CH |
| 852 | Q35 | H | COOEt | Me | OMe | CH |
| 853 | Q35 | H | COOEt | OMe | OMe | CH |
| 854 | Q35 | Me | COOMe | Me | OMe | CH |
| 855 | Q35 | Me | COOMe | OMe | OMe | CH |
| 856 | Q35 | Me | COOEt | Me | OMe | CH |
| 857 | Q35 | Me | COOEt | OMe | OMe | CH |
| 858 | Q35 | H | H | Me | OMe | CH |
| 859 | Q35 | H | H | OMe | OMe | CH |
| 860 | Me | H | Q35 | Me | OMe | CH |
| 861 | Me | H | Q35 | OMe | OMe | CH |
| 862 | Q36 | H | COOMe | Me | OMe | CH |
| 863 | Q36 | H | COOMe | OMe | OMe | CH |
| 864 | Q36 | H | COOEt | Me | OMe | CH |
| 865 | Q36 | H | COOEt | OMe | OMe | CH |
| 866 | Q36 | Me | COOMe | Me | OMe | CH |
| 867 | Q36 | Me | COOMe | OMe | OMe | CH |
| 868 | Q36 | Me | COOEt | Me | OMe | CH |
| 869 | Q36 | Me | COOEt | OMe | OMe | CH |
| 870 | Q36 | H | H | Me | OMe | CH |
| 871 | Q36 | H | H | OMe | OMe | CH |
| 872 | Me | H | Q36 | Me | OMe | CH |
| 873 | Me | H | Q36 | OMe | OMe | CH |
| 874 | Q37 | H | COOMe | Me | OMe | CH |
| 875 | Q37 | H | COOMe | OMe | OMe | CH |
| 876 | Q37 | H | COOEt | Me | OMe | CH |
| 877 | Q37 | H | COOEt | OMe | OMe | CH |
| 878 | Q37 | Me | COOMe | Me | OMe | CH |
| 879 | Q37 | Me | COOMe | OMe | OMe | CH |
| 880 | Q37 | Me | COOEt | Me | OMe | CH |
| 881 | Q37 | Me | COOEt | OMe | OMe | CH |
| 882 | Q37 | H | H | Me | OMe | CH |
| 883 | Q37 | H | H | OMe | OMe | CH |
| 884 | Me | H | Q37 | Me | OMe | CH |
| 885 | Me | H | Q37 | OMe | OMe | CH |
| 886 | Q38 | H | COOMe | Me | OMe | CH |
| 887 | Q38 | H | COOMe | OMe | OMe | CH |
| 888 | Q38 | H | COOEt | Me | OMe | CH |
| 889 | Q38 | H | COOEt | OMe | OMe | CH |
| 890 | Q38 | Me | COOMe | Me | OMe | CH |
| 891 | Q38 | Me | COOMe | OMe | OMe | CH |
| 892 | Q38 | Me | COOEt | Me | OMe | CH |
| 893 | Q38 | Me | COOEt | OMe | OMe | CH |
| 932 | Me | H | Q41 | Me | OMe | CH |
| 933 | Me | H | Q41 | OMe | OMe | CH |
| 934 | Q42 | H | COOMe | Me | OMe | CH |
| 935 | Q42 | H | COOMe | OMe | OMe | CH |
| 936 | Q42 | H | COOEt | Me | OMe | CH |
| 937 | Q42 | H | COOEt | OMe | OMe | CH |
| 938 | Q42 | Me | COOMe | Me | OMe | CH |
| 939 | Q42 | Me | COOMe | OMe | OMe | CH |
| 940 | Q42 | Me | COOEt | Me | OMe | CH |
| 941 | Q42 | Me | COOEt | OMe | OMe | CH |
| 942 | Q42 | H | H | Me | OMe | CH |
| 943 | Q42 | H | H | OMe | OMe | CH |
| 944 | Me | H | Q42 | Me | OMe | CH |
| 945 | Me | H | Q42 | OMe | OMe | CH |
| 946 | Q43 | H | COOMe | Me | OMe | CH |
| 947 | Q43 | H | COOMe | OMe | OMe | CH |
| 948 | Q43 | H | COOEt | Me | OMe | CH |
| 949 | Q43 | H | COOEt | OMe | OMe | CH |
| 950 | Q43 | Me | COOMe | Me | OMe | CH |
| 951 | Q43 | Me | COOMe | OMe | OMe | CH |
| 952 | Q43 | Me | COOEt | Me | OMe | CH |
| 953 | Q43 | Me | COOEt | OMe | OMe | CH |
| 954 | Q43 | H | H | Me | OMe | CH |
| 955 | Q43 | H | H | OMe | OMe | CH |
| 956 | Me | H | Q43 | Me | OMe | CH |
| 957 | Me | H | Q43 | OMe | OMe | CH |
| 958 | Q44 | H | COOMe | Me | OMe | CH |
| 959 | Q44 | H | COOMe | OMe | OMe | CH |
| 960 | Q44 | H | COOEt | Me | OMe | CH |
| 961 | Q44 | H | COOEt | OMe | OMe | CH |
| 962 | Q44 | Me | COOMe | Me | OMe | CH |
| 963 | Q44 | Me | COOMe | OMe | OMe | CH |
| 964 | Q44 | Me | COOEt | Me | OMe | CH |
| 965 | Q44 | Me | COOEt | OMe | OMe | CH |
| 966 | Q44 | H | H | Me | OMe | CH |
| 967 | Q44 | H | H | OMe | OMe | CH |
| 968 | Me | H | Q44 | Me | OMe | CH |

TABLE 1-continued

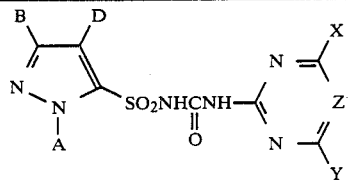

| No. | A | B | D | X | Y | Z |
|---|---|---|---|---|---|---|
| 969 | Me | H | Q44 | OMe | OMe | CH |
| 970 | Q45 | H | COOMe | Me | OMe | CH |
| 971 | Q45 | H | COOMe | OMe | OMe | CH |
| 972 | Q45 | H | COOEt | Me | OMe | CH |
| 973 | Q45 | H | COOEt | OMe | OMe | CH |
| 974 | Q45 | Me | COOMe | Me | OMe | CH |
| 975 | Q45 | Me | COOMe | OMe | OMe | CH |
| 976 | Q45 | Me | COOEt | Me | OMe | CH |
| 977 | Q45 | Me | COOEt | OMe | OMe | CH |
| 978 | Q45 | H | H | Me | OMe | CH |
| 979 | Q45 | H | H | OMe | OMe | CH |
| 980 | Me | H | Q45 | Me | OMe | CH |
| 981 | Me | H | Q45 | OMe | OMe | CH |
| 982 | Q46 | H | COOMe | Me | OMe | CH |
| 983 | Q46 | H | COOMe | OMe | OMe | CH |
| 984 | Q46 | H | COOEt | Me | OMe | CH |
| 985 | Q46 | H | COOEt | OMe | OMe | CH |
| 986 | Q46 | Me | COOMe | Me | OMe | CH |
| 987 | Q46 | Me | COOMe | OMe | OMe | CH |
| 988 | Q46 | Me | COOEt | Me | OMe | CH |
| 989 | Q46 | Me | COOEt | OMe | OMe | CH |
| 990 | Q46 | H | H | Me | OMe | CH |
| 991 | Q46 | H | H | OMe | OMe | CH |
| 992 | Me | H | Q46 | Me | OMe | CH |
| 993 | Me | H | Q46 | OMe | OMe | CH |
| 994 | Q47 | H | COOMe | Me | OMe | CH |
| 995 | Q47 | H | COOMe | OMe | OMe | CH |
| 996 | Q47 | H | COOEt | Me | OMe | CH |
| 997 | Q47 | H | COOEt | OMe | OMe | CH |
| 998 | Q47 | Me | COOMe | Me | OMe | CH |
| 999 | Q47 | Me | COOMe | OMe | OMe | CH |
| 1000 | Q47 | Me | COOEt | Me | OMe | CH |
| 1001 | Q47 | Me | COOEt | OMe | OMe | CH |
| 1002 | Q47 | H | H | Me | OMe | CH |
| 1003 | Q47 | H | H | OMe | OMe | CH |
| 1004 | Me | H | Q47 | Me | OMe | CH |
| 1005 | Me | H | Q47 | OMe | OMe | CH |
| 2001 | Q48 | H | COOMe | Me | Me | CH |
| 2002 | Q48 | H | COOMe | Me | OMe | CH |
| 2003 | Q48 | H | COOMe | OMe | OMe | CH |
| 2004 | Q48 | H | COOEt | Me | OMe | CH |
| 2005 | Q48 | H | COOEt | OMe | OMe | CH |
| 2006 | Q48 | Me | COOMe | Me | Me | CH |
| 2007 | Q48 | Me | COOMe | Me | OMe | CH |
| 2008 | Q48 | Me | COOMe | OMe | OMe | CH |
| 2009 | Q48 | Me | COOEt | Me | OMe | CH |
| 2010 | Q48 | Me | COOEt | OMe | OMe | CH |
| 2011 | Q48 | H | H | Me | OMe | CH |
| 2012 | Q48 | H | H | OMe | OMe | CH |
| 2013 | Me | H | Q48 | Me | OMe | CH |
| 2014 | Me | H | Q48 | OMe | OMe | CH |
| 2015 | Q49 | H | COOMe | Me | Me | CH |
| 2016 | Q49 | H | COOMe | Me | OMe | CH |
| 2017 | Q49 | H | COOMe | OMe | OMe | CH |
| 2018 | Q49 | H | COOEt | Me | OMe | CH |
| 2019 | Q49 | H | COOEt | OMe | OMe | CH |
| 2020 | Q49 | Me | COOMe | Me | Me | CH |
| 2021 | Q49 | Me | COOMe | Me | OMe | CH |
| 2022 | Q49 | Me | COOMe | OMe | OMe | CH |
| 2023 | Q49 | Me | COOEt | Me | OMe | CH |
| 2024 | Q49 | Me | COOEt | OMe | OMe | CH |
| 2025 | Q49 | H | H | Me | OMe | CH |
| 2026 | Q49 | H | H | OMe | OMe | CH |
| 2027 | Me | H | Q49 | Me | OMe | CH |
| 2028 | Me | H | Q49 | OMe | OMe | CH |
| 2029 | Q50 | H | COOMe | Me | Me | CH |
| 2030 | Q50 | H | COOMe | Me | OMe | CH |
| 2031 | Q50 | H | COOMe | OMe | OMe | CH |
| 2032 | Q50 | H | COOEt | Me | OMe | CH |
| 2033 | Q50 | H | COOEt | OMe | OMe | CH |
| 2034 | Q50 | Me | COOMe | Me | Me | CH |
| 2035 | Q50 | Me | COOMe | Me | OMe | CH |
| 2036 | Q50 | Me | COOMe | OMe | OMe | CH |
| 2037 | Q50 | Me | COOEt | Me | OMe | CH |
| 2038 | Q50 | Me | COOEt | OMe | OMe | CH |
| 2039 | Q50 | H | H | Me | OMe | CH |
| 2040 | Q50 | H | H | OMe | OMe | CH |
| 2041 | Me | H | Q50 | Me | OMe | CH |
| 2042 | Me | H | Q50 | OMe | OMe | CH |
| 2043 | Q51 | H | COOMe | Me | Me | CH |
| 2044 | Q51 | H | COOMe | Me | OMe | CH |
| 2045 | Q51 | H | COOMe | OMe | OMe | CH |
| 2046 | Q51 | H | COOEt | Me | OMe | CH |
| 2047 | Q51 | H | COOEt | OMe | OMe | CH |
| 2048 | Q51 | Me | COOMe | Me | Me | CH |
| 2049 | Q51 | Me | COOMe | Me | OMe | CH |
| 2050 | Q51 | Me | COOMe | OMe | OMe | CH |
| 2051 | Q51 | Me | COOEt | Me | OMe | CH |
| 2052 | Q51 | Me | COOEt | OMe | OMe | CH |
| 2053 | Q51 | H | H | Me | OMe | CH |
| 2054 | Q51 | H | H | OMe | OMe | CH |
| 2055 | Me | H | Q51 | Me | OMe | CH |
| 2056 | Me | H | Q51 | OMe | OMe | CH |
| 2057 | Q52 | H | COOMe | Me | Me | CH |
| 2058 | Q52 | H | COOMe | Me | OMe | CH |
| 2059 | Q52 | H | COOMe | OMe | OMe | CH |
| 2060 | Q52 | H | COOEt | Me | OMe | CH |
| 2061 | Q52 | H | COOEt | OMe | OMe | CH |
| 2062 | Q52 | Me | COOMe | Me | Me | CH |
| 2063 | Q52 | Me | COOMe | Me | OMe | CH |
| 2064 | Q52 | Me | COOMe | OMe | OMe | CH |
| 2065 | Q52 | Me | COOEt | Me | OMe | CH |
| 2066 | Q52 | Me | COOEt | OMe | OMe | CH |
| 2067 | Q52 | H | H | Me | OMe | CH |
| 2068 | Q52 | H | H | OMe | OMe | CH |
| 2069 | Me | H | Q52 | Me | OMe | CH |
| 2070 | Me | H | Q52 | OMe | OMe | CH |
| 2071 | Q53 | H | COOMe | Me | Me | CH |
| 2072 | Q53 | H | COOMe | Me | OMe | CH |
| 2073 | Q53 | H | COOMe | OMe | OMe | CH |
| 2074 | Q53 | H | COOMe | Me | OMe | N |
| 2075 | Q53 | H | COOMe | OMe | OMe | N |
| 2076 | Q53 | H | COOEt | Me | Me | CH |
| 2077 | Q53 | H | COOEt | Me | OMe | CH |
| 2078 | Q53 | H | COOEt | OMe | OMe | CH |
| 2079 | Q53 | H | COOEt | Me | OMe | N |
| 2080 | Q53 | H | COOEt | OMe | OMe | N |
| 2081 | Q53 | Me | COOMe | Me | Me | CH |
| 2082 | Q53 | Me | COOMe | Me | OMe | CH |
| 2083 | Q53 | Me | COOMe | OMe | OMe | CH |
| 2084 | Q53 | Me | COOMe | Me | OMe | N |
| 2085 | Q53 | Me | COOEt | Me | OMe | CH |
| 2086 | Q53 | Me | COOEt | OMe | OMe | CH |
| 2087 | Q53 | Me | COOEt | Me | OMe | N |
| 2088 | Q53 | H | CN | Me | OMe | CH |
| 2089 | Q53 | H | CN | OMe | OMe | CH |
| 2090 | Q53 | H | CN | Me | OMe | N |
| 2091 | Q53 | H | H | Me | OMe | CH |
| 2092 | Q53 | H | H | OMe | OMe | CH |
| 2093 | Q53 | H | H | Me | OMe | N |
| 2094 | Me | H | Q53 | Me | Me | CH |
| 2095 | Me | H | Q53 | Me | OMe | CH |
| 2096 | Me | H | Q53 | OMe | OMe | CH |
| 2097 | Me | H | Q53 | Me | OMe | N |
| 2098 | Me | H | Q53 | OMe | OMe | N |
| 2099 | Q54 | H | COOMe | Me | Me | CH |
| 2100 | Q54 | H | COOMe | Me | OMe | CH |
| 2101 | Q54 | H | COOMe | OMe | OMe | CH |
| 2102 | Q54 | H | COOEt | Me | OMe | CH |
| 2103 | Q54 | H | COOEt | OMe | OMe | CH |
| 2104 | Q54 | Me | COOMe | Me | Me | CH |
| 2105 | Q54 | Me | COOMe | Me | OMe | CH |

TABLE 1-continued

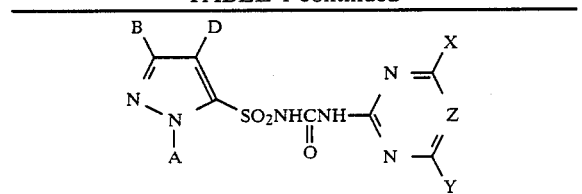

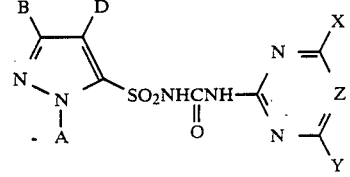

| No. | A | B | D | X | Y | Z |
|---|---|---|---|---|---|---|
| 2106 | Q54 | Me | COOMe | OMe | OMe | CH |
| 2107 | Q54 | Me | COOEt | Me | OMe | CH |
| 2108 | Q54 | Me | COOEt | OMe | OMe | CH |
| 2109 | Q54 | H | H | Me | OMe | CH |
| 2110 | Q54 | H | H | OMe | OMe | CH |
| 2111 | Me | H | Q54 | Me | OMe | CH |
| 2112 | Me | H | Q54 | OMe | OMe | CH |
| 2113 | Q55 | H | COOMe | Me | Me | CH |
| 2114 | Q55 | H | COOMe | Me | OMe | CH |
| 2115 | Q55 | H | COOMe | OMe | OMe | CH |
| 2116 | Q55 | H | COOEt | Me | OMe | CH |
| 2117 | Q55 | H | COOEt | OMe | OMe | CH |
| 2118 | Q55 | Me | COOMe | Me | Me | CH |
| 2119 | Q55 | Me | COOMe | Me | OMe | CH |
| 2120 | Q55 | Me | COOMe | OMe | OMe | CH |
| 2121 | Q55 | Me | COOEt | Me | OMe | CH |
| 2122 | Q55 | Me | COOEt | OMe | OMe | CH |
| 2123 | Q55 | H | H | Me | OMe | CH |
| 2124 | Q55 | H | H | OMe | OMe | CH |
| 2125 | Me | H | Q55 | Me | OMe | CH |
| 2126 | Me | H | Q55 | OMe | OMe | CH |
| 2127 | Q56 | H | COOMe | Me | Me | CH |
| 2128 | Q56 | H | COOMe | Me | OMe | CH |
| 2129 | Q56 | H | COOMe | OMe | OMe | CH |
| 2130 | Q56 | H | COOEt | Me | OMe | CH |
| 2131 | Q56 | H | COOEt | OMe | OMe | CH |
| 2132 | Q56 | Me | COOMe | Me | Me | CH |
| 2133 | Q56 | Me | COOMe | Me | OMe | CH |
| 2134 | Q56 | Me | COOMe | OMe | OMe | CH |
| 2135 | Q56 | Me | COOEt | Me | OMe | CH |
| 2136 | Q56 | Me | COOEt | OMe | OMe | CH |
| 2137 | Q56 | H | H | Me | OMe | CH |
| 2138 | Q56 | H | H | OMe | OMe | CH |
| 2139 | Me | H | Q56 | Me | OMe | CH |
| 2140 | Me | H | Q56 | OMe | OMe | CH |
| 2141 | Q57 | H | COOMe | Me | Me | CH |
| 2142 | Q57 | H | COOMe | Me | OMe | CH |
| 2143 | Q57 | H | COOMe | OMe | OMe | CH |
| 2144 | Q57 | H | COOEt | Me | OMe | CH |
| 2145 | Q57 | H | COOEt | OMe | OMe | CH |
| 2146 | Q57 | Me | COOMe | Me | Me | CH |
| 2147 | Q57 | Me | COOMe | Me | OMe | CH |
| 2148 | Q57 | Me | COOMe | OMe | OMe | CH |
| 2149 | Q57 | Me | COOEt | Me | OMe | CH |
| 2150 | Q57 | Me | COOEt | OMe | OMe | CH |
| 2151 | Q57 | H | H | Me | OMe | CH |
| 2152 | Q57 | H | H | OMe | OMe | CH |
| 2153 | Me | H | Q57 | Me | OMe | CH |
| 2154 | Me | H | Q57 | OMe | OMe | C |
| 2155 | Q58 | H | COOMe | Me | Me | CH |
| 2156 | Q58 | H | COOMe | Me | OMe | CH |
| 2157 | Q58 | H | COOMe | OMe | OMe | CH |
| 2158 | Q58 | H | COOEt | Me | OMe | CH |
| 2159 | Q58 | H | COOEt | OMe | OMe | CH |
| 2160 | Q58 | Me | COOMe | Me | Me | CH |
| 2161 | Q58 | Me | COOMe | Me | OMe | CH |
| 2162 | Q58 | Me | COOMe | OMe | OMe | CH |
| 2163 | Q58 | Me | COOEt | Me | OMe | CH |
| 2164 | Q58 | Me | COOEt | OMe | OMe | CH |
| 2165 | Q58 | H | H | Me | OMe | CH |
| 2166 | Q58 | H | H | OMe | OMe | CH |
| 2167 | Me | H | Q58 | Me | OMe | CH |
| 2168 | Me | H | Q58 | OMe | OMe | CH |
| 2169 | Q59 | H | COOMe | Me | Me | CH |
| 2170 | Q59 | H | COOMe | Me | OMe | CH |
| 2171 | Q59 | H | COOMe | OMe | OMe | CH |
| 2172 | Q59 | H | COOEt | Me | OMe | CH |
| 2173 | Q59 | H | COOEt | OMe | OMe | CH |
| 2174 | Q59 | Me | COOMe | Me | Me | CH |
| 2175 | Q59 | Me | COOMe | Me | OMe | CH |
| 2176 | Q59 | Me | COOMe | OMe | OMe | CH |
| 2177 | Q59 | Me | COOEt | Me | OMe | CH |
| 2178 | Q59 | Me | COOEt | OMe | OMe | CH |
| 2179 | Q59 | H | H | Me | OMe | CH |
| 2180 | Q59 | H | H | OMe | OMe | CH |
| 2181 | Me | H | Q59 | Me | OMe | CH |
| 2182 | Me | H | Q59 | OMe | OMe | CH |
| 2183 | Q60 | H | COOMe | Me | Me | CH |
| 2184 | Q60 | H | COOMe | Me | OMe | CH |
| 2185 | Q60 | H | COOMe | OMe | OMe | CH |
| 2186 | Q60 | H | COOMe | Me | OMe | N |
| 2187 | Q60 | H | COOMe | OMe | OMe | N |
| 2188 | Q60 | H | COOEt | Me | Me | CH |
| 2189 | Q60 | H | COOEt | Me | OMe | CH |
| 2190 | Q60 | H | COOEt | OMe | OMe | CH |
| 2191 | Q60 | H | COOEt | Me | OMe | N |
| 2192 | Q60 | H | COOEt | OMe | OMe | N |
| 2193 | Q60 | Me | COOMe | Me | Me | CH |
| 2194 | Q60 | Me | COOMe | Me | OMe | CH |
| 2195 | Q60 | Me | COOMe | OMe | OMe | CH |
| 2196 | Q60 | Me | COOMe | Me | OMe | N |
| 2197 | Q60 | Me | COOEt | Me | OMe | CH |
| 2198 | Q60 | Me | COOEt | OMe | OMe | CH |
| 2199 | Q60 | Me | COOEt | Me | OMe | N |
| 2200 | Q60 | H | CN | Me | OMe | CH |
| 2201 | Q60 | H | CN | OMe | OMe | CH |
| 2202 | Q60 | H | CN | Me | OMe | N |
| 2203 | Q60 | H | H | Me | OMe | CH |
| 2204 | Q60 | H | H | OMe | OMe | CH |
| 2205 | Q60 | H | H | Me | OMe | N |
| 2206 | Me | H | Q60 | Me | Me | CH |
| 2207 | Me | H | Q60 | Me | OMe | CH |
| 2208 | Me | H | Q60 | OMe | OMe | CH |
| 2209 | Me | H | Q60 | Me | OMe | N |
| 2210 | Me | H | Q60 | OMe | OMe | N |
| 2211 | Q61 | H | COOMe | Me | Me | CH |
| 2212 | Q61 | H | COOMe | Me | OMe | CH |
| 2213 | Q61 | H | COOMe | OMe | OMe | CH |
| 2214 | Q61 | H | COOEt | Me | OMe | CH |
| 2215 | Q61 | H | COOEt | OMe | OMe | CH |
| 2216 | Q61 | Me | COOMe | Me | Me | CH |
| 2217 | Q61 | Me | COOMe | Me | OMe | CH |
| 2218 | Q61 | Me | COOMe | OMe | OMe | CH |
| 2219 | Q61 | Me | COOEt | Me | OMe | CH |
| 2220 | Q61 | Me | COOEt | OMe | OMe | CH |
| 2221 | Q61 | H | H | Me | OMe | CH |
| 2222 | Q61 | H | H | OMe | OMe | CH |
| 2223 | Me | H | Q61 | Me | OMe | CH |
| 2234 | Me | H | Q61 | OMe | OMe | CH |
| 2224 | Me | H | Q61 | Me | Me | CH |
| 2225 | Q62 | H | COOMe | Me | Me | CH |
| 2226 | Q62 | H | COOMe | Me | OMe | CH |
| 2227 | Q62 | H | COOMe | OMe | OMe | CH |
| 2228 | Q62 | H | COOEt | Me | OMe | CH |
| 2229 | Q62 | H | COOEt | OMe | OMe | CH |
| 2230 | Q62 | Me | COOMe | Me | Me | CH |
| 2231 | Q62 | Me | COOMe | Me | OMe | CH |
| 2232 | Q62 | Me | COOEt | OMe | OMe | CH |
| 2233 | Q62 | Me | COOEt | Me | OMe | CH |
| 2234 | Q62 | Me | COOEt | OMe | OMe | CH |
| 2235 | Q62 | H | H | Me | OMe | CH |
| 2236 | Q62 | H | H | OMe | OMe | CH |
| 2237 | Me | H | Q62 | Me | OMe | CH |
| 2238 | Me | H | Q62 | OMe | OMe | CH |
| 2239 | Q63 | H | COOMe | Me | Me | CH |
| 2240 | Q63 | H | COOMe | Me | OMe | CH |
| 2241 | Q63 | H | COOMe | OMe | OMe | CH |
| 2242 | Q63 | H | COOEt | Me | OMe | CH |
| 2243 | Q63 | H | COOEt | OMe | OMe | CH |
| 2244 | Q63 | Me | COOMe | Me | Me | CH |
| 2245 | Q63 | Me | COOMe | Me | OMe | CH |
| 2246 | Q63 | Me | COOMe | OMe | OMe | CH |
| 2247 | Q63 | Me | COOEt | Me | OMe | CH |

TABLE 1-continued

| No. | A | B | D | X | Y | Z |
|---|---|---|---|---|---|---|
| 2248 | Q63 | Me | COOEt | OMe | OMe | CH |
| 2249 | Q63 | H | H | Me | OMe | CH |
| 2250 | Q63 | H | H | OMe | OMe | CH |
| 2251 | Me | H | Q63 | Me | OMe | CH |
| 2252 | Me | H | Q63 | OMe | OMe | CH |
| 2253 | Q64 | H | COOMe | Me | Me | CH |
| 2254 | Q64 | H | COOMe | Me | OMe | CH |
| 2255 | Q64 | H | COOMe | OMe | OMe | CH |
| 2256 | Q64 | H | COOEt | Me | OMe | CH |
| 2257 | Q64 | H | COOEt | OMe | OMe | CH |
| 2258 | Q64 | Me | COOMe | Me | Me | CH |
| 2259 | Q64 | Me | COOMe | Me | OMe | CH |
| 2260 | Q64 | Me | COOMe | OMe | OMe | CH |
| 2261 | Q64 | Me | COOEt | Me | OMe | CH |
| 2262 | Q64 | Me | COOEt | OMe | OMe | CH |
| 2263 | Q64 | H | H | Me | OMe | CH |
| 2264 | Q64 | H | H | OMe | OMe | CH |
| 2265 | Me | H | Q64 | Me | OMe | CH |
| 2266 | Me | H | Q64 | OMe | OMe | CH |
| 2267 | Q65 | H | COOMe | Me | Me | CH |
| 2268 | Q65 | H | COOMe | Me | OMe | CH |
| 2269 | Q65 | H | COOMe | OMe | OMe | CH |
| 2270 | Q65 | H | COOMe | Me | OMe | N |
| 2271 | Q65 | H | COOMe | OMe | OMe | N |
| 2272 | Q65 | H | COOEt | Me | Me | CH |
| 2273 | Q65 | H | COOEt | Me | OMe | CH |
| 2274 | Q65 | H | COOEt | OMe | OMe | CH |
| 2275 | Q65 | H | COOEt | Me | OMe | N |
| 2276 | Q65 | H | COOEt | OMe | OMe | N |
| 2277 | Q65 | Me | COOMe | Me | Me | CH |
| 2278 | Q65 | Me | COOMe | Me | OMe | CH |
| 2279 | Q65 | Me | COOMe | OMe | OMe | CH |
| 2280 | Q65 | Me | COOMe | Me | OMe | N |
| 2281 | Q65 | Me | COOEt | Me | OMe | CH |
| 2282 | Q65 | Me | COOEt | OMe | OMe | CH |
| 2283 | Q65 | Me | COOEt | Me | OMe | N |
| 2284 | Q65 | H | CN | Me | OMe | CH |
| 2285 | Q65 | H | CN | OMe | OMe | CH |
| 2286 | Q65 | H | CN | Me | OMe | N |
| 2287 | Q65 | H | H | Me | OMe | CH |
| 2288 | Q65 | H | H | OMe | OMe | CH |
| 2289 | Q65 | H | H | Me | OMe | N |
| 2290 | Me | H | Q65 | Me | Me | CH |
| 2291 | Me | H | Q65 | Me | OMe | CH |
| 2292 | Me | H | Q65 | OMe | OMe | CH |
| 2293 | Me | H | Q65 | Me | OMe | N |
| 2294 | Me | H | Q65 | OMe | OMe | N |
| 2295 | Q66 | H | COOMe | Me | Me | CH |
| 2296 | Q66 | H | COOMe | Me | OMe | CH |
| 2297 | Q66 | H | COOMe | OMe | OMe | CH |
| 2298 | Q66 | H | COOEt | Me | OMe | CH |
| 2299 | Q66 | H | COOEt | OMe | OMe | CH |
| 2300 | Q66 | Me | COOMe | Me | Me | CH |
| 2301 | Q66 | Me | COOMe | Me | OMe | CH |
| 2302 | Q66 | Me | COOMe | OMe | OMe | CH |
| 2303 | Q66 | Me | COOEt | Me | OMe | CH |
| 2304 | Q66 | Me | COOEt | OMe | OMe | CH |
| 2305 | Q66 | H | H | Me | OMe | CH |
| 2306 | Q66 | H | H | OMe | OMe | CH |
| 2307 | Me | H | Q66 | Me | OMe | CH |
| 2308 | Me | H | Q66 | OMe | OMe | CH |
| 2309 | Q67 | H | COOMe | Me | Me | CH |
| 2310 | Q67 | H | COOMe | Me | OMe | CH |
| 2311 | Q67 | H | COOMe | OMe | OMe | CH |
| 2312 | Q67 | H | COOEt | Me | OMe | CH |
| 2313 | Q67 | H | COOEt | OMe | OMe | CH |
| 2314 | Q67 | Me | COOMe | Me | Me | CH |
| 2315 | Q67 | Me | COOMe | Me | OMe | CH |
| 2316 | Q67 | Me | COOMe | OMe | OMe | CH |
| 2317 | Q67 | Me | COOEt | Me | OMe | CH |
| 2318 | Q67 | Me | COOEt | OMe | OMe | CH |
| 2319 | Q67 | H | H | Me | OMe | CH |
| 2320 | Q67 | H | H | OMe | OMe | CH |
| 2321 | Me | H | Q67 | Me | OMe | CH |
| 2322 | Me | H | Q67 | OMe | OMe | CH |
| 2323 | Q68 | H | COOMe | Me | Me | CH |
| 2324 | Q68 | H | COOMe | Me | OMe | CH |
| 2325 | Q68 | H | COOMe | OMe | OMe | CH |
| 2326 | Q68 | H | COOMe | Me | OMe | N |
| 2327 | Q68 | H | COOMe | OMe | OMe | N |
| 2328 | Q68 | H | COOEt | Me | Me | CH |
| 2329 | Q68 | H | COOEt | Me | OMe | CH |
| 2330 | Q68 | H | COOEt | OMe | OMe | CH |
| 2331 | Q68 | H | COOEt | Me | OMe | N |
| 2332 | Q68 | H | COOEt | OMe | OMe | N |
| 2333 | Q68 | Me | COOMe | Me | Me | CH |
| 2334 | Q68 | Me | COOMe | Me | OMe | CH |
| 2335 | Q68 | Me | COOMe | OMe | OMe | CH |
| 2336 | Q68 | Me | COOMe | Me | OMe | N |
| 2337 | Q68 | Me | COOEt | Me | OMe | CH |
| 2338 | Q68 | Me | COOEt | OMe | OMe | CH |
| 2339 | Q68 | Me | COOEt | Me | OMe | N |
| 2340 | Q68 | H | CN | Me | OMe | CH |
| 2341 | Q68 | H | CN | OMe | OMe | CH |
| 2342 | Q68 | H | CN | Me | OMe | N |
| 2343 | Q68 | H | H | Me | OMe | CH |
| 2344 | Q68 | H | H | OMe | OMe | CH |
| 2345 | Q68 | H | H | Me | OMe | N |
| 2346 | Me | H | Q68 | Me | Me | CH |
| 2347 | Me | H | Q68 | Me | OMe | CH |
| 2348 | Me | H | Q68 | OMe | OMe | CH |
| 2349 | Me | H | Q68 | Me | OMe | N |
| 2350 | Me | H | Q68 | OMe | OMe | N |
| 2351 | Q69 | H | COOMe | Me | Me | CH |
| 2352 | Q69 | H | COOMe | Me | OMe | CH |
| 2353 | Q69 | H | COOMe | OMe | OMe | CH |
| 2354 | Q69 | H | COOEt | Me | OMe | CH |
| 2355 | Q69 | H | COOEt | OMe | OMe | CH |
| 2356 | Q69 | Me | COOMe | Me | Me | CH |
| 2357 | Q69 | Me | COOMe | Me | OMe | CH |
| 2358 | Q69 | Me | COOMe | OMe | OMe | CH |
| 2359 | Q69 | Me | COOEt | Me | OMe | CH |
| 2360 | Q69 | Me | COOEt | OMe | OMe | CH |
| 2361 | Q69 | H | H | Me | OMe | CH |
| 2362 | Q69 | H | H | OMe | OMe | CH |
| 2363 | Me | H | Q69 | Me | OMe | CH |
| 2364 | Me | H | Q69 | OMe | OMe | CH |
| 2365 | Q70 | H | COOMe | Me | Me | CH |
| 2366 | Q70 | H | COOMe | Me | OMe | CH |
| 2367 | Q70 | H | COOMe | OMe | OMe | CH |
| 2368 | Q70 | H | COOEt | Me | OMe | CH |
| 2369 | Q70 | H | COOEt | OMe | OMe | CH |
| 2370 | Q70 | Me | COOMe | Me | Me | CH |
| 2371 | Q70 | Me | COOMe | Me | OMe | CH |
| 2372 | Q70 | Me | COOMe | OMe | OMe | CH |
| 2373 | Q70 | Me | COOEt | Me | OMe | CH |
| 2374 | Q70 | Me | COOEt | OMe | OMe | CH |
| 2375 | Q70 | H | H | Me | OMe | CH |
| 2376 | Q70 | H | H | OMe | OMe | CH |
| 2377 | Me | H | Q70 | Me | OMe | CH |
| 2378 | Me | H | Q70 | OMe | OMe | CH |
| 2379 | Q71 | H | COOMe | Me | Me | CH |
| 2380 | Q71 | H | COOMe | Me | OMe | CH |
| 2381 | Q71 | H | COOMe | OMe | OMe | CH |
| 2382 | Q71 | H | COOMe | Me | OMe | N |
| 2383 | Q71 | H | COOMe | OMe | OMe | N |
| 2384 | Q71 | H | COOEt | Me | Me | CH |
| 2385 | Q71 | H | COOEt | Me | OMe | CH |
| 2386 | Q71 | H | COOEt | OMe | OMe | CH |
| 2387 | Q71 | H | COOEt | Me | OMe | N |
| 2388 | Q71 | H | COOEt | OMe | OMe | N |
| 2389 | Q71 | Me | COOMe | Me | Me | CH |

TABLE 1-continued

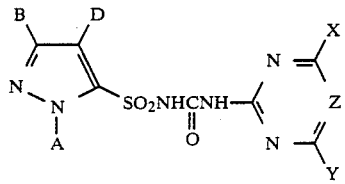

| No. | A | B | D | X | Y | Z |
|---|---|---|---|---|---|---|
| 2390 | Q71 | Me | COOMe | Me | OMe | CH |
| 2391 | Q71 | Me | COOMe | OMe | OMe | CH |
| 2392 | Q71 | Me | COOMe | Me | OMe | N |
| 2393 | Q71 | Me | COOEt | Me | OMe | CH |
| 2394 | Q71 | Me | COOEt | OMe | OMe | CH |
| 2395 | Q71 | Me | COOEt | Me | OMe | N |
| 2396 | Q71 | H | CN | Me | OMe | CH |
| 2397 | Q71 | H | CN | OMe | OMe | CH |
| 2398 | Q71 | H | CN | Me | OMe | N |
| 2399 | Q71 | H | H | Me | OMe | CH |
| 2400 | Q71 | H | H | OMe | OMe | CH |
| 2401 | Q71 | H | H | Me | OMe | N |
| 2402 | Me | H | Q71 | Me | Me | CH |
| 2403 | Me | H | Q71 | Me | OMe | CH |
| 2404 | Me | H | Q71 | OMe | OMe | CH |
| 2405 | Me | H | Q71 | Me | OMe | N |
| 2406 | Me | H | Q71 | OMe | OMe | N |
| 2407 | Q72 | H | COOMe | Me | Me | CH |
| 2408 | Q72 | H | COOMe | Me | OMe | CH |
| 2409 | Q72 | H | COOMe | OMe | OMe | CH |
| 2410 | Q72 | H | COOEt | Me | OMe | CH |
| 2411 | Q72 | H | COOEt | OMe | OMe | CH |
| 2412 | Q72 | Me | COOMe | Me | Me | CH |
| 2413 | Q72 | Me | COOMe | Me | OMe | CH |
| 2414 | Q72 | Me | COOMe | OMe | OMe | CH |
| 2415 | Q72 | Me | COOEt | Me | OMe | CH |
| 2416 | Q72 | Me | COOEt | OMe | OMe | CH |
| 2417 | Q72 | H | H | Me | OMe | CH |
| 2418 | Q72 | H | H | OMe | OMe | CH |
| 2419 | Me | H | Q72 | Me | OMe | CH |
| 2420 | Me | H | Q72 | OMe | OMe | CH |
| 2421 | Q73 | H | COOMe | Me | Me | CH |
| 2422 | Q73 | H | COOMe | Me | OMe | CH |
| 2423 | Q73 | H | COOMe | OMe | OMe | CH |
| 2424 | Q73 | H | COOEt | Me | OMe | CH |
| 2425 | Q73 | H | COOEt | OMe | OMe | CH |
| 2426 | Q73 | Me | COOMe | Me | Me | CH |
| 2427 | Q73 | Me | COOMe | Me | OMe | CH |
| 2428 | Q73 | Me | COOMe | OMe | OMe | CH |
| 2429 | Q73 | Me | COOEt | Me | OMe | CH |
| 2430 | Q73 | Me | COOEt | OMe | OMe | CH |
| 2431 | Q73 | H | H | Me | OMe | CH |
| 2432 | Q73 | H | H | OMe | OMe | CH |
| 2433 | Me | H | Q73 | Me | OMe | CH |
| 2434 | Me | H | Q73 | OMe | OMe | CH |
| 2435 | Q74 | H | COOMe | Me | Me | CH |
| 2436 | Q74 | H | COOMe | Me | OMe | CH |
| 2437 | Q74 | H | COOMe | OMe | OMe | CH |
| 2438 | Q74 | H | COOEt | Me | OMe | CH |
| 2439 | Q74 | H | COOEt | OMe | OMe | CH |
| 2440 | Q74 | Me | COOMe | Me | Me | CH |
| 2441 | Q74 | Me | COOMe | Me | OMe | CH |
| 2442 | Q74 | Me | COOMe | OMe | OMe | CH |
| 2443 | Q74 | Me | COOEt | Me | OMe | CH |
| 2444 | Q74 | Me | COOEt | OMe | OMe | CH |
| 2445 | Q74 | H | H | Me | OMe | CH |
| 2446 | Q74 | H | H | OMe | OMe | CH |
| 2447 | Me | H | Q74 | Me | OMe | CH |
| 2448 | Me | H | Q74 | OMe | OMe | CH |
| 2449 | Q75 | H | COOMe | Me | Me | CH |
| 2450 | Q75 | H | COOMe | Me | OMe | CH |
| 2451 | Q75 | H | COOMe | OMe | OMe | CH |
| 2452 | Q75 | H | COOEt | Me | OMe | CH |
| 2453 | Q75 | H | COOEt | OMe | OMe | CH |
| 2454 | Q75 | Me | COOMe | Me | Me | CH |
| 2455 | Q75 | Me | COOMe | Me | OMe | CH |
| 2456 | Q75 | Me | COOMe | OMe | OMe | CH |
| 2457 | Q75 | Me | COOEt | Me | OMe | CH |
| 2458 | Q75 | Me | COOEt | OMe | OMe | CH |
| 2459 | Q75 | H | H | Me | OMe | CH |
| 2460 | Q75 | H | H | OMe | OMe | CH |

TABLE 1-continued

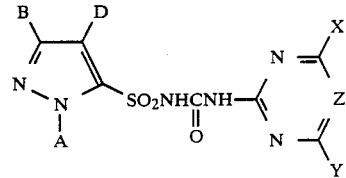

| No. | A | B | D | X | Y | Z |
|---|---|---|---|---|---|---|
| 2461 | Me | H | Q75 | Me | OMe | CH |
| 2462 | Me | H | Q75 | OMe | OMe | CH |
| 2463 | Q76 | H | COOMe | Me | Me | CH |
| 2464 | Q76 | H | COOMe | Me | OMe | CH |
| 2465 | Q76 | H | COOMe | OMe | OMe | CH |
| 2466 | Q76 | H | COOEt | Me | OMe | CH |
| 2467 | Q76 | H | COOEt | OMe | OMe | CH |
| 2468 | Q76 | Me | COOMe | Me | Me | CH |
| 2469 | Q76 | Me | COOMe | Me | OMe | CH |
| 2470 | Q76 | Me | COOMe | OMe | OMe | CH |
| 2471 | Q76 | Me | COOEt | Me | OMe | CH |
| 2472 | Q76 | Me | COOEt | OMe | OMe | CH |
| 2473 | Q76 | H | H | Me | OMe | CH |
| 2474 | Q76 | H | H | OMe | OMe | CH |
| 2475 | Me | H | Q76 | Me | OMe | CH |
| 2476 | Me | H | Q76 | OMe | OMe | CH |
| 2477 | Q77 | H | COOMe | Me | Me | CH |
| 2478 | Q77 | H | COOMe | Me | OMe | CH |
| 2479 | Q77 | H | COOMe | OMe | OMe | CH |
| 2480 | Q77 | H | COOEt | Me | OMe | CH |
| 2481 | Q77 | H | COOEt | OMe | OMe | CH |
| 2482 | Q77 | Me | COOMe | Me | Me | CH |
| 2483 | Q77 | Me | COOMe | Me | OMe | CH |
| 2484 | Q77 | Me | COOMe | OMe | OMe | CH |
| 2485 | Q77 | Me | COOEt | Me | OMe | CH |
| 2486 | Q77 | Me | COOEt | OMe | OMe | CH |
| 2487 | Q77 | H | H | Me | OMe | CH |
| 2488 | Q77 | H | H | OMe | OMe | CH |
| 2489 | Me | H | Q77 | Me | OMe | CH |
| 2490 | Me | H | Q77 | OMe | OMe | CH |
| 2491 | Q78 | H | COOMe | Me | Me | CH |
| 2492 | Q78 | H | COOMe | Me | OMe | CH |
| 2493 | Q78 | H | COOMe | OMe | OMe | CH |
| 2494 | Q78 | H | COOEt | Me | OMe | CH |
| 2495 | Q78 | H | COOEt | OMe | OMe | CH |
| 2496 | Q78 | Me | COOMe | Me | Me | CH |
| 2497 | Q78 | Me | COOMe | Me | OMe | CH |
| 2498 | Q78 | Me | COOMe | OMe | OMe | CH |
| 2499 | Q78 | Me | COOEt | Me | OMe | CH |
| 2500 | Q78 | Me | COOEt | OMe | OMe | CH |
| 2501 | Q78 | H | H | Me | OMe | CH |
| 2502 | Q78 | H | H | OMe | OMe | CH |
| 2503 | Me | H | Q78 | Me | OMe | CH |
| 2504 | Me | H | Q78 | OMe | OMe | CH |
| 2505 | Q79 | H | COOMe | Me | Me | CH |
| 2506 | Q79 | H | COOMe | Me | OMe | CH |
| 2507 | Q79 | H | COOMe | OMe | OMe | CH |
| 2508 | Q79 | H | COOEt | Me | OMe | CH |
| 2509 | Q79 | H | COOEt | OMe | OMe | CH |
| 2510 | Q79 | Me | COOMe | Me | Me | CH |
| 2511 | Q79 | Me | COOMe | Me | OMe | CH |
| 2512 | Q79 | Me | COOMe | OMe | OMe | CH |
| 2513 | Q79 | Me | COOEt | Me | OMe | CH |
| 2514 | Q79 | Me | COOEt | OMe | OMe | CH |
| 2515 | Q79 | H | H | Me | OMe | CH |
| 2516 | Q79 | H | H | OMe | OMe | CH |
| 2517 | Me | H | Q79 | Me | OMe | CH |
| 2518 | Me | H | Q79 | OMe | OMe | CH |
| 2519 | Q80 | H | COOMe | Me | Me | CH |
| 2520 | Q80 | H | COOMe | Me | OMe | CH |
| 2521 | Q80 | H | COOMe | OMe | OMe | CH |
| 2522 | Q80 | H | COOEt | Me | OMe | CH |
| 2523 | Q80 | H | COOEt | OMe | OMe | CH |
| 2524 | Q80 | Me | COOMe | Me | Me | CH |
| 2525 | Q80 | Me | COOMe | Me | OMe | CH |
| 2526 | Q80 | Me | COOMe | OMe | OMe | CH |
| 2527 | Q80 | Me | COOEt | Me | OMe | CH |
| 2528 | Q80 | Me | COOEt | OMe | OMe | CH |
| 2529 | Q80 | H | H | Me | OMe | CH |
| 2530 | Q80 | H | H | OMe | OMe | CH |
| 2531 | Me | H | Q80 | Me | OMe | CH |

TABLE 1-continued

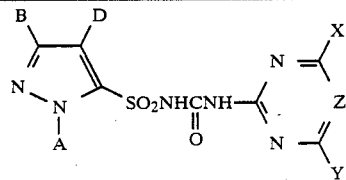

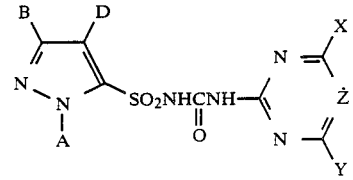

| No. | A | B | D | X | Y | Z |
|---|---|---|---|---|---|---|
| 2532 | Me | H | Q80 | OMe | OMe | CH |
| 2533 | Q81 | H | COOMe | Me | Me | CH |
| 2534 | Q81 | H | COOMe | Me | OMe | CH |
| 2535 | Q81 | H | COOMe | OMe | OMe | CH |
| 2536 | Q81 | H | COOEt | Me | OMe | CH |
| 2537 | Q81 | H | COOEt | OMe | OMe | CH |
| 2538 | Q81 | Me | COOMe | Me | Me | CH |
| 2539 | Q81 | Me | COOMe | Me | OMe | CH |
| 2540 | Q81 | Me | COOMe | OMe | OMe | CH |
| 2541 | Q81 | Me | COOEt | Me | OMe | CH |
| 2542 | Q81 | Me | COOEt | OMe | OMe | CH |
| 2543 | Q81 | H | H | Me | OMe | CH |
| 2544 | Q81 | H | H | OMe | OMe | CH |
| 2545 | Me | H | Q81 | Me | OMe | CH |
| 2546 | Me | H | Q81 | OMe | OMe | CH |
| 2547 | Q82 | H | COOMe | Me | Me | CH |
| 2548 | Q82 | H | COOMe | Me | OMe | CH |
| 2549 | Q82 | H | COOMe | OMe | OMe | CH |
| 2550 | Q82 | H | COOEt | Me | OMe | CH |
| 2551 | Q82 | H | COOEt | OMe | OMe | CH |
| 2552 | Q82 | Me | COOMe | Me | Me | CH |
| 2553 | Q82 | Me | COOMe | Me | OMe | CH |
| 2554 | Q82 | Me | COOMe | OMe | OMe | CH |
| 2555 | Q82 | Me | COOEt | Me | OMe | CH |
| 2556 | Q82 | Me | COOEt | OMe | OMe | CH |
| 2557 | Q82 | H | H | Me | OMe | CH |
| 2558 | Q82 | H | H | OMe | OMe | CH |
| 2559 | Me | H | Q82 | Me | OMe | CH |
| 2560 | Me | H | Q82 | OMe | OMe | CH |
| 2561 | Q83 | H | COOMe | Me | Me | CH |
| 2562 | Q83 | H | COOMe | Me | OMe | CH |
| 2563 | Q83 | H | COOMe | OMe | OMe | CH |
| 2564 | Q83 | H | COOEt | Me | OMe | CH |
| 2565 | Q83 | H | COOEt | OMe | OMe | CH |
| 2566 | Q83 | Me | COOMe | Me | Me | CH |
| 2567 | Q83 | Me | COOMe | Me | OMe | CH |
| 2568 | Q83 | Me | COOMe | OMe | OMe | CH |
| 2569 | Q83 | Me | COOEt | Me | OMe | CH |
| 2570 | Q83 | Me | COOEt | OMe | OMe | CH |
| 2571 | Q83 | H | H | Me | OMe | CH |
| 2572 | Q83 | H | H | OMe | OMe | CH |
| 2573 | Me | H | Q83 | Me | OMe | CH |
| 2574 | Me | H | Q83 | OMe | OMe | CH |
| 2575 | Q84 | H | COOMe | Me | Me | CH |
| 2576 | Q84 | H | COOMe | Me | OMe | CH |
| 2577 | Q84 | H | COOMe | OMe | OMe | CH |
| 2578 | Q84 | H | COOEt | Me | OMe | CH |
| 2579 | Q84 | H | COOEt | OMe | OMe | CH |
| 2580 | Q84 | Me | COOMe | Me | Me | CH |
| 2581 | Q84 | Me | COOMe | Me | OMe | CH |
| 2582 | Q84 | Me | COOMe | OMe | OMe | CH |
| 2583 | Q84 | Me | COOEt | Me | OMe | CH |
| 2584 | Q84 | Me | COOEt | OMe | OMe | CH |
| 2585 | Q84 | H | H | Me | OMe | CH |
| 2586 | Q84 | H | H | OMe | OMe | CH |
| 2587 | Me | H | Q84 | Me | OMe | CH |
| 2588 | Me | H | Q84 | OMe | OMe | CH |
| 2589 | Q85 | H | COOMe | Me | Me | CH |
| 2590 | Q85 | H | COOMe | Me | OMe | CH |
| 2591 | Q85 | H | COOMe | OMe | OMe | CH |
| 2592 | Q85 | H | COOEt | Me | OMe | CH |
| 2593 | Q85 | H | COOEt | OMe | OMe | CH |
| 2594 | Q85 | Me | COOMe | Me | Me | CH |
| 2595 | Q85 | Me | COOMe | Me | OMe | CH |
| 2596 | Q85 | Me | COOMe | OMe | OMe | CH |
| 2597 | Q85 | Me | COOEt | Me | OMe | CH |
| 2598 | Q85 | Me | COOEt | OMe | OMe | CH |
| 2599 | Q85 | H | H | Me | OMe | CH |
| 2600 | Q85 | H | H | OMe | OMe | CH |
| 2601 | Me | H | Q85 | Me | OMe | CH |
| 2602 | Me | H | Q85 | OMe | OMe | CH |
| 2603 | Q86 | H | COOMe | Me | Me | CH |
| 2604 | Q86 | H | COOMe | Me | OMe | CH |
| 2605 | Q86 | H | COOMe | OMe | OMe | CH |
| 2606 | Q86 | H | COOEt | Me | OMe | CH |
| 2607 | Q86 | H | COOEt | OMe | OMe | CH |
| 2608 | Q86 | Me | COOMe | Me | Me | CH |
| 2609 | Q86 | Me | COOMe | Me | OMe | CH |
| 2610 | Q86 | Me | COOMe | OMe | OMe | CH |
| 2611 | Q86 | Me | COOEt | Me | OMe | CH |
| 2612 | Q86 | Me | COOEt | OMe | OMe | CH |
| 2613 | Q86 | H | H | Me | OMe | CH |
| 2614 | Q86 | H | H | OMe | OMe | CH |
| 2615 | Me | H | Q86 | Me | OMe | CH |
| 2616 | Me | H | Q86 | OMe | OMe | CH |
| 2617 | Q87 | H | COOMe | Me | Me | CH |
| 2618 | Q87 | H | COOMe | Me | OMe | CH |
| 2619 | Q87 | H | COOMe | OMe | OMe | CH |
| 2620 | Q87 | H | COOEt | Me | OMe | CH |
| 2621 | Q87 | H | COOEt | OMe | OMe | CH |
| 2622 | Q87 | Me | COOMe | Me | Me | CH |
| 2623 | Q87 | Me | COOMe | Me | OMe | CH |
| 2624 | Q87 | Me | COOMe | OMe | OMe | CH |
| 2625 | Q87 | Me | COOEt | Me | OMe | CH |
| 2626 | Q87 | Me | COOEt | OMe | OMe | CH |
| 2627 | Q87 | H | H | Me | OMe | CH |
| 2628 | Q87 | H | H | OMe | OMe | CH |
| 2629 | Me | H | Q87 | Me | OMe | CH |
| 2630 | Me | H | Q87 | OMe | OMe | CH |
| 2631 | Q88 | H | COOMe | Me | Me | CH |
| 2632 | Q88 | H | COOMe | Me | OMe | CH |
| 2633 | Q88 | H | COOMe | OMe | OMe | CH |
| 2634 | Q88 | H | COOEt | Me | OMe | CH |
| 2635 | Q88 | H | COOEt | OMe | OMe | CH |
| 2636 | Q88 | Me | COOMe | Me | Me | CH |
| 2637 | Q88 | Me | COOMe | Me | OMe | CH |
| 2638 | Q88 | Me | COOMe | OMe | OMe | CH |
| 2639 | Q88 | Me | COOEt | Me | OMe | CH |
| 2640 | Q88 | Me | COOEt | OMe | OMe | CH |
| 2641 | Q88 | H | H | Me | OMe | CH |
| 2642 | Q88 | H | H | OMe | OMe | CH |
| 2643 | Me | H | Q88 | Me | OMe | CH |
| 2644 | Me | H | Q88 | OMe | OMe | CH |
| 2645 | Q89 | H | COOMe | Me | Me | CH |
| 2646 | Q89 | H | COOMe | Me | OMe | CH |
| 2647 | Q89 | H | COOMe | OMe | OMe | CH |
| 2648 | Q89 | H | COOEt | Me | OMe | CH |
| 2649 | Q89 | H | COOEt | OMe | OMe | CH |
| 2650 | Q89 | Me | COOMe | Me | Me | CH |
| 2651 | Q89 | Me | COOMe | Me | OMe | CH |
| 2652 | Q89 | Me | COOMe | OMe | OMe | CH |
| 2653 | Q89 | Me | COOEt | Me | OMe | CH |
| 2654 | Q89 | Me | COOEt | OMe | OMe | CH |
| 2655 | Q89 | H | H | Me | OMe | CH |
| 2656 | Q89 | H | H | OMe | OMe | CH |
| 2657 | Me | H | Q89 | Me | OMe | CH |
| 2658 | Me | H | Q89 | OMe | OMe | CH |
| 2659 | Q90 | H | COOMe | Me | Me | CH |
| 2660 | Q90 | H | COOMe | Me | OMe | CH |
| 2661 | Q90 | H | COOMe | OMe | OMe | CH |
| 2662 | Q90 | H | COOMe | Me | OMe | N |
| 2663 | Q90 | H | COOMe | OMe | OMe | N |
| 2664 | Q90 | H | COOEt | Me | Me | CH |
| 2665 | Q90 | H | COOEt | Me | OMe | CH |
| 2666 | Q90 | H | COOEt | OMe | OMe | CH |
| 2667 | Q90 | H | COOEt | Me | OMe | N |
| 2668 | Q90 | H | COOEt | OMe | OMe | N |
| 2669 | Q90 | Me | COOMe | Me | Me | CH |
| 2670 | Q90 | Me | COOMe | Me | OMe | CH |
| 2671 | Q90 | Me | COOMe | OMe | OMe | CH |
| 2672 | Q90 | Me | COOMe | Me | OMe | N |
| 2673 | Q90 | Me | COOEt | Me | OMe | CH |

TABLE 1-continued

Structure:
$$\text{pyrazole with B, D substituents, N-A, SO}_2\text{NHCNH-C(=O)-pyrimidine(X,Y,Z)}$$

| No. | A | B | D | X | Y | Z |
|---|---|---|---|---|---|---|
| 2674 | $Q_{90}$ | Me | COOEt | OMe | OMe | CH |
| 2675 | $Q_{90}$ | Me | COOEt | Me | OMe | N |
| 2676 | $Q_{90}$ | H | CN | Me | OMe | CH |
| 2677 | $Q_{90}$ | H | CN | OMe | OMe | CH |
| 2678 | $Q_{90}$ | H | CN | Me | OMe | N |
| 2679 | $Q_{90}$ | H | H | Me | OMe | CH |
| 2680 | $Q_{90}$ | H | H | OMe | OMe | CH |
| 2681 | $Q_{90}$ | H | H | Me | OMe | N |
| 2682 | Me | H | $Q_{90}$ | Me | Me | CH |
| 2683 | Me | H | $Q_{90}$ | Me | OMe | CH |
| 2684 | Me | H | $Q_{90}$ | OMe | OMe | CH |
| 2685 | Me | H | $Q_{90}$ | Me | OMe | N |
| 2686 | Me | H | $Q_{90}$ | OMe | OMe | N |
| 2687 | $Q_{91}$ | H | COOMe | Me | Me | CH |
| 2688 | $Q_{91}$ | H | COOMe | Me | OMe | CH |
| 2689 | $Q_{91}$ | H | COOMe | OMe | OMe | CH |
| 2690 | $Q_{91}$ | H | COOEt | Me | OMe | CH |
| 2691 | $Q_{91}$ | H | COOEt | OMe | OMe | CH |
| 2692 | $Q_{91}$ | Me | COOMe | Me | Me | CH |
| 2693 | $Q_{91}$ | Me | COOMe | Me | OMe | CH |
| 2694 | $Q_{91}$ | Me | COOMe | OMe | OMe | CH |
| 2695 | $Q_{91}$ | Me | COOEt | Me | OMe | CH |
| 2696 | $Q_{91}$ | Me | COOEt | OMe | OMe | CH |
| 2697 | $Q_{91}$ | H | H | Me | OMe | CH |
| 2698 | $Q_{91}$ | H | H | OMe | OMe | CH |
| 2699 | Me | H | $Q_{91}$ | Me | OMe | CH |
| 2700 | Me | H | $Q_{91}$ | OMe | OMe | CH |
| 2701 | $Q_{92}$ | H | COOMe | Me | Me | CH |
| 2702 | $Q_{92}$ | H | COOMe | Me | OMe | CH |
| 2703 | $Q_{92}$ | H | COOMe | OMe | OMe | CH |
| 2704 | $Q_{92}$ | H | COOMe | Me | OMe | N |
| 2705 | $Q_{92}$ | H | COOMe | OMe | OMe | N |
| 2706 | $Q_{92}$ | H | COOEt | Me | Me | CH |
| 2707 | $Q_{92}$ | H | COOEt | Me | OMe | CH |
| 2708 | $Q_{92}$ | H | COOEt | OMe | OMe | CH |
| 2709 | $Q_{92}$ | H | COOEt | Me | OMe | N |
| 2710 | $Q_{92}$ | H | COOEt | OMe | OMe | N |
| 2711 | $Q_{92}$ | Me | COOMe | Me | Me | CH |
| 2712 | $Q_{92}$ | Me | COOMe | Me | OMe | CH |
| 2713 | $Q_{92}$ | Me | COOMe | OMe | OMe | CH |
| 2714 | $Q_{92}$ | Me | COOMe | Me | OMe | N |
| 2715 | $Q_{92}$ | Me | COOEt | Me | OMe | CH |
| 2716 | $Q_{92}$ | Me | COOEt | OMe | OMe | CH |
| 2717 | $Q_{92}$ | Me | COOEt | Me | OMe | N |
| 2718 | $Q_{92}$ | H | CN | Me | OMe | CH |
| 2719 | $Q_{92}$ | H | CN | OMe | OMe | CH |
| 2720 | $Q_{92}$ | H | CN | Me | OMe | N |
| 2721 | $Q_{92}$ | H | H | Me | OMe | CH |
| 2722 | $Q_{92}$ | H | H | OMe | OMe | CH |
| 2723 | $Q_{92}$ | H | H | Me | OMe | N |
| 2724 | Me | H | $Q_{92}$ | Me | Me | CH |
| 2725 | Me | H | $Q_{92}$ | Me | OMe | CH |
| 2726 | Me | H | $Q_{92}$ | OMe | OMe | CH |
| 2727 | Me | H | $Q_{92}$ | Me | OMe | N |
| 2728 | Me | H | $Q_{92}$ | OMe | OMe | N |
| 2729 | $Q_{93}$ | H | COOMe | Me | Me | CH |
| 2730 | $Q_{93}$ | H | COOMe | Me | OMe | CH |
| 2731 | $Q_{93}$ | H | COOMe | OMe | OMe | CH |
| 2732 | $Q_{93}$ | H | COOEt | Me | OMe | CH |
| 2733 | $Q_{93}$ | H | COOEt | OMe | OMe | CH |
| 2734 | $Q_{93}$ | Me | COOMe | Me | Me | CH |
| 2735 | $Q_{93}$ | Me | COOMe | Me | OMe | CH |
| 2736 | $Q_{93}$ | Me | COOMe | OMe | OMe | CH |
| 2737 | $Q_{93}$ | Me | COOEt | Me | OMe | CH |
| 2738 | $Q_{93}$ | Me | COOEt | OMe | OMe | CH |
| 2739 | $Q_{93}$ | H | H | Me | OMe | CH |
| 2740 | $Q_{93}$ | H | H | OMe | OMe | CH |
| 2741 | Me | H | $Q_{93}$ | Me | OMe | CH |
| 2742 | Me | H | $Q_{93}$ | OMe | OMe | CH |
| 2743 | $Q_{94}$ | H | COOMe | Me | Me | CH |
| 2744 | $Q_{94}$ | H | COOMe | Me | OMe | CH |
| 2745 | $Q_{94}$ | H | COOMe | OMe | OMe | CH |
| 2746 | $Q_{94}$ | H | COOEt | Me | OMe | CH |
| 2747 | $Q_{94}$ | H | COOEt | OMe | OMe | CH |
| 2748 | $Q_{94}$ | Me | COOMe | Me | Me | CH |
| 2749 | $Q_{94}$ | Me | COOMe | Me | OMe | CH |
| 2750 | $Q_{94}$ | Me | COOMe | OMe | OMe | CH |
| 2751 | $Q_{94}$ | Me | COOEt | Me | OMe | CH |
| 2752 | $Q_{94}$ | Me | COOEt | OMe | OMe | CH |
| 2753 | $Q_{94}$ | H | H | Me | OMe | CH |
| 2754 | $Q_{94}$ | H | H | OMe | OMe | CH |
| 2755 | Me | H | $Q_{94}$ | Me | OMe | CH |
| 2756 | Me | H | $Q_{94}$ | OMe | OMe | CH |
| 2757 | $Q_{95}$ | H | COOMe | Me | Me | CH |
| 2758 | $Q_{95}$ | H | COOMe | Me | OMe | CH |
| 2759 | $Q_{95}$ | H | COOMe | OMe | OMe | CH |
| 2760 | $Q_{95}$ | H | COOEt | Me | OMe | CH |
| 2761 | $Q_{95}$ | H | COOEt | OMe | OMe | CH |
| 2762 | $Q_{95}$ | Me | COOMe | Me | Me | CH |
| 2763 | $Q_{95}$ | Me | COOMe | Me | OMe | CH |
| 2764 | $Q_{95}$ | Me | COOMe | OMe | OMe | CH |
| 2765 | $Q_{95}$ | Me | COOEt | Me | OMe | CH |
| 2766 | $Q_{95}$ | Me | COOEt | OMe | OMe | CH |
| 2767 | $Q_{95}$ | H | H | Me | OMe | CH |
| 2768 | $Q_{95}$ | H | H | OMe | OMe | CH |
| 2769 | Me | H | $Q_{95}$ | Me | OMe | CH |
| 2770 | Me | H | $Q_{95}$ | OMe | OMe | CH |
| 2771 | $Q_{96}$ | H | COOMe | Me | Me | CH |
| 2772 | $Q_{96}$ | H | COOMe | Me | OMe | CH |
| 2773 | $Q_{96}$ | H | COOMe | OMe | OMe | CH |
| 2774 | $Q_{96}$ | H | COOEt | Me | OMe | CH |
| 2775 | $Q_{96}$ | H | COOEt | OMe | OMe | CH |
| 2776 | $Q_{96}$ | Me | COOMe | Me | Me | CH |
| 2777 | $Q_{96}$ | Me | COOMe | Me | OMe | CH |
| 2778 | $Q_{96}$ | Me | COOMe | OMe | OMe | CH |
| 2779 | $Q_{96}$ | Me | COOEt | Me | OMe | CH |
| 2780 | $Q_{96}$ | Me | COOEt | OMe | OMe | CH |
| 2781 | $Q_{96}$ | H | H | Me | OMe | CH |
| 2782 | $Q_{96}$ | H | H | OMe | OMe | CH |
| 2783 | Me | H | $Q_{96}$ | Me | OMe | CH |
| 2784 | Me | H | $Q_{96}$ | OMe | OMe | CH |
| 2785 | $Q_{97}$ | H | COOMe | Me | Me | CH |
| 2786 | $Q_{97}$ | H | COOMe | Me | OMe | CH |
| 2787 | $Q_{97}$ | H | COOMe | OMe | OMe | CH |
| 2788 | $Q_{97}$ | H | COOEt | Me | OMe | CH |
| 2789 | $Q_{97}$ | H | COOEt | OMe | OMe | CH |
| 2790 | $Q_{97}$ | Me | COOMe | Me | Me | CH |
| 2791 | $Q_{97}$ | Me | COOMe | Me | OMe | CH |
| 2792 | $Q_{97}$ | Me | COOMe | OMe | OMe | CH |
| 2793 | $Q_{97}$ | Me | COOEt | Me | OMe | CH |
| 2794 | $Q_{97}$ | Me | COOEt | OMe | OMe | CH |
| 2795 | $Q_{97}$ | H | H | Me | OMe | CH |
| 2796 | $Q_{97}$ | H | H | OMe | OMe | CH |
| 2797 | Me | H | $Q_{97}$ | Me | OMe | CH |
| 2798 | Me | H | $Q_{97}$ | OMe | OMe | CH |
| 2799 | $Q_{98}$ | H | COOMe | Me | Me | CH |
| 2800 | $Q_{98}$ | H | COOMe | Me | OMe | CH |
| 2801 | $Q_{98}$ | H | COOMe | OMe | OMe | CH |
| 2802 | $Q_{98}$ | H | COOMe | Me | OMe | N |
| 2803 | $Q_{98}$ | H | COOMe | OMe | OMe | N |
| 2804 | $Q_{98}$ | H | COOEt | Me | Me | CH |
| 2805 | $Q_{98}$ | H | COOEt | Me | OMe | CH |
| 2806 | $Q_{98}$ | H | COOEt | OMe | OMe | CH |
| 2807 | $Q_{98}$ | H | COOEt | Me | OMe | N |
| 2808 | $Q_{98}$ | H | COOEt | OMe | OMe | N |
| 2809 | $Q_{98}$ | Me | COOMe | Me | OMe | CH |
| 2810 | $Q_{98}$ | Me | COOMe | OMe | OMe | CH |
| 2811 | $Q_{98}$ | Me | COOMe | Me | OMe | N |
| 2812 | $Q_{98}$ | Me | COOEt | Me | OMe | CH |
| 2813 | $Q_{98}$ | Me | COOEt | OMe | OMe | CH |
| 2814 | $Q_{98}$ | Me | COOEt | Me | OMe | N |
| 2815 | $Q_{98}$ | H | CN | Me | OMe | CH |

TABLE 1-continued

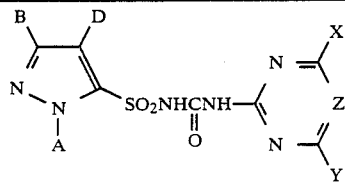

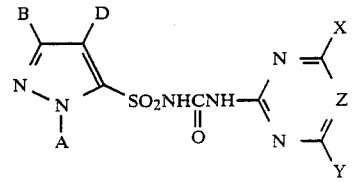

| No. | A | B | D | X | Y | Z |
|---|---|---|---|---|---|---|
| 2816 | Q98 | H | CN | OMe | OMe | CH |
| 2817 | Q98 | H | CN | Me | OMe | N |
| 2818 | Q98 | H | H | Me | OMe | CH |
| 2819 | Q98 | H | H | OMe | OMe | CH |
| 2820 | Q98 | H | H | Me | OMe | N |
| 2821 | Me | H | Q98 | Me | Me | CH |
| 2822 | Me | H | Q98 | Me | OMe | CH |
| 2823 | Me | H | Q98 | OMe | OMe | CH |
| 2824 | Me | H | Q98 | Me | OMe | N |
| 2825 | Me | H | Q98 | OMe | OMe | N |
| 2826 | Q99 | H | COOMe | Me | Me | CH |
| 2827 | Q99 | H | COOMe | Me | OMe | CH |
| 2828 | Q99 | H | COOMe | OMe | OMe | CH |
| 2829 | Q99 | H | COOEt | Me | OMe | CH |
| 2830 | Q99 | H | COOEt | OMe | OMe | CH |
| 2831 | Q99 | Me | COOMe | Me | Me | CH |
| 2832 | Q99 | Me | COOMe | Me | OMe | CH |
| 2833 | Q99 | Me | COOMe | OMe | OMe | CH |
| 2834 | Q99 | Me | COOEt | Me | OMe | CH |
| 2835 | Q99 | Me | COOEt | OMe | OMe | CH |
| 2836 | Q99 | H | H | Me | OMe | CH |
| 2837 | Q99 | H | H | OMe | OMe | CH |
| 2838 | Me | H | Q99 | Me | OMe | CH |
| 2839 | Me | H | Q99 | OMe | OMe | CH |
| 2840 | Q100 | H | COOMe | Me | Me | CH |
| 2841 | Q100 | H | COOMe | Me | OMe | CH |
| 2842 | Q100 | H | COOMe | OMe | OMe | CH |
| 2843 | Q100 | H | COOMe | Me | OMe | N |
| 2844 | Q100 | H | COOMe | OMe | OMe | N |
| 2845 | Q100 | H | COOEt | Me | Me | CH |
| 2846 | Q100 | H | COOEt | Me | OMe | CH |
| 2847 | Q100 | H | COOEt | OMe | OMe | CH |
| 2848 | Q100 | H | COOEt | Me | OMe | N |
| 2849 | Q100 | H | COOEt | OMe | OMe | N |
| 2850 | Q100 | Me | COOMe | Me | OMe | CH |
| 2851 | Q100 | Me | COOMe | OMe | OMe | CH |
| 2852 | Q100 | Me | COOMe | Me | OMe | N |
| 2853 | Q100 | Me | COOEt | Me | OMe | CH |
| 2854 | Q100 | Me | COOEt | OMe | OMe | CH |
| 2855 | Q100 | Me | COOEt | Me | OMe | N |
| 2856 | Q100 | H | CN | Me | OMe | CH |
| 2857 | Q100 | H | CN | OMe | OMe | CH |
| 2858 | Q100 | H | CN | Me | OMe | N |
| 2859 | Q100 | H | H | Me | OMe | CH |
| 2860 | Q100 | H | H | OMe | OMe | CH |
| 2861 | Q100 | H | H | Me | OMe | N |
| 2862 | Me | H | Q100 | Me | Me | CH |
| 2863 | Me | H | Q100 | Me | OMe | CH |
| 2864 | Me | H | Q100 | OMe | OMe | CH |
| 2865 | Me | H | Q100 | Me | OMe | N |
| 2866 | Me | H | Q100 | OMe | OMe | N |
| 2867 | Q101 | H | COOMe | Me | Me | CH |
| 2868 | Q101 | H | COOMe | Me | OMe | CH |
| 2869 | Q101 | H | COOMe | OMe | OMe | CH |
| 2870 | Q101 | H | COOEt | Me | OMe | CH |
| 2871 | Q101 | H | COOEt | OMe | OMe | CH |
| 2872 | Q101 | Me | COOMe | Me | Me | CH |
| 2873 | Q101 | Me | COOMe | Me | OMe | CH |
| 2874 | Q101 | Me | COOMe | OMe | OMe | CH |
| 2875 | Q101 | Me | COOEt | Me | OMe | CH |
| 2876 | Q101 | Me | COOEt | OMe | OMe | CH |
| 2877 | Q101 | H | H | Me | OMe | CH |
| 2878 | Q101 | H | H | OMe | OMe | CH |
| 2879 | Me | H | Q101 | Me | OMe | CH |
| 2880 | Me | H | Q101 | OMe | OMe | CH |
| 2881 | Q102 | H | COOMe | Me | Me | CH |
| 2882 | Q102 | H | COOMe | Me | OMe | CH |
| 2883 | Q102 | H | COOMe | OMe | OMe | CH |
| 2884 | Q102 | H | COOEt | Me | OMe | CH |
| 2885 | Q102 | H | COOEt | OMe | OMe | CH |
| 2886 | Q102 | Me | COOMe | Me | Me | CH |
| 2887 | Q102 | Me | COOMe | Me | OMe | CH |
| 2888 | Q102 | Me | COOMe | OMe | OMe | CH |
| 2889 | Q102 | Me | COOEt | Me | OMe | CH |
| 2890 | Q102 | Me | COOEt | OMe | OMe | CH |
| 2891 | Q102 | H | H | Me | OMe | CH |
| 2892 | Q102 | H | H | OMe | OMe | CH |
| 2893 | Me | H | Q102 | Me | OMe | CH |
| 2894 | Me | H | Q102 | OMe | OMe | CH |
| 2895 | Q103 | H | COOMe | Me | Me | CH |
| 2896 | Q103 | H | COOMe | Me | OMe | CH |
| 2897 | Q103 | H | COOMe | OMe | OMe | CH |
| 2898 | Q103 | H | COOEt | Me | OMe | CH |
| 2899 | Q103 | H | COOEt | OMe | OMe | CH |
| 2900 | Q103 | Me | COOMe | Me | Me | CH |
| 2901 | Q103 | Me | COOMe | Me | OMe | CH |
| 2902 | Q103 | Me | COOMe | OMe | OMe | CH |
| 2903 | Q103 | Me | COOEt | Me | OMe | CH |
| 2904 | Q103 | Me | COOEt | OMe | OMe | CH |
| 2905 | Q103 | H | H | Me | OMe | CH |
| 2906 | Q103 | H | H | OMe | OMe | CH |
| 2907 | Me | H | Q103 | Me | OMe | CH |
| 2908 | Me | H | Q103 | OMe | OMe | CH |
| 2909 | Q104 | H | COOMe | Me | Me | CH |
| 2910 | Q104 | H | COOMe | Me | OMe | CH |
| 2911 | Q104 | H | COOMe | OMe | OMe | CH |
| 2912 | Q104 | H | COOEt | Me | OMe | CH |
| 2913 | Q104 | H | COOEt | OMe | OMe | CH |
| 2914 | Q104 | Me | COOMe | Me | Me | CH |
| 2915 | Q104 | Me | COOMe | Me | OMe | CH |
| 2916 | Q104 | Me | COOMe | OMe | OMe | CH |
| 2917 | Q104 | Me | COOEt | Me | OMe | CH |
| 2918 | Q104 | Me | COOEt | OMe | OMe | CH |
| 2919 | Q104 | H | H | Me | OMe | CH |
| 2920 | Q104 | H | H | OMe | OMe | CH |
| 2921 | Me | H | Q104 | Me | OMe | CH |
| 2922 | Me | H | Q104 | OMe | OMe | CH |
| 2923 | Q105 | H | COOMe | Me | Me | CH |
| 2924 | Q105 | H | COOMe | Me | OMe | CH |
| 2925 | Q105 | H | COOMe | OMe | OMe | CH |
| 2926 | Q105 | H | COOEt | Me | OMe | CH |
| 2927 | Q105 | H | COOEt | OMe | OMe | CH |
| 2928 | Q105 | Me | COOMe | Me | Me | CH |
| 2929 | Q105 | Me | COOMe | Me | OMe | CH |
| 2930 | Q105 | Me | COOMe | OMe | OMe | CH |
| 2931 | Q105 | Me | COOEt | Me | OMe | CH |
| 2932 | Q105 | Me | COOEt | OMe | OMe | CH |
| 2933 | Q105 | H | H | Me | OMe | CH |
| 2934 | Q105 | H | H | OMe | OMe | CH |
| 2935 | Me | H | Q105 | Me | OMe | CH |
| 2936 | Me | H | Q105 | OMe | OMe | CH |
| 2937 | Q106 | H | COOMe | Me | Me | CH |
| 2938 | Q106 | H | COOMe | Me | OMe | CH |
| 2939 | Q106 | H | COOMe | OMe | OMe | CH |
| 2940 | Q106 | H | COOEt | Me | OMe | CH |
| 2941 | Q106 | H | COOEt | OMe | OMe | CH |
| 2942 | Q106 | Me | COOMe | Me | Me | CH |
| 2943 | Q106 | Me | COOMe | Me | OMe | CH |
| 2944 | Q106 | Me | COOEt | OMe | OMe | CH |
| 2945 | Q106 | Me | COOEt | Me | OMe | CH |
| 2946 | Q106 | Me | COOEt | OMe | OMe | CH |
| 2947 | Q106 | H | H | Me | OMe | CH |
| 2948 | Q106 | H | H | OMe | OMe | CH |
| 2949 | Me | H | Q106 | Me | OMe | CH |
| 2950 | Me | H | Q106 | OMe | OMe | CH |
| 2951 | Q107 | H | COOMe | Me | Me | CH |
| 2952 | Q107 | H | COOMe | Me | OMe | CH |
| 2953 | Q107 | H | COOMe | OMe | OMe | CH |
| 2954 | Q107 | H | COOEt | Me | OMe | CH |
| 2955 | Q107 | H | COOEt | OMe | OMe | CH |
| 2956 | Q107 | Me | COOMe | Me | Me | CH |
| 2957 | Q107 | Me | COOMe | Me | OMe | CH |

TABLE 1-continued structure: pyrazole with B at 4-position, D at 3-position(?), N-A, SO₂NHCNH-C(=O)-N=C(X)-Z=C(Y)-N (pyrimidine)

| No. | A | B | D | X | Y | Z |
|---|---|---|---|---|---|---|
| 2958 | Q107 | Me | COOMe | OMe | OMe | CH |
| 2959 | Q107 | Me | COOEt | Me | OMe | CH |
| 2960 | Q107 | Me | COOEt | OMe | OMe | CH |
| 2961 | Q107 | H | H | Me | OMe | CH |
| 2962 | Q107 | H | H | OMe | OMe | CH |
| 2963 | Me | H | Q107 | Me | OMe | CH |
| 2964 | Me | H | Q107 | OMe | OMe | CH |
| 2965 | Q108 | H | COOMe | Me | Me | CH |
| 2966 | Q108 | H | COOMe | Me | OMe | CH |
| 2967 | Q108 | H | COOMe | OMe | OMe | CH |
| 2968 | Q108 | H | COOEt | Me | OMe | CH |
| 2969 | Q108 | H | COOEt | OMe | OMe | CH |
| 2970 | Q108 | Me | COOMe | Me | Me | CH |
| 2971 | Q108 | Me | COOMe | Me | OMe | CH |
| 2972 | Q108 | Me | COOMe | OMe | OMe | CH |
| 2973 | Q108 | Me | COOEt | Me | OMe | CH |
| 2974 | Q108 | Me | COOEt | OMe | OMe | CH |
| 2975 | Q108 | H | H | Me | OMe | CH |
| 2976 | Q108 | H | H | OMe | OMe | CH |
| 2977 | Me | H | Q108 | Me | OMe | CH |
| 2978 | Me | H | Q108 | OMe | OMe | CH |
| 2979 | Q109 | H | COOMe | Me | Me | CH |
| 2980 | Q109 | H | COOMe | Me | OMe | CH |
| 2981 | Q109 | H | COOMe | OMe | OMe | CH |
| 2982 | Q109 | H | COOEt | Me | OMe | CH |
| 2983 | Q109 | H | COOEt | OMe | OMe | CH |
| 2984 | Q109 | Me | COOMe | Me | Me | CH |
| 2985 | Q109 | Me | COOMe | Me | OMe | CH |
| 2986 | Q109 | Me | COOMe | OMe | OMe | CH |
| 2987 | Q109 | Me | COOEt | Me | OMe | CH |
| 2988 | Q109 | Me | COOEt | OMe | OMe | CH |
| 2989 | Q109 | H | H | Me | OMe | CH |
| 2990 | Q109 | H | H | OMe | OMe | CH |
| 2991 | Me | H | Q109 | Me | OMe | CH |
| 2992 | Me | H | Q109 | OMe | OMe | CH |
| 2993 | Q110 | H | COOMe | Me | Me | CH |
| 2994 | Q110 | H | COOMe | Me | OMe | CH |
| 2995 | Q110 | H | COOMe | OMe | OMe | CH |
| 2996 | Q110 | H | COOEt | Me | OMe | CH |
| 2997 | Q110 | H | COOEt | OMe | OMe | CH |
| 2998 | Q110 | Me | COOMe | Me | Me | CH |
| 2999 | Q110 | Me | COOMe | Me | OMe | CH |
| 3000 | Q110 | Me | COOMe | OMe | OMe | CH |
| 3001 | Q110 | Me | COOEt | Me | OMe | CH |
| 3002 | Q110 | Me | COOEt | OMe | OMe | CH |
| 3003 | Q110 | H | H | Me | OMe | CH |
| 3004 | Q110 | H | H | OMe | OMe | CH |
| 3005 | Me | H | Q110 | Me | OMe | CH |
| 3006 | Me | H | Q110 | OMe | OMe | CH |
| 3007 | Q111 | H | COOMe | Me | Me | CH |
| 3008 | Q111 | H | COOMe | Me | OMe | CH |
| 3009 | Q111 | H | COOMe | OMe | OMe | CH |
| 3010 | Q111 | H | COOEt | Me | OMe | CH |
| 3011 | Q111 | H | COOEt | OMe | OMe | CH |
| 3012 | Q111 | Me | COOMe | Me | Me | CH |
| 3013 | Q111 | Me | COOMe | Me | OMe | CH |
| 3014 | Q111 | Me | COOMe | OMe | OMe | CH |
| 3015 | Q111 | Me | COOEt | Me | OMe | CH |
| 3016 | Q111 | Me | COOEt | OMe | OMe | CH |
| 3017 | Q111 | H | H | Me | OMe | CH |
| 3018 | Q111 | H | H | OMe | OMe | CH |
| 3019 | Me | H | Q111 | Me | OMe | CH |
| 3020 | Me | H | Q111 | OMe | OMe | CH |
| 3021 | Q112 | H | COOMe | Me | Me | CH |
| 3022 | Q112 | H | COOMe | Me | OMe | CH |
| 3023 | Q112 | H | COOMe | OMe | OMe | CH |
| 3024 | Q112 | H | COOEt | Me | OMe | CH |
| 3025 | Q112 | H | COOEt | OMe | OMe | CH |
| 3026 | Q112 | Me | COOMe | Me | Me | CH |
| 3027 | Q112 | Me | COOMe | Me | OMe | CH |
| 3028 | Q112 | Me | COOMe | OMe | OMe | CH |
| 3029 | Q112 | Me | COOEt | Me | OMe | CH |
| 3030 | Q112 | Me | COOEt | OMe | OMe | CH |
| 3031 | Q112 | H | H | Me | OMe | CH |
| 3032 | Q112 | H | H | OMe | OMe | CH |
| 3033 | Me | H | Q112 | Me | OMe | CH |
| 3034 | Me | H | Q112 | OMe | OMe | CH |
| 3035 | Q113 | H | COOMe | Me | Me | CH |
| 3036 | Q113 | H | COOMe | Me | OMe | CH |
| 3037 | Q113 | H | COOMe | OMe | OMe | CH |
| 3038 | Q113 | H | COOEt | Me | OMe | CH |
| 3039 | Q113 | H | COOEt | OMe | OMe | CH |
| 3040 | Q113 | Me | COOMe | Me | Me | CH |
| 3041 | Q113 | Me | COOMe | Me | OMe | CH |
| 3042 | Q113 | Me | COOMe | OMe | OMe | CH |
| 3043 | Q113 | Me | COOEt | Me | OMe | CH |
| 3044 | Q113 | Me | COOEt | OMe | OMe | CH |
| 3045 | Q113 | H | H | Me | OMe | CH |
| 3046 | Q113 | H | H | OMe | OMe | CH |
| 3047 | Me | H | Q113 | Me | OMe | CH |
| 3048 | Me | H | Q113 | OMe | OMe | CH |
| 3049 | Q114 | H | COOMe | Me | Me | CH |
| 3050 | Q114 | H | COOMe | Me | OMe | CH |
| 3051 | Q114 | H | COOMe | OMe | OMe | CH |
| 3052 | Q114 | H | COOEt | Me | OMe | CH |
| 3053 | Q114 | H | COOEt | OMe | OMe | CH |
| 3054 | Q114 | Me | COOMe | Me | Me | CH |
| 3055 | Q114 | Me | COOMe | Me | OMe | CH |
| 3056 | Q114 | Me | COOMe | OMe | OMe | CH |
| 3057 | Q114 | Me | COOEt | Me | OMe | CH |
| 3058 | Q114 | Me | COOEt | OMe | OMe | CH |
| 3059 | Q114 | H | H | Me | OMe | CH |
| 3060 | Q114 | H | H | OMe | OMe | CH |
| 3061 | Me | H | Q114 | Me | OMe | CH |
| 3062 | Me | H | Q114 | OMe | OMe | CH |
| 3063 | Q115 | H | COOMe | Me | Me | CH |
| 3064 | Q115 | H | COOMe | Me | OMe | CH |
| 3065 | Q115 | H | COOMe | OMe | OMe | CH |
| 3066 | Q115 | H | COOEt | Me | OMe | CH |
| 3067 | Q115 | H | COOEt | OMe | OMe | CH |
| 3068 | Q115 | Me | COOMe | Me | Me | CH |
| 3069 | Q115 | Me | COOMe | Me | OMe | CH |
| 3070 | Q115 | Me | COOMe | OMe | OMe | CH |
| 3071 | Q115 | Me | COOEt | Me | OMe | CH |
| 3072 | Q115 | Me | COOEt | OMe | OMe | CH |
| 3073 | Q115 | H | H | Me | OMe | CH |
| 3074 | Q115 | H | H | OMe | OMe | CH |
| 3075 | Me | H | Q115 | Me | OMe | CH |
| 3076 | Me | H | Q115 | OMe | OMe | CH |
| 3077 | Q116 | H | COOMe | Me | Me | CH |
| 3078 | Q116 | H | COOMe | Me | OMe | CH |
| 3079 | Q116 | H | COOMe | OMe | OMe | CH |
| 3080 | Q116 | H | COOEt | Me | OMe | CH |
| 3081 | Q116 | H | COOEt | OMe | OMe | CH |
| 3082 | Q116 | Me | COOMe | Me | Me | CH |
| 3083 | Q116 | Me | COOMe | Me | OMe | CH |
| 3084 | Q116 | Me | COOMe | OMe | OMe | CH |
| 3085 | Q116 | Me | COOEt | Me | OMe | CH |
| 3086 | Q116 | Me | COOEt | OMe | OMe | CH |
| 3087 | Q116 | H | H | Me | OMe | CH |
| 3088 | Q116 | H | H | OMe | OMe | CH |
| 3089 | Me | H | Q116 | Me | OMe | CH |
| 3090 | Me | H | Q116 | OMe | OMe | CH |
| 3091 | Q117 | H | COOMe | Me | Me | CH |
| 3092 | Q117 | H | COOMe | Me | OMe | CH |
| 3093 | Q117 | H | COOMe | OMe | OMe | CH |
| 3094 | Q117 | H | COOEt | Me | OMe | CH |
| 3095 | Q117 | H | COOEt | OMe | OMe | CH |
| 3096 | Q117 | Me | COOMe | Me | Me | CH |
| 3097 | Q117 | Me | COOMe | Me | OMe | CH |
| 3098 | Q117 | Me | COOMe | OMe | OMe | CH |
| 3099 | Q117 | Me | COOEt | Me | OMe | CH |

TABLE 1-continued

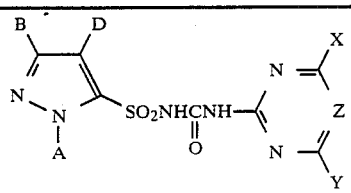

| No. | A | B | D | X | Y | Z |
|---|---|---|---|---|---|---|
| 3100 | $Q_{117}$ | Me | COOEt | OMe | OMe | CH |
| 3101 | $Q_{117}$ | H | H | Me | OMe | CH |
| 3102 | $Q_{117}$ | H | H | OMe | OMe | CH |
| 3103 | Me | H | $Q_{117}$ | Me | OMe | CH |
| 3104 | Me | H | $Q_{117}$ | OMe | OMe | CH |
| 3105 | $Q_{118}$ | H | COOMe | Me | Me | CH |
| 3106 | $Q_{118}$ | H | COOMe | Me | OMe | CH |
| 3107 | $Q_{118}$ | H | COOMe | OMe | OMe | CH |
| 3108 | $Q_{118}$ | H | COOEt | Me | OMe | CH |
| 3109 | $Q_{118}$ | H | COOEt | OMe | OMe | CH |
| 3110 | $Q_{118}$ | Me | COOMe | Me | Me | CH |
| 3111 | $Q_{118}$ | Me | COOMe | Me | OMe | CH |
| 3112 | $Q_{118}$ | Me | COOMe | OMe | OMe | CH |
| 3113 | $Q_{118}$ | Me | COOEt | Me | OMe | CH |
| 3114 | $Q_{118}$ | Me | COOEt | OMe | OMe | CH |
| 3115 | $Q_{118}$ | H | H | Me | OMe | CH |
| 3116 | $Q_{118}$ | H | H | OMe | OMe | CH |
| 3117 | Me | H | $Q_{118}$ | Me | OMe | CH |
| 3118 | Me | H | $Q_{118}$ | OMe | OMe | CH |
| 3119 | $Q_{119}$ | H | COOMe | Me | Me | CH |
| 3120 | $Q_{119}$ | H | COOMe | Me | OMe | CH |
| 3121 | $Q_{119}$ | H | COOMe | OMe | OMe | CH |
| 3122 | $Q_{119}$ | H | COOEt | Me | OMe | CH |
| 3123 | $Q_{119}$ | H | COOEt | OMe | OMe | CH |
| 3124 | $Q_{119}$ | Me | COOMe | Me | Me | CH |
| 3125 | $Q_{119}$ | Me | COOMe | Me | OMe | CH |
| 3126 | $Q_{119}$ | Me | COOMe | OMe | OMe | CH |
| 3127 | $Q_{119}$ | Me | COOEt | Me | OMe | CH |
| 3128 | $Q_{119}$ | Me | COOEt | OMe | OMe | CH |
| 3129 | $Q_{119}$ | H | H | Me | OMe | CH |
| 3130 | $Q_{119}$ | H | H | OMe | OMe | CH |
| 3131 | Me | H | $Q_{119}$ | Me | OMe | CH |
| 3132 | Me | H | $Q_{119}$ | OMe | OMe | CH |
| 3133 | $Q_{120}$ | H | COOMe | Me | Me | CH |
| 3134 | $Q_{120}$ | H | COOMe | Me | OMe | CH |
| 3135 | $Q_{120}$ | H | COOMe | OMe | OMe | CH |
| 3136 | $Q_{120}$ | H | COOEt | Me | OMe | CH |
| 3137 | $Q_{120}$ | H | COOEt | OMe | OMe | CH |
| 3138 | $Q_{120}$ | Me | COOMe | Me | Me | CH |
| 3139 | $Q_{120}$ | Me | COOMe | Me | OMe | CH |
| 3140 | $Q_{120}$ | Me | COOMe | OMe | OMe | CH |
| 3141 | $Q_{120}$ | Me | COOEt | Me | OMe | CH |
| 3142 | $Q_{120}$ | Me | COOEt | OMe | OMe | CH |
| 3143 | Me | H | $Q_{120}$ | Me | OMe | CH |
| 3144 | Me | H | $Q_{120}$ | OMe | OMe | CH |
| 3145 | Me | Me | $Q_{120}$ | Me | OMe | CH |
| 3146 | Me | Me | $Q_{120}$ | OMe | OMe | CH |
| 3147 | $Q_{121}$ | H | COOMe | Me | Me | CH |
| 3148 | $Q_{121}$ | H | COOMe | Me | OMe | CH |
| 3149 | $Q_{121}$ | H | COOMe | OMe | OMe | CH |
| 3150 | $Q_{121}$ | H | COOEt | Me | OMe | CH |
| 3151 | $Q_{121}$ | H | COOEt | OMe | OMe | CH |
| 3152 | $Q_{121}$ | Me | COOMe | Me | Me | CH |
| 3153 | $Q_{121}$ | Me | COOMe | Me | OMe | CH |
| 3154 | $Q_{121}$ | Me | COOMe | OMe | OMe | CH |
| 3155 | $Q_{121}$ | Me | COOEt | Me | OMe | CH |
| 3156 | $Q_{121}$ | Me | COOEt | OMe | OMe | CH |
| 3157 | Me | H | $Q_{121}$ | Me | OMe | CH |
| 3158 | Me | H | $Q_{121}$ | OMe | OMe | CH |
| 3159 | Me | Me | $Q_{121}$ | Me | OMe | CH |
| 3160 | Me | Me | $Q_{121}$ | OMe | OMe | CH |
| 3161 | $Q_{122}$ | H | COOMe | Me | Me | CH |
| 3162 | $Q_{122}$ | H | COOMe | Me | OMe | CH |
| 3163 | $Q_{122}$ | H | COOMe | OMe | OMe | CH |
| 3164 | $Q_{122}$ | H | COOEt | Me | OMe | CH |
| 3165 | $Q_{122}$ | H | COOEt | OMe | OMe | CH |
| 3166 | $Q_{122}$ | Me | COOMe | Me | Me | CH |
| 3167 | $Q_{122}$ | Me | COOMe | Me | OMe | CH |
| 3168 | $Q_{122}$ | Me | COOMe | OMe | OMe | CH |
| 3169 | $Q_{122}$ | Me | COOEt | Me | OMe | CH |
| 3170 | $Q_{122}$ | Me | COOEt | OMe | OMe | CH |

TABLE 1-continued

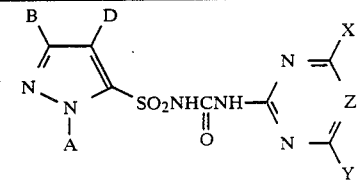

| No. | A | B | D | X | Y | Z |
|---|---|---|---|---|---|---|
| 3171 | Me | H | $Q_{122}$ | Me | OMe | CH |
| 3172 | Me | H | $Q_{122}$ | OMe | OMe | CH |
| 3173 | Me | Me | $Q_{122}$ | Me | OMe | CH |
| 3174 | Me | Me | $Q_{122}$ | OMe | OMe | CH |
| 3175 | $Q_{123}$ | H | COOMe | Me | Me | CH |
| 3176 | $Q_{123}$ | H | COOMe | Me | OMe | CH |
| 3177 | $Q_{123}$ | H | COOMe | OMe | OMe | CH |
| 3178 | $Q_{123}$ | H | COOEt | Me | OMe | CH |
| 3179 | $Q_{123}$ | H | COOEt | OMe | OMe | CH |
| 3180 | $Q_{123}$ | Me | COOMe | Me | Me | CH |
| 3181 | $Q_{123}$ | Me | COOMe | Me | OMe | CH |
| 3182 | $Q_{123}$ | Me | COOMe | OMe | OMe | CH |
| 3183 | $Q_{123}$ | Me | COOEt | Me | OMe | CH |
| 3184 | $Q_{123}$ | Me | COOEt | OMe | OMe | CH |
| 3185 | Me | H | $Q_{123}$ | Me | OMe | CH |
| 3186 | Me | H | $Q_{123}$ | OMe | OMe | CH |
| 3187 | Me | Me | $Q_{123}$ | Me | OMe | CH |
| 3188 | Me | Me | $Q_{123}$ | OMe | OMe | CH |
| 3189 | $Q_{124}$ | H | COOMe | Me | Me | CH |
| 3190 | $Q_{124}$ | H | COOMe | Me | OMe | CH |
| 3191 | $Q_{124}$ | H | COOMe | OMe | OMe | CH |
| 3192 | $Q_{124}$ | H | COOEt | Me | OMe | CH |
| 3193 | $Q_{124}$ | H | COOEt | OMe | OMe | CH |
| 3194 | $Q_{124}$ | Me | COOMe | Me | Me | CH |
| 3195 | $Q_{124}$ | Me | COOMe | Me | OMe | CH |
| 3196 | $Q_{124}$ | Me | COOMe | OMe | OMe | CH |
| 3197 | $Q_{124}$ | Me | COOEt | Me | OMe | CH |
| 3198 | $Q_{124}$ | Me | COOEt | OMe | OMe | CH |
| 3199 | Me | H | $Q_{124}$ | Me | OMe | CH |
| 3200 | Me | H | $Q_{124}$ | OMe | OMe | CH |
| 3201 | Me | Me | $Q_{124}$ | Me | OMe | CH |
| 3202 | Me | Me | $Q_{124}$ | OMe | OMe | CH |
| 3203 | $Q_{125}$ | H | COOMe | Me | Me | CH |
| 3204 | $Q_{125}$ | H | COOMe | Me | OMe | CH |
| 3205 | $Q_{125}$ | H | COOMe | OMe | OMe | CH |
| 3206 | $Q_{125}$ | H | COOEt | Me | OMe | CH |
| 3207 | $Q_{125}$ | H | COOEt | OMe | OMe | CH |
| 3208 | $Q_{125}$ | Me | COOMe | Me | Me | CH |
| 3209 | $Q_{125}$ | Me | COOMe | Me | OMe | CH |
| 3210 | $Q_{125}$ | Me | COOMe | OMe | OMe | CH |
| 3211 | $Q_{125}$ | Me | COOEt | Me | OMe | CH |
| 3212 | $Q_{125}$ | Me | COOEt | OMe | OMe | CH |
| 3213 | Me | H | $Q_{125}$ | Me | OMe | CH |
| 3214 | Me | H | $Q_{125}$ | OMe | OMe | CH |
| 3215 | Me | Me | $Q_{125}$ | Me | OMe | CH |
| 3216 | Me | Me | $Q_{125}$ | OMe | OMe | CH |
| 3217 | $Q_{126}$ | H | COOMe | Me | Me | CH |
| 3218 | $Q_{126}$ | H | COOMe | Me | OMe | CH |
| 3219 | $Q_{126}$ | H | COOMe | OMe | OMe | CH |
| 3220 | $Q_{126}$ | H | COOEt | Me | OMe | CH |
| 3221 | $Q_{126}$ | H | COOEt | OMe | OMe | CH |
| 3222 | $Q_{126}$ | Me | COOMe | Me | Me | CH |
| 3223 | $Q_{126}$ | Me | COOMe | Me | OMe | CH |
| 3224 | $Q_{126}$ | Me | COOMe | OMe | OMe | CH |
| 3225 | $Q_{126}$ | Me | COOEt | Me | OMe | CH |
| 3226 | $Q_{126}$ | Me | COOEt | OMe | OMe | CH |
| 3227 | Me | H | $Q_{126}$ | Me | OMe | CH |
| 3228 | Me | H | $Q_{126}$ | OMe | OMe | CH |
| 3229 | Me | Me | $Q_{126}$ | Me | OMe | CH |
| 3230 | Me | Me | $Q_{126}$ | OMe | OMe | CH |
| 3231 | $Q_{127}$ | H | COOMe | Me | Me | CH |
| 3232 | $Q_{127}$ | H | COOMe | Me | OMe | CH |
| 3233 | $Q_{127}$ | H | COOMe | OMe | OMe | CH |
| 3234 | $Q_{127}$ | H | COOEt | Me | OMe | CH |
| 3235 | $Q_{127}$ | H | COOEt | OMe | OMe | CH |
| 3236 | $Q_{127}$ | Me | COOMe | Me | Me | CH |
| 3237 | $Q_{127}$ | Me | COOMe | Me | OMe | CH |
| 3238 | $Q_{127}$ | Me | COOMe | OMe | OMe | CH |
| 3239 | $Q_{127}$ | Me | COOEt | Me | OMe | CH |
| 3240 | $Q_{127}$ | Me | COOEt | OMe | OMe | CH |
| 3241 | Me | H | $Q_{127}$ | Me | OMe | CH |

TABLE 1-continued

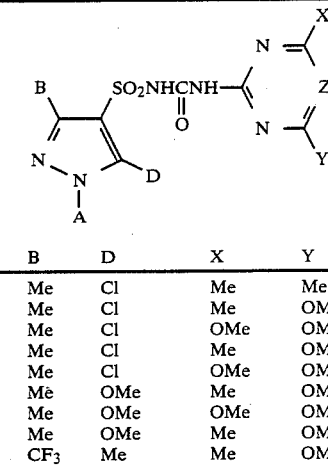

| No. | A | B | D | X | Y | Z |
|---|---|---|---|---|---|---|
| 3242 | Me | H | $Q_{127}$ | OMe | OMe | CH |
| 3243 | Me | Me | $Q_{127}$ | Me | OMe | CH |
| 3244 | Me | Me | $Q_{127}$ | OMe | OMe | CH |
| 3245 | $Q_{128}$ | H | COOMe | Me | Me | CH |
| 3246 | $Q_{128}$ | H | COOMe | Me | OMe | CH |
| 3247 | $Q_{127}$ | H | COOMe | OMe | OMe | CH |
| 3248 | $Q_{128}$ | H | COOEt | Me | OMe | CH |
| 3249 | $Q_{128}$ | H | COOEt | OMe | OMe | CH |
| 3250 | $Q_{128}$ | Me | COOMe | Me | Me | CH |
| 3251 | $Q_{128}$ | Me | COOMe | Me | OMe | CH |
| 3252 | $Q_{128}$ | Me | COOMe | OMe | OMe | CH |
| 3253 | $Q_{128}$ | Me | COOEt | Me | OMe | CH |
| 3254 | $Q_{128}$ | Me | COOEt | OMe | OMe | CH |
| 3255 | Me | H | $Q_{128}$ | Me | OMe | CH |
| 3256 | Me | H | $Q_{128}$ | OMe | OMe | CH |
| 3257 | Me | Me | $Q_{128}$ | Me | OMe | CH |
| 3258 | Me | Me | $Q_{128}$ | OMe | OMe | CH |
| 3259 | $Q_{129}$ | H | COOMe | Me | Me | CH |
| 3260 | $Q_{129}$ | H | COOMe | Me | OMe | CH |
| 3261 | $Q_{129}$ | H | COOMe | OMe | OMe | CH |
| 3262 | $Q_{129}$ | H | COOEt | Me | OMe | CH |
| 3263 | $Q_{129}$ | H | COOEt | OMe | OMe | CH |
| 3264 | $Q_{129}$ | Me | COOMe | Me | Me | CH |
| 3265 | $Q_{129}$ | Me | COOMe | Me | OMe | CH |
| 3266 | $Q_{129}$ | Me | COOMe | OMe | OMe | CH |
| 3267 | $Q_{129}$ | Me | COOEt | Me | OMe | CH |
| 3268 | $Q_{129}$ | Me | COOEt | OMe | OMe | CH |
| 3269 | Me | H | $Q_{129}$ | Me | OMe | CH |
| 3270 | Me | H | $Q_{129}$ | OMe | OMe | CH |
| 3271 | Me | Me | $Q_{129}$ | Me | OMe | CH |
| 3272 | Me | Me | $Q_{129}$ | OMe | OMe | CH |
| 3273 | $Q_{130}$ | H | COOMe | Me | Me | CH |
| 3274 | $Q_{130}$ | H | COOMe | Me | OMe | CH |
| 3275 | $Q_{130}$ | H | COOMe | OMe | OMe | CH |
| 3276 | $Q_{130}$ | H | COOEt | Me | OMe | CH |
| 3277 | $Q_{130}$ | H | COOEt | OMe | OMe | CH |
| 3278 | $Q_{130}$ | Me | COOMe | Me | Me | CH |
| 3279 | $Q_{130}$ | Me | COOMe | Me | OMe | CH |
| 3280 | $Q_{130}$ | Me | COOMe | OMe | OMe | CH |
| 3281 | $Q_{130}$ | Me | COOEt | Me | OMe | CH |
| 3282 | $Q_{130}$ | Me | COOEt | OMe | OMe | CH |
| 3283 | Me | H | $Q_{130}$ | Me | OMe | CH |
| 3284 | Me | H | $Q_{130}$ | OMe | OMe | CH |
| 3285 | Me | Me | $Q_{130}$ | Me | OMe | CH |
| 3286 | Me | Me | $Q_{130}$ | OMe | OMe | CH |
| 3287 | $Q_{131}$ | H | COOMe | Me | Me | CH |
| 3288 | $Q_{131}$ | H | COOMe | Me | OMe | CH |
| 3289 | $Q_{131}$ | H | COOMe | OMe | OMe | CH |
| 3290 | $Q_{131}$ | H | COOEt | Me | OMe | CH |
| 3291 | $Q_{131}$ | H | COOEt | OMe | OMe | CH |
| 3292 | $Q_{131}$ | Me | COOMe | Me | Me | CH |
| 3293 | $Q_{131}$ | Me | COOMe | Me | OMe | CH |
| 3294 | $Q_{131}$ | Me | COOMe | OMe | OMe | CH |
| 3295 | $Q_{131}$ | Me | COOEt | Me | OMe | CH |
| 3296 | $Q_{131}$ | Me | COOEt | OMe | OMe | CH |
| 3297 | Me | H | $Q_{131}$ | Me | OMe | CH |
| 3298 | Me | H | $Q_{131}$ | OMe | OMe | CH |
| 3299 | Me | Me | $Q_{131}$ | Me | OMe | CH |
| 3300 | Me | Me | $Q_{131}$ | OMe | OMe | CH |
| 3301 | $Q_{132}$ | H | COOMe | Me | Me | CH |
| 3302 | $Q_{132}$ | H | COOMe | Me | OMe | CH |
| 3303 | $Q_{132}$ | H | COOMe | OMe | OMe | CH |
| 3304 | $Q_{132}$ | H | COOEt | Me | OMe | CH |
| 3305 | $Q_{132}$ | H | COOEt | OMe | OMe | CH |
| 3306 | $Q_{132}$ | Me | COOMe | Me | Me | CH |
| 3307 | $Q_{132}$ | Me | COOMe | Me | OMe | CH |
| 3308 | $Q_{132}$ | Me | COOMe | OMe | OMe | CH |
| 3309 | $Q_{132}$ | Me | COOEt | Me | OMe | CH |
| 3310 | $Q_{132}$ | Me | COOEt | OMe | OMe | CH |
| 3311 | Me | H | $Q_{132}$ | Me | OMe | CH |
| 3312 | Me | H | $Q_{132}$ | OMe | OMe | CH |
| 3313 | Me | Me | $Q_{132}$ | Me | OMe | CH |
| 3314 | Me | Me | $Q_{132}$ | OMe | OMe | CH |

TABLE 2

| No. | A | B | D | X | Y | Z |
|---|---|---|---|---|---|---|
| 1006 | $Q_1$ | Me | Cl | Me | Me | CH |
| 1007 | $Q_1$ | Me | Cl | Me | OMe | CH |
| 1008 | $Q_1$ | Me | Cl | OMe | OMe | CH |
| 1009 | $Q_1$ | Me | Cl | Me | OMe | N |
| 1010 | $Q_1$ | Me | Cl | OMe | OMe | N |
| 1011 | $Q_1$ | Me | OMe | Me | OMe | CH |
| 1012 | $Q_1$ | Me | OMe | OMe | OMe | CH |
| 1013 | $Q_1$ | Me | OMe | Me | OMe | N |
| 1014 | $Q_1$ | $CF_3$ | Me | Me | Me | CH |
| 1015 | $Q_1$ | $CF_3$ | Me | Me | OMe | CH |
| 1016 | $Q_1$ | $CF_3$ | Me | Me | OMe | N |
| 1017 | $Q_1$ | Me | COOMe | Me | Me | CH |
| 1018 | $Q_1$ | Me | COOMe | Me | OMe | CH |
| 1019 | $Q_1$ | Me | COOMe | OMe | OMe | CH |
| 1020 | $Q_1$ | Me | COOMe | Me | OMe | N |
| 1021 | $Q_1$ | Me | COOMe | OMe | OMe | N |
| 1022 | $Q_1$ | Me | COOMe | Me | $OCHF_2$ | CH |
| 1023 | $Q_1$ | Me | COOMe | Me |  | CH |
| 1024 | $Q_1$ | Me | $SO_2Me$ | Me | OMe | CH |
| 1025 | $Q_1$ | Me | $SO_2Me$ | OMe | OMe | CH |
| 1026 | $Q_1$ | Me | $SO_2Me$ | Me | OMe | N |
| 1027 | H | $Q_1$ | Me | Me | OMe | CH |
| 1028 | H | $Q_1$ | Me | OMe | OMe | CH |
| 1029 | H | $Q_1$ | Me | Me | OMe | N |
| 1030 | Me | $Q_1$ | Me | Me | Me | CH |
| 1031 | Me | $Q_1$ | Me | Me | OMe | CH |
| 1032 | Me | $Q_1$ | Me | Me | OMe | N |
| 1033 | Me | $Q_1$ | Cl | Me | OMe | CH |
| 1034 | Me | $Q_1$ | Cl | OMe | OMe | CH |
| 1035 | Me | $Q_1$ | Cl | Me | OMe | N |
| 1036 | Me | $Q_1$ | COOMe | Me | OMe | CH |
| 1037 | Me | $Q_1$ | COOMe | OMe | OMe | CH |
| 1038 | Me | $Q_1$ | COOMe | Me | OMe | N |
| 1039 | Me | $Q_1$ | Ph | Me | OMe | CH |
| 1040 | Me | $Q_1$ | Ph | OMe | OMe | CH |
| 1041 | Me | $Q_1$ | Ph | Me | OMe | N |
| 1042 | Me | Me | $Q_1$ | Me | OMe | CH |
| 1043 | Me | Me | $Q_1$ | OMe | OMe | CH |
| 1044 | Me | Me | $Q_1$ | Me | OMe | N |
| 1045 | $Q_2$ | Me | COOMe | Me | Me | CH |
| 1046 | $Q_2$ | Me | COOMe | Me | OMe | CH |
| 1047 | $Q_2$ | Me | COOMe | OMe | OMe | CH |
| 1048 | $Q_2$ | Me | COOMe | Me | OMe | N |
| 1049 | $Q_2$ | Me | COOMe | OMe | OMe | N |
| 1050 | Me | $Q_2$ | Me | Me | OMe | CH |
| 1051 | Me | $Q_2$ | Me | Me | OMe | CH |
| 1052 | Me | $Q_2$ | Me | Me | OMe | N |

TABLE 2-continued

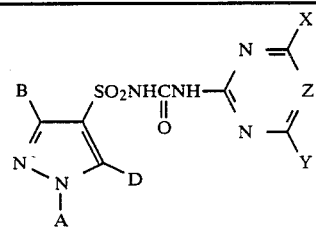
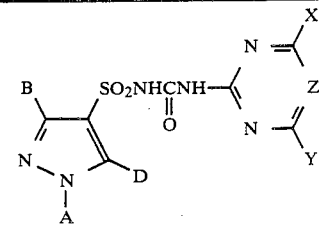

| No. | A | B | D | X | Y | Z |
|---|---|---|---|---|---|---|
| 1053 | Me | Me | Q2 | Me | OMe | CH |
| 1054 | Me | Me | Q2 | OMe | OMe | CH |
| 1055 | Me | Me | Q2 | Me | OMe | N |
| 1056 | Q3 | Me | COOMe | Me | Me | CH |
| 1057 | Q3 | Me | COOMe | Me | OMe | CH |
| 1058 | Q3 | Me | COOMe | OMe | OMe | CH |
| 1059 | Q3 | Me | COOMe | Me | OMe | N |
| 1060 | Q3 | Me | COOMe | OMe | OMe | N |
| 1061 | Me | Q3 | Me | Me | OMe | CH |
| 1062 | Me | Q3 | Me | OMe | OMe | CH |
| 1063 | Me | Q3 | Me | Me | OMe | N |
| 1064 | Me | Me | Q3 | Me | OMe | CH |
| 1065 | Me | Me | Q3 | OMe | OMe | CH |
| 1066 | Me | Me | Q3 | Me | OMe | N |
| 1067 | Q4 | Me | COOMe | Me | Me | CH |
| 1068 | Q4 | Me | COOMe | Me | OMe | CH |
| 1069 | Q4 | Me | COOMe | OMe | OMe | CH |
| 1070 | Q4 | Me | COOMe | Me | OMe | N |
| 1071 | Q4 | Me | COOMe | OMe | OMe | N |
| 1072 | Me | Q4 | Me | Me | OMe | CH |
| 1073 | Me | Q4 | Me | OMe | OMe | CH |
| 1074 | Me | Q4 | Me | Me | OMe | N |
| 1075 | Me | Me | Q4 | Me | OMe | CH |
| 1076 | Me | Me | Q4 | OMe | OMe | CH |
| 1077 | Me | Me | Q4 | Me | OMe | N |
| 1078 | Q5 | Me | COOMe | Me | Me | CH |
| 1079 | Q5 | Me | COOMe | Me | OMe | CH |
| 1080 | Q5 | Me | COOMe | OMe | OMe | CH |
| 1081 | Q5 | Me | COOMe | Me | OMe | N |
| 1082 | Q5 | Me | COOMe | OMe | OMe | N |
| 1083 | Me | Q5 | Me | Me | OMe | CH |
| 1084 | Me | Q5 | Me | OMe | OMe | CH |
| 1085 | Me | Q5 | Me | Me | OMe | N |
| 1086 | Me | Me | Q5 | Me | OMe | CH |
| 1087 | Me | Me | Q5 | OMe | OMe | CH |
| 1088 | Me | Me | Q5 | Me | OMe | N |
| 1089 | Q6 | Me | COOMe | Me | Me | CH |
| 1090 | Q6 | Me | COOMe | Me | OMe | CH |
| 1091 | Q6 | Me | COOMe | OMe | OMe | CH |
| 1092 | Q6 | Me | COOMe | Me | OMe | N |
| 1093 | Q6 | Me | COOMe | OMe | OMe | N |
| 1094 | Me | Q6 | Me | Me | OMe | CH |
| 1095 | Me | Q6 | Me | OMe | OMe | CH |
| 1096 | Me | Q6 | Me | Me | OMe | N |
| 1097 | Me | Me | Q6 | Me | OMe | CH |
| 1098 | Me | Me | Q6 | OMe | OMe | CH |
| 1099 | Me | Me | Q6 | Me | OMe | N |
| 1100 | Q7 | Me | COOMe | Me | OMe | CH |
| 1101 | Q7 | Me | COOMe | OMe | OMe | CH |
| 1102 | Q7 | Me | COOMe | Me | OMe | N |
| 1103 | Me | Me | Q7 | OMe | OMe | CH |
| 1104 | Me | Me | Q7 | Me | OMe | N |
| 1105 | Q8 | Me | COOMe | Me | OMe | CH |
| 1106 | Q8 | Me | COOMe | OMe | OMe | CH |
| 1107 | Q8 | Me | COOMe | Me | OMe | N |
| 1108 | Me | Me | Q8 | OMe | OMe | CH |
| 1109 | Me | Me | Q8 | Me | OMe | N |
| 1110 | Q9 | Me | COOMe | Me | OMe | CH |
| 1111 | Q9 | Me | COOMe | OMe | OMe | CH |
| 1112 | Q9 | Me | COOMe | Me | OMe | N |
| 1113 | Me | Me | Q9 | OMe | OMe | CH |
| 1114 | Me | Me | Q9 | Me | OMe | N |
| 1115 | Q10 | Me | COOMe | Me | OMe | CH |
| 1116 | Q10 | Me | COOMe | OMe | OMe | CH |
| 1117 | Q10 | Me | COOMe | Me | OMe | N |
| 1118 | Me | Me | Q10 | OMe | OMe | CH |
| 1119 | Me | Me | Q10 | Me | OMe | N |
| 1120 | Q11 | Me | COOMe | Me | Me | CH |
| 1121 | Q11 | Me | COOMe | Me | OMe | CH |
| 1122 | Q11 | Me | COOMe | OMe | OMe | CH |
| 1123 | Q11 | Me | COOMe | Me | OMe | N |
| 1124 | Q11 | Me | COOMe | OMe | OMe | N |
| 1125 | Me | Q11 | Me | Me | OMe | CH |
| 1126 | Me | Q11 | Me | OMe | OMe | CH |
| 1127 | Me | Q11 | Me | Me | OMe | N |
| 1128 | Me | Me | Q11 | Me | OMe | CH |
| 1129 | Me | Me | Q11 | OMe | OMe | CH |
| 1130 | Me | Me | Q11 | Me | OMe | N |
| 1131 | Q12 | Me | Cl | Me | Me | CH |
| 1132 | Q12 | Me | Cl | Me | OMe | CH |
| 1133 | Q12 | Me | Cl | OMe | OMe | CH |
| 1134 | Q12 | Me | Cl | Me | OMe | N |
| 1135 | Q12 | Me | Cl | OMe | OMe | N |
| 1136 | Q12 | Me | OMe | Me | OMe | CH |
| 1137 | Q12 | Me | OMe | OMe | OMe | CH |
| 1138 | Q12 | Me | OMe | Me | OMe | N |
| 1139 | Q12 | CF3 | Me | Me | OMe | CH |
| 1140 | Q12 | CF3 | Me | OMe | OMe | CH |
| 1141 | Q12 | CF3 | Me | Me | OMe | N |
| 1142 | Q12 | Me | COOMe | Me | Me | CH |
| 1143 | Q12 | Me | COOMe | Me | OMe | CH |
| 1144 | Q12 | Me | COOMe | OMe | OMe | CH |
| 1145 | Q12 | Me | COOMe | Me | OMe | N |
| 1146 | Q12 | Me | COOMe | OMe | OMe | N |
| 1147 | Q12 | Me | COOMe | Me | OCHF2 | CH |
| 1148 | Q12 | Me | COOMe | Me | ▷ | CH |
| 1149 | Q12 | Me | SO2Me | Me | OMe | CH |
| 1150 | Q12 | Me | SO2Me | OMe | OMe | CH |
| 1151 | Q12 | Me | SO2Me | Me | OMe | N |
| 1152 | H | Q12 | Me | Me | OMe | CH |
| 1153 | H | Q12 | Me | OMe | OMe | CH |
| 1154 | H | Q12 | Me | Me | OMe | N |
| 1155 | Me | Q12 | Me | Me | OMe | CH |
| 1156 | Me | Q12 | Me | OMe | OMe | CH |
| 1157 | Me | Q12 | Me | Me | OMe | N |
| 1158 | Me | Q12 | Cl | Me | OMe | CH |
| 1159 | Me | Q12 | Cl | OMe | OMe | CH |
| 1160 | Me | Q12 | Cl | Me | OMe | N |
| 1161 | Me | Q12 | COOMe | Me | OMe | CH |
| 1162 | Me | Q12 | COOMe | OMe | OMe | CH |
| 1163 | Me | Q12 | COOMe | Me | OMe | N |
| 1164 | Me | Q12 | Ph | Me | OMe | CH |
| 1165 | Me | Q12 | Ph | OMe | OMe | CH |
| 1166 | Me | Q12 | Ph | Me | OMe | N |
| 1167 | Me | Me | Q12 | Me | OMe | CH |
| 1168 | Me | Me | Q12 | OMe | OMe | CH |
| 1169 | Me | Me | Q12 | Me | OMe | N |
| 1170 | Q13 | Me | COOMe | Me | Me | CH |
| 1171 | Q13 | Me | COOMe | Me | OMe | CH |
| 1172 | Q13 | Me | COOMe | OMe | OMe | CH |
| 1173 | Q13 | Me | COOMe | Me | OMe | N |
| 1174 | Q13 | Me | COOMe | OMe | OMe | N |
| 1175 | Me | Q13 | Me | Me | OMe | CH |
| 1176 | Me | Q13 | Me | OMe | OMe | CH |
| 1177 | Me | Q13 | Me | Me | OMe | N |
| 1178 | Me | Me | Q13 | Me | OMe | CH |
| 1179 | Me | Me | Q13 | OMe | OMe | CH |
| 1180 | Me | Me | Q13 | Me | OMe | N |
| 1181 | Q14 | Me | COOMe | Me | Me | CH |
| 1182 | Q14 | Me | COOMe | Me | OMe | CH |
| 1183 | Q14 | Me | COOMe | OMe | OMe | CH |
| 1184 | Q14 | Me | COOMe | Me | OMe | N |
| 1185 | Q14 | Me | COOMe | OMe | OMe | N |
| 1186 | Me | Q14 | Me | Me | OMe | CH |

TABLE 2-continued

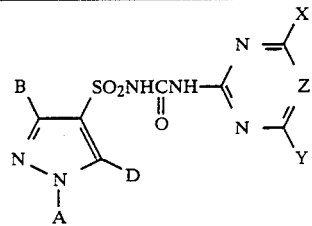

| No. | A | B | D | X | Y | Z |
|---|---|---|---|---|---|---|
| 1187 | Me | Q14 | Me | OMe | OMe | CH |
| 1188 | Me | Q14 | Me | Me | OMe | N |
| 1189 | Me | Me | Q14 | OMe | OMe | CH |
| 1190 | Me | Me | Q14 | OMe | OMe | CH |
| 1191 | Me | Me | Q14 | Me | OMe | N |
| 1192 | Q15 | Me | COOMe | Me | OMe | CH |
| 1193 | Q15 | Me | COOMe | OMe | OMe | CH |
| 1194 | Q15 | Me | COOMe | Me | OMe | N |
| 1195 | Me | Me | Q15 | OMe | OMe | CH |
| 1196 | Me | Me | Q15 | Me | OMe | N |
| 1197 | Q17 | Me | COOMe | Me | OMe | CH |
| 1198 | Q16 | Me | COOMe | Me | OMe | CH |
| 1199 | Q16 | Me | COOMe | Me | OMe | N |
| 1200 | Me | Me | Q16 | OMe | OMe | CH |
| 1201 | Me | Me | Q16 | Me | OMe | N |
| 1202 | Q17 | Me | COOMe | Me | OMe | CH |
| 1203 | Q17 | Me | COOMe | OMe | OMe | CH |
| 1204 | Q17 | Me | COOMe | Me | OMe | N |
| 1205 | Me | Me | Q17 | OMe | OMe | CH |
| 1206 | Me | Me | Q17 | Me | OMe | N |
| 1207 | Q18 | Me | COOMe | Me | OMe | CH |
| 1208 | Q18 | Me | COOMe | OMe | OMe | CH |
| 1209 | Q18 | Me | COOMe | Me | OMe | N |
| 1210 | Me | Me | Q18 | OMe | OMe | CH |
| 1211 | Me | Me | Q18 | Me | OMe | N |
| 1212 | Q19 | Me | COOMe | Me | Me | CH |
| 1213 | Q19 | Me | COOMe | Me | OMe | CH |
| 1214 | Q19 | Me | COOMe | OMe | OMe | CH |
| 1215 | Q19 | Me | COOMe | Me | OMe | N |
| 1216 | Q19 | Me | COOMe | OMe | OMe | N |
| 1217 | Me | Q19 | Me | Me | OMe | CH |
| 1218 | Me | Q19 | Me | OMe | OMe | CH |
| 1219 | Me | Q19 | Me | Me | OMe | N |
| 1220 | Me | Me | Q19 | Me | OMe | CH |
| 1221 | Me | Me | Q19 | OMe | OMe | CH |
| 1222 | Me | Me | Q19 | Me | OMe | N |
| 1223 | Q20 | Me | COOMe | Me | OMe | CH |
| 1224 | Q20 | Me | COOMe | OMe | OMe | CH |
| 1225 | Q20 | Me | COOMe | Me | OMe | N |
| 1226 | Me | Me | Q20 | OMe | OMe | CH |
| 1227 | Me | Me | Q20 | Me | OMe | N |
| 1228 | Q21 | Me | COOMe | Me | OMe | CH |
| 1229 | Q21 | Me | COOMe | OMe | OMe | CH |
| 1230 | Q21 | Me | COOMe | Me | OMe | N |
| 1231 | Me | Me | Q21 | OMe | OMe | CH |
| 1232 | Me | Me | Q21 | Me | OMe | N |
| 1233 | Q22 | Me | Cl | Me | Me | CH |
| 1234 | Q22 | Me | Cl | Me | OMe | CH |
| 1235 | Q22 | Me | Cl | OMe | OMe | CH |
| 1236 | Q22 | Me | Cl | Me | OMe | N |
| 1237 | Q22 | Me | Cl | OMe | OMe | N |
| 1238 | Q22 | Me | OMe | Me | OMe | CH |
| 1239 | Q22 | Me | OMe | OMe | OMe | CH |
| 1240 | Q22 | Me | OMe | Me | OMe | N |
| 1241 | Q22 | CF3 | Me | Me | OMe | CH |
| 1242 | Q22 | CF3 | Me | OMe | OMe | CH |
| 1243 | Q22 | CF3 | Me | Me | OMe | N |
| 1244 | Q22 | Me | COOMe | Me | Me | CH |
| 1245 | Q22 | Me | COOMe | Me | OMe | CH |
| 1246 | Q22 | Me | COOMe | OMe | OMe | CH |
| 1247 | Q22 | Me | COOMe | Me | OMe | N |
| 1248 | Q22 | Me | COOMe | OMe | OMe | N |
| 1249 | Q22 | Me | COOMe | Me | OCHF2 | CH |
| 1250 | Q22 | Me | COOMe | Me | ◁ | CH |
| 1251 | Q22 | Me | SO2Me | Me | OMe | CH |

TABLE 2-continued

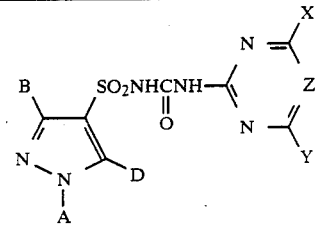

| No. | A | B | D | X | Y | Z |
|---|---|---|---|---|---|---|
| 1252 | Q22 | Me | SO2Me | OMe | OMe | CH |
| 1253 | Q22 | Me | SO2Me | Me | OMe | N |
| 1254 | H | Q22 | Me | Me | OMe | CH |
| 1255 | H | Q22 | Me | OMe | OMe | CH |
| 1256 | H | Q22 | Me | Me | OMe | N |
| 1257 | Me | Q22 | Me | Me | OMe | CH |
| 1258 | Me | Q22 | Me | OMe | OMe | CH |
| 1259 | Me | Q22 | Me | Me | OMe | N |
| 1260 | Me | Q22 | Cl | Me | OMe | CH |
| 1261 | Me | Q22 | Cl | OMe | OMe | CH |
| 1262 | Me | Q22 | Cl | Me | OMe | N |
| 1263 | Me | Q22 | COOMe | Me | OMe | CH |
| 1264 | Me | Q22 | COOMe | OMe | OMe | CH |
| 1265 | Me | Q22 | COOMe | Me | OMe | N |
| 1266 | Me | Q22 | Ph | Me | OMe | CH |
| 1267 | Me | Q22 | Ph | OMe | OMe | CH |
| 1268 | Me | Q22 | Ph | Me | OMe | N |
| 1269 | Me | Me | Q22 | Me | OMe | CH |
| 1270 | Me | Me | Q22 | OMe | OMe | CH |
| 1271 | Me | Me | Q22 | Me | OMe | N |
| 1272 | Q23 | Me | COOMe | Me | Me | CH |
| 1273 | Q23 | Me | COOMe | Me | OMe | CH |
| 1274 | Q23 | Me | COOMe | OMe | OMe | CH |
| 1275 | Q23 | Me | COOMe | Me | OMe | N |
| 1276 | Q23 | Me | COOMe | OMe | OMe | N |
| 1277 | Me | Q23 | Me | Me | OMe | CH |
| 1278 | Me | Q23 | Me | OMe | OMe | CH |
| 1279 | Me | Q23 | Me | Me | OMe | N |
| 1280 | Me | Me | Q23 | Me | OMe | CH |
| 1281 | Me | Me | Q23 | OMe | OMe | CH |
| 1282 | Me | Me | Q23 | Me | OMe | N |
| 1283 | Q24 | Me | COOMe | Me | Me | CH |
| 1284 | Q24 | Me | COOMe | Me | OMe | CH |
| 1285 | Q24 | Me | COOMe | OMe | OMe | CH |
| 1286 | Q24 | Me | COOMe | Me | OMe | N |
| 1287 | Q24 | Me | COOMe | OMe | OMe | N |
| 1288 | Me | Q24 | Me | Me | OMe | CH |
| 1289 | Me | Q24 | Me | OMe | OMe | CH |
| 1290 | Me | Q24 | Me | Me | OMe | N |
| 1291 | Me | Me | Q24 | Me | OMe | CH |
| 1292 | Me | Me | Q24 | OMe | OMe | CH |
| 1293 | Me | Me | Q24 | Me | OMe | N |
| 1294 | Q25 | Me | COOMe | Me | Me | CH |
| 1295 | Q25 | Me | COOMe | Me | OMe | CH |
| 1296 | Q25 | Me | COOMe | OMe | OMe | CH |
| 1297 | Q25 | Me | COOMe | Me | OMe | N |
| 1298 | Q25 | Me | COOMe | OMe | OMe | N |
| 1299 | Me | Q25 | Me | Me | OMe | CH |
| 1300 | Me | Q25 | Me | OMe | OMe | CH |
| 1301 | Me | Q25 | Me | Me | OMe | N |
| 1302 | Me | Me | Q25 | Me | OMe | CH |
| 1303 | Me | Me | Q25 | OMe | OMe | CH |
| 1304 | Me | Me | Q25 | Me | OMe | N |
| 1305 | Q26 | Me | COOMe | Me | OMe | CH |
| 1306 | Q26 | Me | COOMe | OMe | OMe | CH |
| 1307 | Q26 | Me | COOMe | Me | OMe | N |
| 1308 | Me | Me | Q26 | OMe | OMe | CH |
| 1309 | Me | Me | Q26 | Me | OMe | N |
| 1310 | Q27 | Me | COOMe | Me | OMe | CH |
| 1311 | Q27 | Me | COOMe | OMe | OMe | CH |
| 1312 | Q27 | Me | COOMe | Me | OMe | N |
| 1313 | Me | Me | Q27 | OMe | OMe | CH |
| 1314 | Me | Me | Q27 | Me | OMe | N |
| 1315 | Q28 | Me | COOMe | Me | OMe | CH |
| 1316 | Q28 | Me | COOMe | OMe | OMe | CH |
| 1317 | Q28 | Me | COOMe | Me | OMe | N |
| 1318 | Me | Me | Q28 | OMe | OMe | CH |
| 1319 | Me | Me | Q28 | Me | OMe | N |
| 1320 | Q29 | Me | COOMe | Me | OMe | CH |

TABLE 2-continued

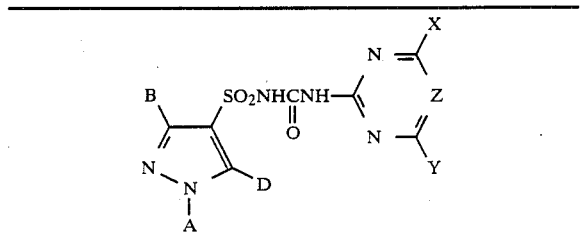

| No. | A | B | D | X | Y | Z |
|---|---|---|---|---|---|---|
| 1321 | $Q_{29}$ | Me | COOMe | Me | OMe | CH |
| 1322 | $Q_{29}$ | Me | COOMe | Me | OMe | N |
| 1323 | Me | Me | $Q_{29}$ | OMe | OMe | CH |
| 1324 | Me | Me | $Q_{29}$ | Me | OMe | N |
| 1325 | $Q_{30}$ | Me | COOMe | Me | OMe | CH |
| 1326 | $Q_{30}$ | Me | COOMe | OMe | OMe | CH |
| 1327 | $Q_{30}$ | Me | COOMe | Me | OMe | N |
| 1328 | Me | Me | $Q_{30}$ | OMe | OMe | CH |
| 1329 | Me | Me | $Q_{30}$ | Me | OMe | N |
| 1330 | $Q_{31}$ | Me | COOMe | Me | OMe | CH |
| 1331 | $Q_{31}$ | Me | COOMe | OMe | OMe | CH |
| 1332 | $Q_{31}$ | Me | COOMe | Me | OMe | N |
| 1333 | Me | Me | $Q_{31}$ | OMe | OMe | CH |
| 1334 | Me | Me | $Q_{31}$ | Me | OMe | N |
| 1335 | $Q_{32}$ | Me | COOMe | Me | Me | CH |
| 1336 | $Q_{32}$ | Me | COOMe | Me | OMe | CH |
| 1337 | $Q_{32}$ | Me | COOMe | OMe | OMe | CH |
| 1338 | $Q_{32}$ | Me | COOMe | Me | OMe | N |
| 1339 | $Q_{32}$ | Me | COOMe | OMe | OMe | N |
| 1340 | Me | $Q_{32}$ | Me | Me | OMe | CH |
| 1341 | Me | $Q_{32}$ | Me | OMe | OMe | CH |
| 1342 | Me | $Q_{32}$ | Me | Me | OMe | N |
| 1343 | Me | Me | $Q_{32}$ | Me | OMe | CH |
| 1344 | Me | Me | $Q_{32}$ | OMe | OMe | CH |
| 1345 | Me | Me | $Q_{32}$ | Me | OMe | N |
| 1346 | $Q_{33}$ | Me | COOMe | Me | OMe | CH |
| 1347 | $Q_{33}$ | Me | COOMe | OMe | OMe | CH |
| 1348 | $Q_{33}$ | Me | COOMe | Me | OMe | N |
| 1349 | Me | Me | $Q_{33}$ | OMe | OMe | CH |
| 1350 | Me | Me | $Q_{33}$ | Me | OMe | N |
| 1351 | $Q_{34}$ | Me | COOMe | Me | OMe | CH |
| 1352 | $Q_{34}$ | Me | COOMe | OMe | OMe | CH |
| 1353 | $Q_{34}$ | Me | COOMe | Me | OMe | N |
| 1354 | Me | Me | $Q_{34}$ | OMe | OMe | CH |
| 1355 | Me | Me | $Q_{34}$ | Me | OMe | N |
| 1356 | $Q_{35}$ | Me | COOMe | Me | OMe | CH |
| 1357 | $Q_{35}$ | Me | COOMe | OMe | OMe | CH |
| 1358 | $Q_{35}$ | Me | COOMe | Me | OMe | N |
| 1359 | Me | Me | $Q_{35}$ | OMe | OMe | CH |
| 1360 | Me | Me | $Q_{35}$ | Me | OMe | N |
| 1361 | $Q_{36}$ | Me | COOMe | Me | OMe | CH |
| 1362 | $Q_{36}$ | Me | COOMe | OMe | OMe | CH |
| 1363 | $Q_{36}$ | Me | COOMe | Me | OMe | N |
| 1364 | Me | Me | $Q_{36}$ | OMe | OMe | CH |
| 1365 | Me | Me | $Q_{36}$ | Me | OMe | N |
| 1366 | $Q_{37}$ | Me | COOMe | Me | OMe | CH |
| 1367 | $Q_{37}$ | Me | COOMe | OMe | OMe | CH |
| 1368 | $Q_{37}$ | Me | COOMe | Me | OMe | N |
| 1369 | Me | Me | $Q_{37}$ | OMe | OMe | CH |
| 1370 | Me | Me | $Q_{37}$ | Me | OMe | N |
| 1371 | $Q_{38}$ | Me | COOMe | Me | OMe | CH |
| 1372 | $Q_{38}$ | Me | COOMe | OMe | OMe | CH |
| 1373 | $Q_{38}$ | Me | COOMe | Me | OMe | N |
| 1374 | Me | Me | $Q_{38}$ | OMe | OMe | CH |
| 1375 | Me | Me | $Q_{38}$ | Me | OMe | N |
| 1376 | $Q_{39}$ | Me | COOMe | Me | OMe | CH |
| 1377 | $Q_{39}$ | Me | COOMe | OMe | OMe | CH |
| 1378 | $Q_{39}$ | Me | COOMe | Me | OMe | N |
| 1379 | Me | Me | $Q_{39}$ | OMe | OMe | CH |
| 1380 | Me | Me | $Q_{39}$ | Me | OMe | N |
| 1381 | $Q_{40}$ | Me | COOMe | Me | OMe | CH |
| 1382 | $Q_{40}$ | Me | COOMe | OMe | OMe | CH |
| 1383 | $Q_{40}$ | Me | COOMe | Me | OMe | N |
| 1384 | Me | Me | $Q_{40}$ | OMe | OMe | CH |
| 1385 | Me | Me | $Q_{40}$ | Me | OMe | N |
| 1386 | $Q_{41}$ | Me | COOMe | Me | OMe | CH |
| 1387 | $Q_{41}$ | Me | COOMe | OMe | OMe | CH |
| 1388 | $Q_{41}$ | Me | COOMe | Me | OMe | N |
| 1389 | Me | Me | $Q_{41}$ | OMe | OMe | CH |

TABLE 2-continued

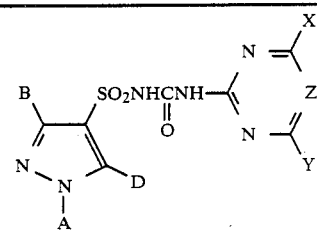

| No. | A | B | D | X | Y | Z |
|---|---|---|---|---|---|---|
| 1390 | Me | Me | $Q_{41}$ | Me | OMe | N |
| 1391 | $Q_{42}$ | Me | COOMe | Me | OMe | CH |
| 1392 | $Q_{42}$ | Me | COOMe | OMe | OMe | CH |
| 1393 | $Q_{42}$ | Me | COOMe | Me | OMe | N |
| 1394 | Me | Me | $Q_{42}$ | OMe | OMe | CH |
| 1395 | Me | Me | $Q_{42}$ | Me | OMe | N |
| 1396 | $Q_{43}$ | Me | COOMe | Me | OMe | CH |
| 1397 | $Q_{43}$ | Me | COOMe | OMe | OMe | CH |
| 1398 | $Q_{43}$ | Me | COOMe | Me | OMe | N |
| 1399 | Me | Me | $Q_{43}$ | OMe | OMe | CH |
| 1400 | Me | Me | $Q_{43}$ | Me | OMe | N |
| 1401 | $Q_{44}$ | Me | COOMe | Me | OMe | CH |
| 1402 | $Q_{44}$ | Me | COOMe | OMe | OMe | CH |
| 1403 | $Q_{44}$ | Me | COOMe | Me | OMe | N |
| 1404 | Me | Me | $Q_{44}$ | OMe | OMe | CH |
| 1405 | Me | Me | $Q_{44}$ | Me | OMe | N |
| 1406 | $Q_{45}$ | Me | COOMe | Me | OMe | CH |
| 1407 | $Q_{45}$ | Me | COOMe | OMe | OMe | CH |
| 1408 | $Q_{45}$ | Me | COOMe | Me | OMe | N |
| 1409 | Me | Me | $Q_{45}$ | OMe | OMe | CH |
| 1410 | Me | Me | $Q_{45}$ | Me | OMe | N |
| 1411 | $Q_{46}$ | Me | COOMe | Me | OMe | CH |
| 1412 | $Q_{46}$ | Me | COOMe | OMe | OMe | CH |
| 1413 | $Q_{46}$ | Me | COOMe | Me | OMe | N |
| 1414 | Me | Me | $Q_{46}$ | OMe | OMe | CH |
| 1415 | Me | Me | $Q_{46}$ | Me | OMe | N |
| 1416 | $Q_{47}$ | Me | COOMe | Me | OMe | CH |
| 1417 | $Q_{47}$ | Me | COOMe | OMe | OMe | CH |
| 1418 | $Q_{47}$ | Me | COOMe | Me | OMe | N |
| 1419 | Me | Me | $Q_{47}$ | OMe | OMe | CH |
| 1420 | Me | Me | $Q_{47}$ | Me | OMe | N |
| 3315 | $Q_{48}$ | Me | COOMe | OMe | OMe | CH |
| 3316 | Me | $Q_{48}$ | Me | Me | Me | CH |
| 3317 | Me | $Q_{48}$ | Me | Me | OMe | CH |
| 3318 | Me | $Q_{48}$ | Me | OMe | OMe | CH |
| 3319 | Me | Me | $Q_{48}$ | Me | Me | CH |
| 3320 | Me | Me | $Q_{48}$ | Me | OMe | CH |
| 3321 | Me | Me | $Q_{48}$ | OMe | OMe | CH |
| 3322 | H | Me | $Q_{48}$ | OMe | OMe | CH |
| 3323 | $Q_{49}$ | Me | COOMe | OMe | OMe | CH |
| 3324 | Me | $Q_{49}$ | Me | Me | Me | CH |
| 3325 | Me | $Q_{49}$ | Me | Me | OMe | CH |
| 3326 | Me | $Q_{49}$ | Me | OMe | OMe | CH |
| 3327 | Me | Me | $Q_{49}$ | Me | Me | CH |
| 3328 | Me | Me | $Q_{49}$ | Me | OMe | CH |
| 3329 | Me | Me | $Q_{49}$ | OMe | OMe | CH |
| 3330 | H | Me | $Q_{49}$ | OMe | OMe | CH |
| 3331 | $Q_{50}$ | Me | COOMe | OMe | OMe | CH |
| 3332 | Me | $Q_{50}$ | Me | Me | Me | CH |
| 3333 | Me | $Q_{50}$ | Me | Me | OMe | CH |
| 3334 | Me | $Q_{50}$ | Me | OMe | OMe | CH |
| 3335 | Me | Me | $Q_{50}$ | Me | Me | CH |
| 3336 | Me | Me | $Q_{50}$ | Me | OMe | CH |
| 3337 | Me | Me | $Q_{50}$ | OMe | OMe | CH |
| 3338 | H | Me | $Q_{50}$ | OMe | OMe | CH |
| 3339 | $Q_{51}$ | Me | COOMe | OMe | OMe | CH |
| 3340 | Me | $Q_{51}$ | Me | Me | Me | CH |
| 3341 | Me | $Q_{51}$ | Me | Me | OMe | CH |
| 3342 | Me | $Q_{51}$ | Me | OMe | OMe | CH |
| 3343 | Me | Me | $Q_{51}$ | Me | Me | CH |
| 3344 | Me | Me | $Q_{51}$ | Me | OMe | CH |
| 3345 | Me | Me | $Q_{51}$ | OMe | OMe | CH |
| 3346 | H | Me | $Q_{51}$ | OMe | OMe | CH |
| 3347 | $Q_{52}$ | Me | COOMe | OMe | OMe | CH |
| 3348 | Me | $Q_{52}$ | Me | Me | Me | CH |
| 3349 | Me | $Q_{52}$ | Me | Me | OMe | CH |
| 3350 | Me | $Q_{52}$ | Me | OMe | OMe | CH |
| 3351 | Me | Me | $Q_{52}$ | Me | Me | CH |
| 3352 | Me | Me | $Q_{52}$ | Me | OMe | CH |

TABLE 2-continued

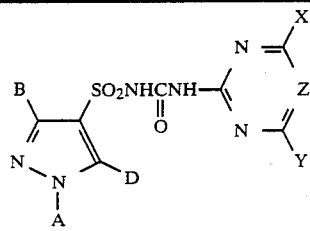

| No. | A | B | D | X | Y | Z |
|---|---|---|---|---|---|---|
| 3353 | Me | Me | $Q_{52}$ | OMe | OMe | CH |
| 3354 | H | Me | $Q_{52}$ | OMe | OMe | CH |
| 3355 | $Q_{53}$ | Me | COOMe | Me | Me | CH |
| 3356 | $Q_{53}$ | Me | COOMe | Me | OMe | CH |
| 3357 | $Q_{53}$ | Me | COOMe | OMe | OMe | CH |
| 3358 | $Q_{53}$ | Me | COOMe | Me | OMe | N |
| 3359 | $Q_{53}$ | Me | COOMe | OMe | OMe | N |
| 3360 | Me | $Q_{53}$ | Me | Me | OMe | CH |
| 3361 | Me | $Q_{53}$ | Me | OMe | OMe | CH |
| 3362 | Me | $Q_{53}$ | Me | OMe | OMe | N |
| 3363 | Me | Me | $Q_{53}$ | Me | OMe | CH |
| 3364 | Me | Me | $Q_{53}$ | OMe | OMe | CH |
| 3365 | Me | Me | $Q_{53}$ | Me | OMe | N |
| 3366 | H | Me | $Q_{53}$ | OMe | OMe | CH |
| 3367 | $Q_{54}$ | Me | COOMe | OMe | OMe | CH |
| 3368 | Me | $Q_{54}$ | Me | Me | Me | CH |
| 3369 | Me | $Q_{54}$ | Me | Me | OMe | CH |
| 3370 | Me | $Q_{54}$ | Me | OMe | OMe | CH |
| 3371 | Me | Me | $Q_{54}$ | Me | Me | CH |
| 3372 | Me | Me | $Q_{54}$ | Me | OMe | CH |
| 3373 | Me | Me | $Q_{54}$ | OMe | OMe | CH |
| 3374 | H | Me | $Q_{54}$ | OMe | OMe | CH |
| 3375 | $Q_{55}$ | Me | COOMe | OMe | OMe | CH |
| 3376 | Me | $Q_{55}$ | Me | Me | Me | CH |
| 3377 | Me | $Q_{55}$ | Me | Me | OMe | CH |
| 3378 | Me | $Q_{55}$ | Me | OMe | OMe | CH |
| 3379 | Me | Me | $Q_{55}$ | Me | Me | CH |
| 3380 | Me | Me | $Q_{55}$ | Me | OMe | CH |
| 3381 | Me | Me | $Q_{55}$ | OMe | OMe | CH |
| 3382 | H | Me | $Q_{55}$ | OMe | OMe | CH |
| 3383 | $Q_{56}$ | Me | COOMe | OMe | OMe | CH |
| 3384 | Me | $Q_{56}$ | Me | Me | Me | CH |
| 3385 | Me | $Q_{56}$ | Me | Me | OMe | CH |
| 3386 | Me | $Q_{56}$ | Me | OMe | OMe | CH |
| 3387 | Me | Me | $Q_{56}$ | Me | Me | CH |
| 3388 | Me | Me | $Q_{56}$ | Me | OMe | CH |
| 3389 | Me | Me | $Q_{56}$ | OMe | OMe | CH |
| 3390 | H | Me | $Q_{56}$ | OMe | OMe | CH |
| 3391 | $Q_{57}$ | Me | COOMe | OMe | OMe | CH |
| 3392 | Me | $Q_{57}$ | Me | Me | Me | CH |
| 3393 | Me | $Q_{57}$ | Me | Me | OMe | CH |
| 3394 | Me | $Q_{57}$ | Me | OMe | OMe | CH |
| 3395 | Me | Me | $Q_{57}$ | Me | Me | CH |
| 3396 | Me | Me | $Q_{57}$ | Me | OMe | CH |
| 3397 | Me | Me | $Q_{57}$ | OMe | OMe | CH |
| 3398 | H | Me | $Q_{57}$ | OMe | OMe | CH |
| 3399 | $Q_{58}$ | Me | COOMe | OMe | OMe | CH |
| 3400 | Me | $Q_{58}$ | Me | Me | Me | CH |
| 3401 | Me | $Q_{58}$ | Me | Me | OMe | CH |
| 3402 | Me | $Q_{58}$ | Me | OMe | OMe | CH |
| 3403 | Me | Me | $Q_{58}$ | Me | Me | CH |
| 3404 | Me | Me | $Q_{58}$ | Me | OMe | CH |
| 3405 | Me | Me | $Q_{58}$ | OMe | OMe | CH |
| 3406 | H | Me | $Q_{58}$ | OMe | OMe | CH |
| 3407 | $Q_{59}$ | Me | COOMe | OMe | OMe | CH |
| 3408 | Me | $Q_{59}$ | Me | Me | Me | CH |
| 3409 | Me | $Q_{59}$ | Me | Me | OMe | CH |
| 3410 | Me | $Q_{59}$ | Me | OMe | OMe | CH |
| 3411 | Me | Me | $Q_{59}$ | Me | Me | CH |
| 3412 | Me | Me | $Q_{59}$ | Me | OMe | CH |
| 3413 | Me | Me | $Q_{59}$ | OMe | OMe | CH |
| 3414 | H | Me | $Q_{59}$ | OMe | OMe | CH |
| 3415 | $Q_{60}$ | Me | COOMe | Me | Me | CH |
| 3416 | $Q_{60}$ | Me | COOMe | Me | OMe | CH |
| 3417 | $Q_{60}$ | Me | COOMe | OMe | OMe | CH |
| 3418 | $Q_{60}$ | Me | COOMe | Me | OMe | N |
| 3419 | $Q_{60}$ | Me | COOMe | OMe | OMe | N |
| 3420 | Me | $Q_{60}$ | Me | Me | Me | CH |
| 3421 | Me | $Q_{60}$ | Me | OMe | OMe | CH |
| 3422 | Me | $Q_{60}$ | Me | Me | OMe | N |
| 3423 | Me | Me | $Q_{60}$ | Me | OMe | CH |
| 3424 | Me | Me | $Q_{60}$ | OMe | OMe | CH |
| 3425 | Me | Me | $Q_{60}$ | Me | OMe | N |
| 3426 | H | Me | $Q_{60}$ | OMe | OMe | CH |
| 3427 | $Q_{61}$ | Me | COOMe | OMe | OMe | CH |
| 3428 | Me | $Q_{61}$ | Me | Me | Me | CH |
| 3429 | Me | $Q_{61}$ | Me | Me | OMe | CH |
| 3430 | Me | $Q_{61}$ | Me | OMe | OMe | CH |
| 3431 | Me | Me | $Q_{61}$ | Me | Me | CH |
| 3432 | Me | Me | $Q_{61}$ | Me | OMe | CH |
| 3433 | Me | Me | $Q_{61}$ | OMe | OMe | CH |
| 3434 | H | Me | $Q_{61}$ | OMe | OMe | CH |
| 3435 | $Q_{62}$ | Me | COOMe | OMe | OMe | CH |
| 3436 | Me | $Q_{62}$ | Me | Me | Me | CH |
| 3437 | Me | $Q_{62}$ | Me | Me | OMe | CH |
| 3438 | Me | $Q_{62}$ | Me | OMe | OMe | CH |
| 3439 | Me | Me | $Q_{62}$ | Me | Me | CH |
| 3440 | Me | Me | $Q_{62}$ | Me | OMe | CH |
| 3441 | Me | Me | $Q_{62}$ | OMe | OMe | CH |
| 3442 | H | Me | $Q_{62}$ | OMe | OMe | CH |
| 3443 | $Q_{63}$ | Me | COOMe | OMe | OMe | CH |
| 3444 | Me | $Q_{63}$ | Me | Me | Me | CH |
| 3445 | Me | $Q_{63}$ | Me | Me | OMe | CH |
| 3446 | Me | $Q_{63}$ | Me | OMe | OMe | CH |
| 3447 | Me | Me | $Q_{63}$ | Me | Me | CH |
| 3448 | Me | Me | $Q_{63}$ | Me | OMe | CH |
| 3449 | Me | Me | $Q_{63}$ | OMe | OMe | CH |
| 3450 | H | Me | $Q_{63}$ | OMe | OMe | CH |
| 3451 | $Q_{64}$ | Me | COOMe | OMe | OMe | CH |
| 3452 | Me | $Q_{64}$ | Me | Me | Me | CH |
| 3453 | Me | $Q_{64}$ | Me | Me | OMe | CH |
| 3454 | Me | $Q_{64}$ | Me | OMe | OMe | CH |
| 3455 | Me | Me | $Q_{64}$ | Me | Me | CH |
| 3456 | Me | Me | $Q_{64}$ | Me | OMe | CH |
| 3457 | Me | Me | $Q_{64}$ | OMe | OMe | CH |
| 3458 | H | Me | $Q_{64}$ | OMe | OMe | CH |
| 3459 | $Q_{65}$ | Me | COOMe | Me | Me | CH |
| 3460 | $Q_{65}$ | Me | COOMe | Me | OMe | CH |
| 3461 | $Q_{65}$ | Me | COOMe | OMe | OMe | CH |
| 3462 | $Q_{65}$ | Me | COOMe | Me | OMe | N |
| 3463 | $Q_{65}$ | Me | COOMe | OMe | OMe | N |
| 3464 | Me | $Q_{65}$ | Me | Me | OMe | CH |
| 3465 | Me | $Q_{65}$ | Me | OMe | OMe | CH |
| 3466 | Me | $Q_{65}$ | Me | Me | OMe | N |
| 3467 | Me | Me | $Q_{65}$ | Me | OMe | CH |
| 3468 | Me | Me | $Q_{65}$ | OMe | OMe | CH |
| 3469 | Me | Me | $Q_{65}$ | Me | OMe | N |
| 3470 | H | Me | $Q_{65}$ | OMe | OMe | CH |
| 3471 | $Q_{66}$ | Me | COOMe | OMe | OMe | CH |
| 3472 | Me | $Q_{66}$ | Me | Me | Me | CH |
| 3473 | Me | $Q_{66}$ | Me | Me | OMe | CH |
| 3474 | Me | $Q_{66}$ | Me | OMe | OMe | CH |
| 3475 | Me | Me | $Q_{66}$ | Me | Me | CH |
| 3476 | Me | Me | $Q_{66}$ | Me | OMe | CH |
| 3477 | Me | Me | $Q_{66}$ | OMe | OMe | CH |
| 3478 | H | Me | $Q_{66}$ | OMe | OMe | CH |
| 3479 | $Q_{67}$ | Me | COOMe | OMe | OMe | CH |
| 3480 | Me | $Q_{67}$ | Me | Me | Me | CH |
| 3481 | Me | $Q_{67}$ | Me | Me | OMe | CH |
| 3482 | Me | $Q_{67}$ | Me | OMe | OMe | CH |
| 3483 | Me | Me | $Q_{67}$ | Me | Me | CH |
| 3484 | Me | Me | $Q_{67}$ | Me | OMe | CH |
| 3485 | Me | Me | $Q_{67}$ | OMe | OMe | CH |
| 3486 | H | Me | $Q_{67}$ | OMe | OMe | CH |
| 3487 | $Q_{68}$ | Me | COOMe | Me | Me | CH |
| 3488 | $Q_{68}$ | Me | COOMe | Me | OMe | CH |
| 3489 | $Q_{68}$ | Me | COOMe | OMe | OMe | CH |
| 3490 | $Q_{68}$ | Me | COOMe | Me | OMe | N |

TABLE 2-continued $$\underset{\underset{A}{N}\diagdown N}{\overset{B}{\diagdown}}\overset{SO_2NHCNH}{\underset{D}{\diagup}}\overset{O}{\underset{}{\parallel}}\overset{N=\overset{X}{\diagdown}}{\underset{N=\underset{Y}{\diagdown}}{\diagup Z}}$$

| No. | A | B | D | X | Y | Z |
|---|---|---|---|---|---|---|
| 3491 | Q68 | Me | COOMe | OMe | OMe | N |
| 3492 | Me | Q68 | Me | Me | OMe | CH |
| 3493 | Me | Q68 | Me | OMe | OMe | CH |
| 3494 | Me | Q68 | Me | Me | OMe | N |
| 3495 | Me | Me | Q68 | Me | OMe | CH |
| 3496 | Me | Me | Q68 | OMe | OMe | CH |
| 3497 | Me | Me | Q68 | Me | OMe | N |
| 3498 | H | Me | Q68 | OMe | OMe | CH |
| 3499 | Q69 | Me | COOMe | OMe | OMe | CH |
| 3500 | Me | Q69 | Me | Me | Me | CH |
| 3501 | Me | Q69 | Me | Me | OMe | CH |
| 3502 | Me | Q69 | Me | OMe | OMe | CH |
| 3503 | Me | Me | Q69 | Me | Me | CH |
| 3504 | Me | Me | Q69 | Me | OMe | CH |
| 3505 | Me | Me | Q69 | OMe | OMe | CH |
| 3506 | H | Me | Q69 | OMe | OMe | CH |
| 3507 | Q70 | Me | COOMe | OMe | OMe | CH |
| 3508 | Me | Q70 | Me | Me | Me | CH |
| 3509 | Me | Q70 | Me | Me | OMe | CH |
| 3510 | Me | Q70 | Me | OMe | OMe | CH |
| 3511 | Me | Me | Q70 | Me | Me | CH |
| 3512 | Me | Me | Q70 | Me | OMe | CH |
| 3513 | Me | Me | Q70 | OMe | OMe | CH |
| 3514 | H | Me | Q70 | OMe | OMe | CH |
| 3515 | Q71 | Me | COOMe | Me | Me | CH |
| 3516 | Q71 | Me | COOMe | Me | OMe | CH |
| 3517 | Q71 | Me | COOMe | OMe | OMe | CH |
| 3518 | Q71 | Me | COOMe | Me | OMe | N |
| 3519 | Q71 | Me | COOMe | OMe | OMe | N |
| 3519 | Me | Q71 | Me | Me | OMe | CH |
| 3520 | Me | Q71 | Me | OMe | OMe | CH |
| 3520 | Me | Q71 | Me | Me | OMe | N |
| 3521 | Me | Me | Q71 | Me | OMe | CH |
| 3522 | Me | Me | Q71 | OMe | OMe | CH |
| 3523 | Me | Me | Q71 | Me | OMe | N |
| 3524 | H | Me | Q71 | OMe | OMe | CH |
| 3525 | Q72 | Me | COOMe | OMe | OMe | CH |
| 3526 | Me | Q72 | Me | Me | Me | CH |
| 3527 | Me | Q72 | Me | Me | OMe | CH |
| 3528 | Me | Q72 | Me | OMe | OMe | CH |
| 3529 | Me | Me | Q72 | Me | Me | CH |
| 3530 | Me | Me | Q72 | Me | OMe | CH |
| 3531 | Me | Me | Q72 | OMe | OMe | CH |
| 3532 | H | Me | Q72 | OMe | OMe | CH |
| 3533 | Q73 | Me | COOMe | OMe | OMe | CH |
| 3534 | Me | Q73 | Me | Me | Me | CH |
| 3535 | Me | Q73 | Me | Me | OMe | CH |
| 3536 | Me | Q73 | Me | OMe | OMe | CH |
| 3537 | Me | Me | Q73 | Me | Me | CH |
| 3538 | Me | Me | Q73 | Me | OMe | CH |
| 3539 | Me | Me | Q73 | OMe | OMe | CH |
| 3540 | H | Me | Q73 | OMe | OMe | CH |
| 3541 | Q74 | Me | COOMe | OMe | OMe | CH |
| 3542 | Me | Q74 | Me | Me | Me | CH |
| 3543 | Me | Q74 | Me | Me | OMe | CH |
| 3544 | Me | Q74 | Me | OMe | OMe | CH |
| 3545 | Me | Me | Q74 | Me | Me | CH |
| 3546 | Me | Me | Q74 | Me | OMe | CH |
| 3547 | Me | Me | Q74 | OMe | OMe | CH |
| 3548 | H | Me | Q74 | OMe | OMe | CH |
| 3549 | Q75 | Me | COOMe | OMe | OMe | CH |
| 3550 | Me | Q75 | Me | Me | Me | CH |
| 3551 | Me | Q75 | Me | Me | OMe | CH |
| 3552 | Me | Q75 | Me | OMe | OMe | CH |
| 3553 | Me | Me | Q75 | Me | Me | CH |
| 3554 | Me | Me | Q75 | Me | OMe | CH |
| 3555 | Me | Me | Q75 | OMe | OMe | CH |
| 3556 | H | Me | Q75 | OMe | OMe | CH |
| 3557 | Q76 | Me | COOMe | OMe | OMe | CH |
| 3558 | Me | Q76 | Me | Me | Me | CH |
| 3559 | Me | Q76 | Me | Me | OMe | CH |
| 3560 | Me | Q76 | Me | OMe | OMe | CH |
| 3561 | Me | Me | Q76 | Me | Me | CH |
| 3562 | Me | Me | Q76 | Me | OMe | CH |
| 3563 | Me | Me | Q76 | OMe | OMe | CH |
| 3564 | H | Me | Q76 | OMe | OMe | CH |
| 3565 | Q77 | Me | COOMe | OMe | OMe | CH |
| 3566 | Me | Q77 | Me | Me | Me | CH |
| 3567 | Me | Q77 | Me | Me | OMe | CH |
| 3568 | Me | Q77 | Me | OMe | OMe | CH |
| 3569 | Me | Me | Q77 | Me | Me | CH |
| 3570 | Me | Me | Q77 | Me | OMe | CH |
| 3571 | Me | Me | Q77 | OMe | OMe | CH |
| 3572 | H | Me | Q77 | OMe | OMe | CH |
| 3573 | Q78 | Me | COOMe | OMe | OMe | CH |
| 3574 | Me | Q78 | Me | Me | Me | CH |
| 3575 | Me | Q78 | Me | Me | OMe | CH |
| 3576 | Me | Q78 | Me | OMe | OMe | CH |
| 3577 | Me | Me | Q78 | Me | Me | CH |
| 3578 | Me | Me | Q78 | Me | OMe | CH |
| 3579 | Me | Me | Q78 | OMe | OMe | CH |
| 3580 | H | Me | Q78 | OMe | OMe | CH |
| 3581 | Q79 | Me | COOMe | OMe | OMe | CH |
| 3582 | Me | Q79 | Me | Me | Me | CH |
| 3583 | Me | Q79 | Me | Me | OMe | CH |
| 3584 | Me | Q79 | Me | OMe | OMe | CH |
| 3585 | Me | Me | Q79 | Me | Me | CH |
| 3586 | Me | Me | Q79 | Me | OMe | CH |
| 3587 | Me | Me | Q79 | OMe | OMe | CH |
| 3588 | H | Me | Q79 | OMe | OMe | CH |
| 3589 | Q80 | Me | COOMe | OMe | OMe | CH |
| 3590 | Me | Q80 | Me | Me | Me | CH |
| 3591 | Me | Q80 | Me | Me | OMe | CH |
| 3592 | Me | Q80 | Me | OMe | OMe | CH |
| 3593 | Me | Me | Q80 | Me | Me | CH |
| 3594 | Me | Me | Q80 | Me | OMe | CH |
| 3595 | Me | Me | Q80 | OMe | OMe | CH |
| 3596 | H | Me | Q80 | OMe | OMe | CH |
| 3597 | Q81 | Me | COOMe | OMe | OMe | CH |
| 3598 | Me | Q81 | Me | Me | Me | CH |
| 3599 | Me | Q81 | Me | Me | OMe | CH |
| 3600 | Me | Q81 | Me | OMe | OMe | CH |
| 3601 | Me | Me | Q81 | Me | Me | CH |
| 3602 | Me | Me | Q81 | Me | OMe | CH |
| 3603 | Me | Me | Q81 | OMe | OMe | CH |
| 3604 | H | Me | Q81 | OMe | OMe | CH |
| 3605 | Q79 | Me | COOMe | OMe | OMe | CH |
| 3606 | Me | Q82 | Me | Me | Me | CH |
| 3607 | Me | Q82 | Me | Me | OMe | CH |
| 3608 | Me | Q82 | Me | OMe | OMe | CH |
| 3609 | Me | Me | Q82 | Me | Me | CH |
| 3610 | Me | Me | Q82 | Me | OMe | CH |
| 3611 | Me | Me | Q82 | OMe | OMe | CH |
| 3612 | H | Me | Q82 | OMe | OMe | CH |
| 3613 | Q83 | Me | COOMe | OMe | OMe | CH |
| 3614 | Me | Q83 | Me | Me | Me | CH |
| 3615 | Me | Q83 | Me | Me | OMe | CH |
| 3616 | Me | Q83 | Me | OMe | OMe | CH |
| 3617 | Me | Me | Q83 | Me | Me | CH |
| 3618 | Me | Me | Q83 | Me | OMe | CH |
| 3619 | Me | Me | Q83 | OMe | OMe | CH |
| 3620 | H | Me | Q83 | OMe | OMe | CH |
| 3619 | Q84 | Me | COOMe | OMe | OMe | CH |
| 3620 | Me | Q84 | Me | Me | Me | CH |
| 3621 | Me | Q84 | Me | Me | OMe | CH |
| 3622 | Me | Q84 | Me | OMe | OMe | CH |
| 3623 | Me | Me | Q84 | Me | Me | CH |
| 3624 | Me | Me | Q84 | Me | OMe | CH |

TABLE 2-continued

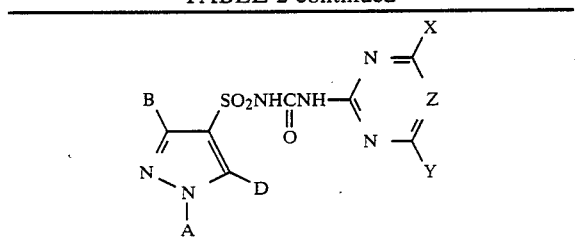

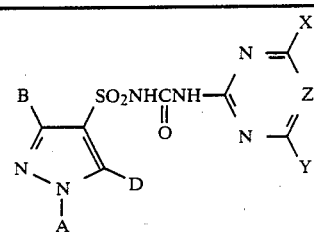

| No. | A | B | D | X | Y | Z |
|---|---|---|---|---|---|---|
| 3625 | Me | Me | Q84 | OMe | OMe | CH |
| 3626 | H | Me | Q84 | OMe | OMe | CH |
| 3627 | Q85 | Me | COOMe | OMe | OMe | CH |
| 3628 | Me | Q85 | Me | Me | Me | CH |
| 3629 | Me | Q85 | Me | OMe | OMe | CH |
| 3630 | Me | Q85 | Me | OMe | OMe | CH |
| 3631 | Me | Me | Q85 | Me | Me | CH |
| 3632 | Me | Me | Q85 | Me | OMe | CH |
| 3633 | Me | Me | Q85 | OMe | OMe | CH |
| 3634 | H | Me | Q85 | OMe | OMe | CH |
| 3635 | Q86 | Me | COOMe | OMe | OMe | CH |
| 3636 | Me | Q86 | Me | Me | Me | CH |
| 3637 | Me | Q86 | Me | Me | OMe | CH |
| 3638 | Me | Q86 | Me | OMe | OMe | CH |
| 3639 | Me | Me | Q86 | Me | Me | CH |
| 3640 | Me | Me | Q86 | Me | OMe | CH |
| 3641 | Me | Me | Q86 | OMe | OMe | CH |
| 3642 | H | Me | Q86 | OMe | OMe | CH |
| 3643 | Q87 | Me | COOMe | OMe | OMe | CH |
| 3644 | Me | Q87 | Me | Me | Me | CH |
| 3645 | Me | Q87 | Me | Me | OMe | CH |
| 3646 | Me | Q87 | Me | OMe | OMe | CH |
| 3647 | Me | Me | Q87 | Me | Me | CH |
| 3648 | Me | Me | Q87 | Me | OMe | CH |
| 3649 | Me | Me | Q87 | OMe | OMe | CH |
| 3650 | H | Me | Q87 | OMe | OMe | CH |
| 3651 | Q88 | Me | COOMe | OMe | OMe | CH |
| 3652 | Me | Q88 | Me | Me | Me | CH |
| 3653 | Me | Q88 | Me | Me | OMe | CH |
| 3654 | Me | Q88 | Me | OMe | OMe | CH |
| 3655 | Me | Me | Q88 | Me | Me | CH |
| 3656 | Me | Me | Q88 | Me | OMe | CH |
| 3657 | Me | Me | Q88 | OMe | OMe | CH |
| 3658 | H | Me | Q88 | OMe | OMe | CH |
| 3659 | Q89 | Me | COOMe | OMe | OMe | CH |
| 3660 | Me | Q89 | Me | Me | Me | CH |
| 3661 | Me | Q89 | Me | Me | OMe | CH |
| 3662 | Me | Q89 | Me | OMe | OMe | CH |
| 3663 | Me | Me | Q89 | Me | Me | CH |
| 3664 | Me | Me | Q89 | Me | OMe | CH |
| 3665 | Me | Me | Q89 | OMe | OMe | CH |
| 3666 | H | Me | Q89 | OMe | OMe | CH |
| 3667 | Q90 | Me | COOMe | Me | Me | CH |
| 3668 | Q90 | Me | COOMe | Me | OMe | CH |
| 3669 | Q90 | Me | COOMe | OMe | OMe | CH |
| 3670 | Q90 | Me | COOMe | Me | OMe | N |
| 3671 | Q90 | Me | COOMe | OMe | OMe | N |
| 3672 | Me | Q90 | Me | Me | Me | CH |
| 3673 | Me | Q90 | Me | Me | OMe | CH |
| 3674 | Me | Q90 | Me | Me | OMe | N |
| 3675 | Me | Me | Q90 | Me | Me | CH |
| 3676 | Me | Me | Q90 | Me | OMe | CH |
| 3677 | Me | Me | Q90 | Me | OMe | N |
| 3678 | H | Me | Q90 | OMe | OMe | CH |
| 3679 | Q91 | Me | COOMe | OMe | OMe | CH |
| 3680 | Me | Q91 | Me | Me | Me | CH |
| 3681 | Me | Q91 | Me | Me | OMe | CH |
| 3682 | Me | Q91 | Me | OMe | OMe | CH |
| 3683 | Me | Me | Q91 | Me | Me | CH |
| 3684 | Me | Me | Q91 | Me | OMe | CH |
| 3685 | Me | Me | Q91 | OMe | OMe | CH |
| 3686 | H | Me | Q91 | OMe | OMe | CH |
| 3687 | Q92 | Me | COOMe | Me | Me | CH |
| 3688 | Q92 | Me | COOMe | Me | OMe | CH |
| 3689 | Q92 | Me | COOMe | OMe | OMe | CH |
| 3690 | Q92 | Me | COOMe | Me | OMe | N |
| 3691 | Q92 | Me | COOMe | OMe | OMe | N |
| 3692 | Me | Q92 | Me | Me | Me | CH |
| 3693 | Me | Q92 | Me | OMe | OMe | CH |
| 3694 | Me | Q92 | Me | Me | OMe | N |
| 3695 | Me | Me | Q92 | Me | OMe | CH |
| 3696 | Me | Me | Q92 | OMe | OMe | CH |
| 3697 | Me | Me | Q92 | Me | OMe | N |
| 3698 | H | Me | Q92 | OMe | OMe | CH |
| 3699 | Q93 | Me | COOMe | OMe | OMe | CH |
| 3700 | Me | Q93 | Me | Me | Me | CH |
| 3701 | Me | Q93 | Me | Me | OMe | CH |
| 3702 | Me | Q93 | Me | OMe | OMe | CH |
| 3703 | Me | Me | Q93 | Me | Me | CH |
| 3704 | Me | Me | Q93 | Me | OMe | CH |
| 3705 | Me | Me | Q93 | OMe | OMe | CH |
| 3706 | H | Me | Q93 | OMe | OMe | CH |
| 3707 | Q94 | Me | COOMe | OMe | OMe | CH |
| 3708 | Me | Q94 | Me | Me | Me | CH |
| 3709 | Me | Q94 | Me | Me | OMe | CH |
| 3710 | Me | Q94 | Me | OMe | OMe | CH |
| 3711 | Me | Me | Q94 | Me | Me | CH |
| 3712 | Me | Me | Q94 | Me | OMe | CH |
| 3713 | Me | Me | Q94 | OMe | OMe | CH |
| 3714 | H | Me | Q94 | OMe | OMe | CH |
| 3715 | Q95 | Me | COOMe | OMe | OMe | CH |
| 3716 | Me | Q95 | Me | Me | Me | CH |
| 3717 | Me | Q95 | Me | Me | OMe | CH |
| 3718 | Me | Q95 | Me | OMe | OMe | CH |
| 3719 | Me | Me | Q95 | Me | Me | CH |
| 3720 | Me | Me | Q95 | Me | OMe | CH |
| 3721 | Me | Me | Q95 | OMe | OMe | CH |
| 3722 | H | Me | Q95 | OMe | OMe | CH |
| 3723 | Q96 | Me | COOMe | OMe | OMe | CH |
| 3724 | Me | Q96 | Me | Me | Me | CH |
| 3725 | Me | Q96 | Me | Me | OMe | CH |
| 3726 | Me | Q96 | Me | OMe | OMe | CH |
| 3727 | Me | Me | Q96 | Me | Me | CH |
| 3728 | Me | Me | Q96 | Me | OMe | CH |
| 3729 | Me | Me | Q96 | OMe | OMe | CH |
| 3730 | H | Me | Q96 | OMe | OMe | CH |
| 3731 | Q97 | Me | COOMe | OMe | OMe | CH |
| 3732 | Me | Q97 | Me | Me | Me | CH |
| 3733 | Me | Q97 | Me | Me | OMe | CH |
| 3734 | Me | Q97 | Me | OMe | OMe | CH |
| 3735 | Me | Me | Q97 | Me | Me | CH |
| 3736 | Me | Me | Q97 | Me | OMe | CH |
| 3737 | Me | Me | Q97 | OMe | OMe | CH |
| 3738 | H | Me | Q97 | OMe | OMe | CH |
| 3739 | Q98 | Me | COOMe | Me | Me | CH |
| 3740 | Q98 | Me | COOMe | Me | OMe | CH |
| 3741 | Q98 | Me | COOMe | OMe | OMe | CH |
| 3742 | Q98 | Me | COOMe | Me | OMe | N |
| 3743 | Q98 | Me | COOMe | OMe | OMe | N |
| 3744 | Me | Q98 | Me | Me | OMe | CH |
| 3745 | Me | Q98 | Me | Me | OMe | CH |
| 3746 | Me | Q98 | Me | Me | OMe | N |
| 3747 | Me | Me | Q98 | Me | OMe | CH |
| 3748 | Me | Me | Q98 | OMe | OMe | CH |
| 3749 | Me | Me | Q98 | Me | OMe | N |
| 3750 | H | Me | Q98 | OMe | OMe | CH |
| 3751 | Q99 | Me | COOMe | OMe | OMe | CH |
| 3752 | Me | Q99 | Me | Me | Me | CH |
| 3753 | Me | Q99 | Me | Me | OMe | CH |
| 3754 | Me | Q99 | Me | OMe | OMe | CH |
| 3755 | Me | Me | Q99 | Me | Me | CH |
| 3756 | Me | Me | Q99 | Me | OMe | CH |
| 3757 | Me | Me | Q99 | OMe | OMe | CH |
| 3758 | H | Me | Q99 | OMe | OMe | CH |
| 3759 | Q100 | Me | COOMe | Me | Me | CH |
| 3760 | Q100 | Me | COOMe | Me | OMe | CH |
| 3761 | Q100 | Me | COOMe | OMe | OMe | CH |
| 3762 | Q100 | Me | COOMe | Me | OMe | N |

TABLE 2-continued

| No. | A | B | D | X | Y | Z |
|---|---|---|---|---|---|---|
| 3763 | Q100 | Me | COOMe | OMe | OMe | N |
| 3764 | Me | Q100 | Me | Me | OMe | CH |
| 3765 | Me | Q100 | Me | OMe | OMe | CH |
| 3766 | Me | Q100 | Me | Me | OMe | N |
| 3767 | Me | Me | Q100 | Me | OMe | CH |
| 3768 | Me | Me | Q100 | OMe | OMe | CH |
| 3769 | Me | Me | Q100 | Me | OMe | N |
| 3770 | H | Me | Q100 | OMe | OMe | CH |
| 3771 | Q101 | Me | COOMe | OMe | OMe | CH |
| 3772 | Me | Q101 | Me | Me | Me | CH |
| 3773 | Me | Q101 | Me | Me | OMe | CH |
| 3774 | Me | Q101 | Me | OMe | OMe | CH |
| 3775 | Me | Me | Q101 | Me | Me | CH |
| 3776 | Me | Me | Q101 | Me | OMe | CH |
| 3777 | Me | Me | Q101 | OMe | OMe | CH |
| 3778 | H | Me | Q101 | OMe | OMe | CH |
| 3779 | Q102 | Me | COOMe | OMe | OMe | CH |
| 3780 | Me | Q102 | Me | Me | Me | CH |
| 3781 | Me | Q102 | Me | Me | OMe | CH |
| 3782 | Me | Q102 | Me | OMe | OMe | CH |
| 3783 | Me | Me | Q102 | Me | Me | CH |
| 3784 | Me | Me | Q102 | Me | OMe | CH |
| 3785 | Me | Me | Q102 | OMe | OMe | CH |
| 3786 | H | Me | Q102 | OMe | OMe | CH |
| 3787 | Q103 | Me | COOMe | OMe | OMe | CH |
| 3788 | Me | Q103 | Me | Me | Me | CH |
| 3789 | Me | Q103 | Me | Me | OMe | CH |
| 3790 | Me | Q103 | Me | OMe | OMe | CH |
| 3791 | Me | Me | Q103 | Me | Me | CH |
| 3792 | Me | Me | Q103 | Me | OMe | CH |
| 3793 | Me | Me | Q103 | OMe | OMe | CH |
| 3794 | H | Me | Q103 | OMe | OMe | CH |
| 3795 | Q104 | Me | COOMe | OMe | OMe | CH |
| 3796 | Me | Q104 | Me | Me | Me | CH |
| 3797 | Me | Q104 | Me | Me | OMe | CH |
| 3798 | Me | Q104 | Me | OMe | OMe | CH |
| 3799 | Me | Me | Q104 | Me | Me | CH |
| 3800 | Me | Me | Q104 | Me | OMe | CH |
| 3801 | Me | Me | Q104 | OMe | OMe | CH |
| 3802 | H | Me | Q104 | OMe | OMe | CH |
| 3803 | Q105 | Me | COOMe | OMe | OMe | CH |
| 3804 | Me | Q105 | Me | Me | Me | CH |
| 3805 | Me | Q105 | Me | Me | OMe | CH |
| 3806 | Me | Q105 | Me | OMe | OMe | CH |
| 3807 | Me | Me | Q105 | Me | Me | CH |
| 3808 | Me | Me | Q105 | Me | OMe | CH |
| 3809 | Me | Me | Q105 | OMe | OMe | CH |
| 3810 | H | Me | Q105 | OMe | OMe | CH |
| 3811 | Q106 | Me | COOMe | OMe | OMe | CH |
| 3812 | Me | Q106 | Me | Me | Me | CH |
| 3813 | Me | Q106 | Me | Me | OMe | CH |
| 3814 | Me | Q106 | Me | OMe | OMe | CH |
| 3815 | Me | Me | Q106 | Me | Me | CH |
| 3816 | Me | Me | Q106 | Me | OMe | CH |
| 3817 | Me | Me | Q106 | OMe | OMe | CH |
| 3818 | H | Me | Q106 | OMe | OMe | CH |
| 3819 | Q107 | Me | COOMe | OMe | OMe | CH |
| 3820 | Me | Q107 | Me | Me | Me | CH |
| 3819 | Me | Q107 | Me | Me | OMe | CH |
| 3820 | Me | Q107 | Me | OMe | OMe | CH |
| 3821 | Me | Me | Q107 | Me | Me | CH |
| 3822 | Me | Me | Q107 | Me | OMe | CH |
| 3823 | Me | Me | Q107 | OMe | OMe | CH |
| 3824 | H | Me | Q107 | OMe | OMe | CH |
| 3825 | Q108 | Me | COOMe | OMe | OMe | CH |
| 3826 | Me | Q108 | Me | Me | Me | CH |
| 3827 | Me | Q108 | Me | Me | OMe | CH |
| 3828 | Me | Q108 | Me | OMe | OMe | CH |
| 3829 | Me | Me | Q108 | Me | Me | CH |
| 3830 | Me | Me | Q108 | Me | OMe | CH |
| 3831 | Me | Me | Q108 | OMe | OMe | CH |
| 3832 | H | Me | Q108 | OMe | OMe | CH |
| 3833 | Q109 | Me | COOMe | OMe | OMe | CH |
| 3834 | Me | Q109 | Me | Me | Me | CH |
| 3835 | Me | Q109 | Me | Me | OMe | CH |
| 3836 | Me | Q109 | Me | OMe | OMe | CH |
| 3837 | Me | Me | Q109 | Me | Me | CH |
| 3838 | Me | Me | Q109 | Me | OMe | CH |
| 3839 | Me | Me | Q109 | OMe | OMe | CH |
| 3840 | H | Me | Q109 | OMe | OMe | CH |
| 3841 | Q110 | Me | COOMe | OMe | OMe | CH |
| 3842 | Me | Q110 | Me | Me | Me | CH |
| 3843 | Me | Q110 | Me | Me | OMe | CH |
| 3844 | Me | Q110 | Me | OMe | OMe | CH |
| 3845 | Me | Me | Q110 | Me | Me | CH |
| 3846 | Me | Me | Q110 | Me | OMe | CH |
| 3847 | Me | Me | Q110 | OMe | OMe | CH |
| 3848 | H | Me | Q110 | OMe | OMe | CH |
| 3849 | Q111 | Me | COOMe | OMe | OMe | CH |
| 3850 | Me | Q111 | Me | Me | Me | CH |
| 3851 | Me | Q111 | Me | Me | OMe | CH |
| 3852 | Me | Q111 | Me | OMe | OMe | CH |
| 3853 | Me | Me | Q111 | Me | Me | CH |
| 3854 | Me | Me | Q111 | Me | OMe | CH |
| 3855 | Me | Me | Q111 | OMe | OMe | CH |
| 3856 | H | Me | Q111 | OMe | OMe | CH |
| 3857 | Q112 | Me | COOMe | OMe | OMe | CH |
| 3858 | Me | Q112 | Me | Me | Me | CH |
| 3859 | Me | Q112 | Me | Me | OMe | CH |
| 3860 | Me | Q112 | Me | OMe | OMe | CH |
| 3861 | Me | Me | Q112 | Me | Me | CH |
| 3862 | Me | Me | Q112 | Me | OMe | CH |
| 3863 | Me | Me | Q112 | OMe | OMe | CH |
| 3864 | H | Me | Q112 | OMe | OMe | CH |
| 3865 | Q113 | Me | COOMe | OMe | OMe | CH |
| 3866 | Me | Q113 | Me | Me | Me | CH |
| 3867 | Me | Q113 | Me | Me | OMe | CH |
| 3868 | Me | Q113 | Me | OMe | OMe | CH |
| 3869 | Me | Me | Q113 | Me | Me | CH |
| 3870 | Me | Me | Q113 | Me | OMe | CH |
| 3871 | Me | Me | Q113 | OMe | OMe | CH |
| 3872 | H | Me | Q113 | OMe | OMe | CH |
| 3873 | Q114 | Me | COOMe | OMe | OMe | CH |
| 3874 | Me | Q114 | Me | Me | Me | CH |
| 3875 | Me | Q114 | Me | Me | OMe | CH |
| 3876 | Me | Q114 | Me | OMe | OMe | CH |
| 3877 | Me | Me | Q114 | Me | Me | CH |
| 3878 | Me | Me | Q114 | Me | OMe | CH |
| 3879 | Me | Me | Q114 | OMe | OMe | CH |
| 3880 | H | Me | Q114 | OMe | OMe | CH |
| 3881 | Q115 | Me | COOMe | OMe | OMe | CH |
| 3882 | Me | Q115 | Me | Me | Me | CH |
| 3883 | Me | Q115 | Me | Me | OMe | CH |
| 3884 | Me | Q115 | Me | OMe | OMe | CH |
| 3885 | Me | Me | Q115 | Me | Me | CH |
| 3886 | Me | Me | Q115 | Me | OMe | CH |
| 3887 | Me | Me | Q115 | OMe | OMe | CH |
| 3888 | H | Me | Q115 | OMe | OMe | CH |
| 3889 | Q116 | Me | COOMe | OMe | OMe | CH |
| 3890 | Me | Q116 | Me | Me | Me | CH |
| 3891 | Me | Q116 | Me | Me | OMe | CH |
| 3892 | Me | Q116 | Me | OMe | OMe | CH |
| 3893 | Me | Me | Q116 | Me | Me | CH |
| 3894 | Me | Me | Q116 | Me | OMe | CH |
| 3895 | Me | Me | Q116 | OMe | OMe | CH |
| 3896 | H | Me | Q116 | OMe | OMe | CH |
| 3897 | Q117 | Me | COOMe | OMe | OMe | CH |
| 3898 | Me | Q117 | Me | Me | Me | CH |

TABLE 2-continued

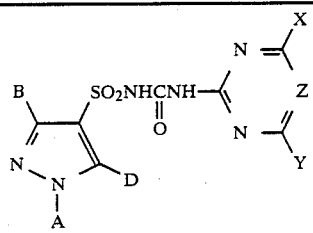

| No. | A | B | D | X | Y | Z |
|---|---|---|---|---|---|---|
| 3899 | Me | Q117 | Me | Me | OMe | CH |
| 3900 | Me | Q117 | Me | OMe | OMe | CH |
| 3901 | Me | Me | Q117 | Me | Me | CH |
| 3902 | Me | Me | Q117 | Me | OMe | CH |
| 3903 | Me | Me | Q117 | OMe | OMe | CH |
| 3904 | H | Me | Q117 | OMe | OMe | CH |
| 3905 | Q118 | Me | COOMe | OMe | OMe | CH |
| 3906 | Me | Q118 | Me | Me | Me | CH |
| 3907 | Me | Q118 | Me | Me | OMe | CH |
| 3908 | Me | Q118 | Me | OMe | OMe | CH |
| 3909 | Me | Me | Q118 | Me | Me | CH |
| 3910 | Me | Me | Q118 | Me | OMe | CH |
| 3911 | Me | Me | Q118 | OMe | OMe | CH |
| 3912 | H | Me | Q118 | OMe | OMe | CH |
| 3913 | Q119 | Me | COOMe | OMe | OMe | CH |
| 3914 | Me | Q119 | Me | Me | Me | CH |
| 3915 | Me | Q119 | Me | Me | OMe | CH |
| 3916 | Me | Q119 | Me | OMe | OMe | CH |
| 3917 | Me | Me | Q119 | Me | Me | CH |
| 3918 | Me | Me | Q119 | Me | OMe | CH |
| 3919 | Me | Me | Q119 | OMe | OMe | CH |
| 3920 | H | Me | Q119 | OMe | OMe | CH |
| 3919 | Q120 | Me | COOMe | OMe | OMe | CH |
| 3920 | Me | Q120 | Me | Me | Me | CH |
| 3921 | Me | Q120 | Me | Me | OMe | CH |
| 3922 | Me | Q120 | Me | OMe | OMe | CH |
| 3923 | Me | Me | Q120 | Me | Me | CH |
| 3924 | Me | Me | Q120 | Me | OMe | CH |
| 3925 | Me | Me | Q120 | OMe | OMe | CH |
| 3926 | H | Me | Q120 | OMe | OMe | CH |
| 3927 | Q121 | Me | COOMe | OMe | OMe | CH |
| 3928 | Me | Q121 | Me | Me | Me | CH |
| 3929 | Me | Q121 | Me | Me | OMe | CH |
| 3930 | Me | Q121 | Me | OMe | OMe | CH |
| 3931 | Me | Me | Q121 | Me | Me | CH |
| 3932 | Me | Me | Q121 | Me | OMe | CH |
| 3933 | Me | Me | Q121 | OMe | OMe | CH |
| 3934 | H | Me | Q121 | OMe | OMe | CH |
| 3935 | Q122 | Me | COOMe | OMe | OMe | CH |
| 3936 | Me | Q122 | Me | Me | Me | CH |
| 3937 | Me | Q122 | Me | Me | OMe | CH |
| 3938 | Me | Q122 | Me | OMe | OMe | CH |
| 3939 | Me | Me | Q122 | Me | Me | CH |
| 3940 | Me | Me | Q122 | Me | OMe | CH |
| 3941 | Me | Me | Q122 | OMe | OMe | CH |
| 3942 | H | Me | Q122 | OMe | OMe | CH |
| 3943 | Q123 | Me | COOMe | OMe | OMe | CH |
| 3944 | Me | Q123 | Me | Me | Me | CH |
| 3945 | Me | Q123 | Me | Me | OMe | CH |
| 3946 | Me | Q123 | Me | OMe | OMe | CH |
| 3947 | Me | Me | Q123 | Me | Me | CH |
| 3948 | Me | Me | Q123 | Me | OMe | CH |
| 3949 | Me | Me | Q123 | OMe | OMe | CH |
| 3950 | H | Me | Q123 | OMe | OMe | CH |
| 3951 | Q124 | Me | COOMe | OMe | OMe | CH |
| 3952 | Me | Q124 | Me | Me | Me | CH |
| 3953 | Me | Q124 | Me | Me | OMe | CH |
| 3954 | Me | Q124 | Me | OMe | OMe | CH |
| 3955 | Me | Me | Q124 | Me | Me | CH |
| 3956 | Me | Me | Q124 | Me | OMe | CH |
| 3957 | Me | Me | Q124 | OMe | OMe | CH |
| 3958 | H | Me | Q124 | OMe | OMe | CH |
| 3959 | Q125 | Me | COOMe | OMe | OMe | CH |
| 3960 | Me | Q125 | Me | Me | Me | CH |
| 3961 | Me | Q125 | Me | Me | OMe | CH |
| 3962 | Me | Q125 | Me | OMe | OMe | CH |
| 3963 | Me | Me | Q125 | Me | Me | CH |
| 3964 | Me | Me | Q125 | Me | OMe | CH |
| 3965 | Me | Me | Q125 | OMe | OMe | CH |
| 3966 | H | Me | Q125 | OMe | OMe | CH |
| 3967 | Q126 | Me | COOMe | OMe | OMe | CH |
| 3968 | Me | Q126 | Me | Me | Me | CH |
| 3969 | Me | Q126 | Me | Me | OMe | CH |
| 3970 | Me | Q126 | Me | OMe | OMe | CH |
| 3971 | Me | Me | Q126 | Me | Me | CH |
| 3972 | Me | Me | Q126 | Me | OMe | CH |
| 3973 | Me | Me | Q126 | OMe | OMe | CH |
| 3974 | H | Me | Q126 | OMe | OMe | CH |
| 3975 | Q127 | Me | COOMe | OMe | OMe | CH |
| 3976 | Me | Q127 | Me | Me | Me | CH |
| 3977 | Me | Q127 | Me | Me | OMe | CH |
| 3978 | Me | Q127 | Me | OMe | OMe | CH |
| 3979 | Me | Me | Q127 | Me | Me | CH |
| 3980 | Me | Me | Q127 | Me | OMe | CH |
| 3981 | Me | Me | Q127 | OMe | OMe | CH |
| 3982 | H | Me | Q127 | OMe | OMe | CH |
| 3983 | Q128 | Me | COOMe | OMe | OMe | CH |
| 3984 | Me | Q128 | Me | Me | Me | CH |
| 3985 | Me | Q128 | Me | Me | OMe | CH |
| 3986 | Me | Q128 | Me | OMe | OMe | CH |
| 3987 | Me | Me | Q128 | Me | Me | CH |
| 3988 | Me | Me | Q128 | Me | OMe | CH |
| 3989 | Me | Me | Q128 | OMe | OMe | CH |
| 3990 | H | Me | Q128 | OMe | OMe | CH |
| 3991 | Q129 | Me | COOMe | OMe | OMe | CH |
| 3992 | Me | Q129 | Me | Me | Me | CH |
| 3993 | Me | Q129 | Me | Me | OMe | CH |
| 3994 | Me | Q129 | Me | OMe | OMe | CH |
| 3995 | Me | Me | Q129 | Me | Me | CH |
| 3996 | Me | Me | Q129 | Me | OMe | CH |
| 3997 | Me | Me | Q129 | OMe | OMe | CH |
| 3998 | H | Me | Q129 | OMe | OMe | CH |
| 3999 | Q130 | Me | COOMe | OMe | OMe | CH |
| 4000 | Me | Q130 | Me | Me | Me | CH |
| 4001 | Me | Q130 | Me | Me | OMe | CH |
| 4002 | Me | Q130 | Me | OMe | OMe | CH |
| 4003 | Me | Me | Q130 | Me | Me | CH |
| 4004 | Me | Me | Q130 | Me | OMe | CH |
| 4005 | Me | Me | Q130 | OMe | OMe | CH |
| 4006 | H | Me | Q130 | OMe | OMe | CH |
| 4007 | Q131 | Me | COOMe | OMe | OMe | CH |
| 4008 | Me | Q131 | Me | Me | Me | CH |
| 4009 | Me | Q131 | Me | Me | OMe | CH |
| 4010 | Me | Q131 | Me | OMe | OMe | CH |
| 4011 | Me | Me | Q131 | Me | Me | CH |
| 4012 | Me | Me | Q131 | Me | OMe | CH |
| 4013 | Me | Me | Q131 | OMe | OMe | CH |
| 4014 | H | Me | Q131 | OMe | OMe | CH |
| 4015 | Q132 | Me | COOMe | OMe | OMe | CH |
| 4016 | Me | Q132 | Me | Me | Me | CH |
| 4017 | Me | Q132 | Me | Me | OMe | CH |
| 4018 | Me | Q132 | Me | OMe | OMe | CH |
| 4019 | Me | Me | Q132 | Me | Me | CH |
| 4020 | Me | Me | Q132 | Me | OMe | CH |
| 4021 | Me | Me | Q132 | OMe | OMe | CH |
| 4022 | H | Me | Q132 | OMe | OMe | CH |

TABLE 3

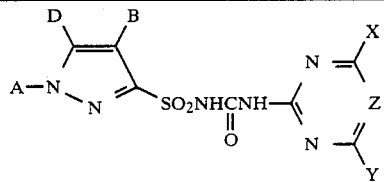

| No. | A | B | D | X | Y | Z |
|---|---|---|---|---|---|---|
| 1421 | Q1 | H | H | Me | OMe | CH |
| 1422 | Q1 | H | H | OMe | OMe | CH |
| 1423 | Q1 | H | H | Me | OMe | N |
| 1424 | Q1 | Me | H | Me | OMe | CH |
| 1425 | Q1 | Me | H | OMe | OMe | CH |
| 1426 | Q1 | Me | H | Me | OMe | N |
| 1427 | Q1 | Cl | H | Me | OMe | CH |
| 1428 | Q1 | Cl | H | OMe | OMe | CH |
| 1429 | Q1 | Cl | H | Me | OMe | N |
| 1430 | Q1 | Br | H | Me | OMe | CH |
| 1431 | Q1 | Br | H | OMe | OMe | CH |
| 1432 | Q1 | Br | H | Me | OMe | N |
| 1433 | Q1 | COOMe | H | Me | OMe | CH |
| 1434 | Q1 | COOMe | H | OMe | OMe | CH |
| 1435 | Q1 | COOMe | H | Me | OMe | N |
| 1436 | Q1 | COOEt | H | Me | OMe | CH |
| 1437 | Q1 | COOEt | H | OMe | OMe | CH |
| 1438 | Q1 | COOEt | H | Me | OMe | N |
| 1439 | Me | Q1 | H | Me | Me | CH |
| 1440 | Me | Q1 | H | Me | OMe | CH |
| 1441 | Me | Q1 | H | OMe | OMe | CH |
| 1442 | Me | Q1 | H | Me | OMe | N |
| 1443 | Me | Q1 | H | OMe | OMe | N |
| 1444 | COMe | Q1 | H | Me | OMe | CH |
| 1445 | COMe | Q1 | H | OMe | OMe | CH |
| 1446 | COMe | Q1 | H | Me | OMe | N |
| 1447 | Q2 | H | H | Me | OMe | CH |
| 1448 | Q2 | H | H | OMe | OMe | CH |
| 1449 | Q2 | H | H | Me | OMe | N |
| 1450 | Q2 | Cl | H | Me | OMe | CH |
| 1451 | Q2 | Cl | H | OMe | OMe | CH |
| 1452 | Q2 | Cl | H | Me | OMe | N |
| 1453 | Q2 | COOMe | H | Me | OMe | CH |
| 1454 | Q2 | COOMe | H | OMe | OMe | CH |
| 1455 | Q2 | COOMe | H | Me | OMe | N |
| 1456 | Me | Q2 | H | Me | OMe | CH |
| 1457 | Me | Q2 | H | OMe | OMe | CH |
| 1458 | Me | Q2 | H | Me | OMe | N |
| 1459 | Q3 | H | H | Me | OMe | CH |
| 1460 | Q3 | H | H | OMe | OMe | CH |
| 1461 | Q3 | H | H | Me | OMe | N |
| 1462 | Q3 | Cl | H | Me | OMe | CH |
| 1463 | Q3 | Cl | H | OMe | OMe | CH |
| 1464 | Q3 | Cl | H | Me | OMe | N |
| 1465 | Q3 | COOMe | H | Me | OMe | CH |
| 1466 | Q3 | COOMe | H | OMe | OMe | CH |
| 1467 | Q3 | COOMe | H | Me | OMe | N |
| 1468 | Me | Q3 | H | Me | OMe | CH |
| 1469 | Me | Q3 | H | OMe | OMe | CH |
| 1470 | Me | Q3 | H | Me | OMe | N |
| 1471 | Q4 | H | H | Me | OMe | CH |
| 1471 | Q4 | H | H | OMe | OMe | CH |
| 1473 | Q4 | H | H | Me | OMe | N |
| 1474 | Q4 | Cl | H | Me | OMe | CH |
| 1475 | Q4 | Cl | H | OMe | OMe | CH |
| 1476 | Q4 | Cl | H | Me | OMe | N |
| 1477 | Q4 | COOMe | H | Me | OMe | CH |
| 1478 | Q4 | COOMe | H | OMe | OMe | CH |
| 1479 | Q4 | COOMe | H | Me | OMe | N |
| 1480 | Me | Q4 | H | Me | OMe | CH |
| 1481 | Me | Q4 | H | OMe | OMe | CH |
| 1482 | Me | Q4 | H | Me | OMe | N |
| 1483 | Q5 | H | H | Me | OMe | CH |
| 1484 | Q5 | H | H | OMe | OMe | CH |
| 1485 | Q5 | H | H | Me | OMe | N |
| 1486 | Q5 | Cl | H | Me | OMe | CH |
| 1487 | Q5 | Cl | H | OMe | OMe | CH |
| 1488 | Q5 | Cl | H | Me | OMe | N |
| 1489 | Q5 | COOMe | H | Me | OMe | CH |
| 1490 | Q5 | COOMe | H | OMe | OMe | CH |
| 1491 | Q5 | COOMe | H | Me | OMe | N |
| 1492 | Me | Q5 | H | Me | OMe | CH |
| 1493 | Me | Q5 | H | OMe | OMe | CH |
| 1494 | Me | Q5 | H | Me | OMe | N |
| 1495 | Q6 | H | H | Me | OMe | CH |
| 1496 | Q6 | H | H | OMe | OMe | CH |
| 1497 | Q6 | H | H | Me | OMe | N |
| 1498 | Q6 | Cl | H | Me | OMe | CH |
| 1499 | Q6 | Cl | H | OMe | OMe | CH |
| 1500 | Q6 | Cl | H | Me | OMe | N |
| 1501 | Q6 | COOMe | H | Me | OMe | CH |
| 1502 | Q6 | COOMe | H | OMe | OMe | CH |
| 1503 | Q6 | COOMe | H | Me | OMe | N |
| 1504 | Me | Q6 | H | Me | OMe | CH |
| 1505 | Me | Q6 | H | OMe | OMe | CH |
| 1506 | Me | Q6 | H | Me | OMe | N |
| 1507 | Q7 | Cl | H | Me | OMe | CH |
| 1508 | Q7 | Cl | H | OMe | OMe | CH |
| 1509 | Q7 | Cl | H | Me | OMe | N |
| 1510 | Q7 | COOMe | H | Me | OMe | CH |
| 1511 | Q7 | COOMe | H | OMe | OMe | CH |
| 1512 | Q7 | COOMe | H | Me | OMe | N |
| 1513 | Me | Q7 | H | Me | OMe | CH |
| 1514 | Me | Q7 | H | OMe | OMe | CH |
| 1515 | Me | Q7 | H | Me | OMe | N |
| 1516 | Q8 | Cl | H | Me | OMe | CH |
| 1517 | Q8 | Cl | H | OMe | OMe | CH |
| 1518 | Q8 | Cl | H | Me | OMe | N |
| 1519 | Q8 | COOMe | H | Me | OMe | CH |
| 1520 | Q8 | COOMe | H | OMe | OMe | CH |
| 1521 | Q8 | COOMe | H | Me | OMe | N |
| 1522 | Me | Q8 | H | Me | OMe | CH |
| 1523 | Me | Q8 | H | OMe | OMe | CH |
| 1524 | Me | Q8 | H | Me | OMe | N |
| 1525 | Q9 | Cl | H | Me | OMe | CH |
| 1526 | Q9 | Cl | H | OMe | OMe | CH |
| 1527 | Q9 | Cl | H | Me | OMe | N |
| 1528 | Q9 | COOMe | H | Me | OMe | CH |
| 1529 | Q9 | COOMe | H | OMe | OMe | CH |
| 1530 | Q9 | COOMe | H | Me | OMe | N |
| 1531 | Me | Q9 | H | Me | OMe | CH |
| 1532 | Me | Q9 | H | OMe | OMe | CH |
| 1533 | Me | Q9 | H | Me | OMe | N |
| 1534 | Q10 | Cl | H | Me | OMe | CH |
| 1535 | Q10 | Cl | H | OMe | OMe | CH |
| 1536 | Q10 | Cl | H | Me | OMe | N |
| 1537 | Q10 | COOMe | H | Me | OMe | CH |
| 1538 | Q10 | COOMe | H | OMe | OMe | CH |
| 1539 | Q10 | COOMe | H | Me | OMe | N |
| 1540 | Me | Q10 | H | Me | OMe | CH |
| 1541 | Me | Q10 | H | OMe | OMe | CH |
| 1542 | Me | Q10 | H | Me | OMe | N |
| 1543 | Q11 | H | H | Me | OMe | CH |
| 1544 | Q11 | H | H | OMe | OMe | CH |
| 1545 | Q11 | H | H | Me | OMe | N |
| 1546 | Q11 | Cl | H | Me | OMe | CH |
| 1547 | Q11 | Cl | H | OMe | OMe | CH |
| 1548 | Q11 | Cl | H | Me | OMe | N |
| 1549 | Q11 | COOMe | H | Me | OMe | CH |
| 1550 | Q11 | COOMe | H | OMe | OMe | CH |
| 1551 | Q11 | COOMe | H | Me | OMe | N |
| 1552 | Me | Q11 | H | Me | OMe | CH |
| 1553 | Me | Q11 | H | OMe | OMe | CH |
| 1554 | Me | Q11 | H | Me | OMe | N |
| 1555 | Q12 | H | H | Me | OMe | CH |
| 1556 | Q12 | H | H | OMe | OMe | CH |
| 1557 | Q12 | H | H | Me | OMe | N |
| 1558 | Q12 | Me | H | Me | OMe | CH |
| 1559 | Q12 | Me | H | OMe | OMe | CH |
| 1560 | Q12 | Me | H | Me | OMe | N |
| 1561 | Q12 | Cl | H | Me | OMe | CH |
| 1562 | Q12 | Cl | H | OMe | OMe | CH |

TABLE 3-continued

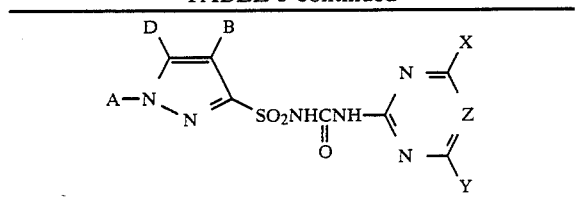

| No. | A | B | D | X | Y | Z |
|---|---|---|---|---|---|---|
| 1563 | Q12 | Cl | H | Me | OMe | N |
| 1564 | Q12 | Br | H | Me | OMe | CH |
| 1565 | Q12 | Br | H | OMe | OMe | CH |
| 1566 | Q12 | Br | H | Me | OMe | N |
| 1567 | Q12 | COOMe | H | Me | OMe | CH |
| 1568 | Q12 | COOMe | H | OMe | OMe | CH |
| 1569 | Q12 | COOMe | H | Me | OMe | N |
| 1570 | Q12 | COOEt | H | Me | OMe | CH |
| 1571 | Q12 | COOEt | H | OMe | OMe | CH |
| 1572 | Q12 | COOEt | H | Me | OMe | N |
| 1573 | Me | Q12 | H | Me | Me | CH |
| 1574 | Me | Q12 | H | Me | OMe | CH |
| 1575 | Me | Q12 | H | OMe | OMe | CH |
| 1576 | Me | Q12 | H | Me | OMe | N |
| 1577 | Me | Q12 | H | OMe | OMe | N |
| 1578 | COMe | Q12 | H | Me | OMe | CH |
| 1579 | COMe | Q12 | H | OMe | OMe | CH |
| 1580 | COMe | Q12 | H | Me | OMe | N |
| 1581 | Q13 | H | H | Me | OMe | CH |
| 1582 | Q13 | H | H | OMe | OMe | CH |
| 1583 | Q13 | H | H | Me | OMe | N |
| 1584 | Q13 | Cl | H | Me | OMe | CH |
| 1585 | Q13 | Cl | H | OMe | OMe | CH |
| 1586 | Q13 | Cl | H | Me | OMe | N |
| 1587 | Q13 | COOMe | H | Me | OMe | CH |
| 1588 | Q13 | COOMe | H | OMe | OMe | CH |
| 1589 | Q13 | COOMe | H | Me | OMe | N |
| 1590 | Me | Q13 | H | Me | OMe | CH |
| 1591 | Me | Q13 | H | OMe | OMe | CH |
| 1592 | Me | Q13 | H | Me | OMe | N |
| 1593 | Q14 | H | H | Me | OMe | CH |
| 1594 | Q14 | H | H | OMe | OMe | CH |
| 1595 | Q14 | H | H | Me | OMe | N |
| 1596 | Q14 | Cl | H | Me | OMe | CH |
| 1597 | Q14 | Cl | H | OMe | OMe | CH |
| 1598 | Q14 | Cl | H | Me | OMe | N |
| 1599 | Q14 | COOMe | H | Me | OMe | CH |
| 1600 | Q14 | COOMe | H | OMe | OMe | CH |
| 1601 | Q14 | COOMe | H | Me | OMe | N |
| 1602 | Me | Q14 | H | Me | OMe | CH |
| 1603 | Me | Q14 | H | OMe | OMe | CH |
| 1604 | Me | Q14 | H | Me | OMe | N |
| 1605 | Q15 | Cl | H | Me | OMe | CH |
| 1606 | Q15 | Cl | H | OMe | OMe | CH |
| 1607 | Q15 | Cl | H | Me | OMe | N |
| 1608 | Q15 | COOMe | H | Me | OMe | CH |
| 1609 | Q15 | COOMe | H | OMe | OMe | CH |
| 1610 | Q15 | COOMe | H | Me | OMe | N |
| 1611 | Me | Q15 | H | Me | OMe | CH |
| 1612 | Me | Q15 | H | OMe | OMe | CH |
| 1613 | Me | Q15 | H | Me | OMe | N |
| 1614 | Q16 | Cl | H | Me | OMe | CH |
| 1615 | Q16 | Cl | H | OMe | OMe | CH |
| 1616 | Q16 | Cl | H | Me | OMe | N |
| 1617 | Q16 | COOMe | H | Me | OMe | CH |
| 1618 | Q16 | COOMe | H | OMe | OMe | CH |
| 1619 | Q16 | COOMe | H | Me | OMe | N |
| 1620 | Me | Q16 | H | Me | OMe | CH |
| 1621 | Me | Q16 | H | OMe | OMe | CH |
| 1622 | Me | Q16 | H | Me | OMe | N |
| 1623 | Q17 | Cl | H | Me | OMe | CH |
| 1624 | Q17 | Cl | H | OMe | OMe | CH |
| 1625 | Q17 | Cl | H | Me | OMe | N |
| 1626 | Q17 | COOMe | H | Me | OMe | CH |
| 1627 | Q17 | COOMe | H | OMe | OMe | CH |
| 1628 | Q17 | COOMe | H | Me | OMe | N |
| 1629 | Me | Q17 | H | Me | OMe | CH |
| 1630 | Me | Q17 | H | OMe | OMe | CH |
| 1631 | Me | Q17 | H | Me | OMe | N |
| 1632 | Q18 | Cl | H | Me | OMe | CH |
| 1633 | Q18 | Cl | H | OMe | OMe | CH |
| 1634 | Q18 | Cl | H | Me | OMe | N |
| 1635 | Q18 | COOMe | H | Me | OMe | CH |
| 1636 | Q18 | COOMe | H | OMe | OMe | CH |
| 1637 | Q18 | COOMe | H | Me | OMe | N |
| 1638 | Me | Q18 | H | Me | OMe | CH |
| 1639 | Me | Q18 | H | OMe | OMe | CH |
| 1640 | Me | Q18 | H | Me | OMe | N |
| 1641 | Q19 | H | H | Me | OMe | CH |
| 1642 | Q19 | H | H | OMe | OMe | CH |
| 1643 | Q19 | H | H | Me | OMe | N |
| 1644 | Q19 | Cl | H | Me | OMe | CH |
| 1645 | Q19 | Cl | H | OMe | OMe | CH |
| 1646 | Q19 | Cl | H | Me | OMe | N |
| 1647 | Q19 | COOMe | H | Me | OMe | CH |
| 1648 | Q19 | COOMe | H | OMe | OMe | CH |
| 1649 | Q19 | COOMe | H | Me | OMe | N |
| 1650 | Me | Q19 | H | Me | OMe | CH |
| 1651 | Me | Q19 | H | OMe | OMe | CH |
| 1652 | Me | Q19 | H | Me | OMe | N |
| 1653 | Q20 | Cl | H | Me | OMe | CH |
| 1654 | Q20 | Cl | H | OMe | OMe | CH |
| 1655 | Q20 | Cl | H | Me | OMe | N |
| 1656 | Q20 | COOMe | H | Me | OMe | CH |
| 1657 | Q20 | COOMe | H | OMe | OMe | CH |
| 1658 | Q20 | COOMe | H | Me | OMe | N |
| 1659 | Me | Q20 | H | Me | OMe | CH |
| 1660 | Me | Q20 | H | OMe | OMe | CH |
| 1661 | Me | Q20 | H | Me | OMe | N |
| 1662 | Q21 | Cl | H | Me | OMe | CH |
| 1663 | Q21 | Cl | H | OMe | OMe | CH |
| 1664 | Q21 | Cl | H | Me | OMe | N |
| 1665 | Q21 | COOMe | H | Me | OMe | CH |
| 1666 | Q21 | COOMe | H | OMe | OMe | CH |
| 1667 | Q21 | COOMe | H | Me | OMe | N |
| 1668 | Me | Q21 | H | Me | OMe | CH |
| 1669 | Me | Q21 | H | OMe | OMe | CH |
| 1670 | Me | Q21 | H | Me | OMe | N |
| 1671 | Q22 | H | H | Me | OMe | CH |
| 1672 | Q22 | H | H | OMe | OMe | CH |
| 1673 | Q22 | H | H | Me | OMe | N |
| 1674 | Q22 | Me | H | Me | OMe | CH |
| 1675 | Q22 | Me | H | OMe | OMe | CH |
| 1676 | Q22 | Me | H | Me | OMe | N |
| 1677 | Q22 | Cl | H | Me | OMe | CH |
| 1678 | Q22 | Cl | H | OMe | OMe | CH |
| 1679 | Q22 | Cl | H | Me | OMe | N |
| 1680 | Q22 | Br | H | Me | OMe | CH |
| 1681 | Q22 | Br | H | OMe | OMe | CH |
| 1682 | Q22 | Br | H | Me | OMe | N |
| 1683 | Q22 | COOMe | H | Me | OMe | CH |
| 1684 | Q22 | COOMe | H | OMe | OMe | CH |
| 1685 | Q22 | COOMe | H | Me | OMe | N |
| 1686 | Q22 | COOEt | H | Me | OMe | CH |
| 1687 | Q22 | COOEt | H | OMe | OMe | CH |
| 1688 | Q22 | COOEt | H | Me | OMe | N |
| 1689 | Me | Q22 | H | Me | Me | CH |
| 1690 | Me | Q22 | H | Me | OMe | CH |
| 1691 | Me | Q22 | H | OMe | OMe | CH |
| 1692 | Me | Q22 | H | Me | OMe | N |
| 1693 | Me | Q22 | H | OMe | OMe | N |
| 1694 | COMe | Q22 | H | Me | OMe | CH |
| 1695 | COMe | Q22 | H | OMe | OMe | CH |
| 1696 | COMe | Q22 | H | Me | OMe | N |
| 1697 | Q23 | H | H | Me | OMe | CH |
| 1698 | Q23 | H | H | OMe | OMe | CH |
| 1699 | Q23 | H | H | Me | OMe | N |
| 1700 | Q23 | Cl | H | Me | OMe | CH |
| 1701 | Q23 | Cl | H | OMe | OMe | CH |
| 1702 | Q23 | Cl | H | Me | OMe | N |
| 1703 | Q23 | COOMe | H | Me | OMe | CH |
| 1704 | Q23 | COOMe | H | OMe | OMe | CH |

TABLE 3-continued

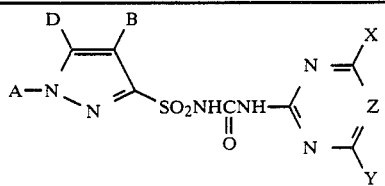
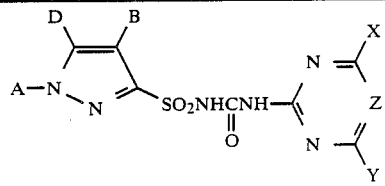

| No. | A | B | D | X | Y | Z |
|---|---|---|---|---|---|---|
| 1705 | Q23 | COOMe | H | Me | OMe | N |
| 1706 | Me | Q23 | H | Me | OMe | CH |
| 1707 | Me | Q23 | H | OMe | OMe | CH |
| 1708 | Me | Q23 | H | Me | OMe | N |
| 1709 | Q24 | H | H | Me | OMe | CH |
| 1710 | Q24 | H | H | OMe | OMe | CH |
| 1711 | Q24 | H | H | Me | OMe | N |
| 1712 | Q24 | Cl | H | Me | OMe | CH |
| 1713 | Q24 | Cl | H | OMe | OMe | CH |
| 1714 | Q24 | Cl | H | Me | OMe | N |
| 1715 | Q24 | COOMe | H | Me | OMe | CH |
| 1716 | Q24 | COOMe | H | OMe | OMe | CH |
| 1717 | Q24 | COOMe | H | Me | OMe | N |
| 1718 | Me | Q24 | H | Me | OMe | CH |
| 1719 | Me | Q24 | H | OMe | OMe | CH |
| 1720 | Me | Q24 | H | Me | OMe | N |
| 1721 | Q25 | H | H | Me | OMe | CH |
| 1722 | Q25 | H | H | OMe | OMe | CH |
| 1723 | Q25 | H | H | Me | OMe | N |
| 1724 | Q25 | Cl | H | Me | OMe | CH |
| 1725 | Q25 | Cl | H | OMe | OMe | CH |
| 1726 | Q25 | Cl | H | Me | OMe | N |
| 1727 | Q25 | COOMe | H | Me | OMe | CH |
| 1728 | Q25 | COOMe | H | OMe | OMe | CH |
| 1729 | Q25 | COOMe | H | Me | OMe | N |
| 1730 | Me | Q25 | H | Me | OMe | CH |
| 1731 | Me | Q25 | H | OMe | OMe | CH |
| 1732 | Me | Q25 | H | Me | OMe | N |
| 1733 | Q26 | Cl | H | Me | OMe | CH |
| 1734 | Q26 | Cl | H | OMe | OMe | CH |
| 1735 | Q26 | Cl | H | Me | OMe | N |
| 1736 | Q26 | COOMe | H | Me | OMe | CH |
| 1737 | Q26 | COOMe | H | OMe | OMe | CH |
| 1738 | Q26 | COOMe | H | Me | OMe | N |
| 1739 | Me | Q26 | H | Me | OMe | CH |
| 1740 | Me | Q26 | H | OMe | OMe | CH |
| 1741 | Me | Q26 | H | Me | OMe | N |
| 1742 | Q27 | Cl | H | Me | OMe | CH |
| 1743 | Q27 | Cl | H | OMe | OMe | CH |
| 1744 | Q27 | Cl | H | Me | OMe | N |
| 1745 | Q27 | COOMe | H | Me | OMe | CH |
| 1746 | Q27 | COOMe | H | OMe | OMe | CH |
| 1747 | Q27 | COOMe | H | Me | OMe | N |
| 1748 | Me | Q47 | H | Me | OMe | CH |
| 1749 | Me | Q47 | H | OMe | OMe | CH |
| 1750 | Me | Q47 | H | Me | OMe | N |
| 1751 | Q28 | Cl | H | Me | OMe | CH |
| 1752 | Q28 | Cl | H | OMe | OMe | CH |
| 1753 | Q28 | Cl | H | Me | OMe | N |
| 1754 | Q28 | COOMe | H | Me | OMe | CH |
| 1755 | Q28 | COOMe | H | OMe | OMe | CH |
| 1756 | Q28 | COOMe | H | Me | OMe | N |
| 1757 | Me | Q28 | H | Me | OMe | CH |
| 1758 | Me | Q28 | H | OMe | OMe | CH |
| 1759 | Me | Q28 | H | Me | OMe | N |
| 1760 | Q29 | Cl | H | Me | OMe | CH |
| 1761 | Q29 | Cl | H | OMe | OMe | CH |
| 1762 | Q29 | Cl | H | Me | OMe | N |
| 1763 | Q29 | COOMe | H | Me | OMe | CH |
| 1764 | Q29 | COOMe | H | OMe | OMe | CH |
| 1765 | Q29 | COOMe | H | Me | OMe | N |
| 1766 | Me | Q29 | H | Me | OMe | CH |
| 1767 | Me | Q29 | H | OMe | OMe | CH |
| 1768 | Me | Q29 | H | Me | OMe | N |
| 1769 | Q30 | Cl | H | Me | OMe | CH |
| 1770 | Q30 | Cl | H | OMe | OMe | CH |
| 1771 | Q30 | Cl | H | Me | OMe | N |
| 1772 | Q30 | COOMe | H | Me | OMe | CH |
| 1773 | Q30 | COOMe | H | OMe | OMe | CH |
| 1774 | Q30 | COOMe | H | Me | OMe | N |
| 1775 | Me | Q30 | H | Me | OMe | CH |
| 1776 | Me | Q30 | H | OMe | OMe | CH |
| 1777 | Me | Q30 | H | Me | OMe | N |
| 1778 | Q31 | Cl | H | Me | OMe | CH |
| 1779 | Q31 | Cl | H | OMe | OMe | CH |
| 1780 | Q31 | Cl | H | Me | OMe | N |
| 1781 | Q31 | COOMe | H | Me | OMe | CH |
| 1782 | Q31 | COOMe | H | OMe | OMe | CH |
| 1783 | Q31 | COOMe | H | Me | OMe | N |
| 1784 | Me | Q31 | H | Me | OMe | CH |
| 1785 | Me | Q31 | H | OMe | OMe | CH |
| 1786 | Me | Q31 | H | Me | OMe | N |
| 1787 | Q32 | H | H | Me | OMe | CH |
| 1788 | Q32 | H | H | OMe | OMe | CH |
| 1789 | Q32 | H | H | Me | OMe | N |
| 1790 | Q32 | Cl | H | Me | OMe | CH |
| 1791 | Q32 | Cl | H | OMe | OMe | CH |
| 1792 | Q32 | Cl | H | Me | OMe | N |
| 1793 | Q32 | COOMe | H | Me | OMe | CH |
| 1794 | Q32 | COOMe | H | OMe | OMe | CH |
| 1795 | Q32 | COOMe | H | Me | OMe | N |
| 1796 | Me | Q32 | H | Me | OMe | CH |
| 1797 | Me | Q32 | H | OMe | OMe | CH |
| 1798 | Me | Q32 | H | Me | OMe | N |
| 1799 | Q33 | Cl | H | Me | OMe | CH |
| 1800 | Q33 | Cl | H | OMe | OMe | CH |
| 1801 | Q33 | Cl | H | Me | OMe | N |
| 1802 | Q33 | COOMe | H | Me | OMe | CH |
| 1803 | Q33 | COOMe | H | OMe | OMe | CH |
| 1804 | Q33 | COOMe | H | Me | OMe | N |
| 1805 | Me | Q33 | H | Me | OMe | CH |
| 1806 | Me | Q33 | H | OMe | OMe | CH |
| 1807 | Me | Q33 | H | Me | OMe | N |
| 1808 | Q34 | Cl | H | Me | OMe | CH |
| 1809 | Q34 | Cl | H | OMe | OMe | CH |
| 1810 | Q34 | Cl | H | Me | OMe | N |
| 1811 | Q34 | COOMe | H | Me | OMe | CH |
| 1812 | Q34 | COOMe | H | OMe | OMe | CH |
| 1813 | Q34 | COOMe | H | Me | OMe | N |
| 1814 | Me | Q34 | H | Me | OMe | CH |
| 1815 | Me | Q34 | H | OMe | OMe | CH |
| 1816 | Me | Q34 | H | Me | OMe | N |
| 1817 | Q35 | Cl | H | Me | OMe | CH |
| 1818 | Q35 | Cl | H | OMe | OMe | CH |
| 1819 | Q35 | Cl | H | Me | OMe | N |
| 1820 | Q35 | COOMe | H | Me | OMe | CH |
| 1821 | Q35 | COOMe | H | OMe | OMe | CH |
| 1822 | Q35 | COOMe | H | Me | OMe | N |
| 1823 | Me | Q35 | H | Me | OMe | CH |
| 1824 | Me | Q35 | H | OMe | OMe | CH |
| 1825 | Me | Q35 | H | Me | OMe | N |
| 1826 | Q36 | Cl | H | Me | OMe | CH |
| 1827 | Q36 | Cl | H | OMe | OMe | CH |
| 1828 | Q36 | Cl | H | Me | OMe | N |
| 1829 | Q36 | COOMe | H | Me | OMe | CH |
| 1830 | Q36 | COOMe | H | OMe | OMe | CH |
| 1831 | Q36 | COOMe | H | Me | OMe | N |
| 1832 | Me | Q36 | H | Me | OMe | CH |
| 1833 | Me | Q36 | H | OMe | OMe | CH |
| 1834 | Me | Q36 | H | Me | OMe | N |
| 1835 | Q37 | Cl | H | Me | OMe | CH |
| 1836 | Q37 | Cl | H | OMe | OMe | CH |
| 1837 | Q37 | Cl | H | Me | OMe | N |
| 1838 | Q37 | COOMe | H | Me | OMe | CH |
| 1839 | Q37 | COOMe | H | OMe | OMe | CH |
| 1840 | Q37 | COOMe | H | Me | OMe | N |
| 1841 | Me | Q37 | H | Me | OMe | CH |
| 1842 | Me | Q37 | H | OMe | OMe | CH |
| 1843 | Me | Q37 | H | Me | OMe | N |
| 1844 | Q38 | Cl | H | Me | OMe | CH |
| 1845 | Q38 | Cl | H | OMe | OMe | CH |
| 1846 | Q38 | Cl | H | Me | OMe | N |

TABLE 3-continued

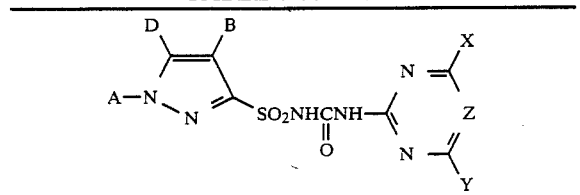

| No. | A | B | D | X | Y | Z |
|---|---|---|---|---|---|---|
| 1847 | $Q_{38}$ | COOMe | H | Me | OMe | CH |
| 1848 | $Q_{38}$ | COOMe | H | OMe | OMe | CH |
| 1849 | $Q_{38}$ | COOMe | H | Me | OMe | N |
| 1850 | Me | $Q_{38}$ | H | Me | OMe | CH |
| 1851 | Me | $Q_{38}$ | H | OMe | OMe | CH |
| 1852 | Me | $Q_{38}$ | H | Me | OMe | N |
| 1853 | $Q_{39}$ | Cl | H | Me | OMe | CH |
| 1854 | $Q_{39}$ | Cl | H | OMe | OMe | CH |
| 1855 | $Q_{39}$ | Cl | H | Me | OMe | N |
| 1856 | $Q_{39}$ | COOMe | H | Me | OMe | CH |
| 1857 | $Q_{39}$ | COOMe | H | OMe | OMe | CH |
| 1858 | $Q_{39}$ | COOMe | H | Me | OMe | N |
| 1859 | Me | $Q_{39}$ | H | Me | OMe | CH |
| 1860 | Me | $Q_{39}$ | H | OMe | OMe | CH |
| 1861 | Me | $Q_{39}$ | H | Me | OMe | N |
| 1862 | $Q_{40}$ | Cl | H | Me | OMe | CH |
| 1863 | $Q_{40}$ | Cl | H | OMe | OMe | CH |
| 1864 | $Q_{40}$ | Cl | H | Me | OMe | N |
| 1865 | $Q_{40}$ | COOMe | H | Me | OMe | CH |
| 1866 | $Q_{40}$ | COOMe | H | OMe | OMe | CH |
| 1867 | $Q_{40}$ | COOMe | H | Me | OMe | N |
| 1868 | Me | $Q_{40}$ | H | Me | OMe | CH |
| 1869 | Me | $Q_{40}$ | H | OMe | OMe | CH |
| 1870 | Me | $Q_{40}$ | H | Me | OMe | N |
| 1871 | $Q_{41}$ | Cl | H | Me | OMe | CH |
| 1872 | $Q_{41}$ | Cl | H | OMe | OMe | CH |
| 1873 | $Q_{41}$ | Cl | H | Me | OMe | N |
| 1874 | $Q_{41}$ | COOMe | H | Me | OMe | CH |
| 1875 | $Q_{41}$ | COOMe | H | OMe | OMe | CH |
| 1876 | $Q_{41}$ | COOMe | H | Me | OMe | N |
| 1877 | Me | $Q_{41}$ | H | Me | OMe | CH |
| 1878 | Me | $Q_{41}$ | H | OMe | OMe | CH |
| 1879 | Me | $Q_{41}$ | H | Me | OMe | N |
| 1880 | $Q_{42}$ | Cl | H | Me | OMe | CH |
| 1881 | $Q_{42}$ | Cl | H | OMe | OMe | CH |
| 1882 | $Q_{42}$ | Cl | H | Me | OMe | N |
| 1883 | $Q_{42}$ | COOMe | H | Me | OMe | CH |
| 1884 | $Q_{42}$ | COOMe | H | OMe | OMe | CH |
| 1885 | $Q_{42}$ | COOMe | H | Me | OMe | N |
| 1886 | Me | $Q_{42}$ | H | Me | OMe | CH |
| 1887 | Me | $Q_{42}$ | H | OMe | OMe | CH |
| 1888 | Me | $Q_{42}$ | H | Me | OMe | N |
| 1889 | $Q_{43}$ | Cl | H | Me | OMe | CH |
| 1890 | $Q_{43}$ | Cl | H | OMe | OMe | CH |
| 1891 | $Q_{43}$ | Cl | H | Me | OMe | N |
| 1892 | $Q_{43}$ | COOMe | H | Me | OMe | CH |
| 1893 | $Q_{43}$ | COOMe | H | OMe | OMe | CH |
| 1894 | $Q_{43}$ | COOMe | H | Me | OMe | N |
| 1895 | Me | $Q_{43}$ | H | Me | OMe | CH |
| 1896 | Me | $Q_{43}$ | H | OMe | OMe | CH |
| 1897 | Me | $Q_{43}$ | H | Me | OMe | N |
| 1898 | $Q_{44}$ | Cl | H | Me | OMe | CH |
| 1899 | $Q_{44}$ | Cl | H | OMe | OMe | CH |
| 1900 | $Q_{44}$ | Cl | H | Me | OMe | N |
| 1901 | $Q_{44}$ | COOMe | H | Me | OMe | CH |
| 1902 | $Q_{44}$ | COOMe | H | OMe | OMe | CH |
| 1903 | $Q_{44}$ | COOMe | H | Me | OMe | N |
| 1904 | Me | $Q_{44}$ | H | Me | OMe | CH |
| 1905 | Me | $Q_{44}$ | H | OMe | OMe | CH |
| 1906 | Me | $Q_{44}$ | H | Me | OMe | N |
| 1907 | $Q_{45}$ | Cl | H | Me | OMe | CH |
| 1908 | $Q_{45}$ | Cl | H | OMe | OMe | CH |
| 1909 | $Q_{45}$ | Cl | H | Me | OMe | N |
| 1910 | $Q_{45}$ | COOMe | H | Me | OMe | CH |
| 1911 | $Q_{45}$ | COOMe | H | OMe | OMe | CH |
| 1912 | $Q_{45}$ | COOMe | H | Me | OMe | N |
| 1913 | Me | $Q_{45}$ | H | Me | OMe | CH |
| 1914 | Me | $Q_{45}$ | H | OMe | OMe | CH |
| 1915 | Me | $Q_{45}$ | H | Me | OMe | N |
| 1916 | $Q_{46}$ | Cl | H | Me | OMe | CH |
| 1917 | $Q_{46}$ | Cl | H | OMe | OMe | CH |
| 1918 | $Q_{46}$ | Cl | H | Me | OMe | N |
| 1919 | $Q_{46}$ | COOMe | H | Me | OMe | CH |
| 1920 | $Q_{46}$ | COOMe | H | OMe | OMe | CH |
| 1921 | $Q_{46}$ | COOMe | H | Me | OMe | N |
| 1922 | Me | $Q_{46}$ | H | Me | OMe | CH |
| 1923 | Me | $Q_{46}$ | H | OMe | OMe | CH |
| 1924 | Me | $Q_{46}$ | H | Me | OMe | N |
| 1925 | $Q_{47}$ | Cl | H | Me | OMe | CH |
| 1926 | $Q_{47}$ | Cl | H | OMe | OMe | CH |
| 1927 | $Q_{47}$ | Cl | H | Me | OMe | N |
| 1928 | $Q_{47}$ | COOMe | H | Me | OMe | CH |
| 1929 | $Q_{47}$ | COOMe | H | OMe | OMe | CH |
| 1930 | $Q_{47}$ | COOMe | H | Me | OMe | N |
| 1931 | Me | $Q_{47}$ | H | Me | OMe | CH |
| 1932 | Me | $Q_{47}$ | H | OMe | OMe | CH |
| 1933 | Me | $Q_{47}$ | H | Me | OMe | N |
| 4023 | $Q_{48}$ | Br | H | Me | OMe | CH |
| 4024 | $Q_{48}$ | Br | H | OMe | OMe | CH |
| 4025 | $Q_{48}$ | Br | H | Me | OMe | N |
| 4026 | Me | $Q_{48}$ | H | OMe | OMe | CH |
| 4027 | $Q_{49}$ | Br | H | Me | OMe | CH |
| 4028 | $Q_{49}$ | Br | H | OMe | OMe | CH |
| 4029 | $Q_{49}$ | Br | H | Me | OMe | N |
| 4030 | Me | $Q_{49}$ | H | OMe | OMe | CH |
| 4031 | $Q_{48}$ | Br | H | Me | OMe | CH |
| 4032 | $Q_{48}$ | Br | H | OMe | OMe | CH |
| 4033 | $Q_{48}$ | Br | H | Me | OMe | N |
| 4034 | Me | $Q_{48}$ | H | OMe | OMe | CH |
| 4035 | $Q_{50}$ | Br | H | Me | OMe | CH |
| 4036 | $Q_{50}$ | Br | H | OMe | OMe | CH |
| 4037 | $Q_{50}$ | Br | H | Me | OMe | N |
| 4038 | Me | $Q_{50}$ | H | OMe | OMe | CH |
| 4039 | $Q_{51}$ | Br | H | Me | OMe | CH |
| 4040 | $Q_{51}$ | Br | H | OMe | OMe | CH |
| 4041 | $Q_{51}$ | Br | H | Me | OMe | N |
| 4042 | Me | $Q_{51}$ | H | OMe | OMe | CH |
| 4043 | $Q_{52}$ | Br | H | Me | OMe | CH |
| 4044 | $Q_{52}$ | Br | H | OMe | OMe | CH |
| 4045 | $Q_{52}$ | Br | H | Me | OMe | N |
| 4046 | Me | $Q_{52}$ | H | OMe | OMe | CH |
| 4047 | $Q_{53}$ | Br | H | Me | OMe | CH |
| 4048 | $Q_{53}$ | Br | H | OMe | OMe | CH |
| 4049 | $Q_{53}$ | Br | H | Me | OMe | N |
| 4050 | Me | $Q_{53}$ | H | OMe | OMe | CH |
| 4051 | $Q_{54}$ | Br | H | Me | OMe | CH |
| 4052 | $Q_{54}$ | Br | H | OMe | OMe | CH |
| 4053 | $Q_{54}$ | Br | H | Me | OMe | N |
| 4054 | Me | $Q_{54}$ | H | OMe | OMe | CH |
| 4055 | $Q_{55}$ | Br | H | Me | OMe | CH |
| 4056 | $Q_{55}$ | Br | H | OMe | OMe | CH |
| 4057 | $Q_{55}$ | Br | H | Me | OMe | N |
| 4058 | Me | $Q_{55}$ | H | OMe | OMe | CH |
| 4059 | $Q_{56}$ | Br | H | Me | OMe | CH |
| 4060 | $Q_{56}$ | Br | H | OMe | OMe | CH |
| 4061 | $Q_{56}$ | Br | H | Me | OMe | N |
| 4062 | Me | $Q_{56}$ | H | OMe | OMe | CH |
| 4063 | $Q_{57}$ | Br | H | Me | OMe | CH |
| 4064 | $Q_{57}$ | Br | H | OMe | OMe | CH |
| 4065 | $Q_{57}$ | Br | H | Me | OMe | N |
| 4066 | Me | $Q_{57}$ | H | OMe | OMe | CH |
| 4067 | $Q_{58}$ | Br | H | Me | OMe | CH |
| 4068 | $Q_{58}$ | Br | H | OMe | OMe | CH |
| 4069 | $Q_{58}$ | Br | H | Me | OMe | N |
| 4070 | Me | $Q_{58}$ | H | OMe | OMe | CH |
| 4071 | $Q_{59}$ | Br | H | Me | OMe | CH |
| 4072 | $Q_{59}$ | Br | H | OMe | OMe | CH |
| 4073 | $Q_{59}$ | Br | H | Me | OMe | N |
| 4074 | Me | $Q_{59}$ | H | OMe | OMe | CH |
| 4075 | $Q_{60}$ | Br | H | Me | OMe | CH |
| 4076 | $Q_{60}$ | Br | H | OMe | OMe | CH |
| 4077 | $Q_{60}$ | Br | H | Me | OMe | N |

TABLE 3-continued

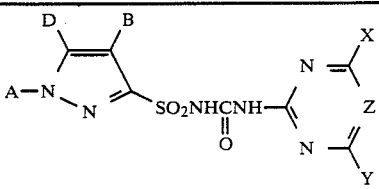
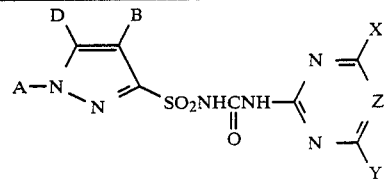

| No. | A | B | D | X | Y | Z |
|---|---|---|---|---|---|---|
| 4078 | Me | $Q_{60}$ | H | OMe | OMe | CH |
| 4079 | $Q_{61}$ | Br | H | Me | OMe | CH |
| 4080 | $Q_{61}$ | Br | H | OMe | OMe | CH |
| 4081 | $Q_{61}$ | Br | H | Me | OMe | N |
| 4082 | Me | $Q_{61}$ | H | OMe | OMe | CH |
| 4083 | $Q_{62}$ | Br | H | Me | OMe | CH |
| 4084 | $Q_{62}$ | Br | H | OMe | OMe | CH |
| 4085 | $Q_{62}$ | Br | H | Me | OMe | N |
| 4086 | Me | $Q_{62}$ | H | OMe | OMe | CH |
| 4087 | $Q_{63}$ | Br | H | Me | OMe | CH |
| 4088 | $Q_{63}$ | Br | H | OMe | OMe | CH |
| 4089 | $Q_{69}$ | Br | H | Me | OMe | N |
| 4090 | Me | $Q_{63}$ | H | OMe | OMe | CH |
| 4091 | $Q_{64}$ | Br | H | Me | OMe | CH |
| 4092 | $Q_{64}$ | Br | H | OMe | OMe | CH |
| 4093 | $Q_{64}$ | Br | H | Me | OMe | N |
| 4094 | Me | $Q_{64}$ | H | OMe | OMe | CH |
| 4095 | $Q_{65}$ | Br | H | Me | OMe | CH |
| 4096 | $Q_{65}$ | Br | H | OMe | OMe | CH |
| 4097 | $Q_{65}$ | Br | H | Me | OMe | N |
| 4098 | Me | $Q_{65}$ | H | OMe | OMe | CH |
| 4099 | $Q_{66}$ | Br | H | Me | OMe | CH |
| 4100 | $Q_{66}$ | Br | H | OMe | OMe | CH |
| 4101 | $Q_{66}$ | Br | H | Me | OMe | N |
| 4102 | Me | $Q_{66}$ | H | OMe | OMe | CH |
| 4103 | $Q_{67}$ | Br | H | Me | OMe | CH |
| 4104 | $Q_{67}$ | Br | H | OMe | OMe | CH |
| 4105 | $Q_{67}$ | Br | H | Me | OMe | N |
| 4106 | Me | $Q_{67}$ | H | OMe | OMe | CH |
| 4107 | $Q_{68}$ | Br | H | Me | OMe | CH |
| 4108 | $Q_{68}$ | Br | H | OMe | OMe | CH |
| 4109 | $Q_{68}$ | Br | H | Me | OMe | N |
| 4110 | Me | $Q_{68}$ | H | OMe | OMe | CH |
| 4111 | $Q_{69}$ | Br | H | Me | OMe | CH |
| 4112 | $Q_{69}$ | Br | H | OMe | OMe | CH |
| 4113 | $Q_{69}$ | Br | H | Me | OMe | N |
| 4114 | Me | $Q_{69}$ | H | OMe | OMe | CH |
| 4115 | $Q_{70}$ | Br | H | Me | OMe | CH |
| 4116 | $Q_{70}$ | Br | H | OMe | OMe | CH |
| 4117 | $Q_{70}$ | Br | H | Me | OMe | N |
| 4118 | Me | $Q_{70}$ | H | OMe | OMe | CH |
| 4119 | $Q_{71}$ | Br | H | Me | OMe | CH |
| 4120 | $Q_{71}$ | Br | H | OMe | OMe | CH |
| 4121 | $Q_{71}$ | Br | H | Me | OMe | N |
| 4122 | Me | $Q_{71}$ | H | OMe | OMe | CH |
| 4123 | $Q_{72}$ | Br | H | Me | OMe | CH |
| 4124 | $Q_{72}$ | Br | H | OMe | OMe | CH |
| 4125 | $Q_{72}$ | Br | H | Me | OMe | N |
| 4126 | Me | $Q_{72}$ | H | OMe | OMe | CH |
| 4127 | $Q_{73}$ | Br | H | Me | OMe | CH |
| 4128 | $Q_{73}$ | Br | H | OMe | OMe | CH |
| 4129 | $Q_{73}$ | Br | H | Me | OMe | N |
| 4130 | Me | $Q_{73}$ | H | OMe | OMe | CH |
| 4131 | $Q_{74}$ | Br | H | Me | OMe | CH |
| 4132 | $Q_{74}$ | Br | H | OMe | OMe | CH |
| 4133 | $Q_{74}$ | Br | H | Me | OMe | N |
| 4134 | Me | $Q_{74}$ | H | OMe | OMe | CH |
| 4135 | $Q_{75}$ | Br | H | Me | OMe | CH |
| 4136 | $Q_{75}$ | Br | H | OMe | OMe | CH |
| 4137 | $Q_{75}$ | Br | H | Me | OMe | N |
| 4138 | Me | $Q_{75}$ | H | OMe | OMe | CH |
| 4139 | $Q_{76}$ | Br | H | Me | OMe | CH |
| 4140 | $Q_{76}$ | Br | H | OMe | OMe | CH |
| 4141 | $Q_{76}$ | Br | H | Me | OMe | N |
| 4142 | Me | $Q_{76}$ | H | OMe | OMe | CH |
| 4143 | $Q_{77}$ | Br | H | Me | OMe | CH |
| 4144 | $Q_{77}$ | Br | H | OMe | OMe | CH |
| 4145 | $Q_{77}$ | Br | H | Me | OMe | N |
| 4146 | Me | $Q_{77}$ | H | OMe | OMe | CH |
| 4147 | $Q_{78}$ | Br | H | Me | OMe | CH |
| 4148 | $Q_{78}$ | Br | H | OMe | OMe | CH |
| 4149 | $Q_{78}$ | Br | H | Me | OMe | N |
| 4150 | Me | $Q_{78}$ | H | OMe | OMe | CH |
| 4151 | $Q_{79}$ | Br | H | Me | OMe | CH |
| 4152 | $Q_{79}$ | Br | H | OMe | OMe | CH |
| 4153 | $Q_{79}$ | Br | H | Me | OMe | N |
| 4154 | Me | $Q_{79}$ | H | OMe | OMe | CH |
| 4155 | $Q_{80}$ | Br | H | Me | OMe | CH |
| 4156 | $Q_{80}$ | Br | H | OMe | OMe | CH |
| 4157 | $Q_{80}$ | Br | H | Me | OMe | N |
| 4158 | Me | $Q_{80}$ | H | OMe | OMe | CH |
| 4159 | $Q_{81}$ | Br | H | Me | OMe | CH |
| 4160 | $Q_{81}$ | Br | H | OMe | OMe | CH |
| 4161 | $Q_{81}$ | Br | H | Me | OMe | N |
| 4162 | Me | $Q_{81}$ | H | OMe | OMe | CH |
| 4163 | $Q_{82}$ | Br | H | Me | OMe | CH |
| 4164 | $Q_{82}$ | Br | H | OMe | OMe | CH |
| 4165 | $Q_{82}$ | Br | H | Me | OMe | N |
| 4166 | Me | $Q_{82}$ | H | OMe | OMe | CH |
| 4167 | $Q_{83}$ | Br | H | Me | OMe | CH |
| 4168 | $Q_{83}$ | Br | H | OMe | OMe | CH |
| 4169 | $Q_{83}$ | Br | H | Me | OMe | N |
| 4170 | Me | $Q_{83}$ | H | OMe | OMe | CH |
| 4171 | $Q_{83}$ | Br | H | Me | OMe | CH |
| 4172 | $Q_{83}$ | Br | H | OMe | OMe | CH |
| 4173 | $Q_{83}$ | Br | H | Me | OMe | N |
| 4174 | Me | $Q_{83}$ | H | OMe | OMe | CH |
| 4175 | $Q_{84}$ | Br | H | Me | OMe | CH |
| 4176 | $Q_{84}$ | Br | H | OMe | OMe | CH |
| 4177 | $Q_{84}$ | Br | H | Me | OMe | N |
| 4178 | Me | $Q_{84}$ | H | OMe | OMe | CH |
| 4179 | $Q_{85}$ | Br | H | Me | OMe | CH |
| 4180 | $Q_{85}$ | Br | H | OMe | OMe | CH |
| 4181 | $Q_{85}$ | Br | H | Me | OMe | N |
| 4182 | Me | $Q_{85}$ | H | OMe | OMe | CH |
| 4183 | $Q_{86}$ | Br | H | Me | OMe | CH |
| 4184 | $Q_{86}$ | Br | H | OMe | OMe | CH |
| 4185 | $Q_{86}$ | Br | H | Me | OMe | N |
| 4186 | Me | $Q_{86}$ | H | OMe | OMe | CH |
| 4187 | $Q_{87}$ | Br | H | Me | OMe | CH |
| 4188 | $Q_{87}$ | Br | H | OMe | OMe | CH |
| 4189 | $Q_{87}$ | Br | H | Me | OMe | N |
| 4190 | Me | $Q_{87}$ | H | OMe | OMe | CH |
| 4191 | $Q_{88}$ | Br | H | Me | OMe | CH |
| 4192 | $Q_{88}$ | Br | H | OMe | OMe | CH |
| 4193 | $Q_{88}$ | Br | H | Me | OMe | N |
| 4194 | Me | $Q_{88}$ | H | OMe | OMe | CH |
| 4195 | $Q_{89}$ | Br | H | Me | OMe | CH |
| 4196 | $Q_{89}$ | Br | H | OMe | OMe | CH |
| 4197 | $Q_{89}$ | Br | H | Me | OMe | N |
| 4198 | Me | $Q_{89}$ | H | OMe | OMe | CH |
| 4199 | $Q_{90}$ | Br | H | Me | OMe | CH |
| 4200 | $Q_{90}$ | Br | H | OMe | OMe | CH |
| 4201 | $Q_{90}$ | Br | H | Me | OMe | N |
| 4202 | Me | $Q_{90}$ | H | OMe | OMe | CH |
| 4203 | $Q_{91}$ | Br | H | Me | OMe | CH |
| 4204 | $Q_{91}$ | Br | H | OMe | OMe | CH |
| 4205 | $Q_{91}$ | Br | H | Me | OMe | N |
| 4206 | Me | $Q_{91}$ | H | OMe | OMe | CH |
| 4207 | $Q_{92}$ | Br | H | Me | OMe | CH |
| 4208 | $Q_{92}$ | Br | H | OMe | OMe | CH |
| 4209 | $Q_{92}$ | Br | H | Me | OMe | N |
| 4210 | Me | $Q_{92}$ | H | OMe | OMe | CH |
| 4211 | $Q_{93}$ | Br | H | Me | OMe | CH |
| 4212 | $Q_{93}$ | Br | H | OMe | OMe | CH |
| 4213 | $Q_{93}$ | Br | H | Me | OMe | N |
| 4214 | Me | $Q_{93}$ | H | OMe | OMe | CH |
| 4215 | $Q_{94}$ | Br | H | Me | OMe | CH |
| 4216 | $Q_{94}$ | Br | H | OMe | OMe | CH |
| 4217 | $Q_{94}$ | Br | H | Me | OMe | N |
| 4218 | Me | $Q_{94}$ | H | OMe | OMe | CH |
| 4219 | $Q_{95}$ | Br | H | Me | OMe | CH |

TABLE 3-continued

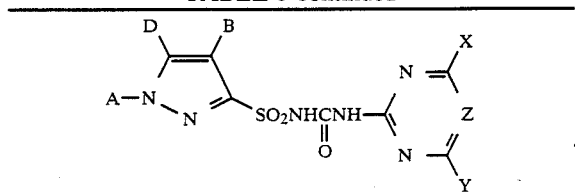

| No. | A | B | D | X | Y | Z |
|---|---|---|---|---|---|---|
| 4220 | Q95 | Br | H | OMe | OMe | CH |
| 4221 | Q95 | Br | H | Me | OMe | N |
| 4222 | Me | Q95 | H | OMe | OMe | CH |
| 4223 | Q96 | Br | H | Me | OMe | CH |
| 4224 | Q96 | Br | H | OMe | OMe | CH |
| 4225 | Q96 | Br | H | Me | OMe | N |
| 4226 | Me | Q96 | H | OMe | OMe | CH |
| 4227 | Q97 | Br | H | Me | OMe | CH |
| 4228 | Q97 | Br | H | OMe | OMe | CH |
| 4229 | Q97 | Br | H | Me | OMe | N |
| 4230 | Me | Q97 | H | OMe | OMe | CH |
| 4231 | Q98 | Br | H | Me | OMe | CH |
| 4232 | Q98 | Br | H | OMe | OMe | CH |
| 4233 | Q98 | Br | H | Me | OMe | N |
| 4234 | Me | Q98 | H | OMe | OMe | CH |
| 4235 | Q99 | Br | H | Me | OMe | CH |
| 4236 | Q99 | Br | H | OMe | OMe | CH |
| 4237 | Q99 | Br | H | Me | OMe | N |
| 4238 | Me | Q99 | H | OMe | OMe | CH |
| 4239 | Q100 | Br | H | Me | OMe | CH |
| 4240 | Q100 | Br | H | OMe | OMe | CH |
| 4241 | Q100 | Br | H | Me | OMe | N |
| 4242 | Me | Q100 | H | OMe | OMe | CH |
| 4243 | Q101 | Br | H | Me | OMe | CH |
| 4244 | Q101 | Br | H | OMe | OMe | CH |
| 4245 | Q101 | Br | H | Me | OMe | N |
| 4246 | Me | Q101 | H | OMe | OMe | CH |
| 4247 | Q102 | Br | H | Me | OMe | CH |
| 4248 | Q102 | Br | H | OMe | OMe | CH |
| 4249 | Q102 | Br | H | Me | OMe | N |
| 4250 | Me | Q102 | H | OMe | OMe | CH |
| 4251 | Q103 | Br | H | Me | OMe | CH |
| 4252 | Q103 | Br | H | OMe | OMe | CH |
| 4253 | Q103 | Br | H | Me | OMe | N |
| 4254 | Me | Q103 | H | OMe | OMe | CH |
| 4255 | Q104 | Br | H | Me | OMe | CH |
| 4256 | Q104 | Br | H | OMe | OMe | CH |
| 4257 | Q104 | Br | H | Me | OMe | N |
| 4258 | Me | Q104 | H | OMe | OMe | CH |
| 4259 | Q105 | Br | H | Me | OMe | CH |
| 4260 | Q105 | Br | H | OMe | OMe | CH |
| 4261 | Q105 | Br | H | Me | OMe | N |
| 4262 | Me | Q105 | H | OMe | OMe | CH |
| 4263 | Q106 | Br | H | Me | OMe | CH |
| 4264 | Q106 | Br | H | OMe | OMe | CH |
| 4265 | Q106 | Br | H | Me | OMe | N |
| 4266 | Me | Q106 | H | OMe | OMe | CH |
| 4267 | Q107 | Br | H | Me | OMe | CH |
| 4268 | Q107 | Br | H | OMe | OMe | CH |
| 4269 | Q107 | Br | H | Me | OMe | N |
| 4270 | Me | Q107 | H | OMe | OMe | CH |
| 4271 | Q108 | Br | H | Me | OMe | CH |
| 4272 | Q108 | Br | H | OMe | OMe | CH |
| 4273 | Q108 | Br | H | Me | OMe | N |
| 4274 | Me | Q108 | H | OMe | OMe | CH |
| 4275 | Q109 | Br | H | Me | OMe | CH |
| 4276 | Q109 | Br | H | OMe | OMe | CH |
| 4277 | Q109 | Br | H | Me | OMe | N |
| 4278 | Me | Q108 | H | OMe | OMe | CH |
| 4279 | Q110 | Br | H | Me | OMe | CH |
| 4280 | Q110 | Br | H | OMe | OMe | CH |
| 4281 | Q110 | Br | H | Me | OMe | N |
| 4282 | Me | Q110 | H | OMe | OMe | CH |
| 4283 | Q111 | Br | H | Me | OMe | CH |
| 4284 | Q111 | Br | H | OMe | OMe | CH |
| 4285 | Q111 | Br | H | Me | OMe | N |
| 4286 | Me | Q111 | H | OMe | OMe | CH |
| 4287 | Q112 | Br | H | Me | OMe | CH |
| 4288 | Q112 | Br | H | OMe | OMe | CH |
| 4289 | Q112 | Br | H | Me | OMe | N |
| 4290 | Me | Q112 | H | OMe | OMe | CH |
| 4291 | Q113 | Br | H | Me | OMe | CH |
| 4292 | Q113 | Br | H | OMe | OMe | CH |
| 4293 | Q113 | Br | H | Me | OMe | N |
| 4294 | Me | Q113 | H | OMe | OMe | CH |
| 4295 | Q114 | Br | H | Me | OMe | CH |
| 4296 | Q114 | Br | H | OMe | OMe | CH |
| 4297 | Q114 | Br | H | Me | OMe | N |
| 4298 | Me | Q114 | H | OMe | OMe | CH |
| 4299 | Q115 | Br | H | Me | OMe | CH |
| 4300 | Q115 | Br | H | OMe | OMe | CH |
| 4301 | Q115 | Br | H | Me | OMe | N |
| 4302 | Me | Q115 | H | OMe | OMe | CH |
| 4303 | Q116 | Br | H | Me | OMe | CH |
| 4304 | Q116 | Br | H | OMe | OMe | CH |
| 4305 | Q116 | Br | H | Me | OMe | N |
| 4306 | Me | Q116 | H | OMe | OMe | CH |
| 4307 | Q117 | Br | H | Me | OMe | CH |
| 4308 | Q117 | Br | H | OMe | OMe | CH |
| 4309 | Q117 | Br | H | Me | OMe | N |
| 4310 | Me | Q117 | H | OMe | OMe | CH |
| 4311 | Q118 | Br | H | Me | OMe | CH |
| 4312 | Q118 | Br | H | OMe | OMe | CH |
| 4313 | Q118 | Br | H | Me | OMe | N |
| 4314 | Me | Q118 | H | OMe | OMe | CH |
| 4315 | Q119 | Br | H | Me | OMe | CH |
| 4316 | Q119 | Br | H | OMe | OMe | CH |
| 4317 | Q119 | Br | H | Me | OMe | N |
| 4318 | Me | Q119 | H | OMe | OMe | CH |
| 4319 | Q120 | Br | H | Me | OMe | CH |
| 4320 | Q120 | Br | H | OMe | OMe | CH |
| 4321 | Q120 | Br | H | Me | OMe | N |
| 4322 | Me | Q120 | H | OMe | OMe | CH |
| 4323 | Q121 | Br | H | Me | OMe | CH |
| 4324 | Q121 | Br | H | OMe | OMe | CH |
| 4325 | Q121 | Br | H | Me | OMe | N |
| 4326 | Me | Q121 | H | OMe | OMe | CH |
| 4327 | Q122 | Br | H | Me | OMe | CH |
| 4328 | Q122 | Br | H | OMe | OMe | CH |
| 4329 | Q122 | Br | H | Me | OMe | N |
| 4330 | Me | Q122 | H | OMe | OMe | CH |
| 4331 | Q123 | Br | H | Me | OMe | CH |
| 4332 | Q123 | Br | H | OMe | OMe | CH |
| 4333 | Q123 | Br | H | Me | OMe | N |
| 4334 | Me | Q123 | H | OMe | OMe | CH |
| 4335 | Q124 | Br | H | Me | OMe | CH |
| 4336 | Q124 | Br | H | OMe | OMe | CH |
| 4337 | Q124 | Br | H | Me | OMe | N |
| 4338 | Me | Q124 | H | OMe | OMe | CH |
| 4339 | Q125 | Br | H | Me | OMe | CH |
| 4340 | Q125 | Br | H | OMe | OMe | CH |
| 4341 | Q125 | Br | H | Me | OMe | N |
| 4342 | Me | Q125 | H | OMe | OMe | CH |
| 4343 | Q126 | Br | H | Me | OMe | CH |
| 4344 | Q126 | Br | H | OMe | OMe | CH |
| 4345 | Q126 | Br | H | Me | OMe | N |
| 4346 | Me | Q126 | H | OMe | OMe | CH |
| 4347 | Q127 | Br | H | Me | OMe | CH |
| 4348 | Q127 | Br | H | OMe | OMe | CH |
| 4349 | Q127 | Br | H | Me | OMe | N |
| 4350 | Me | Q127 | H | OMe | OMe | CH |
| 4351 | Q128 | Br | H | Me | OMe | CH |
| 4352 | Q128 | Br | H | OMe | OMe | CH |
| 4353 | Q128 | Br | H | Me | OMe | N |
| 4354 | Me | Q128 | H | OMe | OMe | CH |
| 4355 | Q129 | Br | H | Me | OMe | CH |
| 4356 | Q129 | Br | H | OMe | OMe | CH |
| 4357 | Q129 | Br | H | Me | OMe | N |
| 4358 | Me | Q129 | H | OMe | OMe | CH |
| 4359 | Q130 | Br | H | Me | OMe | CH |
| 4360 | Q130 | Br | H | OMe | OMe | CH |
| 4361 | Q130 | Br | H | Me | OMe | N |

TABLE 3-continued

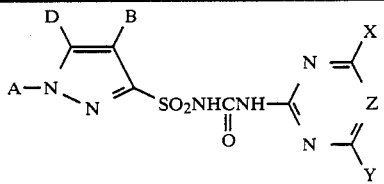

| No. | A | B | D | X | Y | Z |
|-----|---|---|---|---|---|---|
| 4362 | Me | Q130 | H | OMe | OMe | CH |
| 4363 | Q131 | Br | H | Me | OMe | CH |
| 4364 | Q131 | Br | H | OMe | OMe | CH |
| 4365 | Q131 | Br | H | Me | OMe | N |
| 4366 | Me | Q131 | H | OMe | OMe | CH |
| 4367 | Q132 | Br | H | Me | OMe | CH |
| 4368 | Q132 | Br | H | OMe | OMe | CH |
| 4369 | Q132 | Br | H | Me | OMe | N |
| 4370 | Me | Q132 | H | OMe | OMe | CH |

TABLE 4

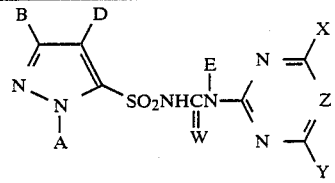

| No. | A | B | D | E | W | X | Y | Z |
|-----|---|---|---|---|---|---|---|---|
| 1934 | Q1 | H | COOMe | H | S | Me | OMe | CH |
| 1935 | Q1 | H | COOMe | H | S | OMe | OMe | CH |
| 1936 | Q1 | H | COOEt | H | S | Me | OMe | CH |
| 1937 | Q1 | H | COOEt | H | S | OMe | OMe | CH |
| 1938 | Q1 | H | COOMe | Me | O | Me | OMe | CH |
| 1939 | Q1 | H | COOMe | Me | O | OMe | OMe | CH |
| 1940 | Q1 | H | COOEt | Me | O | OMe | OMe | CH |
| 1941 | Q1 | H | COOMe | OMe | O | Me | OMe | CH |
| 1942 | Q1 | H | COOMe | OMe | O | OMe | OMe | CH |
| 1943 | Q1 | H | COOEt | OMe | O | OMe | OMe | CH |
| 1944 | Q1 | H | COOMe | $CH_2CH=CH_2$ | O | Me | OMe | CH |
| 1945 | Q1 | H | COOMe | $CH_2CH=CH_2$ | O | OMe | OMe | CH |
| 1946 | Q1 | H | COOEt | $CH_2CH=CH_2$ | O | OMe | OMe | CH |
| 1947 | Q1 | H | COOMe | $CH_2C\equiv CH$ | O | Me | OMe | CH |
| 1948 | Q1 | H | COOMe | $CH_2C\equiv CH$ | O | OMe | OMe | CH |
| 1949 | Q1 | H | COOEt | $CH_2C\equiv CH$ | O | OMe | OMe | CH |
| 1950 | Q12 | H | COOMe | H | S | Me | OMe | CH |
| 1951 | Q12 | H | COOMe | H | S | OMe | OMe | CH |
| 1952 | Q12 | H | COOEt | H | S | Me | OMe | CH |
| 1953 | Q12 | H | COOEt | H | S | OMe | OMe | CH |
| 1954 | Q12 | H | COOMe | Me | O | Me | OMe | CH |
| 1955 | Q12 | H | COOMe | Me | O | OMe | OMe | CH |
| 1956 | Q12 | H | COOEt | Me | O | OMe | OMe | CH |
| 1957 | Q12 | H | COOMe | OMe | O | Me | OMe | CH |
| 1958 | Q12 | H | COOMe | OMe | O | OMe | OMe | CH |
| 1959 | Q12 | H | COOEt | OMe | O | OMe | OMe | CH |
| 1960 | Q12 | H | COOMe | $CH_2CH=CH_2$ | O | Me | OMe | CH |
| 1961 | Q12 | H | COOMe | $CH_2CH=CH_2$ | O | OMe | OMe | CH |
| 1962 | Q12 | H | COOEt | $CH_2CH=CH_2$ | O | OMe | OMe | CH |
| 1963 | Q12 | H | COOMe | $CH_2C\equiv CH$ | O | Me | OMe | CH |
| 1964 | Q12 | H | COOMe | $CH_2C\equiv CH$ | O | OMe | OMe | CH |
| 1965 | Q12 | H | COOEt | $CH_2C\equiv CH$ | O | OMe | OMe | CH |
| 1966 | Q22 | H | COOMe | H | S | Me | OMe | CH |
| 1967 | Q22 | H | COOMe | H | S | OMe | OMe | CH |
| 1968 | Q22 | H | COOEt | H | S | Me | OMe | CH |
| 1969 | Q22 | H | COOEt | H | S | OMe | OMe | CH |
| 1970 | Q22 | H | COOMe | Me | O | Me | OMe | CH |
| 1971 | Q22 | H | COOMe | Me | O | OMe | OMe | CH |
| 1972 | Q22 | H | COOEt | Me | O | OMe | OMe | CH |
| 1973 | Q22 | H | COOMe | OMe | O | Me | OMe | CH |
| 1974 | Q22 | H | COOMe | OMe | O | OMe | OMe | CH |
| 1975 | Q22 | H | COOEt | OMe | O | OMe | OMe | CH |
| 1976 | Q22 | H | cOOMe | $CH_2CH=CH_2$ | O | Me | OMe | CH |
| 1977 | Q22 | H | COOMe | $CH_2CH=CH_2$ | O | OMe | OMe | CH |
| 1978 | Q22 | H | COOEt | $CH_2CH=CH_2$ | O | OMe | OMe | CH |
| 1979 | Q22 | H | COOMe | $CH_2C\equiv CH$ | O | Me | OMe | CH |
| 1980 | Q22 | H | COOMe | $CH_2C\equiv CH$ | O | OMe | OMe | CH |
| 1981 | Q22 | H | COOEt | $CH_2C\equiv CH$ | O | OMe | OMe | CH |
| 4371 | Q1 | H | COOMe | H | =NOMe | Me | OMe | CH |
| 4372 | Q1 | H | COOMe | H | =NOMe | OMe | OMe | CH |
| 4373 | Q1 | H | COOEt | H | =NOMe | Me | OMe | CH |
| 4374 | Q1 | H | COOEt | H | =NOMe | OMe | OMe | CH |
| 4375 | Q1 | H | COOMe | H | =NOEe | Me | OMe | CH |
| 4376 | Q1 | H | COOMe | H | =NOEe | OMe | OMe | CH |
| 4377 | Q1 | H | COOEt | H | =NOEe | Me | OMe | CH |
| 4378 | Q1 | H | COOEt | H | =NOEe | OMe | OMe | CH |
| 4379 | Q1 | H | COOMe | H | =NMe | Me | OMe | CH |
| 4380 | Q1 | H | COOMe | H | =NMe | OMe | OMe | CH |
| 4381 | Q1 | H | COOEt | H | =NMe | Me | OMe | CH |

TABLE 4-continued

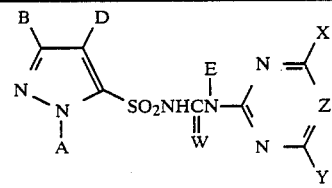

| No. | A | B | D | E | W | X | Y | Z |
|---|---|---|---|---|---|---|---|---|
| 4382 | $Q_1$ | H | COOEt | H | =NMe | OMe | OMe | CH |
| 4383 | $Q_1$ | H | COOMe | H | =NH | Me | OMe | CH |
| 4384 | $Q_1$ | H | COOMe | H | =NH | OMe | OMe | CH |
| 4385 | $Q_1$ | H | COOEt | H | =NH | Me | OMe | CH |
| 4386 | $Q_1$ | H | COOEt | H | =NH | OMe | OMe | CH |
| 4387 | $Q_{12}$ | H | COOMe | H | =NOMe | Me | OMe | CH |
| 4388 | $Q_{12}$ | H | COOMe | H | =NOMe | OMe | OMe | CH |
| 4389 | $Q_{12}$ | H | COOEt | H | =NOMe | Me | OMe | CH |
| 4390 | $Q_{12}$ | H | COOEt | H | =NOMe | OMe | OMe | CH |
| 4391 | $Q_{12}$ | H | COOMe | H | =NOEe | Me | OMe | CH |
| 4392 | $Q_{12}$ | H | COOMe | H | =NOEe | OMe | OMe | CH |
| 4393 | $Q_{12}$ | H | COOEt | H | =NOEe | Me | OMe | CH |
| 4394 | $Q_{12}$ | H | COOEt | H | =NOEe | OMe | OMe | CH |
| 4395 | $Q_{12}$ | H | COOMe | H | =NMe | Me | OMe | CH |
| 4396 | $Q_{12}$ | H | COOMe | H | =NMe | OMe | OMe | CH |
| 4397 | $Q_{12}$ | H | COOEt | H | =NMe | Me | OMe | CH |
| 4398 | $Q_{12}$ | H | COOEt | H | =NMe | OMe | OMe | CH |
| 4399 | $Q_{12}$ | H | COOMe | H | =NH | Me | OMe | CH |
| 4400 | $Q_{12}$ | H | COOMe | H | =NH | OMe | OMe | CH |
| 4401 | $Q_{12}$ | H | COOEt | H | =NH | Me | OMe | CH |
| 4402 | $Q_{12}$ | H | COOEt | H | =NH | OMe | OMe | CH |
| 4403 | $Q_{22}$ | H | COOMe | H | =NOMe | Me | OMe | CH |
| 4404 | $Q_{22}$ | H | COOMe | H | =NOMe | OMe | OMe | CH |
| 4405 | $Q_{22}$ | H | COOEt | H | =NOMe | Me | OMe | CH |
| 4406 | $Q_{22}$ | H | COOEt | H | =NOMe | OMe | OMe | CH |
| 4407 | $Q_{22}$ | H | COOMe | H | =NOEe | Me | OMe | CH |
| 4408 | $Q_{22}$ | H | COOMe | H | =NOEe | OMe | OMe | CH |
| 4409 | $Q_{22}$ | H | COOEt | H | =NOEe | Me | OMe | CH |
| 4410 | $Q_{22}$ | H | COOEt | H | =NOEe | OMe | OMe | CH |
| 4411 | $Q_{22}$ | H | COOMe | H | =NMe | Me | OMe | CH |
| 4412 | $Q_{22}$ | H | COOMe | H | =NMe | OMe | OMe | CH |
| 4413 | $Q_{22}$ | H | COOEt | H | =NMe | Me | OMe | CH |
| 4414 | $Q_{22}$ | H | COOEt | H | =NMe | OMe | OMe | CH |
| 4415 | $Q_{22}$ | H | COOMe | H | =NH | Me | OMe | CH |
| 4416 | $Q_{22}$ | H | COOMe | H | =NH | OMe | OMe | CH |
| 4417 | $Q_{22}$ | H | COOEt | H | =NH | Me | OMe | CH |
| 4418 | $Q_{22}$ | H | COOEt | H | =NH | OMe | OMe | CH |

TABLE 5

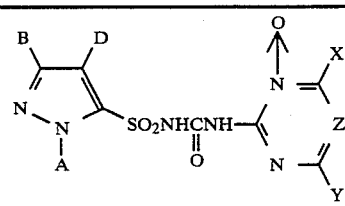

| No. | A | B | D | $X^1$ | $Y^1$ | Z |
|---|---|---|---|---|---|---|
| 1982 | $Q_1$ | H | COOMe | Me | Me | CH |
| 1983 | $Q_1$ | H | COOMe | Me | OMe | CH |
| 1984 | $Q_1$ | H | COOEt | Me | Me | CH |
| 1985 | $Q_1$ | H | COOEt | Me | OMe | CH |
| 1986 | $Q_1$ | H | COOEt | Me | Me | N |
| 1987 | $Q_{12}$ | H | COOMe | Me | Me | CH |
| 1988 | $Q_{12}$ | H | COOMe | Me | OMe | CH |
| 1989 | $Q_{22}$ | H | COOMe | Me | Me | CH |
| 1990 | $Q_{22}$ | H | COOMe | Me | OMe | CH |

TABLE 6

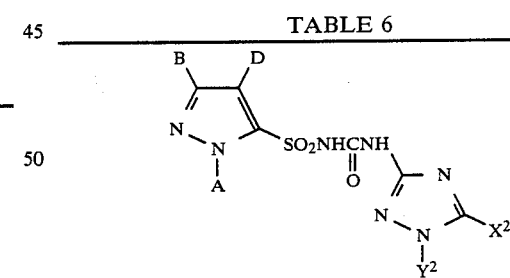

| No. | A | B | D | $X^2$ | $Y^2$ |
|---|---|---|---|---|---|
| 1991 | $Q_1$ | H | COOMe | Me | Me |
| 1992 | $Q_1$ | H | COOMe | OMe | Me |
| 1993 | $Q_1$ | H | COOMe | SMe | Me |
| 1994 | $Q_1$ | H | COOEt | Me | Me |
| 1995 | $Q_1$ | H | COOEt | OMe | Me |
| 1996 | $Q_1$ | H | COOEt | SMe | Me |
| 1997 | $Q_{12}$ | H | COOMe | Me | Me |
| 1998 | $Q_{12}$ | H | COOMe | OMe | Me |
| 1999 | $Q_{22}$ | H | COOMe | Me | Me |
| 2000 | $Q_{22}$ | H | COOMe | OMe | Me |

TABLE 7

| No. | A | B | D | Y⁴ | X³ | Y³ | Z¹ |
|---|---|---|---|---|---|---|---|
| 4419 | Q₁ | H | COOMe | COOMe | Me | Me | CH |
| 4420 | Q₁ | H | COOMe | CN | Me | Me | CH |
| 4421 | Q₁ | H | COOMe | Me | OMe | OMe | N |
| 4422 | Q₁ | H | COOEt | COOMe | Me | Me | CH |
| 4423 | Q₁ | H | COOEt | CN | Me | Me | CH |
| 4424 | Q₁ | H | COOEt | Me | OMe | OMe | N |
| 4425 | Q₁ | Me | COOMe | COOMe | Me | Me | CH |
| 4426 | Q₁ | Me | COOMe | CN | Me | Me | CH |
| 4427 | Q₁ | Me | COOMe | Me | OMe | OMe | N |
| 4428 | Q₁ | Me | COOEt | COOMe | Me | Me | CH |
| 4429 | Q₁ | Me | COOEt | CN | Me | Me | CH |
| 4430 | Q₁ | Me | COOEt | Me | OMe | OMe | N |
| 4431 | Q₁₂ | H | COOMe | COOMe | Me | Me | CH |
| 4432 | Q₁₂ | H | COOMe | CN | Me | Me | CH |
| 4433 | Q₁₂ | H | COOMe | Me | OMe | OMe | N |
| 4434 | Q₁₂ | H | COOEt | COOMe | Me | Me | CH |
| 4435 | Q₁₂ | H | COOEt | CN | Me | Me | CH |
| 4436 | Q₁₂ | H | COOEt | Me | OMe | OMe | N |
| 4437 | Q₁₂ | Me | COOMe | COOMe | Me | Me | CH |
| 4438 | Q₁₂ | Me | COOMe | CN | Me | Me | CH |
| 4439 | Q₁₂ | Me | COOMe | Me | OMe | OMe | N |
| 4440 | Q₁₂ | Me | COOEt | COOMe | Me | Me | CH |
| 4441 | Q₁₂ | Me | COOEt | CN | Me | Me | CH |
| 4442 | Q₁₂ | Me | COOEt | Me | OMe | OMe | N |
| 4443 | Q₂₂ | H | COOMe | COOMe | Me | Me | CH |
| 4444 | Q₂₂ | H | COOMe | CN | Me | Me | CH |
| 4445 | Q₂₂ | H | COOMe | Me | OMe | OMe | N |
| 4446 | Q₂₂ | H | COOEt | COOMe | Me | Me | CH |
| 4447 | Q₂₂ | H | COOEt | CN | Me | Me | CH |
| 4448 | Q₂₂ | H | COOEt | Me | OMe | OMe | N |
| 4449 | Q₂₂ | Me | COOMe | COOMe | Me | Me | CH |
| 4450 | Q₂₂ | Me | COOMe | CN | Me | Me | CH |
| 4451 | Q₂₂ | Me | COOMe | Me | OMe | OMe | N |
| 4452 | Q₂₂ | Me | COOET | COOMe | Me | Me | CH |
| 4453 | Q₂₂ | Me | COOEt | CN | Me | Me | CH |
| 4454 | Q₂₂ | Me | COOEt | Me | OMe | OMe | N |

$Q_1$ to $Q_{132}$ in Tables 1 to 7 each have the meanings shown below:

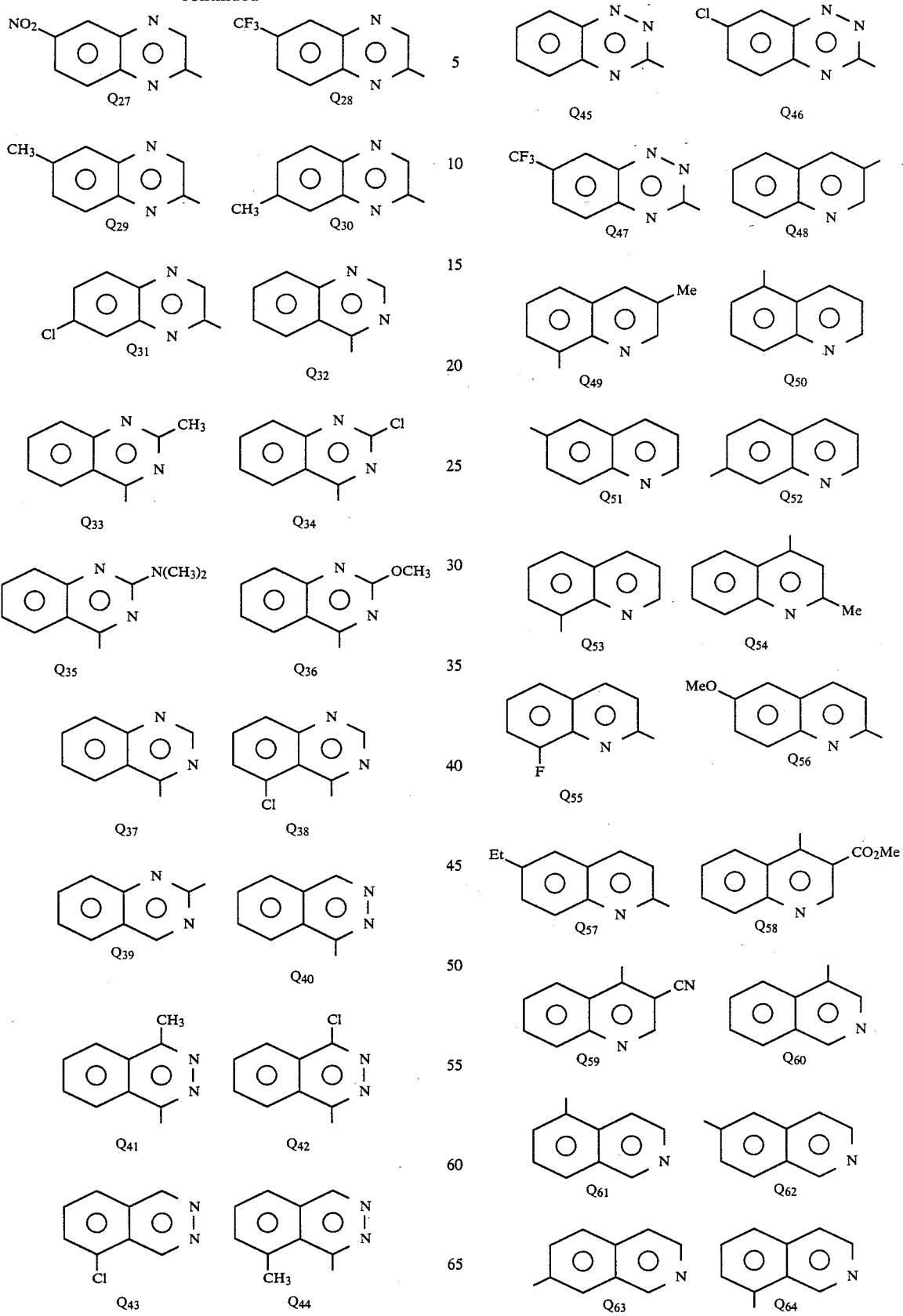

-continued
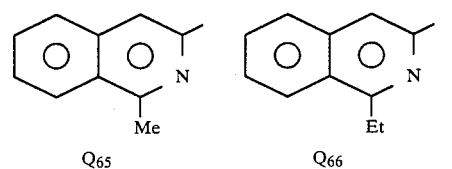
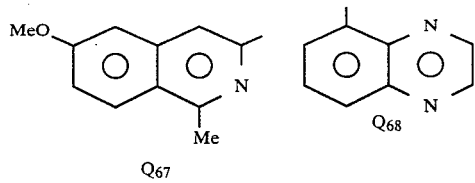
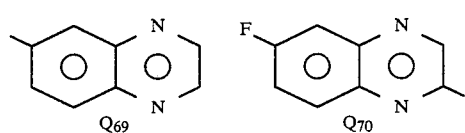
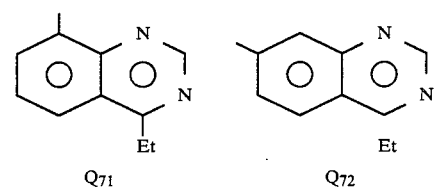
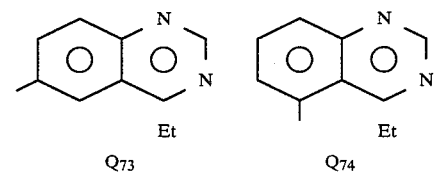
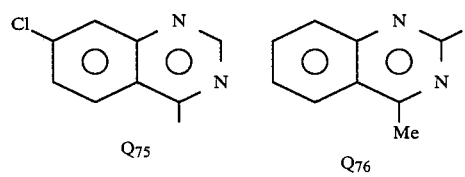
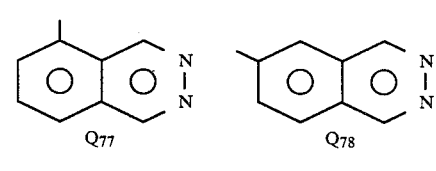
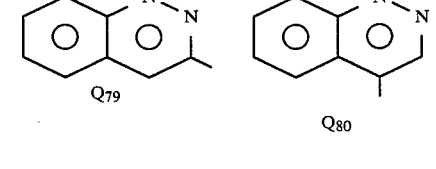
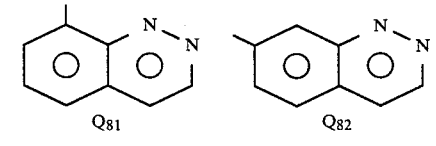
-continued
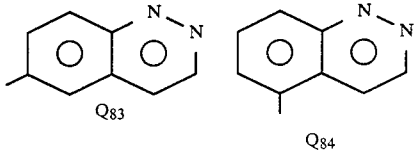
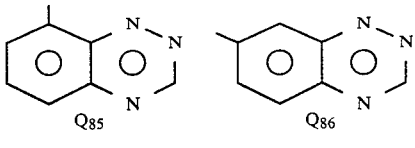
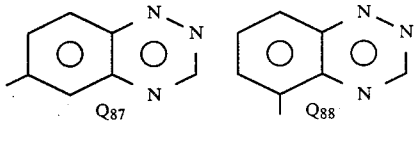
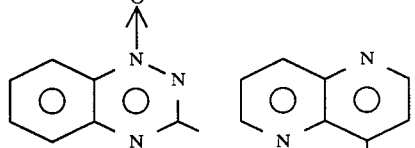
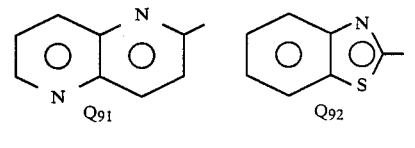
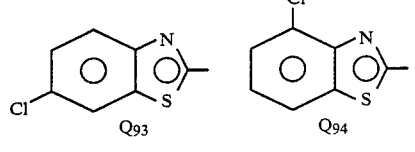
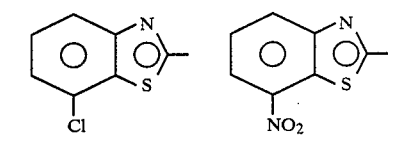
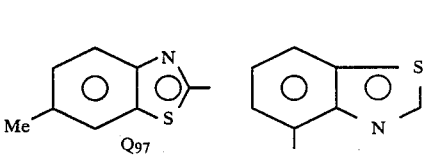
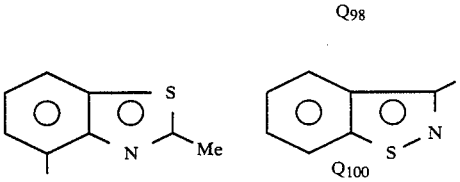

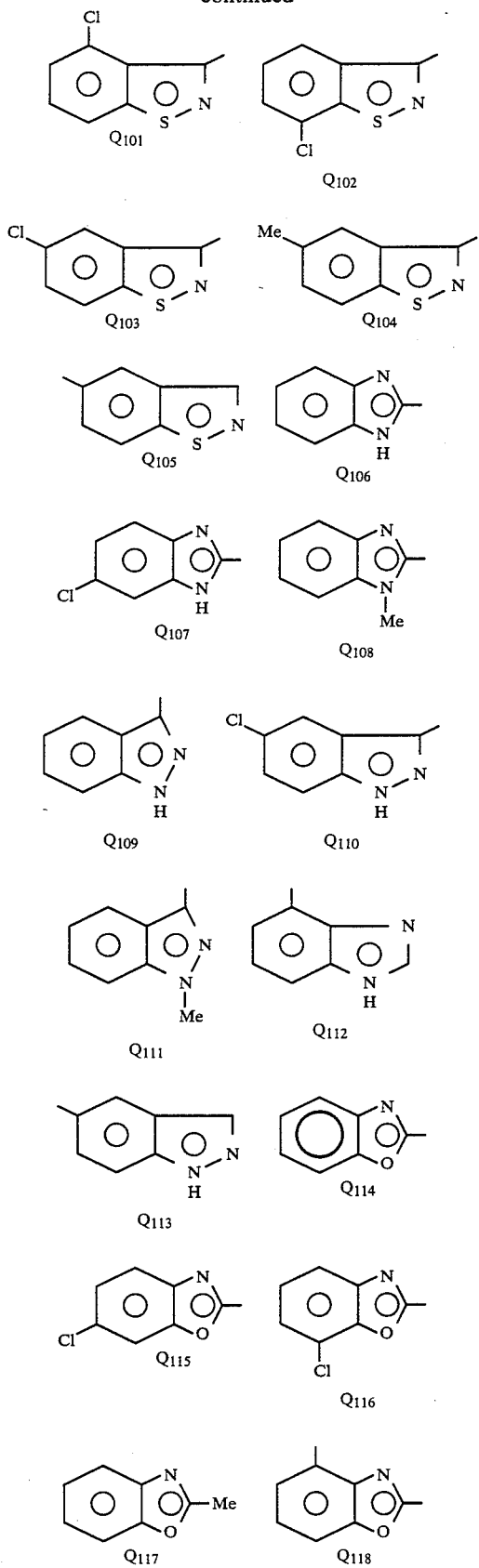
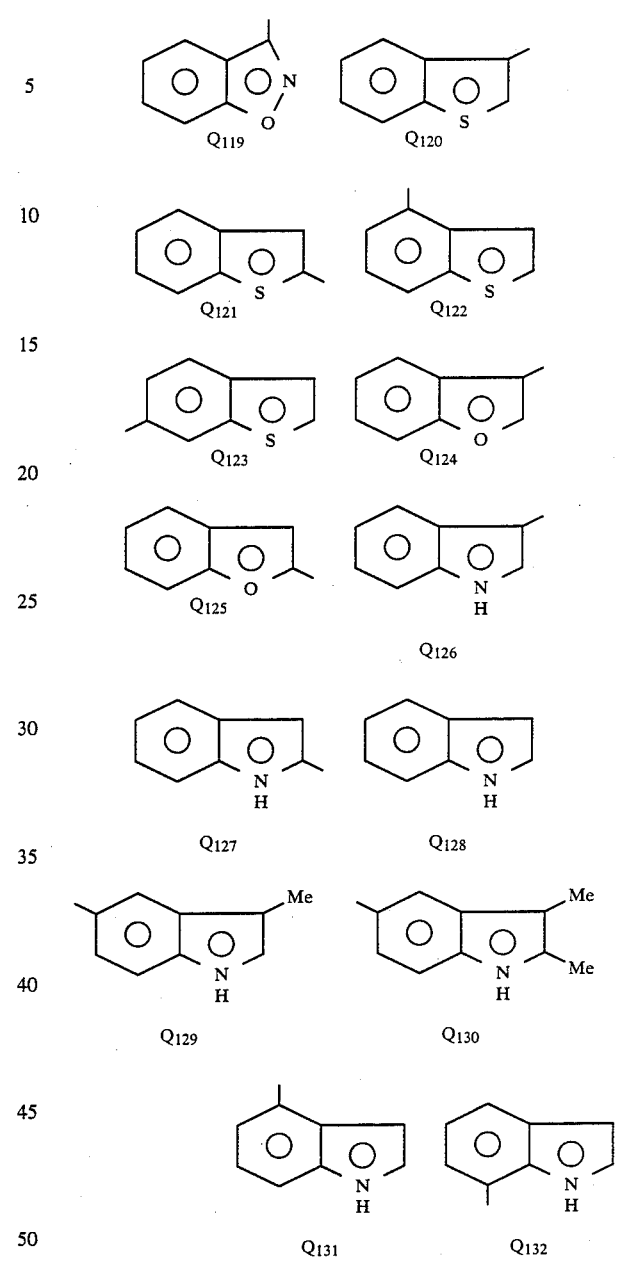
The compounds shown in Table 1 to Table 7 can be synthesized following the procedures in Examples 1 and 2 or the procedures described above. Properties of some of these compounds are shown in Table 8. In Table 8, the compound number correspond to the compound number in Table 1 to Table 7.
TABLE 8
| Comp. No. | m.p. (°C.) |
|---|---|
| 9 | 169–173 |
| 10 | 169–173 |
| 11 | 179–193 |
| 313 | 215–216 |
| 314 | 212–213 |
| 315 | 213–214 |

In application of the compounds of this invention as herbicides, they can be applied by mixing with suitable carriers such as solid carriers, including for example clay, talc, bentonite, diatomaceous earth and others, or liquid carriers, including for example water, alcohols (methanol, ethanol and the like), aromatic hydrocarbons (benzene, toluene, xylene and the like), chlorinated hydrocarbons, ethers, ketones, esters (ethyl acetate, etc.), acid amides (dimethylformamide, etc.) and others. They can be provided for practical use with addition of any desired additive selected from an emulsifier, a dispersing agent, a suspending agent, a penetrating agent, a spreader and a stablizer and in any desired form such as a soluble concentrate, an emulsifiable concentrate, a wettable powder, a dust, a granule, etc.

In the following, there are shown examples of formulations of herbicides containing the compounds of this invention as active ingredients, but they are not limitative of this invention. In the exemplary formulations shown below, "parts" means "parts by weight".

EXEMPLARY FORMULATION 1

Wettable powder

Compound No. 9 of this invention: 50 parts
Zeeklite PFP: 46 parts
   (kaolin type clay; trade name; produced by Zeeklite Kogyo Co., Ltd.)
Solpol 5039: 5 parts
   (anionic surfactant; trade name; produced by Toho Kagaku Co., Ltd.)
Carplex (anticaking agent): 2 parts
   (white carbon; trade name, produced by Shionogi Seiyaku Co., Ltd.)
All of the above components are mixed and pulverized homogeneously to prepare a wettable powder.

EXEMPLARY FORMULATION 2

Wettable powder

Compound No. 315 of this invention: 45 parts
Zeeklite A: 48 parts
   (kaolin type clay; trade name; produced by Zeeklite Kogyo Co., Ltd.)
Solpol 5039: 5 parts
   (anionic surfactant; trade name; produced by Toho Kagaku Co., Ltd.)
Carplex (anticaking agent): 4 parts
   (white carbon; trade name; produced by Shionogi Seiyaku Co., Ltd.)
The above components are mixed and pulverized homogeneously to prepare a wettable powder.

EXEMPLARY FORMULATION 3

Emulsifiable concentrate

Compound No. 313 of this invention: 2 parts
Xylene: 73 parts
Dimethylformamide: 15 parts
Solpol 2680: 10 parts
   (mixture of nonionic surfactant and anionic surfactant; trade name; produced by Toho Kagaku Co., Ltd.)
The above components are homogeneously mixed to prepare an emulsifiable concentrate.
In use, the above emulsifiable concentrate is diluted to 10 to 10,000 times and sprayed in an amount of the active ingredient of 0.005 to 10 kg per hectare.

EXEMPLARY FORMULATION 4

Flowable

Compound No. 11 of this invention: 25 parts
Agrisol S-710: 10 parts
   (nonionic surfactant; trade name; produced by Kao Co., Ltd.)
Runox 1000 C: 0.5 part
   (anionic surfactant; trade name; produced by Toho Kagaku Co., Ltd.)
1% Rodopol water: 20 parts
   (thickener; trade name; produced by Rhone-Poulenc Co., Ltd.)
Water: 44.5 parts
The above components are mixed homogeneously to provide a flowable agent.

EXEMPLARY FORMULATION 5

Granule

Compound No. 314 of this invention: 0.1 part
Bentonite: 55.0 parts
Talc: 44.9 parts
All of the above components are mixed and pulverized homogeneously, then a little amount of water is added and the whole is stirred, kneaded and granulated by excluding granulator, then dried to prepare a granule.

EXEMPLARY FORMULATION 6

Granule

Compound No. 315 of this invention: 0.5 part
Bentonite: 55.0 parts
Talc: 44.5 parts
All of the above components are mixed and pulverized homogeneously, then a little amount of water is added and the whole is stirred, kneaded and granulated by excluding granulator, then dried to prepare a granule.

If desired, the compound of this invention may be applied as a mixture with other kinds of herbicides, various insecticides, sterilizers or adjuvants during preparation or spraying In particular, when applied in beet fields, useful ones include phenmedipham, desmedipham, lenacil, PAC., ethofumesate and so on.

As the other kinds of herbicides mentioned above, there may be included compounds as described in Farm Chemicals Handbook (1986).

The compounds of this invention can also be applied, in addition to the agricultural and horticultural fields such as farm fields, paddy fields, fruit gardens and the like, to the non-agricultural fields such as athletic grounds, vacant lands, belts along railroads and others in order to prevent and eliminate various weeds. The amounts of the herbicide to be applied, which may differ depending on the scenes to be applied, the time of application, the application method, the kinds of the objective grasses and the crops harvested, may generally range suitably from about 0.25 g to about 10 kg per hectare in terms of the active ingredient. When applied to beets in particular, it may range suitably from 0.25 to 1000 g/ha, preferably from 0.5 to 500 g/ha.

The following test examples are set forth for illustration of the utility of the compounds of this invention as herbicides.

TEST EXAMPLE 1

Herbicidal effect test by soil treatment

In a plastic box of 15 cm length, 22 cm width and 6 cm depth, there was placed a sterilized deluvium soil, and seeds of (A) rice (*Oryza sativa*), (B) barnyardgrass (*Echinochloa crusgalli*), (C) large crabgrass (*Digitaria adscendens*), (D) annual sedge (*Cyperus microiria*), (E) black nightshade (*Solanum nigrum* L.), (F) hairly galinosoga (*Galinosoga ciliata*), (G) rorippa spp. (*Rorippa indica*), (H) corn (*Zea mays*), (I) wheat (*Triticum vulgare*), (J) soybean (*Glysine max*) and (K) cotton (*Gossypium spp*) were sown mixedly. After covering soil to about 1.5 cm over the seeds, herbicides were sprayed evenly on the soil surface to predetermined proportions of the active ingredient.

In spraying, the wettable powder as shown in the foregoing exemplary formulations was diluted with water and sprayed over the entire surface by means of a small sprayer. Four weeks after spraying, the herbicidal effect on crops including rice, etc. and the various weeds were examined according to the judgement criteria shown below.

The results are shown in Table 9.

Some of the compounds of this invention show the selectivity on certain crops.

Judgement criteria

5 ... Growth control rates of more than 90% (almost completely withered)
4 ... Growth control rates of 70 to 90%
3 ... Growth control rates of 40 to 70%
2 ... Growth control rates of 20 to 40%
1 ... Growth control rates of 5 to 20%
0 ... Growth control rates of less than 5% (substantially no effect)

The above growth control rates are determined by measuring the top fresh weights of the treated plants and those of the non-treated plants, and calculated from the following formula:

$$\text{Growth control rate}(\%) = \left(1 - \frac{\text{Top fresh weight of the treated plants}}{\text{Top fresh weight of the non-treated plants}}\right) \times 100$$

TEST EXAMPLE 2

Herbicidal effect test by foliage treatment

In a plastic box of 15 cm length, 22 cm width and 6 cm depth, there was placed a sterilized deluvium soil, seeds of (A) rice (*Oryza sativa*), (B) barnyardgrass (*Echinochloa crusgalli*), (C) large crabgrass (*Digitaria adscendens*), (D) annual sedge (*Cyperus microiria*), (E) black nightshade (*Solanum nigrum* L.), (F) hairly galinosoga (*Galinosoga ciliata*), (G) rorippa ssp. (*Rorippa indica*), (H) corn (*Zea mays*), (I) wheat (*Triticum vulgare*), (J) soybean (*Glysine max*), (K) cotton (*Gossypium spp*) and (L) sugar beet (*Beta vulgaris*) were sown in shapes of spots, respectively, followed by covering of soil to about 1.5 cm over the seeds. After respective plants have grown to the second and the third leaf stage, herbicides were sprayed evenly onto the foliage portion at predetermined proportions of the active ingredient. In spraying, the wettable powder as shown in the foregoing exemplary formulations was diluted with water and sprayed over the entire surface of the foliage portions of various weeds by means of a small sprayer. Four weeks after spraying, the herbicidal effect on crops including rice, etc. and the various weeds were examined according to the judgement criteria as shown in Test example 1.

The results are shown in Table 10.

TEST EXAMPLE 3

Agricultural chemical damage test on sugar beet

In a plastic box of 15 cm length, 22 cm width and 6 cm depth, there was placed a sterilized deluvium soil, and seeds of (L) sugar beet (*Beta vulgaris*), (M) groundsel (*Senecio vulgaris*), (N) common field-speedwell (*Veronica persica*), (O) wild mustard (*Sinapis arvensis*) and (P) cleavers (*Galium aparine*) were sown in shapes of spots, respectively, followed by covering of soil to about 1.5 cm over the seeds. After respective plants have grown to the second and the third leaf stage, herbicides were sprayed evenly onto the stem-leaf portion at predetermined proportions of the active ingredient.

On 20 days after treatment, the herbicidal effects on weeds and agricultural chemical damages on sugar beet were examined. The results are shown in Table 11.

TABLE 9

| Compound No. | Amount of active ingredient applied kg/ha | (A) | (B) | (C) | (D) | (E) | (F) | (G) | (H) | (I) | (J) | (K) | (L) |
|---|---|---|---|---|---|---|---|---|---|---|---|---|---|
| 9 | 0.16 | 4 | 5 | 2 | 5 | 5 | 5 | 5 | 0 | 0 | 5 | 3 | — |
|   | 0.32 | 5 | 5 | 5 | 5 | 5 | 5 | 5 | 1 | 1 | 5 | 5 | — |
| 10 | 0.63 | 5 | 5 | 5 | 5 | 5 | 5 | 5 | 0 | 0 | 5 | 5 | — |
| 11 | 0.16 | 5 | 5 | 2 | 5 | 5 | 5 | 5 | 5 | 0 | 5 | 5 | — |
|   | 0.32 | 5 | 5 | 5 | 5 | 5 | 5 | 5 | 5 | 0 | 5 | 0 | — |
| 313 | 0.32 | 5 | 5 | 5 | 5 | 5 | 5 | 5 | 5 | 5 | 5 | 0 | — |
| 314 | 0.16 | 3 | 4 | 2 | 5 | 5 | 5 | 5 | 5 | 5 | 4 | 0 | — |
|   | 0.32 | 5 | 5 | 5 | 5 | 5 | 5 | 5 | 5 | 5 | 5 | 0 | — |
| 315 | 0.82 | 0 | 5 | 2 | 5 | 5 | 5 | 5 | 5 | 5 | 5 | 0 | — |

TABLE 9-continued

| Compound No. | Amount of active ingredient applied kg/ha | (A) | (B) | (C) | (D) | (E) | (F) | (G) | (H) | (I) | (J) | (K) | (L) |
|---|---|---|---|---|---|---|---|---|---|---|---|---|---|
| | 0.16 | 0 | 5 | 5 | 5 | 5 | 5 | 5 | 5 | 5 | 5 | 0 | — |

(A) rice (*oryza sativa*),
(B) barnyardgrass (*Echinochloa crusgalli*),
(C) large crabgrass (*Digitaria adscendens*),
(D) annual sedge (*Cyperus microiria*),
(E) black nightshade (*Solanum nigrum* L.),
(F) hairly galinosoga (*Galinosoga ciliata*),
(G) rorippa spp. (*Rorippa indica*),
(H) corn (*Zea mays*),
(I) wheat (*Triticum vulgare*),
(J) soybean (Glysine max),
(K) cotton (Gossypium spp) and
(L) sugar beet (*Beta vulgaris*).

TABLE 10

| Compound No. | Amount of active ingredient applied kg/ha | (A) | (B) | (C) | (D) | (E) | (F) | (G) | (H) | (I) | (J) | (K) | (L) |
|---|---|---|---|---|---|---|---|---|---|---|---|---|---|
| 9 | 0.04 | 4 | 4 | 2 | 5 | 5 | 5 | 5 | 0 | 0 | 5 | 5 | 5 |
|  | 0.08 | 5 | 5 | 4 | 5 | 5 | 5 | 5 | 1 | 1 | 5 | 5 | 5 |
| 10 | 0.63 | 5 | 5 | 2 | 5 | 5 | 5 | 5 | 4 | 1 | 5 | 1 | 5 |
| 11 | 0.08 | 4 | 5 | 2 | 5 | 5 | 5 | 5 | 4 | 0 | 5 | 0 | 0 |
|  | 0.16 | 5 | 5 | 5 | 5 | 5 | 5 | 5 | 5 | 0 | 5 | 0 | 0 |
| 313 | 0.16 | 0 | 4 | 2 | 5 | 5 | 5 | 5 | 0 | 5 | 5 | 5 |
|  | 0.32 | 0 | 5 | 4 | 5 | 5 | 5 | 5 | 0 | 5 | 5 | 5 |
| 314 | 0.08 | 0 | 4 | 2 | 5 | 5 | 5 | 5 | 0 | 5 | 5 | 4 |
|  | 0.16 | 0 | 5 | 5 | 5 | 5 | 5 | 5 | 0 | 5 | 5 | 5 |
| 315 | 0.04 | 0 | 4 | 2 | 5 | 5 | 5 | 5 | 4 | 5 | 5 | 0 |
|  | 0.08 | 0 | 5 | 4 | 5 | 5 | 5 | 5 | 5 | 5 | 5 | 0 |

(A) rice (*oryza sativa*),
(B) barnyardgrass (*Echinochloa crusgalli*),
(C) large crabgrass (*Digitaria adscendens*),
(D) annual sedge (*Cyperus microiria*),
(E) black nightshade (*Solanum nigrum* L.),
(F) hairly galinosoga (*Galinosoga ciliata*),
(G) rorippa spp. (*Rorippa indica*),
(H) corn (*Zea mays*),
(I) wheat (*Triticum vulgare*),
(J) soybean (Glysine max),
(K) cotton (Gossypium spp) and
(L) sugar beet (*Beta vulgaris*).

TABLE 11

| Compound No. | Amount of active ingredient applied kg/ha | M | N | O | P | L |
|---|---|---|---|---|---|---|
| 11 | 0.04 | 5 | 5 | 5 | 5 | 0 |
|  | 0.08 | 5 | 5 | 5 | 5 | 0 |
|  | 0.16 | 5 | 5 | 5 | 5 | 0 |
| 315 | 0.04 | 5 | 5 | 5 | 5 | 0 |
|  | 0.08 | 5 | 5 | 5 | 5 | 0 |
|  | 0.16 | 5 | 5 | 5 | 5 | 0 |

(L) sugar beet (*Beta vulgaris*),
(M) groundsel (*Senecio vulgaris*),
(N) common field-speedwell (*Veronica persica*),
(O) wild mustard (*Sinapis arvensis*) and
(P) cleavers (*Galium aparine*).

We claim:

1. A pyrazolesulfonamide derivative represented by Formula (I):

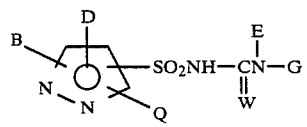

wherein Q represents a group of;

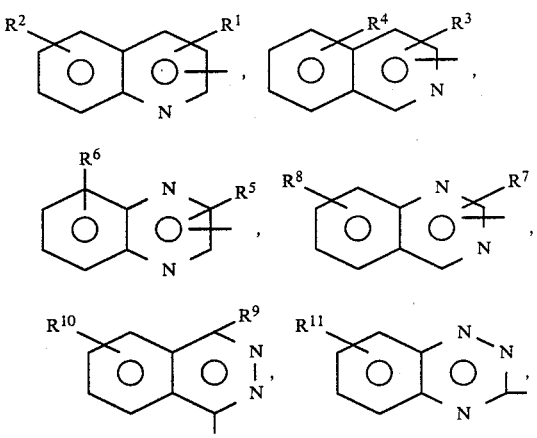

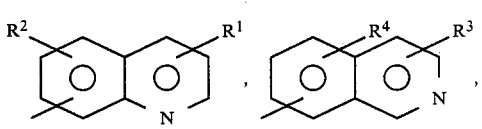

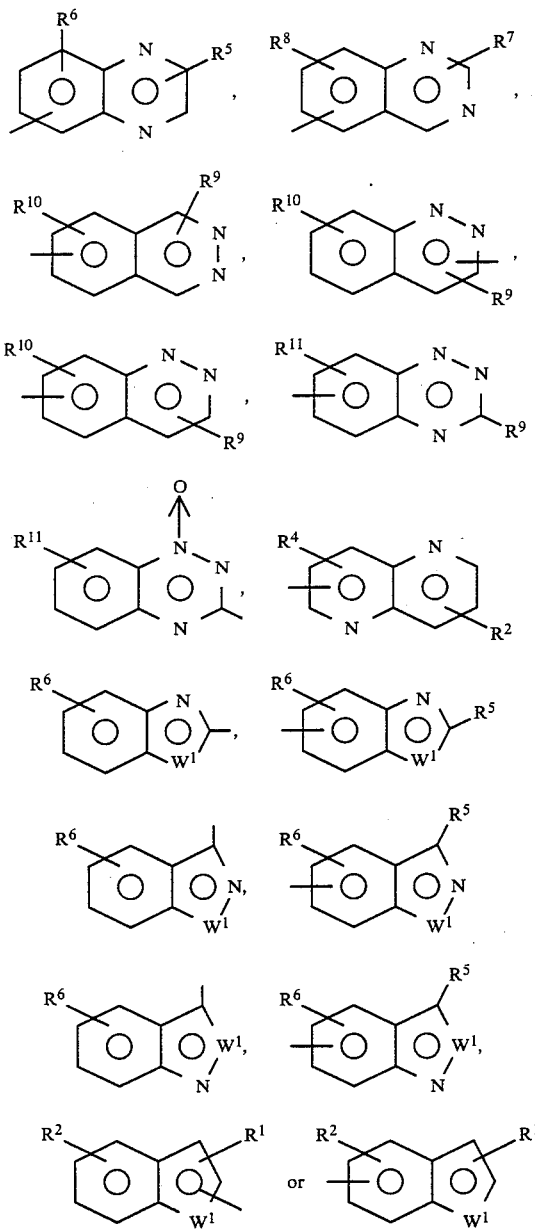

wherein
R¹, R³, R⁹ and R¹⁰ each represent a hydrogen atom, a halogen atom, a $C_1$-$C_8$ alkyl group, a cyano group or a group of $CO_2R^{13}$;
R² and R⁴ each represent a hydrogen atom, a halogen atom, a nitro group, a $C_1$-$C_8$ alkyl group, a halogenated $C_1$-$C_8$ alkyl group or a $C_1$-$C_8$ alkoxy group;
R⁵ represents a hydrogen atom, a halogen atom, a $C_1$-$C_8$ alkyl group, a $C_1$-$C_8$ alkoxy group or a group of $S(O)_nR^{12}$;
R⁶ represents a hydrogen atom, a halogen atom, a nitro group, a $C_1$-$C_8$ alkyl group, a halogenated $C_1$-$C_8$ alkyl group, a $C_1$-$C_8$ alkoxy group or a group of $CO_2R^{13}$;
R⁷ represents a hydrogen atom, a halogen atom, a $C_1$-$C_8$ alkyl group, a $C_1$-$C_8$ alkoxy group or a dialkylamino group;

R⁸ represents a hydrogen atom, a halogen atom, a $C_1$-$C_8$ alkyl group or a nitro group;
R¹¹ represents a hydrogen atom, a halogen atom, a $C_1$-$C_8$ alkyl group or a halogenated $C_1$-$C_8$ alkyl group;
W¹ represents an oxygen atom, a sulfur atom or a group of $NR^{13}$;
R¹² represents a $C_1$-$C_8$ alkyl group;
R¹³ represents a hydrogen atom or a $C_1$-$C_8$ alkyl group; and n represents an integer of 0, 1 or 2;
B and D each independently represent a hydrogen atom, a halogen atom, a nitro group, a $C_1$-$C_8$ alkyl group, a $C_1$-$C_8$ alkenyl group, a $C_1$-$C_8$ alkynyl group a $C_1$-$C_8$ alkoxy group, a $C_1$-$C_8$ alkoxy-$C_1$-$C_8$ alkyl group, a $C_1$-$C_8$ alkylthio-$C_1$-$C_8$ alkyl group, a halogenated $C_1$-$C_8$ alkyl group, a group of $COOR^{14}$, a group of $CH_2COOR^{14}$, a group of $CONR^{15}R^{16}$, a group of $S(O)_nR^{17}$, a cyano group, a group of $CH_2CN$, a group of $NR^{18}R^{19}$, a group of $SO_2NR^{20}R^{21}$, a group of $COR^{13}$, a group of OH, a benzoyl group which may be substituted (the substituent is selected from a halogen atom or a $C_1$-$C_8$ alkyl group) or a phenyl group which may be substituted (the substituent is selected from a halogen atom, a nitro group, a group of $COOR^{13}$ or a $C_1$-$C_8$ alkyl group);
R¹⁴ represents a hydrogen atom, an unsubstituted $C_1$-$C_8$ alkyl group (or a $C_1$-$C_8$ alkyl group substituted with an unsubstituted $C_1$-$C_8$ alkoxy group or a $C_1$-$C_8$ alkoxy group substituted with a group of $OR^{13}$, a halogenated $C_1$-$C_8$ alkoxy group, a cyano group, a phenoxy group, a $C_1$-$C_8$ alkoxycarbonyl group, a group of $NR^{12}R^{13}$, a $C_3$-$C_7$ cycloalkyl group, a $C_1$-$C_8$ alkylthio group or a $C_1$-$C_8$ alkylcarbonyl group), an unsubstituted $C_1$-$C_8$ alkenyl group or a $C_1$-$C_8$ alkenyl group substituted with a halogen atom, an unsubstituted $C_1$-$C_8$ alkynyl group or a $C_1$-$C_8$ alkynyl group substituted with a halogen atom, a halogenated $C_1$-$C_8$ alkyl group, a $C_3$-$C_7$ cycloalkyl group or a benzyl group;
R¹⁵ represents a hydrogen atom, a $C_1$-$C_8$ alkyl group or a phenyl group;
R¹⁶ represents a hydrogen atom, a $C_1$-$C_8$ alkyl group or a $C_1$-$C_8$ alkoxy group;
R¹⁷ represents a $C_1$-$C_8$ alkyl group, a $C_1$-$C_8$ alkoxy group, a phenyl group, a halogenated $C_1$-$C_8$ alkyl group, a $C_1$-$C_8$ alkenyloxy group or a $C_1$-$C_8$ alkynyloxy group; n represents an integer of 0, 1 or 2;
R¹⁸ and R¹⁹ each independently represent a hydrogen atom, a $C_1$-$C_8$ alkyl group, a $C_1$-$C_8$ alkylcarbonyl group or a $C_1$-$C_8$ alkylsulfonyl group;
R²⁰ and R²¹ each independently represent a hydrogen atom, a $C_1$-$C_8$ alkyl group, a $C_1$-$C_8$ alkenyl group or a $C_1$-$C_8$ alkynyl group;
E represents a hydrogen atom, a $C_1$-$C_8$ alkyl group, a $C_1$-$C_8$ alkenyl group, a $C_1$-$C_8$ alkynyl group or a $C_1$-$C_8$ alkoxy group;
W represents an oxygen atom, a sulfur atom or a group of $NR^{16}$;
G represents

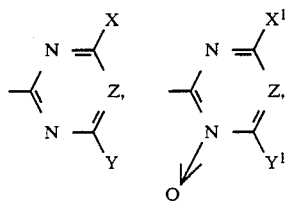

wherein X and Y each independently represent a hydrogen atom, a halogen atom, a $C_1$–$C_8$ alkyl group, a $C_1$–$C_8$ alkoxy group, a $C_1$–$C_8$ alkoxyalkyl group, a halogenated $C_1$–$C_8$ alkyl group, a halogenated $C_1$–$C_8$ alkoxy group, a group of $NR^{22}R^{23}$, a group of $OCH(R^{13})COOR^{13}$, a group of $COOR^{13}$, a cyclopropyl group, a group of $CH(OR^{24})_2$, a $C_1$–$C_8$ alkylthio group or a halogenated $C_1$–$C_8$ alkylthio group;

$R^{22}$ and $R^{23}$ each independently represent a hydrogen atom, a $C_1$–$C_8$ alkyl group or a $C_1$–$C_8$ alkoxy group;

$R^{24}$ represents a $C_1$–$C_8$ alkyl group;

$X^1$ and $Y^1$ each independently represent a hydrogen atom, a halogen atom, a $C_1$–$C_8$ alkyl group or a $C_1$–$C_8$ alkoxy group;

Z represents a group of C—$R^{25}$;

$R^{25}$ represents a hydrogen atom, a $C_1$–$C_8$ alkyl group, a halogenated $C_1$–$C_8$ alkyl group, a halogen atom, a $C_1$–$C_8$ alkoxy group or a 5-membered ring structure containing an oxygen atom together with Y or $Y^1$;

with the proviso that the group:

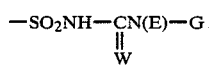

in Formula (I) is not substituted on the nitrogen atom in the pyrazole ring, and, when Q is not substituted on the nitrogen atom in the pyrazole ring, the substituent for B or D on the nitrogen atom is selected from a hydrogen atom, a $C_1$–$C_8$ alkyl group, a $C_1$–$C_8$ alkenyl group, a $C_1$–$C_8$ alkynyl group, a group of —$CH_2CN$, a $C_1$–$C_8$ alkoxy-$C_1$–$C_8$ alkyl group, a $C_1$–$C_8$ alkylthio-$C_1$–$C_8$ alkyl group, a group of —$CH_2COOR^{13}$, a group of —$COR^{13}$, a group of —$SO_2R^{24}$, a group of —$SO_2NR^{13}R^{24}$ or a phenyl group which may be substituted (the substituent is selected from a halogen atom, a nitro group, a group of $COOR^{13}$ or a $C_1$–$C_8$ alkyl group).

2. The pyrazolesulfonamide derivative according to claim 1, wherein the derivative is represented by the formula:

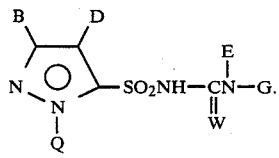

3. The pyrazolesulfonamide derivative according to claim 2, werein

B represents a hydrogen atom, a $C_1$–$C_8$ alkyl group, a $C_1$–$C_8$ alkoxy group, a halogen atom;

D represents a hydrogen atom, a halogen atom, a $C_1$–$C_8$ alkyl group, a group of $COOR^{14}$, a group of $S(O)_nR^{17}$, a group of $SO_2NR^{20}R^{21}$ or $COR^{13}$;

W represents an oxygen atom;

E represents a hydrogen atom; and

G represents a group of

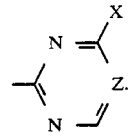

4. The pyrazolesulfonamide derivative according to claim 3, wherein

D represents a group of —$COOR^{14}$ (wherein $R^{14}$ is selected from the group of a $C_1$–$C_8$ alkyl group which may be substituted with a $C_1$–$C_8$ alkoxy group or a halogen atom, a $C_1$–$C_8$ alkenyl group and a $C_1$–$C_8$ alkynyl group);

X and Y each represent a $C_1$–$C_8$ alkyl group, a $C_1$–$C_8$ alkoxy group, a halogen atom or a group of —$OCHF_2$; and Z represents a nitrogen atom or a group of —CH.

5. The pyrazolesulfonamide derivative according to claim 3, wherein

Q represents

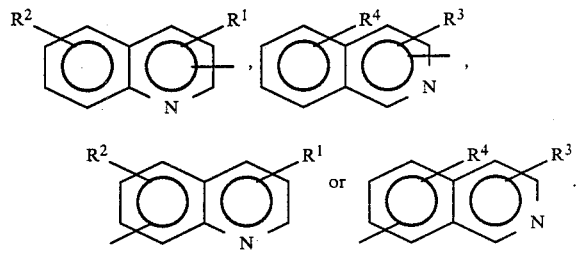

6. The pyrazolesulfonamide derivative according to claim 3, wherein

Q represents

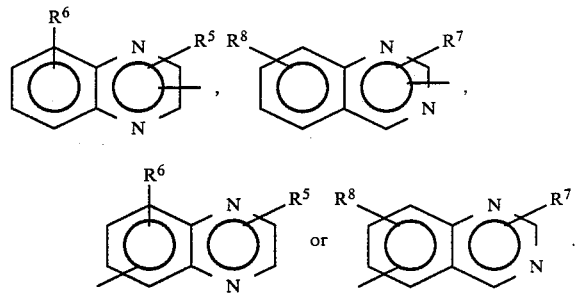

7. The pyrazolesulfonamide derivative according to claim 3, wherein

Q represents

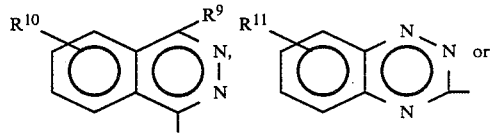

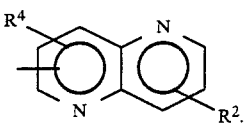

8. The pyrazolesulfonamide derivative according to claim 3, wherein
Q represents

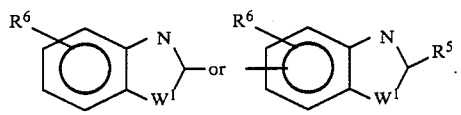

9. The pyrazolesulfonamide derivative according to claim 3, wherein
Q represents

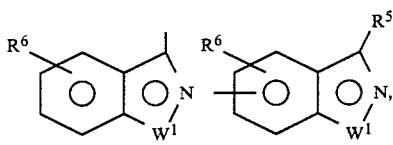

10. The pyrazolesulfonamide derivative according to claim 1, wherein the derivative is represented by the formula:

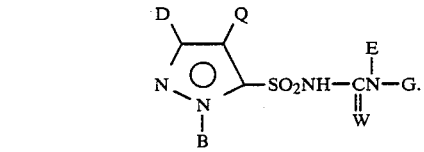

11. The pyrazolesulfonamide derivative according to claim 10, wherein
B represents a hydrogen atom, a $C_1$-$C_8$ alkyl group, a $C_1$-$C_8$ alkenyl group, a $C_1$-$C_8$ alkynyl group, $C_1$-$C_8$ alkoxyalkyl group or a phenyl group which may be substituted (The substituent is selected from a halogen atom, a nitro group, a group of $COOR^{13}$ or a $C_1$-$C_8$ alkyl group);
D represents a hydrogen atom, a $C_1$-$C_8$ alkyl group, a $C_1$-$C_8$ alkoxy group, a halogen atom;
W represents an oxygen atom;
E represents a hydrogen atom; and
G represents a group of

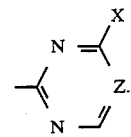

12. The pyrazolesulfonamide derivative according to claim 1, wherein the derivative is represents by the formula:

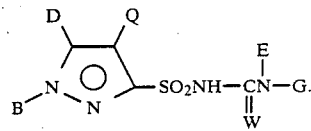

13. The pyrazolesulfonamide derivative according to claim 12, wherein
B represents a $C_1$-$C_8$ alkyl group, a $C_1$-$C_8$ alkenyl group, a $C_1$-$C_8$ alkynyl group or a $C_1$-$C_8$ alkoxyalkyl group;
D represents a hydrogen atom or a $C_1$-$C_8$ alkyl group;
W represents an oxygen atom;
E represents a hydrogen atom; and
G represents a group of

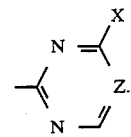

14. The pyrazolesulfonamide derivative according to claim 1, wherein the derivative is represented by the formula:

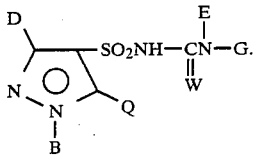

15. The pyrazolesulfonamide derivative according to claim 2, wherein
B represents a hydrogen atom or a $C_1$-$C_8$ alkyl group;
D represents a hydrogen atom, a $C_1$-$C_8$ alkyl group or a halogen atom;
W represents an oxygen atom;
E represents a hydrogen atom; and
G represents a group of

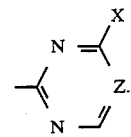

16. The pyrazolesulfonamide derivative according to claim 1, wherein
Q represents

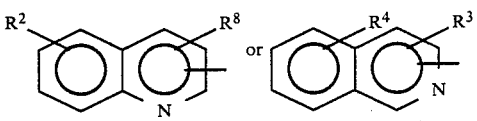

B represents a hydrogen atom, a $C_1$-$C_8$ alkyl group, a $C_1$-$C_8$ alkenyl group, a $C_1$-$C_8$ alkynyl group, a $C_1$-$C_8$ alkoxyalkyl group or a phenyl group which may be substituted (the substituent is selected from a halogen atom, a nitro group, a group of COOR$^{13}$ or a $C_1$-$C_8$ alkyl group);

D represents a hydrogen atom, a $C_1$-$C_8$ alkyl group, a $C_1$-$C_8$ alkoxyl group, a halogen atom;

W represents an oxygen atom;

E represents a hydrogen atom;

G represents the group

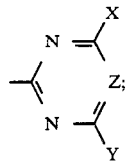

and Z represents CH.

17. The pyrazolesulfonamide derivative according to claim 16, wherein the derivative is represented by the formula;

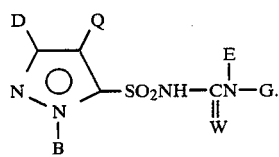

18. The pyrazolesulfonamide derivative according to claim 16, wherein the derivative is represented by the formula:

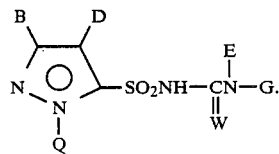

19. The pyrazolesulfonamide derivative according to claim 16, wherein the derivative is represented by the formula:

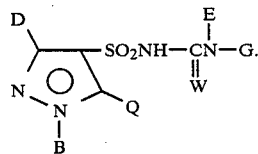

20. The pyrazolesulfonamide derivative according to claim 16, wherein the derivative is represented by the formula:

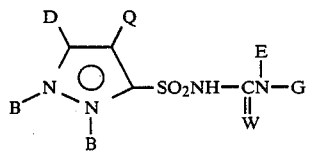

21. The pyrazolesulfonamide derivative according to claim 1, wherein the derivative is N-[(4,6-dimethoxypyrimidin-2-yl)-aminocarbonyl]-4-ethoxycarbonyl-1-(2-quinolyl)pyrazole-5-sulfonamide.

22. The pyrazolesulfonamide derivative according to claim 1, wherein the derivative is N-[(4,6-dimethoxypyrimidin-2-yl)-aminocarbonyl]-4-ethoxycarbonyl-3-methyl-1-(2-quinolyl)pyrazole-5-sulfonamide.

23. The pyrazolesulfonamide derivative according to claim 1, wherein the derivative is N-[(4,6-dimethoxypyrimidin-2-yl)-aminocarbonyl]-4-methoxycarbonyl-1-(2-quinolyl)pyrazole-5-sulfonamide.

24. The pyrazolesulfonamide derivative according to claim 1, wherein the derivative is N-[(4,6-dimethoxypyrimidin-2-yl)-aminocarbonyl]-4-methoxycarbonyl-3-methyl-1-(2-quinolyl)pyrazole-5-sulfonamide.

25. The pyrazolesulfonamide derivative according to claim 1, wherein the derivative is N-[(4,6-dimethoxypyrimidin-2-yl)-aminocarbonyl]-4-ethoxycarbonyl-1-(1-isoquinolyl)pyrazole-5-sulfonamide.

26. The pyrazolesulfonamide derivative according to claim 1, wherein the derivative is N-[(4,6-dimethoxypyrimidin-2-yl)-aminocarbonyl]-4-ethoxycarbonyl-3-methyl-1-(1-isoquinolyl)pyrazole-5-sulfonamide.

27. The pyrazolesulfonamide derivative according to claim 1, wherein the derivative is N-[(4,6-dimethoxypyrimidin-2-yl)-aminocarbonyl]-4-methoxycarbonyl-1-(1-isoquinolyl)pyrazole-5-sulfonamide.

28. The pyrazolesulfonamide derivative according to claim 1, wherein the derivative is N-[(4,6-dimethoxypyrimidin-2-yl)-aminocarbonyl]-4-methoxycarbonyl-3-methyl-1-(1-isoquinolyl)pyrazole-5-sulfonamide.

29. A herbicidal composition comprising an agricultural carrier and as an active component one or more kinds of a pyrazolesulfonamide derivative represented by Formula (I):

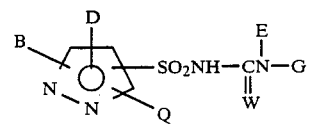 (I)

wherein

Q represents a group of;

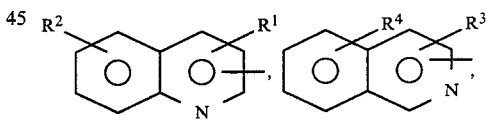

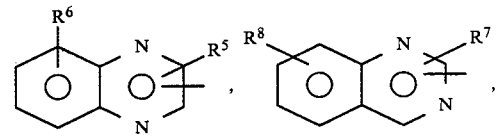

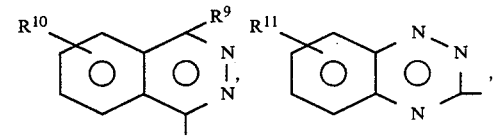

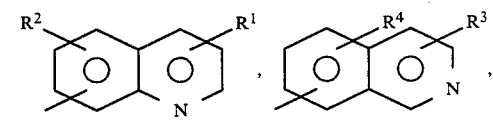

-continued

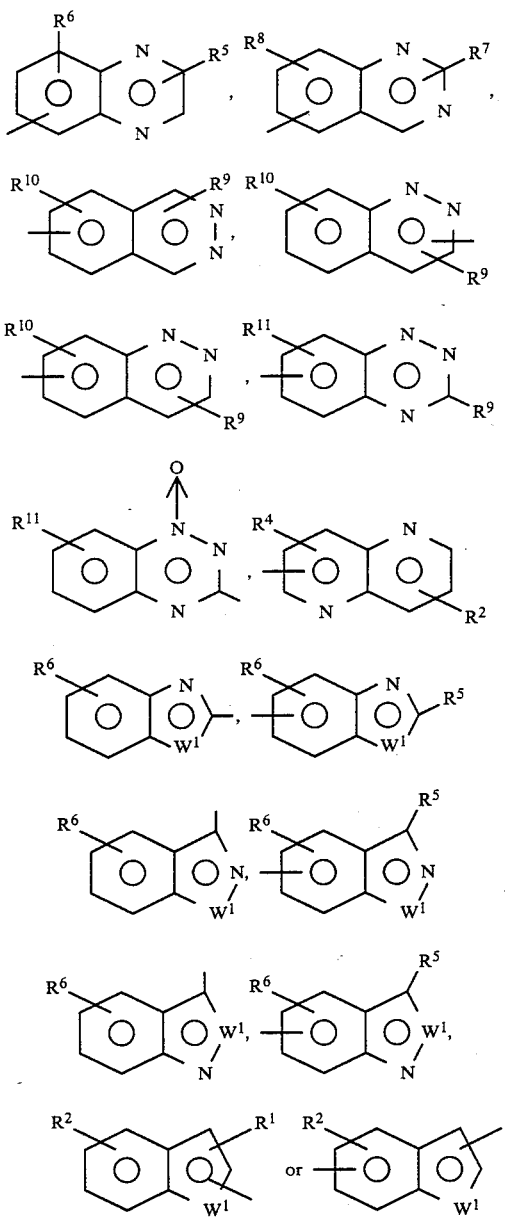

wherein
$R^1$, $R^3$, $R^9$ and $R^{10}$ each represent a hydrogen atom, a halogen atom, a $C_1$-$C_8$ alkyl group, a cyano group or a group of $CO_2R^{13}$;

$R^2$ and $R^4$ each represent a hydrogen atom, a halogen atom, a nitro group, a $C_1$-$C_8$ alkyl group, a halogenated $C_1$-$C_8$ alkyl group or a $C_1$-$C_8$ alkoxy group;

$R^5$ represents a hydrogen atom, a halogen atom, a $C_1$-$C_8$ alkyl group, a $C_1$-$C_8$ alkoxy group or a group of $S(O)_nR^{12}$;

$R^6$ represents a hydrogen atom, a halogen atom, a nitro group, a $C_1$-$C_8$ alkyl group, a halogenated $C_1$-$C_8$ alkyl group, a $C_1$-$C_8$ alkoxy group or a group of $CO_2R^{13}$;

$R^7$ represents a hydrogen atom, a halogen atom, a $C_1$-$C_8$ alkyl group, a $C_1$-$C_8$ alkoxy group or a dialkylamino group;

$R^8$ represents a hydrogen atom, a halogen atom, a $C_1$-$C_8$ alkyl group or a nitro group;

$R^{11}$ represents a hydrogen atom, a halogen atom, a $C_1$-$C_8$ alkyl group or a halogenated $C_1$-$C_8$ alkyl group;

$W^1$ represents an oxygen atom, a sulfur atom or a group of $NR^{13}$;

$R^{12}$ represents a $C_1$-$C_8$ alkyl group;

$R^{13}$ represents a hydrogen atom or a $C_1$-$C_8$ alkyl group; and n represents an integer of 0, 1 or 2;

B and D each independently represent a hydrogen atom, a halogen atom, a nitro group, a $C_1$-$C_8$ alkyl group, a $C_1$-$C_8$ alkenyl group, a $C_1$-$C_8$ alkynyl group a $C_1$-$C_8$ alkoxy group, a $C_1$-$C_8$ alkoxy-$C_1$-$C_8$ alkyl group, a $C_1$-$C_8$ alkylthio-$C_1$-$C_8$ alkyl group, a halogenated $C_1$-$C_8$ alkyl group, a group of $COOR^{14}$, a group of $CH_2COOR^{14}$, a group of $CONR^{15}R^{16}$, a group of $S(O)_nR^{17}$, a cyano group, a group of $CH_2CN$, a group of $NR^{18}R^{19}$, a group of $SO_2NR^{20}R^{21}$, a group of $COR^{13}$, a group of OH, a benzoyl group which may be substituted (the substituent is selected from a halogen atom or a $C_1$-$C_8$ alkyl group) or a phenyl group which may be substituted (the substituent is selected from a halogen atom, a nitro group, a group of $COOR^{13}$ or a $C_1$-$C_8$ alkyl group);

$R^{14}$ represents a hydrogen atom, an unsubstituted $C_1$-$C_8$ alkyl group (or a $C_1$-$C_8$ alkyl group substituted with an unsubstituted $C_1$-$C_8$ alkoxy group or a $C_1$-$C_8$ alkoxy group substituted with a group of $OR^{13}$, a halogenated $C_1$-$C_8$ alkoxy group, a cyano group, a phenoxy group, a $C_1$-$C_8$ alkoxycarbonyl group, a group of $NR^{12}R^{13}$, a $C_3$-$C_7$ cycloalkyl group, a $C_1$-$C_8$ alkylthio group or a $C_1$-$C_8$ alkylcarbonyl group), an unsubstituted $C_1$-$C_8$ alkenyl group or a $C_1$-$C_8$ alkenyl group substituted with a halogen atom, an unsubstituted $C_1$-$C_8$ alkynyl group or a $C_1$-$C_8$ alkynyl group substituted with a halogen atom, a halogenated $C_1$-$C_8$ alkyl group, a $C_3$-$C_7$ cycloalkyl group or a benzyl group;

$R^{15}$ represents a hydrogen atom, a $C_1$-$C_8$ alkyl group or a phenyl group;

$R^{16}$ represents a hydrogen atom, a $C_1$-$C_8$ alkyl group or a $C_1$-$C_8$ alkoxy group;

$R^{17}$ represents a $C_1$-$C_8$ alkyl group, a $C_1$-$C_8$ alkoxy group, a phenyl group, a halogenated $C_1$-$C_8$ alkyl group, a $C_1$-$C_8$ alkenyloxy group or a $C_1$-$C_8$ alkynyloxy group;

n represents an integer of 0, 1 or 2;

$R^{18}$ and $R^{19}$ each independently represent a hydrogen atom, a $C_1$-$C_8$ alkyl group, a $C_1$-$C_8$ alkylcarbonyl group or a $C_1$-$C_8$ alkylsulfonyl group;

$R^{20}$ and $R^{21}$ each independently represent a hydrogen atom, a $C_1$-$C_8$ alkyl group, a $C_1$-$C_8$ alkenyl group or a $C_1$-$C_8$ alkynyl group;

E represents a hydrogen atom, a $C_1$-$C_8$ alkyl group, a $C_1$-$C_8$ alkenyl group, a $C_1$-$C_8$ alkynyl group or a $C_1$-$C_8$ alkoxy group;

W represents an oxygen atom, a sulfur atom or a group of $NR^{16}$;

G represents

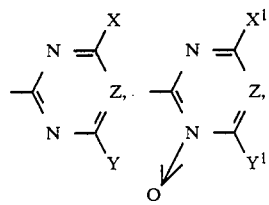

wherein
X and Y each independently represent a hydrogen atom, a halogen atom, a $C_1$-$C_8$ alkyl group, a $C_1$-$C_8$ alkoxy group, a $C_1$-$C_8$ alkoxyalkyl group, a halogenated $C_1$-$C_8$ alkyl group, a halogenated $C_1$-$C_8$ alkoxy group, a group of $NR^{22}R^{23}$, a group of $OCH(R^{13})COOR^{13}$, a group of $COOR^{13}$, a cyclopropyl group, a group of $CH(OR^{24})_2$, a $C_1$-$C_8$ alkylthio group or a halogenated $C_1$-$C_8$ alkylthio group;

$R^{22}$ and $R^{23}$ each independently represent a hydrogen atom, a $C_1$-$C_8$ alkyl group or a $C_1$-$C_8$ alkoxy group;

$R^{24}$ represents a $C_1$-$C_8$ alkyl group;

$X^1$ and $Y^1$ each independently represent a hydrogen atom, a halogen atom, a $C_1$-$C_8$ alkyl group or a $C_1$-$C_8$ alkoxy group;

Z represents a group of $C-R^{25}$;

$R^{25}$ represents a hydrogen atom, a $C_1$-$C_8$ alkyl group, a $C_1$-$C_8$ halogenated alkyl group, a halogen atom, a $C_1$-$C_8$ alkoxy group or a 5-membered ring structure containing an oxygen atom together with Y or $Y^1$;

with the proviso that the group:

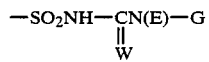

in Formula (I) is not substituted on the nitrogen atom in the pyrazole ring, and, when Q is not substituted on the nitrogen atom in the pyrazole ring, the substituent for B or D on the nitrogen atom is selected from a hydrogen atom, a $C_1$-$C_8$ alkyl group, a $C_1$-$C_8$ alkenyl group, a $C_1$-$C_8$ alkynyl group, a group of $-CH_2CN$, a $C_1$-$C_8$ alkoxy-$C_1$-$C_8$ alkyl group, a $C_1$-$C_8$ alkylthio-$C_1$-$C_8$ alkyl group, a group of $-CH_2COOR^{13}$, a group of $-COR^{13}$, a group of $-SO_2R^{24}$, a group of $-SO_2NR^{13}R^{24}$ or a phenyl group which may be substituted (the substituent is selected from a halogen atom, a nitro group, a group of $COOR^{13}$ or a $C_1$-$C_8$ alkyl group);
and an agriculturally acceptable salt thereof.

30. The herbicidal composition according to claim 29, wherein
Q represents

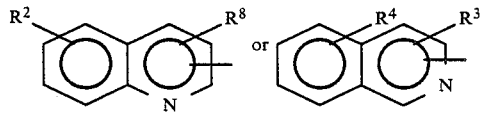

B represents a hydrogen atom, a $C_1$-$C_8$ alkyl group, a $C_1$-$C_8$ alkenyl group, a $C_1$-$C_8$ alkynyl group, a $C_1$-$C_8$ alkoxyalkyl group or a phenyl group which may be substituted (the substituent is selected from a halogen atom, a nitro group, a group of $COOR^{13}$ or a $C_1$-$C_8$ alkyl group);

D represents a hydrogen atom, a $C_1$-$C_8$ alkyl group, a $C_1$-$C_8$ alkoxyl group, a halogen atom W represents an oxygen atom;

E represents a hydrogen atom;

G represents the group

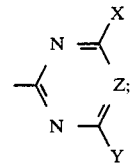

Z represents CH.

31. The herbicidal composition according to claim 24, wherein the derivative is represented by the formula:

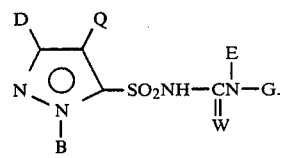

32. The herbicidal composition according to claim 30, wherein the derivative is represented by the formula:

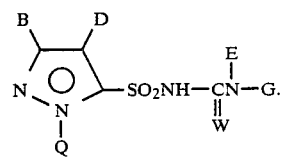

33. The herbicidal composition according to claim 30, wherein the derivative is represented by the formula:

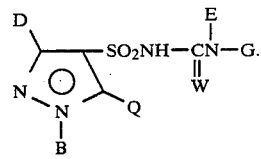

34. The herbicidal composition according to claim 30, wherein the derivative is represented by the formula:

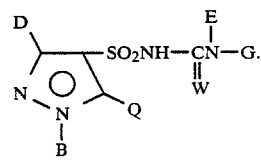

* * * * *

UNITED STATES PATENT AND TRADEMARK OFFICE
CERTIFICATE OF CORRECTION

PATENT NO. : 4,844,728
DATED : July 4, 1989
INVENTOR(S) : YAMAMOTO et al

It is certified that error appears in the above-identified patent and that said Letters Patent is hereby corrected as shown below:

In the title page, the name of the second inventor should read --Takuya Kakuta--.

Column 95, claim 3, line 2, change "werein" to --wherein--.

Column 96, claim 3, insert "Y" in the formula below "Z".

Column 97, claim 11, insert "Y" in the formula below "Z".

Column 98, claim 13, insert "Y" in the formula below "Z".

Column 98, claim 15, insert "Y" in the formula below "Z".

Column 104, claim 31, line 2, change "to claim 24" to --to claim 30--.

Columns 87 and 88 should be reversed with columns 85 and 86.

Signed and Sealed this

Thirty-first Day of March, 1992

Attest:

HARRY F. MANBECK, JR.

Attesting Officer    Commissioner of Patents and Trademarks